(12) United States Patent
Bromley

(10) Patent No.: US 9,351,517 B2
(45) Date of Patent: May 31, 2016

(54) FORMULATIONS OF WATER-SOLUBLE DERIVATIVES OF VITAMIN E AND COMPOSITIONS CONTAINING SAME

(71) Applicant: Philip J. Bromley, Fullerton, CA (US)

(72) Inventor: Philip J. Bromley, Fullerton, CA (US)

(73) Assignee: Virun, Inc., Walnut, CA (US)

( * ) Notice: Subject to any disclaimer, the term of this patent is extended or adjusted under 35 U.S.C. 154(b) by 0 days.

(21) Appl. No.: 14/207,310

(22) Filed: Mar. 12, 2014

(65) Prior Publication Data

US 2014/0271593 A1     Sep. 18, 2014

Related U.S. Application Data

(60) Provisional application No. 61/852,243, filed on Mar. 15, 2013.

(51) Int. Cl.

| | |
|---|---|
| A61K 38/43 | (2006.01) |
| A23L 2/52 | (2006.01) |
| A61K 31/355 | (2006.01) |
| A61K 31/122 | (2006.01) |
| A61K 31/202 | (2006.01) |
| A23L 1/30 | (2006.01) |
| A23L 1/302 | (2006.01) |
| A23L 1/304 | (2006.01) |
| A23L 2/02 | (2006.01) |
| A23L 2/60 | (2006.01) |
| A61K 31/05 | (2006.01) |
| A61K 31/201 | (2006.01) |
| A61K 31/59 | (2006.01) |
| A61K 9/00 | (2006.01) |
| A61K 47/36 | (2006.01) |
| A61K 9/107 | (2006.01) |
| A61K 47/44 | (2006.01) |

(52) U.S. Cl.
CPC ... *A23L 2/52* (2013.01); *A23L 1/30* (2013.01); *A23L 1/3002* (2013.01); *A23L 1/302* (2013.01); *A23L 1/304* (2013.01); *A23L 1/3006* (2013.01); *A23L 1/3008* (2013.01); *A23L 2/02* (2013.01); *A23L 2/60* (2013.01); *A61K 9/0095* (2013.01); *A61K 9/1075* (2013.01); *A61K 31/05* (2013.01); *A61K 31/122* (2013.01); *A61K 31/201* (2013.01); *A61K 31/202* (2013.01); *A61K 31/355* (2013.01); *A61K 31/59* (2013.01); *A61K 47/36* (2013.01); *A61K 47/44* (2013.01)

(58) Field of Classification Search
CPC ...................................................... A61K 38/43
See application file for complete search history.

(56) References Cited

U.S. PATENT DOCUMENTS

| | | | |
|---|---|---|---|
| 2,680,749 A | 6/1954 | Cawley et al. | 549/410 |
| 3,102,078 A | 8/1963 | Robeson et al. | 514/458 |
| 3,156,614 A | 11/1964 | Macdonnell | 514/659 |
| 3,480,616 A | 11/1969 | Osipow et al. | 536/119 |
| 3,538,119 A | 11/1970 | Grant | 549/410 |
| 3,574,859 A | 4/1971 | Kosti | 424/330 |
| 3,644,333 A | 2/1972 | Osipow et al. | 536/119 |
| 3,714,144 A | 1/1973 | Feuge et al. | 536/119 |
| 3,822,349 A | 7/1974 | Kosti | 424/54 |
| 4,035,235 A | 7/1977 | Richards | 435/99 |
| 4,312,861 A | 1/1982 | Boskay et al. | 424/220 |
| 4,353,365 A | 10/1982 | Hallworth et al. | 128/203.15 |
| 4,524,769 A | 6/1985 | Wetterlin et al. | 128/203.15 |
| 4,572,915 A | 2/1986 | Crooks | 514/458 |
| 4,665,204 A | 5/1987 | Wirth | 549/410 |
| 4,670,285 A | 6/1987 | Clandinin et al. | 426/602 |
| 4,710,567 A | 12/1987 | Kea et al. | 536/119 |
| 4,835,002 A | 5/1989 | Wolf et al. | 426/590 |
| 4,849,227 A | 7/1989 | Cho | 424/498 |
| 4,867,986 A | 9/1989 | Desai et al. | 424/464 |
| 4,898,935 A | 2/1990 | Nakamura et al. | 536/119 |
| 4,916,163 A | 4/1990 | Shah et al. | 514/593 |

(Continued)

FOREIGN PATENT DOCUMENTS

| | | |
|---|---|---|
| CN | 101119710 A | 6/2008 |
| DE | 10 2005 049664 | 4/2007 |
| EP | 1 055 374 | 11/2000 |
| EP | 1 972 334 | 9/2010 |
| GB | 576 943 A | 4/1946 |
| GB | 759 577 A | 10/1956 |
| WO | WO 95/31217 | 11/1995 |
| WO | WO 96/36316 | 11/1996 |
| WO | WO 98/08490 | 3/1998 |
| WO | WO 99/59421 | 11/1999 |

(Continued)

OTHER PUBLICATIONS

Gutfinger et al. (Quantitative changes in some Unsaponifiable Components of Soya Bean Oil due to Refining. J. Sci. Fd Agric. 1974, 25, 1143-1147).*

(Continued)

*Primary Examiner* — Karen Cochrane Carlson
*Assistant Examiner* — Natalie Moss
(74) *Attorney, Agent, or Firm* — Dentons US LLP; Stephanie Seidman

(57) ABSTRACT

Provided are compositions that contain water-soluble vitamin E derivative mixtures (compositions), such as tocopheryl polyethylene glycol succinate (TPGS), TPGS analogs, TPGS homologs and TPGS derivatives. The water-soluble vitamin E mixtures contain mixtures that include dimers and monomers of the vitamin E derivative, where the amount of dimer is greater than 12%, such as 29%, 35%, 50%, 60%, and the amount of monomer is less than 87%, by weight, of the water-soluble vitamin E derivative mixture. Also provided are products containing the water-soluble vitamin E derivative mixtures, including concentrates for dilution into aqueous beverages and compositions for direct ingestion.

50 Claims, No Drawings

(56) References Cited

U.S. PATENT DOCUMENTS

| | | | |
|---|---|---|---|
| 4,995,519 A | 2/1991 | Rose et al. | 215/47 |
| 4,995,911 A | 2/1991 | Matsumoto et al. | 127/48 |
| 4,996,309 A | 2/1991 | Matsumoto et al. | 536/119 |
| 5,011,922 A | 4/1991 | Matsumoto et al. | 536/119 |
| 5,017,697 A | 5/1991 | Matsumoto et al. | 536/127 |
| 5,035,237 A | 7/1991 | Newell et al. | 128/203.15 |
| 5,167,950 A | 12/1992 | Lins | 424/47 |
| 5,179,122 A | 1/1993 | Greene et al. | 514/458 |
| 5,234,695 A | 8/1993 | Hobbs et al. | 424/489 |
| 5,236,907 A | 8/1993 | Ueno et al. | 514/530 |
| 5,239,993 A | 8/1993 | Evans et al. | 128/203.15 |
| 5,397,591 A | 3/1995 | Kyle et al. | 426/602 |
| 5,407,957 A | 4/1995 | Kyle et al. | 514/547 |
| 5,415,162 A | 5/1995 | Caspser et al. | 128/203.12 |
| 5,430,021 A | 7/1995 | Rudnic et al. | 514/10.1 |
| 5,492,938 A | 2/1996 | Kyle et al. | 514/786 |
| 5,583,155 A | 12/1996 | Kovacs et al. | 514/20.5 |
| 5,593,682 A | 1/1997 | Papas et al. | 424/401 |
| 5,597,595 A | 1/1997 | Dewille et al. | 426/74 |
| 5,711,983 A | 1/1998 | Kyle et al. | 426/635 |
| 5,715,810 A | 2/1998 | Armstrong et al. | 128/230.15 |
| 5,798,333 A | 8/1998 | Sherman et al. | 514/11 |
| 5,821,264 A | 10/1998 | Lane et al. | 514/458 |
| 5,891,469 A | 4/1999 | Amselem | 424/451 |
| 5,908,940 A | 6/1999 | Lane et al. | 549/453 |
| 5,919,818 A | 7/1999 | Lane et al. | 514/458 |
| 5,977,348 A | 11/1999 | Harris | 536/123.1 |
| 6,045,826 A | 4/2000 | Borowy-Borowski et al. | 424/451 |
| 6,048,566 A | 4/2000 | Behnam et al. | 426/590 |
| 6,054,261 A | 4/2000 | Masterson | 435/1.2 |
| 6,056,971 A | 5/2000 | Goldman | 424/439 |
| 6,086,915 A | 7/2000 | Zeligs et al. | 424/455 |
| 6,136,851 A | 10/2000 | Bonte et al. | 424/455 |
| 6,143,770 A | 11/2000 | Lane et al. | 514/332 |
| 6,162,474 A | 12/2000 | Chen et al. | 426/72 |
| 6,180,130 B1 | 1/2001 | Chen et al. | 424/439 |
| 6,184,255 B1 | 2/2001 | Mae et al. | 514/720 |
| 6,193,985 B1 | 2/2001 | Sonne et al. | 424/400 |
| 6,204,290 B1 | 3/2001 | Lane et al. | 514/456 |
| 6,239,171 B1 | 5/2001 | Lane et al. | 514/458 |
| 6,248,363 B1 | 6/2001 | Patel et al. | 424/497 |
| 6,265,717 B1 | 7/2001 | Sakata et al. | 250/289 |
| 6,267,985 B1 | 7/2001 | Chen et al. | 424/451 |
| 6,284,268 B1 | 9/2001 | Mishra et al. | 424/455 |
| 6,300,677 B1 | 10/2001 | Chopra | 514/715 |
| 6,335,022 B1 | 1/2002 | Simonnet et al. | 424/401 |
| 6,378,519 B1 | 4/2002 | Davies et al. | 128/203.21 |
| 6,383,471 B1 | 5/2002 | Chen et al. | 424/45 |
| 6,391,370 B1 | 5/2002 | Rogers et al. | 426/611 |
| 6,403,116 B1 | 6/2002 | Anderson et al. | 424/439 |
| 6,416,786 B1 | 7/2002 | Mulye et al. | 424/468 |
| 6,441,050 B1 | 8/2002 | Chopra | 514/675 |
| 6,455,512 B1 | 9/2002 | Ward et al. | 514/59 |
| 6,509,044 B2 | 1/2003 | Van Den Braak et al. | 426/2 |
| 6,534,085 B1 | 3/2003 | Zeligs | 424/451 |
| 6,632,443 B2 | 10/2003 | Borowy-Borowski et al. | 424/400 |
| 6,635,293 B2 | 10/2003 | Fullmer et al. | 426/250 |
| 6,635,680 B2 | 10/2003 | Mulye et al. | 424/471 |
| 6,689,387 B1 | 2/2004 | Zeligs | 424/489 |
| 6,761,903 B2 | 7/2004 | Chen et al. | 424/451 |
| 6,870,077 B2 | 3/2005 | Kenaschuk | 800/298 |
| 6,919,378 B2 | 7/2005 | Jacobs et al. | 514/618 |
| 6,946,146 B2 | 9/2005 | Mulye et al. | 424/479 |
| 6,977,166 B1 | 12/2005 | Ratledge et al. | 435/134 |
| 6,982,281 B1 | 1/2006 | Chen et al. | 514/458 |
| 6,982,282 B2 | 1/2006 | Lambert et al. | 424/405 |
| 7,015,252 B2 | 3/2006 | Fujii et al. | 514/690 |
| 7,026,361 B2 | 4/2006 | Minemura et al. | 516/75 |
| 7,030,102 B1 | 4/2006 | Madhavi et al. | 514/58 |
| 7,060,672 B2 | 6/2006 | Naicker et al. | 514/2 |
| 7,094,804 B2 | 8/2006 | Behnam | 514/460 |
| 7,115,565 B2 | 10/2006 | Gao et al. | 514/9 |
| 7,374,779 B2 | 5/2008 | Chen et al. | 424/451 |
| 7,906,140 B2 | 3/2011 | Bromley et al. | 424/450 |
| 8,252,323 B2 | 8/2012 | Bromley | 424/450 |
| 8,282,977 B2 * | 10/2012 | Bromley | A23L 1/30 426/443 |
| 8,337,931 B2 | 12/2012 | Bromley | 426/602 |
| 8,414,914 B2 | 4/2013 | Bromley et al. | 424/450 |
| 8,741,373 B2 | 6/2014 | Bromley | 514/560 |
| 8,765,661 B2 * | 7/2014 | Bromley | 514/1 |
| 2001/0025058 A1 | 9/2001 | Borowy-Borowski et al. | 541/772.4 |
| 2003/0064097 A1 | 4/2003 | Patel et al. | 424/465 |
| 2003/0072798 A1 | 4/2003 | Schwarz | 424/456 |
| 2003/0165438 A1 | 9/2003 | Behnam | 424/49 |
| 2003/0165572 A1 | 9/2003 | Auriou | 264/5 |
| 2003/0180352 A1 | 9/2003 | Patel et al. | 424/465 |
| 2004/0033202 A1 | 2/2004 | Cooper et al. | 424/46 |
| 2004/0043043 A1 | 3/2004 | Schlyter et al. | 424/400 |
| 2004/0072330 A1 | 4/2004 | Ratledge et al. | 435/258.1 |
| 2004/0086576 A1 | 5/2004 | Cianfarani | 424/655 |
| 2004/0086619 A1 | 5/2004 | Zhong et al. | 426/590 |
| 2004/0105889 A1 | 6/2004 | Ryde et al. | 424/489 |
| 2004/0115287 A1 | 6/2004 | Chen et al. | 424/731 |
| 2004/0121043 A1 | 6/2004 | Behnam | 514/458 |
| 2004/0219274 A1 | 11/2004 | Cook | 426/590 |
| 2005/0002992 A1 | 1/2005 | McCleary et al. | 424/439 |
| 2005/0008581 A1 | 1/2005 | Parkhideh | 424/46 |
| 2005/0037073 A1 | 2/2005 | Schwarz | 42/464 |
| 2005/0092969 A1 | 5/2005 | Ueda et al. | 252/399 |
| 2005/0208082 A1 | 9/2005 | Papas et al. | 424/400 |
| 2005/0260752 A1 | 11/2005 | Wilding et al. | 435/373 |
| 2005/0281772 A1 | 12/2005 | Bromley et al. | 424/70.14 |
| 2006/0051462 A1 | 3/2006 | Wang | 426/72 |
| 2006/0088558 A1 | 4/2006 | Jandzinski et al. | 424/400 |
| 2006/0134299 A1 | 6/2006 | Lahteenmaki | 426/590 |
| 2006/0165735 A1 | 7/2006 | Abril | 426/601 |
| 2006/0165769 A1 | 7/2006 | Hyatt et al. | 424/450 |
| 2006/0222716 A1 | 10/2006 | Schwarz et al. | 424/490 |
| 2006/0251690 A1 | 11/2006 | Lipshutz et al. | 424/401 |
| 2006/0286259 A1 | 12/2006 | Hargreaves | 426/590 |
| 2007/0003614 A1 | 1/2007 | Chen et al. | 424/456 |
| 2007/0043106 A1 | 2/2007 | Behnam | 514/440 |
| 2007/0087104 A1 | 4/2007 | Chanamai | 426/602 |
| 2007/0104741 A1 | 5/2007 | Murty et al. | 424/400 |
| 2007/0104778 A1 | 5/2007 | Zeng et al. | 424/451 |
| 2007/0104780 A1 | 5/2007 | Lipari et al. | 424/456 |
| 2007/0134319 A1 | 6/2007 | Zannou et al. | 424/464 |
| 2007/0141203 A1 | 6/2007 | Cook et al. | 426/72 |
| 2007/0141224 A1 | 6/2007 | Zawistowski | 426/611 |
| 2007/0160738 A1 | 7/2007 | Van Bokkelen et al. | 426/601 |
| 2007/0166411 A1 | 7/2007 | Anthony et al. | 424/750 |
| 2007/0184117 A1 | 8/2007 | Gregory et al. | 424/489 |
| 2007/0196480 A1 | 8/2007 | Woo et al. | 424/468 |
| 2007/0207196 A1 | 9/2007 | Zhang | 424/450 |
| 2007/0213234 A1 | 9/2007 | Yaghmur | 508/110 |
| 2007/0218012 A1 | 9/2007 | Bittorf et al. | 424/45 |
| 2007/0218138 A1 | 9/2007 | Bittorf et al. | 424/488 |
| 2007/0248668 A1 | 10/2007 | Michaelis et al. | 424/464 |
| 2007/0298083 A1 | 12/2007 | Mehansho et al. | 426/590 |
| 2007/0298099 A1 | 12/2007 | Peresypkin et al. | 424/456 |
| 2007/0298156 A1 | 12/2007 | Mehansho et al. | 426/590 |
| 2008/0058418 A1 | 3/2008 | D'Angelo et al. | 514/560 |
| 2008/0070981 A1 | 3/2008 | Borowy-Borowski et al. | 514/458 |
| 2008/0233056 A1 | 9/2008 | Berl | 424/49 |
| 2008/0234376 A1 | 9/2008 | Lin et al. | 514/559 |
| 2008/0254188 A1 | 10/2008 | Borowy-Borowski et al. | 424/400 |
| 2009/0018186 A1 | 1/2009 | Chen et al. | 426/590 |
| 2009/0297491 A1 | 12/2009 | Bromley | 424/94.1 |
| 2009/0297665 A1 | 12/2009 | Bromley | 426/72 |
| 2009/0317532 A1 | 12/2009 | Bromley | 426/590 |
| 2010/0041622 A1 | 2/2010 | Bromley et al. | 514/52 |
| 2010/0080785 A1 | 4/2010 | Berl | 424/94.1 |
| 2010/0104730 A1 | 4/2010 | Mehansho et al. | 426/590 |
| 2010/0136175 A1 | 6/2010 | Skiff et al. | 426/72 |
| 2010/0166915 A1 | 7/2010 | Mathisen et al. | 426/477 |
| 2010/0260913 A1 | 10/2010 | Horlacher et al. | 426/546 |
| 2010/0279413 A1 | 11/2010 | Fain | 435/406 |
| 2011/0008305 A1 | 1/2011 | Yu et al. | 424/94.1 |

(56) References Cited

U.S. PATENT DOCUMENTS

| | | |
|---|---|---|
| 2011/0015266 A1 | 1/2011 | Hanefeld et al. ............ 252/363.5 |
| 2011/0117184 A1 | 5/2011 | Bromley ........................ 424/450 |
| 2011/0118351 A1 | 5/2011 | Berl .............................. 514/560 |
| 2011/0130562 A1 | 6/2011 | Berl .............................. 540/604 |
| 2011/0135745 A1 | 6/2011 | Mathisen et al. .............. 424/522 |
| 2011/0184194 A1 | 7/2011 | Berl .............................. 549/410 |
| 2011/0236364 A1 | 9/2011 | Bromley ....................... 424/94.1 |
| 2012/0016026 A1 | 1/2012 | Bromley ........................ 514/560 |
| 2012/0083530 A1 | 4/2012 | Mai et al. ...................... 514/560 |
| 2012/0093998 A1 | 4/2012 | Voelker et al. ................ 426/590 |
| 2012/0251685 A1 | 10/2012 | Wang-Nolan et al. ........ 426/250 |
| 2012/0308644 A1 | 12/2012 | Bromley et al. .............. 424/450 |
| 2013/0017183 A1 | 1/2013 | Bromley ....................... 424/94.1 |
| 2013/0017295 A1 | 1/2013 | Bromley ......................... 426/66 |
| 2013/0309362 A1 | 11/2013 | Bromley ......................... 424/72 |
| 2014/0039052 A1 | 2/2014 | Borowy-Borowski et al. ............................. 514/560 |
| 2014/0086993 A1* | 3/2014 | Guth ...................... A61K 47/22 424/489 |
| 2014/0227242 A1 | 8/2014 | Bromley et al. .............. 424/94.1 |
| 2014/0242055 A1 | 8/2014 | Bromley ....................... 424/94.1 |

FOREIGN PATENT DOCUMENTS

| | | |
|---|---|---|
| WO | WO 00/23545 | 4/2000 |
| WO | WO 02/17879 | 3/2002 |
| WO | WO 02/069981 | 9/2002 |
| WO | WO 02/076970 | 10/2002 |
| WO | WO 2004/098311 | 11/2004 |
| WO | WO 2005/105290 | 11/2005 |
| WO | WO 2005/112654 | 12/2005 |
| WO | WO 2006/080903 | 3/2006 |
| WO | WO 2007/080515 | 7/2007 |
| WO | WO 2007/082149 | 7/2007 |
| WO | WO 2008/039564 | 4/2008 |
| WO | WO 2008/134766 | 11/2008 |
| WO | WO 2009/029046 | 3/2009 |
| WO | WO 2010/008762 | 1/2010 |
| WO | WO 2011/040141 | 4/2011 |
| WO | WO 2011/149854 | 12/2011 |
| WO | WO 2013/120025 | 8/2013 |
| WO | WO 2014/151109 | 9/2014 |

OTHER PUBLICATIONS

Hou et al. (Sugar Variation in Soybean Seed Assessed with a Rapid Extraction and Quantification Method; 2009).*

Global Healing Center (What is Vegetable Glycerin 2012).*

U.S. Appl. No. 90/012,700, filed Oct. 9, 2012.

U.S. Appl. No. 14/271,847, filed May 7, 2014.

U.S. Appl. No. 14/253,773, filed Apr. 15, 2014.

U.S. Appl. No. 60/887,754, filed Feb. 1, 2007, Borowy-Borowski et al.

Letter/Written Disclosure of the Information Disclosure Statement for the above-referenced application, mailed on Jul. 7, 2014, 2 pages.

"Alpha-Tocopherol Polyethylene glycol Succinate (TPGS)," Pure Matters website [online][retrieved on Feb. 26, 2013] Retrieved from:<URL: resources.purematters.com/herbs-supplements/a/alpha- tocopherol-polyethylene-glycol-succinate-tpgs [2 pages].

*Analytical Chemistry An Introduction* 6th Ed., Skoog et al. eds., Chapters 22, "Applications of molecular absorption spectroscopy," (pp. 421-442) and 27, "Applications of chromatography," (pp. 509-530) (1994).

Antares Health Products "Vitamen-E TPGS," product brochure distributed at SupplySide Trade Show Oct. 22, 2008.

Argao et al., "d-Alpha-tocopheryl polyethylene glycol-1000 succinate enhances the absorption of vitamin D in chronic cholestatic liver disease of infancy and childhood," Ped. Res. 31(2):146-150 (1992).

Boukley, B. "'Next Generation' Omega-3 sports drink set to hydrate America" Beveragedaily.com Aug. 1, 2013 [online] Retrieved from:<URL:beveragedaily.com/content/view/print/804977] [accessed on Aug. 16, 2013], 2 pages.

Boukley, B. "Runaway Omega-3 beverage demand 'can be scary'—Virun CEO" Beveragedaily.com Dec. 20, 2013 [online] Retrieved from:<URL:beveragedaily.com/content/view/print/711158] [accessed on Aug. 16, 2013], 2 pages.

Boukley, B. "Searching for the Holy Grail: Science-backed functional beverages" Beveragedaily.com Mar. 3, 2013 [online] [retrieved at Retrieved from:<URL:beveragedaily.com/content/view/print/ 749075] [accessed on Aug. 16, 2013], 2 pages.

Boukley, B. "Stepan Lipid Nutrition and Virun paint bold brushstrokes on clear beverage 'canvas'," Beveragedaily.com Apr. 11, 2013 [online] Retrieved from:<URL:beveragedaily.com/content/ view/print/761692] [accessed on Aug. 16, 2013], 2 pages.

Boukley, B. "Time for a Change . . . Cola? US firm heralds healthy cola revolution," Beveragedaily.com Apr. 30, 2013 [online] [retrieved at Retrieved from:<URL:beveragedaily.com/content/ view/print/769020] [accessed on Aug. 16, 2013], 2 pages.

Bromley, P., "Nanotechnology and nonpolar active compounds in functional foods: An application note," Chapter 39, *Bio-Nanotechnology: A Revolution in Food, Biomedical and Health Sciences* (eds., Bagchi et al.), Blackwell Publishing Ltd., Oxford, UK., pp. 697-703 (2013).

Brouwers et al. "Intraluminal drug and formulation behavior and integration in in vitro permeability estimation: a case study with amprenavir," J. Pharm. Sci. 95:372-383 (2006).

Byberg et al., "Plasminogen activator inhibitor-1 and relations to fatty acid composition in the diet and in serum cholesterol esters," Arteroscler. Thromb. Vasc. Biol., 21:2086-2092 (2001).

Certified English translation of German patent DE 10 2005 049664, published Apr. 19, 2007, entitled: "Liquid Composition and Method for its Production," Inventor—Haller, 9 pages.

Certified English translation of International Patent WO 2011/ 040141, published Apr. 7, 2011, entitled: "Composition Containing Fat-soluble Vitamin," Inventor—Kondo, 17 pages.

Christiansen et al., "Investigating the stability of the nonionic surfactants tocopheryl polyethylene glycol succinate and sucrose laurate by HPLC-MS, DAD, and CAD," J. Pharm. Sci. 100(5):1773-1782 (2011).

Colas et al., "Sensitization by dietary docosahexaenoic acid of rat mammary carcinoma to anthracycline: A role for tumor vascularization," Clin Cancer Res 12(19):5879-5886 (2006).

Collnot et al., "Influence of vitamin E TPGS poly(ethylene glycol) chain length on apical efflux transporters in Caco-2 cell monolayers," J. Controlled Release 111:35-40 (2006).

Compass Foods Website, Food emulsification products, found at compassfoods.com [accessed Sep. 25, 2008]. 22 pages.

Constantinides et al., "Advances in the use of tocols as drug delivery vehicles," Pharm. Res. 23(2):243-255 (2006).

Covington, M., "Omega-3 fatty acids," American Family Physician 70(1):133-140 (2004).

*CRC Handbook of Chemistry and Physics*, Lide, D., ed., 82nd edition, Cleveland, OH:CRC Press 15(14)-15(18) (2001).

DK Ester Sucrose Esters Applications, Montello Inc [online][retrieved on Mar. 24, 2008] Retrieved from:<URL:montelloinc.com/dk_ester2.htm [1 page].

DK Ester Sucrose Esters Properties,, Montello Inc [online][retrieved on Mar. 24, 2008] Retrieved from:<URL:montelloinc.com/dk_ester. htm [2 pages].

DK Ester Sucrose Esters Specifications, Montello Inc [online][retrieved on Mar. 24, 2008] Retrieved from:<URL:montelloinc.com/dk_ester3.htm [1 page].

Eastman PCI-102B Publication, "Vitamin E TPGS NF—Applications and Properties," Eastman Chemical Company, Oct. 2005 [24 pages].

Engreadea News & Analysis, "Virun, Vital Pharmaceuticals expand operations," Published on Nov. 5, 2013 [online][retrieved on Dec. 17, 2013] Retrieved from:<URL:newhope360.com/print/specialty/ virun-vital-pharmaceuticals-expand-operations [2 pages].

(56) References Cited

OTHER PUBLICATIONS

Ernst, E., "The risk-benefit profile of commonly used herbal therapies: Ginkgo, St. John's Wort, Ginseng, Echinacea, Saw Palmetto, and Kava," Ann Intern Med. 136(1):42-53 (2002).
Fan, Y. and R. Chapkin, "Importance of dietary γ-linolenic acid in human health and nutrition," Journal of Nutrition 128(9):1411-1414 (1998).
Fulzele et al., "Inhalation delivery and anti-tumor activity of celecoxib in human orthotopic non-small cell lung cancer xenograft model," Pharm Res. 23(9):2094-2106 (2006).
Gander, P., "Sea changes," Published on Nov. 5, 2013 [online][retrieved on Dec. 17, 2013] Retrieved from:<URL:foodmanufacture.co.uk/content/view/print/843822 [2 pages].
Gelo-Pujic et al., "Synthesis of new antioxidant conjugates and their in vitro hydrolysis with Stratum corneum enzymes," Int. J. Cosmet. Sci. 30(3):195-204 (2008).
Giddings et al., "High pressure gas chromatography of nonvolatile species. Compressed gas is used to cause migration of intractable solutes," Science, 162:67-73 (1968).
Goddeeris et al., "Free flowing solid dispersions of the anti-HIV drug UC 781 with Poloxamer 407 and a maximum amount of TPGS 1000: investigating the relationship between physicochemical characteristics and dissolution behaviour," Eur. J. Pharm. Sci. 35:104-113 (2008).
Goodrum et al., "Gum arabic glycoprotein contains glycomodules of both extensin and arabinogalactan-glycoproteins," Phytochemistry 54(1):99-106 (2000).
Gordon, A. and A. Shaughnessy, "Saw palmetto for prostate disorders," American Family Physician 67(6):1281-1283 (2003).
Green et al., "Dietary docosahexaenoic acid and docosapentaenoic acid ameliorate amyloid-beta tau pathology via a mechanism involving presenilin 1 Levels," J. Neuroscience, 27(16):4385-4395 (2007).
Griffin, W., "Classification of surface-reactive agents by HLB," J. Soc. Cos. Chem. 1:311-326 (1949).
Gutmann, V., "Solvent effects on the reactivities of organometallic compounds," Coord. Chem. Rev. 18:225-255 (1976).
Higgins, K., "Emerging plant technologies help processors make better beverages," Published 2013 [online][retrieved on Dec. 17, 2013] Retrieved from:<URL:foodprocessing.com/articles/2013/beverage-technology/?show=all, 3 pages.
IPEC-Americas News "IPEC-Americas Gains Four New Members in May," pp. 1-12, May 2008.
Ju et al., "Cancer-preventive activities of tocopherols and tocotrienols," Carcinogenesis 31(4):533-542 (2010).
Kong et al., "Direct quantification of mono- and di-D-α-tocopherol polyethylene glycol 1000 succinate by high performance liquid chromatography," J. Chromatography A 1218:8664-8671 (2011).
Kosower, E., "2.6 solvent polarity: empirical measures," found in *An Introduction to Physical Organic Chemistry*, New York: Wiley, p. 293 (1969).
Landfester, K., "Miniemulsions for nanoparticle synthesis: formation of particles in inverse microemulsion," *Colloid Cheimstry II*, vol. 227. M. Antionietti. Ed., New York: Springer, pp. 97-99 (2003).
Lands, W., "Biochemistry and physiology of n-3 fatty acids," The FASEB Journal, 6(8):2530-2536 (1992).
Li et al., "δ-tocopherol is more active than α- or γ-tocopherol in inhibiting lung tumorigenesis in vivo." Cancer Prev. Res. (Phila.) 4(3):404-413 (2011).
Lipshutz et al. "TPGS-750-M: a second-generation amphiphile for metal-catalyzed cross-couplings in water at room temperature." J. Org. Chem. 76(11):4379-4391 (2011).
Lipshutz et al., "Transition-metal-catalyzed cross-couplings going green: in water at room temperature," Aldrichimica Acta 41(3):59-72 (2008).
Miyashita, K., "Effects of chemical properties of oil in water emulsion on lipid peroxidation," Foods Food Ingredients J. Jpn., 209(11):1-2 (2004).
Offer for Sale, "Kaneka Liquid CoQ10" formulation, to Kaneka Nutrients L.P., Pasadena, TX, on Jun. 22-27, 2007, 2 pages.
Okamoto et al., "Effect of sucrose fatty acid esters on transdermal permeation of lidocaine and ketoprofen," Biol. Pharm. Bull., 28(9):1689-1694 (2005).
Osako et al., "Effect of starvation on lipid metabolism and stability of DHA content of lipids in horse mackerel (*Trachurus japonicus*) tissues," Lipids, 38(12):1263-1267 (2003).
Perry, R. and D. Green, *Perry's Chemical Engineers' Handbook*, Sixth Edition, New York:McGraw-Hill, pp. 20-54 to 20-57 (1984).
Press Release, "OmegaH2O® clear shelf stable Omega-3, CoQ10 and other non polar compounds U.S. Appl. No. 12/383,244 approved in Europe and Notice of Allowance in U.S.," Published on Jun. 4, 2012 [online] Retrieved from:<URL:pr.com/press-release/417599 [4 pages].
Press Release: "Virun and Vital Pharmaceuticals expand operations" Retrieved from:<URL:bevnet.com/news/supplier-news/2013/virun-and-vital-pharmaceuticals-expand-operations/ Nov. 15, 2013, accessed on Dec. 17, 2013, 3 pages.
Press Release: "Virun® closes $2.1 million series-A funding to bolster innovation and world-wide expansion," Published on Aug. 2, 2012 [online] Retrieved from:<URL:pr.com/press-release/431579 [4 pages].
Press Release, "Virun® to premiere OmegaH2O® through WEDAR at CPhI and HI/NI in Shanghai, China," Published on May 18, 2010 [online] Retrieved from:<URL:pr.com/press-release/235132 pr.com/press-release/417599 [2 pages].
Randall et al., "The role of the proteinaceous component on the emulsifying properties of gum arabic," Food Hydrocolloids 2(2):131-140 (1988).
Ross et al., "Omega-3 fatty acids as treatments for mental illness: which disorder and which fatty acid?" Lipids in Health and Disease 6:(21):1-19 (2007).
Schultz, H., "PQQ set to make splash in sports nutrition beverages," nutraingredients-usa.com Aug. 6, 2013 [online] Retrieved from:<URL:nutraingredients-usa.com/content/view/print/807624] [accessed on Aug. 16, 2013], 2 pages.
Scientific Panel of the European Food Safety Authority, "Opinion of the Scientific Panel on Food Additives, Flavourings, Processing Aids and Materials in Contact with Food on a request from the Commission related to D-alpha-tocopheryl polyethylene glycol 1000 succinate (TPGS) in use for food for partic ular nutritional purposes." EFSA J. 490:1-20 (2007).
Sheu et al.,"Influence of micelle solubilization by tocopheryl polyethylene glycol succinate (TPGS) on solubility enhancement and percutaneous penetration of estradiol." J. Controlled Release 88:355-368 (2003).
Snyder, L., "Classification of the solvent properties of common liquids," J. Chromatography A 92:223-230 (1974).
Sokol et al., "Improvement of cyclosporin absorption in children after liver transplantation by means of water-soluble vitamin E," Lancet 338:212-214 (1991).
Starling, S., "Virun debuts shelf-stable, H20 soluble, nanotech omega-3," Published on Mar. 12, 2009 [online] Retrieved from:<URL:beveragedaily.com/Products/Virun-debuts-shelf-stable-H20-soluble-nanotech-omega-3 [1 page].
Stojkovic et al., "Coenzyme Q10 in submicron-sized dispersion improves development, hatching, cell proliferation, and adenosine triphosphate content of in vitro-produced bovine embryos," 61:541-547 (1999).
Surfhope SE Pharma, Mitsubishi-Kagaku Foods Corporation, Copyright 2002 [online] Retrieved from:<URL:mfc.co.jp/english/se_pharma/sepharma.htm [accessed on Sep. 25, 2008] 3 pages.
Swanson, E. and K. Chen, "Comparison of pressor action of aliphatic amines," Journal of Pharmacology and Experimental Therapeutics 88(1):10-13 (1946).
Swern, D., *Bailey's Industrial Oil and Fat Products*, vol. 1, 4th edition. John Wiley & Sons, New York, p. 387-391, 424-428 (1979).
Tadros, T., "Emulsion science and technology: a general introduciton," *Emulsion Science and Technology*, T. Tadros ed. Wienheim: Wiley-VCH, pp. 1-56. (2009).
Traber et al. "Absorption of water-miscible forms of vitamin E in a patient with cholestasis and in thoracic duct-cannulated rats." Am. J. Clin. Nutr. 44:914-923 (1986).

(56) References Cited

OTHER PUBLICATIONS

US Pharmacopeia NF-30, Vitamin E Polyethylene Glycol Succinate, pp. 2013-2015 (2012).
Varma et al. "Enhanced oral paclitaxel absorption with vitamin E-TPGS: effect on solubility and permeability in vitro, in situ and in vivo." Eur. J. Pharm. Sci. 25(4-5):445-453 (2005).
Virun Clear Water Soluble Omega-3 DHA, EPA & ALA for Foods & Beverages found at: www.slideshare.net/virun/virun-food-beverage-division-v2 [accessed on May 11, 2009], 6 pages.
Virun Facebook Page, Retrieved from:<URL:facebook.com/pages/Virun/168007462662, [accessed on Aug. 16, 2013], 8 pages.
Virun Facebook Page, Retrieved from:<URL:facebook.com/pages/Virun/168007462662, [accessed on Dec. 17, 2013], 6 pages.
Virun home Webpage found at www.virun.com [accessed on Mar. 24, 2011], 49 pages.
Virun home Webpage found at: www.virun.com [accessed on May 1, 2013], 22 pages.
Virun Improving Life Through Safe & Effective Oral Delivery, Copyright 2009 [online][retrieved on May 11, 2009] Retrieved from:<URL:slideshare.net/virun/virun-improving-life-through-safe-effective-oral- [15 pages].
Virun Intricate Science, Copyright 2011 [online][retrieved on May 25, 2011] Retrieved from:<URL:slideshare.net/virun/virun-intricate-science [22 pages].
Virun on slideshare.net, Philip Bromley's Presentations on SlideShare, Copyright 2009 [online][retrieved on May 8, 2009] Retrieved from:<URL:slideshare.net/virun [5 pages].
Virun Pharmaceutical & Food Beverage Divisions, Copyright 2009 [online][retrieved on May 11, 2009] Retrieved from:<URL:slideshare.net/virun/virun-food-beverage-divisions [9 pages].
Virun Product Sheet "Clear oils for water based beverages," Jan. 16, 2009, 4 pages.
Virun, "Virun Omega 3 Fortified Foods and Beverages," retrieved from the Internet:<URL: slideshare.net/virun/virun-omega-3-fortified-foods-and-beverages, [retrieved on May 7, 2010] [15 pages].
Vraka et al. "Synthesis and study of the cancer cell growth inhibitory properties of alpha-, gamma-tocopheryl and gamma-tocotrienyl 2-phenylselenyl succinates." Bioorg. Med. Chem. 14(8):2684-2696 (2006).
Yang et al. "Inhibition of inflammation and carcinogenesis in the lung and colon by tocopherols." Ann. N.Y. Acad. Sci. 1203:29-34 (2010).
Youan et al., "Evaluation of Sucrose Esters as Alternative Surfactants in Microencapsulation of Proteins by the Solvent Evaporation Method," AAPS PharmSci., 5(2):1-9 (2003).
Yu et al. "Vitamin E-TPGS increases absorption flux of an HIV protease inhibitor by enhancing its solubility and permeability." Pharm. Res. 16:1812-1817 (1999).
Zaghloul et al., "Development, characterization and optimization of ibuprofen self-emulsifying drug delivery system applying face centered experimental design," International Journal of Pharmacy and Technilogy; 3(1):1674-1693 (2011).
Zhao, L. and S. Feng, "Enhanced oral bioavailability of paclitaxel formulated in vitamin E-TPGS emulsified nanoparticles of biodegradable polymers: in vitro and in vivo studies." J. Pharm. Sci. 99(8):3552-3560 (2010).
International Search Report/Written Opinion, issued Jul. 3, 2009, in connection with International Application No. PCT/US2009/001775, 15 pages.
Response to Written Opinion, submitted Jan. 19, 2010, in connection with International Patent Application No. PCT/US2009/001775, 35 pages.
International Search Report/Written Opinion, issued Mar. 2, 2010, in connection with International Application No. PCT/US2009/003761, 13 pages.
International Search Report/Written Opinion, issued Apr. 7, 2010, in connection with International Patent Application No. PCT/US2009/001774, 15 pages.
Response to Written Opinion, submitted Jun. 1, 2010, in connection with International Application No. PCT/US2009/003761, 25 pages.
International Preliminary Report on Patentability, issued Jun. 11, 2010, in connection with International Patent Application No. PCT/US2009/001775, 18 pages.
Response to Written Opinion, submitted Jul. 7, 2010, in connection with International Patent Application No. PCT/US2009/001774, 37 pages.
International Preliminary Report on Patentability, issued Jul. 27, 2010, in connection with International Patent Application No. PCT/US2009/003761, 13 pages.
International Preliminary Report on Patentability, issued Sep. 3, 2010, in connection with International Patent Application No. PCT/US2009/001774, 15 pages.
Examination Report, issued Mar. 7, 2011, in connection with European Patent Application No. 09722985.0, 6 pages.
International Search Report and Written Opinion, issued Jul. 22, 2011, for International Application No. PCT/US2011/000538, 11 pages.
Restriction Requirement, issued Sep. 6, 2011, in connection with U.S. Appl. No. 12/383,241, 6 pages.
Response to Examination Report, submitted Sep. 16, 2011, in connection with European Patent Application No. 09722985.0, 8 pages.
International Search Report and Written Opinion, issued Sep. 26, 2011, in connection with International Application No. PCT/US2011/001099, 9 pages.
Office Action, issued Oct. 4, 2011, in connection with U.S. Appl. No. 12/383,244, 13 pages.
Office Action, issued Nov. 4, 2011, in connection with U.S. Appl. No. 12/456,926, 9 pages.
Itention to Grant European patent, issued Nov. 8, 2011, in connection with European Patent Application No. 09723157.5, 5 pages.
Examination Report, issued Dec. 19, 2011, in connection with European Patent Application No. 09722985.0, 4 pages.
Response to Written Opinion, submitted Jan. 23, 2012, in connection with International Application No. PCT/US2011/000538, 9 pages.
Translation of Office Action, issued Feb. 8, 2012, in connection with Chinese patent Application No. 200980118257.4, 2 pages.
Response to Restriction Requirement, submitted Mar. 6, 2012, in connection with U.S. Appl. No. 12/383,241, 11 pages.
Examiner's Report, issued Mar. 28, 2012, in connection with Canadian Patent Application No. 2,715,018, 2 pages.
Examiner's Report, issued Mar. 28, 2012, in connection with Canadian Patent Application No. 2,718,231, 3 pages.
Response to Office Action, submitted Apr. 4, 2012, in connection with U.S. Appl. No. 12/383,244, 16 pages.
Office Action, issued Apr. 4, 2012, in connection with U.S. Appl. No. 12/383,241, 12 pages.
Response to Examination Report, submitted Apr. 5, 2012, in connection with European Patent Application No. 09722985.0, 60 pages.
Response to Examiner's Report, submitted Apr. 17, 2012, in connection with Canadian Patent Application No. 2,715,018, 7 pages.
Decision to Grant, issued Apr. 19, 2012, in connection with European Patent Application No. 09723157.5, 1 page.
Response to Written Opinion, submitted Apr. 23, 2012, in connection with International Application No. PCT/US2011/001099, 10 pages.
PCT Communication, issued Apr. 25, 2012, in connection with International Patent Application No. PCT/US2011/000538, 4 pages.
Notice of Allowance, issued May 30, 2012, in connection with U.S. Appl. No. 12/383,244, 5 pages.
Response to Office Action, submitted May 4, 2012, in connection with U.S. Appl. No. 12/456,926, 27 pages.
Communication reporting grant, issued May 16, 2012, of European Patent Application No. 09723157.5, 2 pages.
Notice of Allowance, issued May 17, 2012 in connection with Canadian Patent Application No. 2,715,018, 1 page.
Translation of Office Action, issued May 31, 2012, in connection with Chinese Patent Application No. 200980118258.9, 1 page.
Second Written Opinion, issued Jun. 1, 2012 in connection with International Patent Application No. PCT/US2011/001099, 5 pages.
Response to Examiner's Report, submitted Jun. 8, 2012, in connection with Canadian Patent Application No. 2,718,231, 18 pages.
Itention to Grant European patent, issued Jun. 15, 2012, in connection with European Patent Application No. 09722985.0, 5 pages.

(56) References Cited

OTHER PUBLICATIONS

Final Office Action, issued Jun. 19, 2012, in connection with U.S. Appl. No. 12/456,926, 8 pages.
Response to PCT Communication, submitted Jun. 25, 2012, in connection with International Patent Application No. PCT/US2011/000538, 5 pages.
Office Action, Search Report, issued Jun. 25, 2012, and translation, in connection with Chinese Patent Application No. 200980132984.6, 13 pages.
International Preliminary Report on Patentability, mailed Jul. 16, 2012 in connection with International Patent Application No. PCT/US2011/000538, 12 pages.
Response to Office Action, submitted Jul. 16, 2012, and Instructions for response to Office Action, in connection with Chinese patent Application No. 200980118257.4, 27 pages.
Response to Office Action, submitted Jul. 30, 2012, in connection with U.S. Appl. No. 12/383,241, 16 pages.
Response to Written Opinion, submitted Aug. 1, 2012 in connection with International Patent Application No. PCT/US2011/001099, 5 pages.
Amendment after Final, submitted Aug. 6, 2012, in connection with U.S. Appl. No. 12/456,926, 12 pages.
Examination Report, issued Aug. 17, 2012, in connection with Canadian Patent Application No. 2,718,231, 2 pages.
International Preliminary Report on Patentability, issued Aug. 20, 2012, in connection with International Patent Application No. PCT/US2011/001099, 16 pages.
Notice of Allowance, issued Aug. 21, 2012, in connection with U.S. Appl. No. 12/456,926, 10 pages.
Final Office Action, issued Aug. 21, 2012, in connection with U.S. Appl. No. 12/383,241, 17 pages.
Response to Examination Report, submitted Aug. 29, 2012, in connection with Canadian Patent Application No. 2,718,231, 11 pages.
Office Action, issued Sep. 6, 2012, in connection with U.S. Appl. No. 13/065,510, 22 pages.
Third Party Reexamination Request, submitted Oct. 9, 2012, in connection with U.S. Pat. No. 8,282,977, 148 pages.
Response to Office Action, submitted Oct. 15, 2012, in connection with Chinese Patent Application No. 200980118258.9, 17 pages.
Notice of Allowance, issued Nov. 7, 2012, in connection with Canadian Patent Application No. 2,718,231, 3 pages.
Decision to Grant, issued Nov. 8, 2012, in connection with European Patent Application No. 09722985.0, 2 pages.
Office communication, issued Nov. 14, 2012, in connection with U.S. Appl. No. 90/012,700, 3 pages.
Translation of Office Action, issued Nov. 15, 2012, in connection with Israeli Patent Application No. 208133, 3 pages.
Extended European Search Report, issued Dec. 5, 2012, in connection with European Patent Application No. 12188577.6, 7 pages.
Order Granting Request for Ex Parte Reexamination, issued Dec. 10, 2012, in connection with U.S. Appl. No. 90/012,700, 27 pages.
Restriction Requirement, issued Jan. 3, 2013, in connection with U.S. Appl. No. 13/134,927, 7 pages.
Response to Office Action, submitted Jan. 10, 2013, and instructions for response, in connection with Chinese Patent Application No. 200980132984.6, 22 pages.
Office Action, issued Jan. 5, 2013, and translation, in connection with Chinese Patent Application No. 200980118257.4, 8 pages.
Response to Restriction Requirement, submitted Jan. 16, 2013, in connection with U.S. Appl. No. 13/134,927, 9 pages.
Notice of Appeal, submitted Feb. 21, 2013, in connection with U.S. Appl. No. 12/383,241, 1 page.
Office Action, issued Mar. 4, 2013, in connection with U.S. Appl. No. 90/012,700, 40 pages.
Office Action, issued Mar. 4, 2013, and translation, in connection with Chinese Patent Application No. 200980118258.9, 11 pages.
Response to Office Action, submitted Mar. 6, 2013, in connection with U.S. Appl. No. 13/065,510, 25 pages.
Office Action, issued Mar. 7, 2013, in connection with U.S. Appl. No. 13/573,424, 11 pages.
Response to Office Action, submitted Mar. 20, 2013, and instructions for response, in connection with Chinese Patent Application No. 200980118257.4, 17 pages.
Office Action, issued Mar. 26, 2013, in connection with with U.S. Appl. No. 13/134,927, 24 pages.
Office Action, issued Mar. 27, 2013, in connection with Mexican Patent Application No. MX/a/2010/010050, 9 pages.
Response to Office Action, submitted May 6, 2013, in connection with U.S. Appl. No. 90/012,700, 89 pages.
Response to Office Action, submitted May 15, 2013, and instructions for response, in connection with Mexican Patent Application No. MX/a/2010/010050, 16 pages.
Office Action and Search Report, issued May 15, 2013, and translation, in connection with Chinese Patent Application No. 200980132984.6, 15 pages.
International Search Report and Written Opinion, issued May 29, 2013, in connection with International Patent Application No. PCT/US2013/025445, 11 pages.
Request for Continued Examination and Preliminary Amendment filed in response to Final Office Action, submitted Jun. 19, 2013, in connection with U.S. Appl. No. 12/383,241, 31 pages.
Final Office Action, issued Jun. 28, 2013, in connection with U.S. Appl. No. 13/065,510, 28 pages.
Office Action, issued Jul. 4, 2013, in connection with Australian Patent Application No. 2009226019, 2 pages.
Response to Office Action, submitted Jul. 19, 2013, and instructions for response, in connection with Chinese patent Application No. 200980118258.9, 25 pages.
Response to Office Action, submitted Jul. 22, 2013, in connection with Australian Patent Application No. 2009226019, 18 pages.
Response to Rule 70(2) and 70a(2) communication, submitted Jul. 23, 2013, in conneciton with European Patent Application No. 12188577.6, 9 pages.
Supplemental Response to Office Action, submitted Jul. 26, 2013, in connection with Australian Patent Application No. 2009226019, 19 pages.
Office Action, issued Jul. 30, 2013, and translation, in connection with Chinese Patent Application No. 200980118257.4, 6 pages.
Notice of Acceptance, issued Aug. 15, 2013, in connection with Australian Patent Application No. 2009226019, 2 pages.
Office Action and Search Report, issued Aug. 21, 2013, and translation, in connection with Chinese Patent Application No. 201180025197.9, 9 pages.
Translation of Response to Office Action, submitted Sep. 10, 2013, in connection with Israeli Patent Application No. 208133, 16 pages.
Final Office Action, issued Sep. 23, 2013, in connection with U.S. Appl. No. 90/012,700, 46 pages.
Response to Office Action, submitted Sep. 26, 2013, in connection with with U.S. Appl. No. 13/134,927, 25 pages.
Office Action, issued Sep. 27, 2013, in connection with U.S. Appl. No. 12/383,241, 9 pages.
Response to Office Action, submitted Sep. 30, 2013, and instruction for response, in connection with Chinese Patent Application No. 200980132984.6, 23 pages.
Office Action, issued Nov. 21, 2013, and translation, in connection with Chinese patent Application No. 200980118258.9, 9 pages.
Response to Office Action, submitted Nov. 25, 2013, in connection with U.S. Appl. No. 90/012,700, 73 pages.
Office Action, issued Nov. 25, 2013, and translation, in connection with Chinese Patent Application No. 20130096300.X, 4 pages.
Advisory Action, issued Dec. 6, 2013, in connection with U.S. Appl. No. 90/012,700, 4 pages.
Summary of issues to discuss in interview, submitted Dec. 10, 2013, in connection with U.S. Appl. No. 90/012,700, 6 pages.
Response to Office Action, submitted Dec. 16, 2013, and instructions for response to Office Action, in connection with Chinese Patent Application No. 200980118257.4, 30 pages.
Response to International Search Report and Written Opinion, submitted Dec. 10, 2013, in connection with International Patent Application No. PCT/US2013/025445, 43 pages.
Response to Office Action, submitted Dec. 20, 2013, in connection with U.S. Appl. No. 12/383,241, 20 pages.

(56) References Cited

OTHER PUBLICATIONS

Interview Summary, issued Dec. 23, 2013, in connection with U.S. Appl. No. 90/012,700, 11 pages.
Second Response to Office Action, submitted Dec. 23, 2013, in connection with U.S. Appl. No. 90/012,700, 23 pages.
Notice of Allowance, issued Jan. 10, 2014, in connection with with U.S. Appl. No. 13/134,927, 26 pages.
Advisory Action, issued Jan. 10, 2014, in connection with U.S. Appl. No. 90/012,700, 4 pages.
Communication pursuant to Rule 94(3) EPC, issued Jan. 10, 2014, in connection with European Patent Application No. 12 188 577.6, 4 pages.
Third Response to Office Action, submitted Jan. 15, 2014, in connection with U.S. Appl. No. 90/012,700, 12 pages.
Translation of Notification Prior to Allowance, issued Jan. 21, 2014, in connection with Israeli Patent Application No. 208133, 3 pages.
Notice of Appeal and Petition, submitted Jan. 23, 2014, in connection with U.S. Appl. No. 90/012,700, 14 pages.
Advisory Action, issued Jan. 24, 2014, in connection with U.S. Appl. No. 90/012,700, 4 pages.
Written Opinion, issued Jan. 27, 2014, in connection with International Patent Application No. PCT/US2013/025445, 6 pages.
Notice of Allowance, issued Feb. 6, 2014, and replacement PTOL-37 form, issued Feb. 10, 2014, in connection with U.S. Appl. No. 12/383,241, 8 pages.
Response to Office Action, submitted Feb. 7, 2014, and instructions for response, in connection with Chinese patent Application No. 200980118258.9, 15 pages.
Response to Written Opinion, submitted Feb. 27, 2014, in connection with International Patent Application No. PCT/US2013/025445, 30 pages.
Office Action, issued Feb. 7, 2014, and translation, in connection with Chinese Patent Application No. 200980132984.6, 17 pages.
Response to Office Action, submitted Mar. 5, 2014, and instructions for response, in connection with Chinese Patent Application No. 201180025197.9, 33 pages.
Appeal Brief, submitted Mar. 24, 2014, in connection with U.S. Appl. No. 90/012,700, 68 pages.
Response to Office Action, submitted Mar. 26, 2014, and instructions for response, in connection with Chinese Patent Application No. 20130096300.X, 10 pages.
Restriction Requirement, issued Apr. 23, 2014, in connection with U.S. Appl. No. 13/815,193, 10 pages.
Office Action, issued Apr. 25, 2014, and translation, in connection with Korean Patent Application No. 10-2010-7027534, 11 pages.
Examiner's Response to Appeal Brief, issued May 9, 2014, in connection with U.S. Appl. No. 90/012,700, 76 pages.
Amendment and Request for Continued Examination, submitted May 27, 2014, in connection with U.S. Appl. No. 13/065,510, 26 pages.
U.S. Appl. No. 14/449,880, filed Aug. 1, 2014.
Letter/Written Disclosure of the Information Disclosure Statement for the above-referenced application, mailed on Mar. 11, 2015, 2 pages.
Boukley, B, "Straight Dope: Canna Energy hemp oil drink scores sales high," Beveragedaily.com Apr. 2, 2014 [online] [retrieved at http://www.beveragedaily.com/content/view/print/905372] [accessed on Jun. 2, 2014], 2 pages.
Daniells, S. "Abbott Nutrition, Standard Process, Nawgan, and Euromonitor to talk cognitive health" Nutraingredients-usa.com Apr. 30, 2014 [online] [retrieved at http://www.nutraingredients-usa.com/content/view/print/915357] [accessed on Jun. 2, 2014], 2 pages.
NutraBIOsciences™ food-beverage technology evolved product brochure, published May 21, 2014 [online] [available at http://www.beveragedaily.com/smartlead/view/918190/4/NutraBIOsciences-food-beverage-technology-evolved] [accessed on Jun. 2, 2014], 3 pages.
Virun Esolv technology Webpage, found at: http://www.virun.com/omega2.htm [accessed Jun. 2, 2014], 1 page.
Virun Facebook Page found at https://www.facebook.com/pages/Virun/168007462662 [accessed on Mar. 10, 2015], 11 pages.
Virun Facebook Page found at https://www.facebook.com/pages/Virun/168007462662 [accessed on Jun. 2, 2014], 14 pages.
Office Action, issued May 29, 2014, and translation, in connection with Chinese patent Application No. 200980118258.9, 10 pages.
Response to Restriction Requirement, submitted Jun. 3, 2014, in connection with U.S. Appl. No. 13/815,193, 7 pages.
Office Action, issued Jun. 4, 2014, and translation, in connection with Chinese Patent Application No. 200980118257.4, 7 pages.
International Preliminary Report on Patentability, issued Jun. 6, 2014, in connection with International Patent Application No. PCT/US2013/025445, 7 pages.
Response to Office Action, submitted Jun. 20, 2014, in connection with U.S. Appl. No. 12/583,209, 30 pages.
Response to Office Action, submitted Jun. 23, 2014, and instructions for response, in connection with Chinese Patent Application No. 200980132984.6, 33 pages.
Office Action, issued Jul. 1, 2014, and translation, in connection with Chinese Patent Application No. 201180025197.9, 7 pages.
Reply Brief, submitted Jul. 9, 2014, in connection with U.S. Appl. No. 90/012,700, 30 pages.
Office Action, issued Jul. 16, 2014, in connection with U.S. Appl. No. 13/065,510, 25 pages.
Office Action, issued Jul. 18, 2014, and translation, in connection with Chinese Patent Application No. 20130096300.X, 6 pages.
Response to Communication pursuant to Rule 94(3) EPC, submitted Jul. 21, 2014, in connection with European Patent Application No. 12 188 577.6, 6 pages.
International Search Report and Written Opinion, issued Aug. 12, 2014, in connection with International Patent Application No. PCT/US2014/025006, 13 pages.
Response to Office Action, submitted Aug. 25, 2014, and instructions for response, in connection with Korean Patent Application No. 10-2010-7027534, 71 pages.
Amendment after examiner phone interview, submitted Aug. 25, 2014, in connection with Chinese Patent Application No. 200980132984.6, 11 pages.
Response to Office Action and Request for Reexamination, submitted Sep. 15, 2014, and instructions for response, in connection with Chinese patent Application No. 200980118258.9, 24 pages.
Restriction Requirement, issued Sep. 18, 2014, in connection with U.S. Appl. No. 13/815,193, 6 pages.
Response to Office Action and Request for Reexamination, submitted Sep. 19, 2014, and instructions for response, in connection with Chinese Patent Application No. 200980118257.4, 24 pages.
Notification of Grant, issued Sep. 25, 2014, and translation, in connection with Chinese Patent Application No. 200980132984.6, 4 pages.
Response to Office Action, submitted Sep. 28, 2014, and instructions for response, in connection with Chinese Patent Application No. 20130096300.X, 17 pages.
Response to Restriction Requirement, submitted Oct. 7, 2014, in connection with U.S. Appl. No. 13/815,193, 5 pages.
Response to Office Action, submitted Nov. 17, 2014, and instructions for response, in connection with Chinese Patent Application No. 201180025197.9, 23 pages.
Translation of Response to Office Action, submitted Nov. 17, 2014, in connection with Israeli Patent Application No. 208133, 8 pages.
Response to International Search Report and Written Opinion, submitted Jan. 13, 2015, in connection with International Patent Application No. PCT/US2014/025006, 31 pages.
Notice of Hearing, issued Jan. 13, 2015, in connection with U.S. Appl. No. 90/012,700, 3 pages.
Response to Office Action, submitted Jan. 16, 2015, in connection with U.S. Appl. No. 13/065,510, 24 pages.
Office Action, issued Feb. 2, 2015, in connection with U.S. Appl. No. 13/815,193, 9 pages.

(56) References Cited

OTHER PUBLICATIONS

Letter/Written Disclosure of the Supplemental Information Disclosure Statement for the above-referenced application, mailed on Aug. 26, 2015, 2 pages.
Ling, X., "Research on the preparation of Natural Vitamin E Derivatives," Wufang Database, published Sep. 18, 2006. [Document in Chinese], 67 pages.
Partial Translation of Ling, X., "Research on the Preparation of Natural Vitamin E Derivatives," Wufang Database, published Sep. 18, 2006, 15 pages.
Office Action, issued Jan. 21, 2015, in connection with Chinese Patent Application No. 20130096300.X [English language translation and original document in the Chinese language], 24 pages.
Office Action, issued Jan. 30, 2015, in connection with Korean Patent Application No. 10-2010-7027534 [English language translation and original document in the Korean language], 6 pages.
Intention to Grant, issued Feb. 5, 2015, in connection with European Patent Application No. 12 188 577.6, 6 pages.
Summary of Examiner Interview, dated Mar. 11, 2015, in connection with Korean Patent Application No. 10-2010-7027534, 1 page.
International Preliminary Report on Patentability, issued Mar. 23, 2015, in connection with International Patent Application No. PCT/US2014/025006, 6 pages.
Record of Oral Hearing, issued Apr. 21, 2015, in connection with U.S. Appl. No. 90/012,700, 12 pages.
Notification of Reexamination, issued Apr. 28, 2015, in connection with Chinese Patent Application No. 200980118257.4 [English language translation and original document in the Chinese language], 12 pages.
Notification Prior to Acceptance, issued May 13, 2015, in connection with Israeli Patent Application No. 208133, 4 pages.
Office Action, mailed May 26, 2015, in connection with U.S. Appl. No. 13/065,510, 18 pages.
Response, submitted Jun. 5, 2015, to Office Action, dated Feb. 24, 2015, in connection with Chinese Patent Application No. 20130096300.X [English language Instructions with Response as filed in the Chinese language], 27 pages.
Decision to Grant, issued on Jun. 11, 2015, in connection with European Patent Application No. 12188577.6, 2 pages.
Request for Rehearing, submitted Jun. 22, 2015, in connection with U.S. Appl. No. 90/012,700, 28 pages.
Response, filed Jul. 31, 2015, to Office Action, issued Jan. 30, 2015, in connection with Korean Patent Application No. 10-2010-7027534 [English language instructions and pending claims and Arguments and Amendment as filed in Korean language], 46 pages.
Response, filed on Aug. 13, 2015, to Office Action, dated Apr. 28, 2015, in connection with Chinese Patent Application No. 200980118257.4 [English language instructions with response as filed in Chinese language], 13 pages.
Letter/Written Disclosure of the Supplemental Information Disclosure Statement for the above-referenced application, filed herewith on Dec. 4, 2015, 3 pages.
Notification of Grant, issued Oct. 10, 2015, and Search Report, issued Sep. 24, 2015, in connection with Chinese Patent Application No. 201310096300.X [English translation and original document in Chinese], 7 pages.
Notice Forwarding Certified List, Decision, and Decision of Rehearing, dated Dec. 2, 2015, in connection with U.S. Appl. No. 90/012,200, 27 pages.
Letter/Written Disclosure of the Supplemental Information Disclosure Statement for the above-referced application, filed herewith on Mar, 8, 2016, 2 pages.
Notice of Reexamination, issued Nov. 30, 2015, in connection with Chinese patent Application No. 200980118258.9 [English translation and original document in Chinese], 11 pages.
Letter reporting Decision of Reexamination, dated Nov. 26, 2015, in connection with Chinese Patent Application No. 200980118257.4 [English letter and original document in Chinese], 17 pages.

\* cited by examiner

FORMULATIONS OF WATER-SOLUBLE DERIVATIVES OF VITAMIN E AND COMPOSITIONS CONTAINING SAME

RELATED APPLICATIONS

Benefit of priority is claimed to U.S. Provisional Application Ser. No. 61/852,243, filed Mar. 15, 2013, entitled "FORMULATIONS OF PEG-DERIVATIVES OF VITAMIN E AND COMPOSITIONS CONTAINING SAME" to Philip Bromley. The subject matter of this application is incorporated by reference in its entirety.

This application is related to International PCT Application No. PCT/US2014/0250006, filed the same day herewith, entitled "FORMULATIONS OF WATER-SOLUBLE DERIVATIVES OF VITAMIN E AND COMPOSITIONS CONTAINING SAME" to Philip Bromley. The subject matter of this application is incorporated by reference in its entirety.

This application is related to U.S. application Ser. No. 12/383,244, filed Mar. 20, 2009, published as US-2009-0297665-A1, issued as U.S. Pat. No. 8,282,977, and entitled "COMPOSITIONS CONTAINING NON-POLAR COMPOUNDS," and International Application No. PCT/US2009/001775, filed Mar. 20, 2009, published as International PCT Publication No. WO 2009/117152 and entitled "EMULSIONS INCLUDING A PEG-DERIVATIVE OF TOCOPHEROL," all of which claim priority to U.S. Provisional Application Ser. No. 61/070,381, filed Mar. 20, 2008, entitled "COMPOSITIONS CONTAINING NON-POLAR COMPOUNDS" and U.S. Provisional Application Ser. No. 61/132,424, filed Jun. 16, 2008, entitled "COMPOSITIONS CONTAINING NON-POLAR COMPOUNDS," each to Philip Bromley.

This application also is related to U.S. patent application Ser. No. 12/383,241, filed Mar. 20, 2009, published as US-2009-0297491-A1 entitled "COMPOSITIONS CONTAINING NON-POLAR COMPOUNDS" and International Application No. PCT/US2009/001774, filed Mar. 20, 2009, published as International PCT Publication No. WO 2009/117151 and entitled "VITAMIN E DERIVATIVES AND THEIR USES," all of which claim priority to U.S. Provisional Application Ser. No. 61/070,392, filed Mar. 20, 2008, entitled "COMPOSITIONS CONTAINING NON-POLAR COMPOUNDS" and U.S. Provisional Application Ser. No. 61/132,409, filed Jun. 16, 2008, entitled "COMPOSITIONS CONTAINING NON-POLAR COMPOUNDS," each to Philip Bromley.

This application also is related to U.S. Patent Application Ser. No. 13/065,510, filed Mar. 22, 2011, published as US-2011-0236364-A1 entitled "COMPOSITIONS CONTAINING NON-POLAR COMPOUNDS" and International Application No. PCT/US2011/000538, filed Mar. 22, 2011, published as International PCT Publication No. WO 2011/119228 and entitled "COMPOSITIONS CONTAINING NON-POLAR COMPOUNDS," all of which claim priority to U.S. Provisional Application Ser. No. 61/340,944, filed Mar. 23, 2010, entitled "COMPOSITIONS CONTAINING NON-POLAR COMPOUNDS," each to Philip Bromley.

This application also is related to U.S. patent application Ser. No. 13/134,927, filed Jun. 20, 2011, published as US-2012-0016026-A1, entitled "COMPOSITIONS CONTAINING NON-POLAR COMPOUNDS" and International Application No. PCT/US2011/01099, filed Jun. 20, 2011, published as International PCT Publication No. WO 2011/162802 and entitled "COMPOSITIONS CONTAINING NON-POLAR COMPOUNDS," all of which claim priority to U.S. Provisional Application Ser. No. 61/398,192, filed Jun. 21, 2010, entitled "COMPOSITIONS CONTAINING NON-POLAR COMPOUNDS," each to Philip Bromley.

This application also is related to U.S. patent application Ser. No. 13/815,193, filed Feb. 8, 2013, published as US-2013-0309362-A1, entitled "BEVERAGE COMPOSITIONS CONTAINING NON-POLAR COMPOUNDS" and International Application Serial No. PCT/US2013/25445, filed Feb. 8, 2013, entitled "BEVERAGE COMPOSITIONS CONTAINING NON-POLAR COMPOUNDS," both of which claim priority to U.S. Provisional Application Ser. No. 61/633,431, filed Feb. 10, 2012, entitled "BEVERAGE COMPOSITIONS CONTAINING NON-POLAR COMPOUNDS" and U.S. Provisional Application Ser. No. 61/743,466, filed Sep. 4, 2012, entitled "BEVERAGE COMPOSITIONS CONTAINING NON-POLAR COMPOUNDS," each to Philip Bromley.

The subject matter of each of the above-referenced applications is incorporated by reference in its entirety.

FIELD OF THE INVENTION

Provided herein are compositions that contain water-soluble vitamin E derivative mixtures (compositions), such as tocopheryl polyethylene glycol succinate (TPGS), TPGS analogs, TPGS homologs and TPGS derivatives. The water-soluble vitamin E mixtures contain mixtures of dimers and monomers of the vitamin E derivative. Also provided are products containing the water-soluble vitamin E derivative mixtures, including aqueous beverage compositions for human consumption, and methods for preparing the products. Methods for preparing the products are provided.

BACKGROUND

Non-polar compounds are not easily dissolved in aqueous solutions, such as water or other polar solvents. A number of non-polar compounds are used in compositions for human ingestion. These include, for example, pharmaceuticals, nutraceuticals and/or dietary supplements. Exemplary of non-polar compounds are vitamins and minerals, fatty acids, and other non-polar compounds, non-polar active agents and non-polar active ingredients. Because of poor water solubility, inclusion of non-polar compounds in products for human consumption, for example, in supplements, foods and beverages, can be problematic, and the amount of non-polar compound that can be included is limited.

Water-soluble forms of vitamin E, such as TPGS (D-α-tocopheryl polyethylene glycol succinate), in particular TPGS 1000 (D-α-tocopheryl polyethylene glycol 1000 succinate), have been approved by the FDA as vitamin E nutritional supplements. TPGS is a stable, tasteless and odorless source of readily bioavailable vitamin E that does not hydrolyze under normal conditions. TPGS, TPGS homologs, TPGS analogs and TPGS derivatives also are used as surfactants, and have been used to prepare stabilized formulations of food, beverage, pharmaceutical or nutraceutical products containing non-polar compounds. TPGS (and homologs, analogs and derivatives) has been used as a solubilizing agent for such stabilized formulations, such as water-soluble formulations that contain water-insoluble non-polar compounds, such as drugs, vitamins, or other biologically active compounds, such as natural and non-natural omega-fatty acids. Thus, TPGS possesses the dual function of providing additional dietary vitamin E and providing stabilization to a formulation. Available products containing non-polar compounds, particularly products for human consumption, such as food and beverage products containing non-polar compounds, and methods for formulating such products, are limited. In addition, the amount, or concentration, of non-polar compounds in available food and beverage products is limited due to the display of undesirable organoleptic properties when the amount of non-polar compound is increased. Thus, there is a need to develop products for human consumption, such as food and beverage products, that contain non-polar compounds and methods for making the products. There is an additional need to develop products for human consumption, such as food and beverage products, that contain a higher amount of non-polar compound than is offered in available food and beverage products. There also is a need to develop products for human consumption, such as food and beverage products, that retain their organoleptic properties when they contain a higher amount of non-polar compound. Accordingly, it is among the objects herein to provide food and beverage products containing non-polar compounds, in particular, food and beverage products containing more non-polar compounds than available products, that retain desirable organoleptic properties, and methods for making the products.

SUMMARY

Previously, water-soluble vitamin E derivative compositions have been prepared to have as high as possible monomer concentration and typically have at least 87% or more monomer. It is shown herein that the water-soluble vitamin E derivative mixtures (compositions) that contain high amounts of dimer impart advantageous properties to compositions that contain the water-soluble vitamin E derivative composition. Hence, provided herein are compositions that contain a water-soluble vitamin E derivative composition and a non-polar ingredient, such as polyunsaturated fatty acids, coenzyme Q10 compounds, phytosterols, non-polar small molecules, drugs, vitamins and other nutraceuticals, and other such compounds.

Provided herein are compositions that include concentrates and liquid dilution compositions produced from the concentrates, compositions for direct consumption, and dilutions of the concentrates, such as beverages, that contain water-soluble vitamin E derivative mixtures (compositions) and a non-polar ingredient and optionally, additional ingredients. The water-soluble vitamin E derivative mixtures (compositions) contain a relatively high percentage, such as at least 13%, typically greater than 25%, 29%, 35%, 45%, 48%, 49%, 50%, 51%, 52%, or 53%, up to 60-65%, of the dimer form of the vitamin E derivative, generally a PEG-derivative of vitamin E. The remainder of the water-soluble vitamin E derivative composition is the monomer form with a small percentage, less than 5%, 4%, 3%, 2%, or 1% of contaminants, such as higher order polymers and reagents, such as vitamin E.

Provided are compositions, which can be used as concentrates for providing soluble forms of non-polar compounds, for dilution into aqueous beverages and other foods and beverages, or which can be formulated for direct consumption. The compositions, referred to herein as concentrates (although they can be formulated not only for dilution, but for direct consumption), contain a non-polar compound and a water-soluble vitamin E derivative mixture (composition). The water-soluble vitamin E derivative mixture contains at least 13%, typically, at least 20%, 25%, 29%, 30%, 40%, 45%, 50% or more, typically up to 60-65%, of the dimer form of the vitamin E derivative product. Generally, the water-soluble vitamin E derivative mixture contains close to 50% of each of the dimer and monomer, generally more than 30% and up to about 60%, such as about or at 40%-55% dimer, and the rest monomer, with about or at 1% to 5% contaminants, such as vitamin E and higher order polymers of the vitamin E. Exemplary of water-soluble derivatives of vitamin E are PEG-derivatives of vitamin E, such as TPGS and analogs thereof, including PTS. The amount of PEGylation can vary, and includes 1000-PEG-derivatives of vitamin E and 600-PEG-derivative of vitamin E and variations in between. These include, but are not limited to, TPGS-1000, TPGS-600, PTS-1000 and PTS-600. For purposes herein, all are provided as compositions containing the high dimer forms of the water-soluble, such as PEG, derivative of vitamin E.

An advantageous property of the higher dimer containing water-soluble vitamin E derivative compositions is that, when diluted into foods and beverages, the resulting products have greater clarity and/or stability than products produced by dilution of the same concentrates or mixtures where the concentrates or mixtures of the water-soluble derivative contain less than 13% dimer as described above. The inclusion of more dimer form of the water-soluble vitamin E derivative, up to about 50%-65% of the total water-soluble vitamin E derivative mixture, the greater the clarity of the beverage.

Generally, water-soluble vitamin E derivative compositions have been prepared to contain as much monomer form as possible and contain dimer only as an undesired byproduct in low concentration. The water-soluble vitamin E derivative mixtures (compositions) described and used herein are manufactured to contain higher amounts of the dimer form and, consequently, lower amounts of the monomer form of the vitamin E derivative. For example, aqueous beverages that contain these higher dimer content water-soluble vitamin E derivative mixtures (compositions) have substantially greater clarity, typically they are about 2-fold less turbid when measured with a nephelometer in Nephelometric Turbidity Units (NTUs), compared to the same beverages and concentrates that differ only in the water-soluble vitamin E derivative composition that is used. Amounts and particulars of the compositions and the concentrates and resulting liquid dilution compositions, such as aqueous beverages, are described herein. Reference is made to the description and claims set forth below.

The water-soluble vitamin E derivative mixtures (compositions) provided herein can be used as the PEG-derivatives of vitamin E, such as TPGS, and in addition to or in place of another surfactant, such as a polysorbate, in the compositions described in U.S. application Ser. No. 12/383,244, filed Mar. 20, 2009, published as US-2009-0297665-A1, issued as U.S. Pat. No. 8,282,977, and entitled "COMPOSITIONS CONTAINING NON-POLAR COMPOUNDS," and International Application No. PCT/US2009/001775, filed Mar. 20, 2009, published as International PCT Publication No. WO 2009/117152 and entitled "EMULSIONS INCLUDING A PEG-DERIVATIVE OF TOCOPHEROL," U.S. patent application Ser. No. 12/383,241, filed Mar. 20, 2009, published as US-2009-0297491-A1 entitled "COMPOSITIONS CONTAINING NON-POLAR COMPOUNDS" and International Application No. PCT/US2009/001774, filed Mar. 20, 2009, published as International PCT Publication No. WO 2009/117151 and entitled "VITAMIN E DERIVATIVES AND THEIR USES," U.S. patent application Ser. No. 13/065,510, filed Mar. 22, 2011, published as US-2011-0236364-A1 entitled "COMPOSITIONS CONTAINING NON-POLAR COMPOUNDS" and International Application No. PCT/US2011/000538, filed Mar. 22, 2011, published as International PCT Publication No. WO 2011/119228 and entitled "COMPOSITIONS CONTAINING NON-POLAR COMPOUNDS, U.S. patent application Ser. No. 13/134,927, filed Jun. 20, 2011, published as US-2012-0016026-A1, entitled "COMPOSITIONS CONTAINING NON-POLAR COMPOUNDS" and International Application No. PCT/US2011/01099, filed Jun. 20, 2011, published as International PCT Publication No. WO 2011/162802 and entitled "COMPOSITIONS CONTAINING NON-POLAR COMPOUNDS," and U.S. patent application Ser. No. 13/815,193, filed Feb. 8, 2013, entitled "BEVERAGE COMPOSITIONS CONTAINING NON-POLAR COMPOUNDS" and International Application No. PCT/US2013/25445, filed Feb. 8, 2013, entitled "BEVERAGE COMPOSITIONS CONTAINING NON-POLAR COMPOUNDS," and U.S. application. Ser. No. 12/583,209, filed Aug. 13, 2009, published as US-2010-0041622-A, entitled "COMPOSITIONS CONTAINING AMINOALKANES AND AMINOALKANE DERIVATIVES," to Philip Bromley and Paul Edelmann.

High dimer-containing water-soluble derivatives of vitamin E compositions (mixtures) are employed for the preparation of compositions that contain the water-soluble vitamin E mixtures and a non-polar ingredient, such as a fatty acid, a vitamin, a drug, a phytosterol, other nutraceuticals and bioactive components. The water-soluble derivatives of vitamin E mixtures contain a high percentage, greater than or at least 13%, by weight, of the dimer form, of the derivative of vitamin E and the remainder is predominantly the monomer form, with up to 5% other components, such as trace amounts of reagents, other forms of the vitamin, and other minor contaminants. Thus, the water-soluble derivative of vitamin E mixtures (compositions) provide a mixture of the dimer form and monomer form of the water-soluble vitamin E derivative and contain a relatively high concentration of dimer form. These mixtures (or compositions) also are referred to as high dimer vitamin E derivative mixtures, because they are manufactured to be a mixture of forms, with greater than 13%, typically greater than 20%, dimer form. This mixture has advantageous properties, particularly compared to the same derivative of vitamin E that has been used that contains much lower concentrations of dimer, if any, and at least 87% monomer form. The high dimer-containing water-soluble derivatives of vitamin E mixtures are employed to solubilize non-polar ingredients. Thus, provided are compositions that contain high dimer-containing water-soluble derivatives of vitamin E mixtures and a non-polar compound. In particular, the compositions, which include compositions for direct consumption and concentrates, including nanoemulsion concentrates, contain: a water-soluble vitamin E derivative mixture (composition) in an amount from 1% to 99%, inclusive, by weight, of the resulting composition, where the water-soluble vitamin E derivative mixture contains at least 13 wt % water-soluble vitamin E derivative dimer and up to 87 wt % monomer; and a non-polar compound other than the water-soluble vitamin E derivative mixture. In some embodiments, the water-soluble vitamin E derivative mixture contains at least 20%, 25% or 29%, by weight, vitamin E derivative dimer, or the water-soluble vitamin E derivative mixture contains up to 75%, 70%, 69%, 62%, 55%, 50%, 45%, 40%, 35% dimer or 29%-69%, inclusive, of dimer; and/or contains less than 70%, 65%, 63%, 62%, 61%, 55%, 50%, or 48%, by weight, of the vitamin E derivative monomer in the water-soluble vitamin E derivative mixture. In some embodiments, the amount of dimer is greater than 29% and the total amount of dimer and monomer in the water-soluble vitamin E derivative mixture is greater than 95%, 96%, 97%, 98%, or 99%.

The dimer form of the vitamin E derivative is present in an amount between or between about 13% and 15%, 13% and 20%, 13% and 25%, 13% and 30%, 13% and 35%, 13% and 40%, 13% and 45%, 13% and 50%, 13% and 55%, 13% and 60%, 13% and 65%, 13% and 70%, 13% and 75%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 25% and 30%, 25% and 35%, 25% and 40%, 25% and 45%, 25% and 50%, 25% and 55%, 25% and 60%, 25% and 65%, 25% and 70%, 25% and 75%, 30% and 35%, 30% and 40%, 30% and 45%, 30% and 50%, 29% and 52%, 30% and 55%, 30% and 60%, 30% and 65%, 30% and 70%, 30% and 75%, 35% and 40%, 35% and 45%, 35% and 50%, 35% and 55%, 35% and 60%, 35% and 65%, 35% and 70%, 35% and 75%, 40% and 45%, 40% and 50%, 40% and 55%, 40% and 60%, 40% and 65%, 40% and 70%, 40% and 75%, 45% and 50%, 45% and 55%, 45% and 60%, 45% and 65%, 45% and 70%, 45% and 75%, 50% and 55%, 50% and 60%, 50% and 65%, 50% and 69%, 55% and 60%, 55% and 65%, 55% and 70%, 55% and 75%, 60% and 65%, 60% and 70%, 60% and 75%, 65% and 70%, 65% and 75%, or 70% and 75% by weight of the water-soluble vitamin E derivative mixture or is or at least or is at least about 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% or 74%, up to 75%, by weight, of the water-soluble v vitamin E derivative mixture.

The monomer is present in the high dimer-containing water-soluble derivative of vitamin E mixtures in an amount between or between about 25% and 30%, 25% and 35%, 25% and 40%, 25% and 45%, 25% and 50%, 25% and 55%, 25% and 60%, 25% and 65%, 30% and 35%, 30% and 40%, 30% and 45%, 30% and 50%, 30% and 55%, 30% and 60%, 30% and 65%, 30% and 69%, 35% and 40%, 35% and 45%, 35% and 50%, 35% and 55%, 35% and 60%, 35% and 65%, 35% and 69%, 40% and 45%, 40% and 50%, 40% and 55%, 40% and 60%, 40% and 65%, 40% and69%, 45% and 50%, 45% and 55%, 45% and 60%, 45% and 65%, 45% and 69%, 50% and 55%, 50% and 60%, 50% and 65%, 50% and 69%, 55% and 60%, 55% and 65%, 55% and 69%, 60% and 65%, 60% and 69%, or 65% and 69%, by weight, of the water-soluble vitamin E derivative mixture or is or is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, up to and including 69%, by weight, of the water-soluble vitamin E derivative mixture.

In the high dimer-containing water-soluble derivative of vitamin E mixtures, the monomer comprises between or between about 35% and 65%, inclusive, by weight of the water-soluble vitamin E derivative mixture and the dimer comprises between or between about 25% and 65%, by weight, of the water-soluble vitamin E derivative mixture, or the dimer comprises between or between about 29% and 61% or 62%, by weight, of the water-soluble vitamin E derivative mixture, and the monomer and dimer comprise at least 70%, by weight, of the water-soluble vitamin E mixture in the composition.

The water-soluble vitamin E derivative is any suitable derivative of vitamin E that renders it more soluble than it is absence, and can be a mixture of dimers and monomer. Exemplary of such derivatives are polyalkylene glycol derivatives of vitamin E, such as, but not limited to polyethylene glycol (PEG) derivatives of vitamin E. PEG derivatives include those in which the PEG derivative of vitamin E contains a PEG moiety having a molecular weight between or between about 100 Da and 20,000 Da, inclusive, including between 200 Da and 10,000 Da, 200 Da and 8000 Da, 200 Da and 6000 Da, 200 Da and 5000 Da, 200 Da and 3000 Da, 200 Da and 1000 Da, 200 Da and 800 Da, 200 Da and 600 Da, 200 Da and 400 Da, 400 Da and 20,000 Da, 400 Da and 10,000 Da, 400 Da and 8000 Da, 400 Da and 6000 Da, 400 Da and 5000 Da, 400 Da and 3000 Da, 400 Da and 1000 Da, 400 Da and 800 Da, 400 Da and 600 Da, 600 Da and 20,000 Da, 600 Da and 10,000 Da, 600 Da and 8000 Da, 600 Da and 6000 Da, 600 Da and 5000 Da, 600 Da and 3000 Da, 600 Da and 1000 Da, 600 Da and 800 Da, 800 Da and 20,000 Da, 800 Da and 10,000 Da, 800 Da and 8000 Da, 800 Da and 6000 Da, 800 Da and 5000 Da, 800 Da and 3000 Da, 800 Da and 1000 Da, 1000 Da and 20,000 Da, 1000 Da and 10,000 Da, 1000 Da and 8000 Da, 1000 Da and 6000 Da, 1000 Da and 5000 Da, 1000 Da and 3000 Da, 3000 Da and 20,000 Da, 3000 Da and 10,000 Da, 3000 Da and 8000 Da, 3000 Da and 6000 Da, 3000 Da and 5000 Da, 5000 Da and 20,000 Da, 5000 Da and 10,000 Da, 5000 Da and 8000 Da, 5000 Da and 6000 Da, 6000 Da and 20,000 Da, 6000 Da and 10,000 Da, 6000 Da and 8000 Da, 8000 Da and 20,000 Da, 8000 Da and 10,000 Da, or 10000 Da and 20,000 Da, or has a molecular weight of at least 100, 200, 238, 300, 400, 500, 600, 750, 800, 1000, 1200, 1500, 2000, 2500, 3000, 3400, 3500, 4000, 6000, 8000, 10,000, 12,000, 14,000, 16,000, 18,000, up to and including 20,000 Da.

Among the PEG derivatives of vitamin E are, for example, tocopheryl polyethylene glycol succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate.

In some embodiments, the vitamin E derivative is selected from among tocopheryl polyethylene glycol succinate (TPGS), tocopheryl sebacate polyethylene glycol and other TPGS analogs and TPGS homologs, tocopheryl dodecanodioate polyethylene glycol, tocopheryl suberate polyethylene glycol, tocopheryl azelaate polyethylene glycol, tocopheryl citraconate polyethylene glycol, tocopheryl methylcitraconate polyethylene glycol, tocopheryl itaconate polyethylene glycol, tocopheryl maleate polyethylene glycol, tocopheryl glutarate polyethylene glycol, tocopheryl glutaconate polyethylene glycol and tocopheryl phthalate polyethylene glycol.

Exemplary of TPGS is D-α-tocopheryl polyethylene glycol succinate (TPGS).

The compositions provided herein contain, in addition to the high dimer-containing water-soluble derivative of vitamin E mixtures, an additional ingredient, which typically is a bioactive ingredient, such as a drug, vitamin or nutraceutical. Generally, such ingredients are non-polar ingredients and are rendered soluble by the high dimer-containing water-soluble derivative of vitamin E mixture. As provided and shown herein, the high dimer-containing water-soluble derivative of vitamin E mixtures are more effective than vitamin E derivative compositions that contain high amounts of monomer and low amounts, if any, of dimer.

Among the non-polar ingredients are those that contain a non-polar active ingredient, such as, but not limited to, polyunsaturated fatty acids (PUFA), coenzyme Q, phytosterols, resveratrol, carotenoids, micronutrients, alpha lipoic acid and oil-soluble vitamins. Exemplary of such compounds are non-polar compounds that contain PUFAs, such as fish oil, algae (algal) oil, flaxseed oil, borage oil, saw palmetto extract, safflower oil, coconut oil, soybean oil and conjugated linoleic acid (CLA)-containing compounds. These include omega-3 fatty acids, omega-6 fatty acids, omega-9 fatty acids, and conjugated fatty acids, such as, but not limited to, docosahexaenoic acid (DHA), eicosapentaenoic acid (EPA), alpha-linolenic acid (ALA), gamma-linolenic acid (GLA), conjugated linoleic acid (CLA) and oleic acid compounds. Among these are coenzyme Q10; an oil-soluble vitamin that is selected from among vitamin B12, vitamin D3, vitamin A palmitate, vitamin E, vitamin B1, vitamin B3, vitamin B5, vitamin B6, vitamin C and mixtures thereof; a carotenoid-containing compound that is selected from among lycopene, lutein, zeaxanthin and mixtures of lutein and zeaxanthin; and a micronutrient-containing compound that is selected from among yerba mate, *ginkgo biloba* and ginseng.

The concentration of non-polar compound in the composition depends upon the particular compound and desired dosage or amount to be administered and also whether the composition is intended for direct administration or is a concentrate. Hence, the concentration of non-polar compound can be present in an amount from 0.1% to 99%, by weight, such as 0.5% or 1% to 75%, by weight, of the composition, or, for example, 0.1% to 10%, 1% to 5%, 5% to 10%, 5% to 12%, 5% to 15%, 5% to 20%, 5% to 25%, 10% to 14%, 10% to 12%, 10% to 15%, 10% to 20%, 10% to 25%, 5% to 30%, 1% to 30% or 1% to 15%, inclusive, by weight of the composition.

Other ingredients in the compositions include a preservative in an amount sufficient to preserve the composition. The preservative, for example, can contain benzyl alcohol.

The compositions can also include a non-polar solvent that dissolves the non-polar compound and is different therefrom and is present in an amount sufficient to dissolve the non-polar compound. Exemplary non-polar solvents include, for example, a vitamin E oil, a flaxseed oil, an oat oil and mixtures thereof.

The compositions can include a polar solvent, such as a polar protic solvent. Exemplary polar solvents include water and consumable alcohols and mixtures thereof, such as, but not limited to water, glycerin, propylene glycol, ethylene glycol, tetraethylene glycol, triethylene glycol and trimethylene glycol. The amount of polar solvent depends upon the particular composition and whether it is a concentrate or for direct consumption. Hence, the concentration can be, for example, from more than 0.5% or 1% to 95%, by weight, of the composition, such as between 45% to 80%, or 60% to 80%, by weight, of the composition.

The compositions also can contain a co-surfactant present in an amount sufficient to increase stability of the composition compared to the absence of a co-surfactant. Co-surfactants for use with the high dimer-containing water-soluble derivative of vitamin E mixtures include, for example, a phospholipid, such as phosphatidyl choline, a sucrose fatty acid ester, a polysorbate and a polysorbate analog.

The compositions also can include an emulsion stabilizer, such as modified starch and gum mixtures. These include, for example, one or more of a blend of xanthan gum, guar gum and sodium alginate; modified gum acacia; and ester gum.

The compositions include other optional ingredients, such as a pH adjuster present to adjust the pH of the composition to between 2.0 and 4.0. Typically, the pH adjuster is present in an amount of less than 1% by weight. Exemplary pH adjusters include citric acid and phosphoric acid. Other ingredients include a flavor or flavoring agent and/or sweeteners, particularly in the compositions for direct administration. Flavors can be imparted by beverage bases as well as flavoring agents.

The amount of the water-soluble vitamin E derivative mixture is from 16% to 30%, inclusive, or is 1% to 95%, inclusive, or is 10% to 40%, inclusive, 10% to 50%, inclusive, 15% to 25%, inclusive, by weight of the composition, or is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95%, inclusive, by weight, of the composition, such as greater than 1%, 2%, 3%, 4%, 5%, 10%, 15% or 20% or about 20%, greater than 30% or about 30%, between 30% or about 30% and 55% or about 55%, between 16% and 30%, between 30% or about 30% and 50% or about 50%, between 30% or about 30% and 45% or about 45%, or at least 10%, 12%, 15%, 17%, 20%, 22%, 24%, 27%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, or 55%, up to at least 60%, 65%, 70%, 75%, 80%, 85%, 90%, 95%, 97%, 98%, or 99%, all by weight, of the composition. For example, for concentrates, the vitamin E derivative mixture can be present in an amount of about at least 15%, or 15% to 30%, at least 40% or about 40%, 50% or about 50%, or greater than 60% or about 60%, greater than 65% or about 65%, for example, greater than 70% or about 70%, for example, a starting concentration within the concentration range of between 50% or about 50% and 95%, or about 95%, between 60% or about 60% and 95% or about 95%, between 65% or about 65% and 90% or about 90%, for example, between 69% or about 69% and 90% or about 90%, between 69% or about 69% and 89% or about 89%, for example, at least 65%, 66%, 67%, 68%, 69%, 69.5%, 69.9%, 70%, 71%, 72%, 73%, 74%, 75%, 76%, 77%, 78%, 79%, 79.5%, 79.9%, 80%, 81%, 82%, 83%, 84%, 85%, 86%, 87%, 88%, 89%, 89.5%, 89.9%, or 90%, by weight, of the composition.

Exemplary compositions, particularly concentrates, include a composition that contains a water-soluble vitamin E derivative mixture present in an amount from 5% to 95%, by weight, of the composition, wherein the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; and a preservative present in an amount sufficient to preserve the composition.

Another composition contains a water-soluble vitamin E derivative mixture present in an amount from 5% to 95%, by weight, of the composition, where: the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; a preservative present in an amount sufficient to preserve the composition; and a non-polar solvent that differs from the non-polar compound and is present in an amount sufficient to dissolve the non-polar compound.

Another exemplary composition contains a water-soluble vitamin E derivative mixture present in an amount from 5% to 95%, by weight, of the composition, where: the water-soluble vitamin E derivative mixture comprises from 25 wt % to 69 wt % water-soluble vitamin E monomer and from 13 wt % to 75 wt % water-soluble vitamin E dimer; a non-polar compound other than the water-soluble vitamin E derivative mixture, present in an amount from 1% to 75%, by weight, of the composition; a preservative present in an amount sufficient to preserve the composition; a polar solvent present in an amount from 45% to 80%, by weight, of the composition; and a pH adjuster present in an amount sufficient to adjust the pH of the composition to between 2.0 and 4.0.

The compositions provided herein can be concentrates or can be for direct consumption. Among those for direct consumption are dilution compositions, such as beverage compositions into which any of the concentrates provide herein have been diluted. The beverage can contain a beverage base or can be water. Dilution depends upon the desired concentration of active ingredient or non-polar ingredient and the desired volume of the dilution composition. For example, the compositions can be diluted into a polar solvent, such as water or an aqueous beverage, in amounts sufficient whereby: (a) dilution of at least or about 0.5 g, 1 g, 2 g, 5 g or 10 g of the composition into 8 or about 8 fluid ounces of an aqueous medium; or (b) dilution of the composition in an aqueous medium, at a dilution not more than 1:10 or about 1:10, 1:25 or about 1:25, 1:50 or about 1:50, 1:100 or about 1:100, 1:250 or about 1:250, or not more than 1:50; or (c) dilution of the composition into an aqueous medium such that the aqueous medium contains at least or about 25 mg, 35 mg, 50 mg, 100 mg, 250 mg or 500 mg of the non-polar compound per 8 fluid ounces of the aqueous medium, to yield a liquid dilution composition. Such liquid dilution composition can have properties such as: (i) it is at least as clear or at least about as clear as the aqueous medium in the absence of the composition; or (ii) it is an emulsion with particles of size of less than or about 200 nm, less than or about 100 nm, less than or about 50 nm, or less than or about 25 nm, at most or on average; or (iii) is has a turbidity value of less than or about 80, less than or about 50, less than or about 30, less than or about 25, less than or about 10, or less than or about 5, measured in a Nephelometric Turbidity Units (NTUs); or (iv) it does not contain visible particles, does not contain visible crystals, does not exhibit phase separation, and/or does not exhibit ringing. Polar solvents include, but are not limited to water, glycerin, propylene glycol, ethylene glycol, tetraethylene glycol, triethylene glycol and trimethylene glycol.

The compositions provided herein also can contain additional ingredients such as sweeteners, stabilizers, pH adjusters and antifoaming agents. Sweeteners include any known to those of skill in the art, including, but not limited to, sucralose, sucrose, lactose, fructose, an acesulfame salt, aspartame, saccharin, stevia, stevioside and xylitol. Stabilizers include, but are not limited to, carbonates, bicarbonates, acids and antioxidants. The carbonates, bicarbonates, acids and antioxidants can be included in the compositions for direct consumption as they stabilize the compositions as consumed and packaged. Such compositions also are packaged in a sealed container, which contains nitrogen to displace air in the container and to prevent oxygen from entering the sealed container. Such compositions include, but are not limited to juice, water, sports drinks, and sodas.

Methods for preparing the compositions, particularly those that are concentrates, are provided. These methods include steps of: (a) mixing and heating initial ingredients in a vessel, where the initial ingredient(s) comprise: a water-soluble vitamin E derivative mixture present in an amount from 5% to 95%, by weight, of the concentrate; and the water-soluble vitamin E derivative mixture comprises from 25 wt % to 69 wt % water-soluble vitamin E monomer and from 13 wt % to 75 wt % water-soluble vitamin E dimer; (b) adding one or more additional ingredient to the vessel, where the one or more additional ingredients comprise: a non-polar compound at an amount from 1% to 75%, by weight, of the concentrate; (c) homogenizing the ingredients; and then (d) cooling the mixed ingredients, whereby, for compositions with high levels of vitamin E derivatives, the mixed ingredients become waxy in consistency, and lower levels form an emulsion, thereby generating the composition.

Methods for preparing a beverage or other composition for direct consumption containing a non-polar compound also are provided. The beverages are prepared by adding the composition provided herein, such as a nanoemulsion concentrate, to a beverage base. The concentrate is added at a predetermined concentration to produce a beverage supplemented with the active ingredient in the concentrate at an effective or desired concentration. The beverage base comprises the other components of the resulting beverage, including, but not limited to water, juice, a soda, a sports drink and/or a nutritional drink.

Among the compositions provided herein are concentrates and also compositions for direct consumption. Among the compositions for direct consumption are compositions containing either I: (a) an active ingredient; and (b) a water-soluble vitamin E derivative mixture in an amount between at or about 0.1% and at or about 5%, by weight, or 0.1% and 15%, by weight, of the composition; or II: a composition where the water-soluble derivative of vitamin E mixture is present in an amount of less than 20%, 18.5%, 18%, 16%, 15%, 12%, 10%, 5%, 4%, 3%, or 2%, by weight, of the composition; and the non-polar ingredient is in an amount for direct consumption. For direct consumption, the amount of the water-soluble vitamin E derivative mixture can be as low as between at or about 0.1% and at or about 2%, by weight, of the composition, or can be higher, as described herein. The compositions can include a polar solvent, such as at an amount between at or about 25% and at or about 98%, by weight, or between at or about 25% and at or about 92%, by weight, or between at or about 80% and at or about 92%, by weight, of the composition. The polar solvents include water or alcohol or mixtures thereof. Compositions for direct consumption can contain in an aqueous beverage base: (a) a non-polar ingredient in an amount of 0.1% to 25% by weight; and (b) a water-soluble vitamin E derivative mixture in an amount between at or about 0.1% and at or about 5%, by weight, or 0.1% and 15%, by weight, of the composition.

The non-polar ingredient, which is an active ingredient and can be any ingredient of interest, such as a drug, nutraceutical and other supplement, is present in an amount that is suitable for or effective when consumed directly. This includes concentrations of 0.5% or 1% to 25%, 30% or more by weight of the composition. The amount depends upon the particular ingredient. Compositions for direct consumption, if not prepared in a beverage base, typically include additional ingredients, such as taste modifying agents (ingredients) including, flavorings and/or sweeteners to render the compositions palatable. A taste-modifying agent is included in an amount sufficient to improve or enhance the palatability of the composition compared to the absence of the agent, whereby the composition is palatable for direct consumption as a single dosage.

In exemplary embodiments, the composition for direct consumption is one in which an active ingredient is a stimulant, whereby the composition is an energizer composition; or an active ingredient has sedative activity, whereby the composition is a composition that is calming, sedating and/or relaxing. Exemplary active ingredients include, but are not limited to, 4-amino-3-phenylbutyric acid, an aminoalkane or derivative thereof, green tea extract, coQ10, 4-[1-hydroxy-2-(methylamino)ethyl]phenol and caffeine. Also contemplated are agents such as nutritional supplements, vitamins, minerals, fatty acids, amino acids and weight-loss compounds. Other active ingredients include, but are not limited to, vitamins, such as vitamin B12 and vitamin D3 and other vitamins, chromium picolinate, conjugated linoleic acid (CLA), L-taurine, and alpha lipoic acid. The compositions can contain a plurality of active ingredients. The aminoalkane includes those of formula I:

(I)

or a biocompatible derivative thereof, where: R is an alkyl containing from 2 to 20 carbons; and R' is a hydrogen or an alkyl containing from 1 to 20 carbons; and the aminoalkane or derivative thereof has vasoconstrictor activity. Exemplary of an aminoalkane is a 2-aminoalkane, such as one that contains a methyl substitution, including a 2-aminoalkane, and contains a methyl substitution on the fourth carbon of the carbon chain, such as 2-amino-4-methylhexane or a biocompatible derivative thereof. Also included are biocompatible derivatives of the aminoalkane, such as acid addition salts, aldehyde derivatives, amide derivatives, acid derivatives, ester derivatives and carbonate derivatives.

The concentration of the aminoalkane or derivative thereof, for example, is between about 100 mM and about 200 mM. The water-soluble vitamin E derivative mixture is present in an amount between at or about 0.1% and at or about 25%, by weight, of the composition. In exemplary embodiments, the water-soluble vitamin E derivative mixture contains at least 20%, 25% or 29%, by weight, vitamin E derivative dimer.

The compositions for direct consumption can be formulated as an emulsion in a volume of about 1-10 mL for oral ingestion as a single serving to provide a single dose of the aminoalkane of formula I or derivative thereof or any other active agent or non-polar compound. The compositions can be formulated in higher volumes for multiple doses. The compositions can be packaged in a container, such as in a sealed vial, bottle or ampoule, particularly for single dose (one shot) consumption.

The compositions can contain additional ingredients as described above, such as taste-modifying agents, such as flavoring agent and/or a sweetener. Depending upon the non-polar component and other components, rendering the composition palatable requires different amounts of taste modifiers. For example, the taste-modifying agent is present in the composition at an amount between at or about 0.1% and at or about 25%, or between at or about 0.45% and at or about 3%, by weight, of the composition.

Compositions for direct consumption can be provided in low volumes for ease of ingestion and can be packaged as single doses. Low volumes typically are between about or are 1-10 mL, 2-9 mL, 3-8 mL, 3-7 mL, 3-5 mL, 3 mL, 4 mL, 5 mL, up to 10 mL, or any convenient volume. In such compositions, the amount of water-soluble vitamin E derivative mixture is between or between about 0.5%-4%, inclusive, or 1-3% inclusive, or 1-2% inclusive, or 2-3.5% inclusive. The low volume compositions can be packaged in small containers, such as vials, small bottles and ampoules, or other suitable vehicles, particularly sealed containers. Delivery is effected by breaking a seal on the container, such as the ampoule, and ingesting the composition contained in the ampoule.

Depending upon the active ingredient, the low volume composition can be used in a variety of methods. For example, the compositions can be employed in a method for providing energy to a subject by orally administering a composition, wherein the active ingredient is a stimulant. The compositions can be sedating or relaxing, if the active ingredient is one that has a calming or sedating effect. Hence, methods for providing energy to a subject are provided, as are methods for sedating or calming a subject.

Also provided are compositions for direct administration in which the active ingredient is a stimulant, whereby the composition is an energizer composition; or an active ingredient has sedative activity, whereby the composition is a composition that is calming, sedating and/or relaxing. Examples of such ingredients include, but are not limited to, 4-amino-3-phenylbutyric acid, an aminoalkane or derivative thereof, green tea extract, coQ10, 4-[1-hydroxy-2-(methylamino)ethyl]phenol and caffeine. These compositions optionally include flavoring ingredients or taste modifying ingredients to render them more palatable compared to the absence of the agent, whereby the composition is palatable for direct consumption as a single dosage. Exemplary amounts of the flavoring or taste modifying ingredient(s) is 0.1% and at or about 25%, or between at or about 0.45% and at or about 3%, by weight, of the composition.

As an example, provided are compositions in which the compositions contain (a) an active ingredient that is an aminoalkane of formula I:

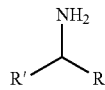

(I)

or a biocompatible derivative thereof, where: R is an alkyl containing from 2 to 20 carbons; and R' is a hydrogen or an alkyl containing from 1 to 20 carbons; the aminoalkane or derivative thereof has vasoconstrictor activity; and the concentration of the aminoalkane or derivative thereof is between about 100 mM and about 200 mM; and (b) a water-soluble vitamin E derivative mixture in an amount between at or about 0.1% and at or about 25%, by weight, such as, 0.1% and at or about 2%, by weight, of the composition. For example, the composition contains at least 20%, 25% or 29%, by weight, vitamin E derivative dimer. The composition can be formulated as an emulsion in a volume of at or about 1-10 mL, such as 1-10 mL, 2-9 mL, 3-8 mL, 3-7 mL, 3-5 mL, 3 mL, 4 mL, 5 mL, up to 10 mL, for oral ingestion as a single serving to provide a single dose of the aminoalkane of formula I or derivative thereof. Exemplary of an aminoalkane is a 2-aminoalkane, such as a 2-aminoalkane, and contains a methyl substitution, such as on the fourth carbon of the carbon chain, such as aminoalkane is 2-amino-4-methylhexane or a biocompatible derivative thereof, such as, but not limited to, acid addition salts, aldehyde derivatives, amide derivatives, acid derivatives, ester derivatives and carbonate derivatives. These compositions, as well as all compositions provided herein, can further contain one or more additional active ingredients selected from any one or more of nutritional supplements, vitamins, minerals, fatty acids, amino acids and weight-loss compounds, such as vitamin B12, chromium picolinate, conjugated linoleic acid (CLA), L-taurine, and alpha lipoic acid. The compositions can include a polar solvent, such as water or an alcohol, at an amount between at or about 25% and at or about 98%, by weight, or between at or about 25% and at or about 92%, by weight, or between at or about 80% and at or about 92%, by weight, of the composition. Exemplary amounts of the high dimer water-soluble vitamin E derivative mixture is between or between about 0.5%-4%, inclusive, or 1-3% inclusive or 1-2% inclusive, or 2-3.5% inclusive. The compositions can further comprise a stabilizer that is selected from among one or more of carbonates, bicarbonates, acids and antioxidants.

All of and any of the compositions provided herein can be provided in a container, such as a sealed container. The container can include nitrogen in place of air in the container. Containers can be bottles and ampoules and other such sealable containers.

Also provided are methods of providing supplements to a subject by orally administering any of the compositions provided herein that are for direct administration. Hence, provided are methods for providing supplementation of omega-3 oils and other such fatty acids, and methods of providing energy or a sedative.

All of the compositions provided herein can be formulated for direct ingestion to deliver an effective amount of a non-polar ingredient.

DETAILED DESCRIPTION

Outline
    A. Definitions
    B. Water-soluble vitamin E derivatives
        1. Vitamin E
        2. Polyalkylene glycol derivatives of vitamin E
            a. Tocopherols and tocotrienols
            b. Linkers
            c. PEG moieties
            d. Surfactant properties
        3. Tocopheryl polyalkylene glycol derivatives
            a. Uses
                i. Nutritional supplement
                ii. Surfactant
        4. Synthesis
        5. Water-soluble vitamin E derivative mixtures (compositions)
    C. Methods for making water-soluble vitamin E derivatives
        1. Reaction mixture
            a. Vitamin E succinate
            b. Polyethylene glycol
            c. Catalyst
            d. Solvent
            e. Exemplary reaction mixtures
        2. Exemplary methods
            a. Preparation of crude water-soluble vitamin E derivative mixtures (compositions)
            b. Processing the reaction mixture to obtain a crude water-soluble vitamin E derivative mixture
            c. Purification of the crude water-soluble vitamin E derivative mixture to obtain a purified high-dimer water-soluble vitamin E derivative mixture
    D. Products containing high dimer-containing water-soluble vitamin E derivative mixtures (compositions)
        1. Concentrates
            a. Pre-emulsion concentrates
                i. Formulating the pre-emulsion concentrates
                ii. Exemplary ingredients and typical concentration ranges -continued

DETAILED DESCRIPTION b. Liquid nanoemulsion concentrates
   i. Formulating the liquid nanoemulsion concentrates
c. Liquid dilution compositions containing the concentrates
d. Evaluation of the concentrates and liquid dilution compositions
   i. Clarity
      (a) Empirical evaluation
      (b) Particle size or number of particles
      (c) Turbidity measurement
   ii. Stability
   iii. Desirable characteristics for human consumption
   iv. Safety
   v. Oral bioavailability
e. Selecting a formulation and modifying formulations
2. Compositions for direct consumption
3. Exemplary ingredients and concentration ranges
   a. Water-soluble vitamin E derivatives
   b. Non-polar compounds containing non-polar active ingredients
      i. Polyunsaturated fatty acid (PUFA)-containing active ingredients
         (a) Omega-3 fatty acid compounds
            (1) DHA/EPA
               (i) Fish oils
               (ii) Algae oil
            (2) Flax seed oil - omega 3 (ALA)
         (b) Omega-6 compounds
         (c) Saw palmetto extract
         (d) Conjugated linoleic acid (CLA)
      ii. Coenzyme Q compounds
      iii. Phytochemical-containing non-polar compounds
         (a) Phytosterols
         (b) Resveratrol
      iv. Carotenoid-containing compounds
         (a) Carotenes
         (b) Xanthophylls
      v. Micronutrient-containing compounds
         (a) Vitamins
         (b) Alpha-lipoic acid (thioctic acid)
   c. Non-polar solvents
   d. Preservatives and sterilizers
   e. Polar solvents
   f. Co-surfactants (emulsifiers)
      i. Phospholipids
      ii. Sugar-derived surfactants
      iii. PEG-derived surfactants
      iv. Sucrose fatty acid ester surfactants
   g. Emulsion stabilizers (co-emulsifiers)
   h. Flavors
   i. pH adjusters
   j. Soluble fibers
   k. Additional ingredients
      i. Active ingredients
         (a) Alkaloids
      ii. Stabilizers
         (a) Bicarbonates or carbonates
         (b) Acids
         (c) Antioxidants
      iii. Beverage base
         (a) Water
         (b) Juices or juice concentrates
         (c) Flavors
         (d) Carbonated beverages
      iv. Sweeteners
      v. pH adjusters
      vi. Antifoaming agents
E. Exemplary methods for preparing products containing high dimer-containing water-soluble vitamin E derivative mixtures
1. Equipment employed in the methods
   a. Scales
   b. Purifiers
   c. Vessels
   d. Mixers
   e. Heating/cooling apparatuses
   f. Transfer device
   g. Evaluation equipment
2. General methods for producing the compositions
   a. Water phase ingredients
   b. Water phase production
   c. Oil phase ingredients
   d. Oil phase production
   e. Combining phases
   f. Cooling
   g. Filtration, additions, evaluation and packaging
   h. Cleaning the equipment
F. Examples A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "vitamin E" refers to any naturally occurring or synthetic form of vitamin E, for example, tocopherols and tocotrienols, and can refer to a single form of the compound or a mixture of forms.

As used herein, "water-soluble vitamin E derivative composition," "water-soluble vitamin E derivative," "water-soluble vitamin E derivative surfactant," "water-soluble vitamin E surfactant," and "water-soluble derivative of vitamin E mixture," which are be used interchangeably, refer to compositions that contain mixtures of water-soluble forms of vitamin E (vitamin E-derivatized with moieties, such as polyalkylene glycol) that increase the water solubility of the water-insoluble vitamin E. The mixtures contain dimers and monomers of the vitamin E derivatives. The water-soluble vitamin E derivative mixtures (compositions) include vitamin E (natural or synthetic forms of vitamin E), such as tocopherol derivatives and tocotrienol derivatives. Derivatives of vitamin E, such as PEG-derivatives previously produced, are manufactured to contain as much monomer form as possible, and to contain minimal amounts of any dimer form (see, e.g., Christiansen et al. (2011) J. Pharm. Sci. 100(5):1773-1782).

In contrast the high dimer vitamin E derivative mixtures, such as PEG-derivative of vitamin E derivative compositions (also referred to herein as high dimer PEG-derivatives of vitamin E mixtures) employed herein, are manufactured to contain dimer forms. The mixtures described herein contain at least 13%, particularly at least or at least about 20%, 25%, 29% or more, dimer form of the water-soluble vitamin E derivative. In particular, the water-soluble vitamin E derivative mixtures (compositions) are manufactured to contain between or between 13 wt % and about or up to 95%, 90%, 85%, 80% or 75%, by weight, particularly at least 29% to 75% or 80%, inclusive, of the water-soluble vitamin E dimer. In general, the high dimer derivatives, such as PEG- derivatives of vitamin E mixtures, such as a high dimer TPGS composition, contain 30%-60%, particularly 35%-52% dimer, and the remainder is the monomer form and less than 5%, generally 3%, 2%, or 1%, other trace components, such as unreacted reagents, such as vitamin E and the hydrophilic derivatizing moiety.

In general, the mixtures contain at least 13% of the dimer form and up to 87% monomer form, particularly at least 25% of the dimer form and up to 70% of monomer form, such as between or between about 25 wt % and 69wt %, inclusive, of the monomer. Hence, the water-soluble vitamin E derivative mixtures (compositions) (high dimer-containing compositions) contain a substantial amount (i.e., 13% or more, particularly 25%, 29%, 35%, 48%, 52% or more) of the dimer form compared to commercially available forms that are manufactured to provide the monomer form.

As manufactured, the high dimer mixtures can include other forms and unreacted components, hence the total amount of dimer and monomer do not necessarily total 100%, by weight, of the composition. It is shown herein that inclusion of at least 13%, 20%, 25%, or 29%, or more of the dimer form, and some monomer form, about less than 87%, 69%, 65%, 60%, 55%, or 50% of the monomer with at least 30% dimer, confers advantageous properties on these water-soluble vitamin E derivative mixtures (compositions) not possessed by such compositions that contain lower amounts of the dimer form.

Examples of water-soluble vitamin E derivatives are those formed by covalently attaching the vitamin E moiety, e.g., a tocopherol or tocotrienol, to a hydrophilic moiety, for example, an alkylene glycol, such as a polyethylene glycol (PEG) moiety, via a linker. The compositions as provided herein are manufactured so that the resulting water-soluble vitamin E derivative mixtures (compositions) include a mixture of monomers and dimers of the water-soluble vitamin E derivatives, and contain a substantial amount (compared to prior art preparations), i.e., 13% to 95%, inclusive, such as at least 13%, 20%, 25%, or 29%, up to as much as 75%, 80%, 85%, 90%, 95%, by weight, of the dimer form, and generally less than 70%, 65%, 63%, 62%, 61%, or 60%, or less of the monomer form. Water-soluble vitamin E derivative mixtures (compositions) include, for example, polyalkylene glycol derivatives of tocopherol, e.g., polyethylene glycol (PEG) derivatives of tocopherol, and polyalkylene glycol derivatives of tocotrienol, e.g., polyethylene glycol (PEG) derivatives of tocotrienol. The water-soluble vitamin E derivatives can include, for example, vitamin E TPGS (D-α-tocopheryl polyethylene glycol succinate), TPGS analogs, TPGS homologs and TPGS derivatives.

As used herein, "tocopherol" and "tocotrienol" refer to any naturally occurring or synthetic form of vitamin E, and can refer to a single compound or a mixture of tocopherols and tocotrienols. Examples of tocopherols include, for example, α-tocopherol, D-α-tocopherol, β-tocopherol, γ-tocopherol and δ-tocopherol. Examples of tocotrienols include, for example, α-tocotrienol, β-tocotrienol, γ-tocotrienol and γ-tocotrienol.

As used herein, a "PEG derivative of vitamin E" or "vitamin E-PEG conjugate" or "vitamin E-PEG derivative," is a compound containing one or more vitamin E moieties (e.g., a tocopherol or tocotrienol) joined by a covalent bond, for example an ester, ether, amide or thioester bond, to one or more polyethylene glycol (PEG) moieties, via a linker, such as a dicarboxylic or tricarboxylic acid. Exemplary of PEG derivatives of vitamin E are D-α-tocopheryl polyethylene glycol succinate (TPGS), TPGS analogs, TPGS homologs and TPGS derivatives.

As used herein, "tocopheryl polyethylene glycol succinate," "TPGS," "tocopheryl polyethylene glycol succinate surfactant" and "TPGS surfactant" refer to tocopheryl polyethylene glycol conjugates that are formed by covalently joining tocopherol succinate, an ester formed through esterification of tocopherol and succinic acid, to a polyethylene glycol (PEG) moiety via an esterification reaction. The PEG moiety of the TPGS surfactant can be any PEG moiety, for example, PEG moieties with a molecular weight of between or about between 200 Da and 20,000 Da or about 20,000 Da, for example, PEG moieties having a molecular weight of or about 200, 300, 400, 500, 600, 800, 1000, 3000, 5000, 6000, 8000, 10,000, 20,000 Da or more; or PEG analogs, including, for example, PEG-NHS (N-hydroxysuccinimide), PEG-aldehyde, PEG-SH, PEG-NH$_2$, PEG-CO$_2$H, and branched PEGs.

As used herein, "TPGS monomer" is a single vitamin E moiety, i.e., D-α-tocopherol, covalently joined to a polyethylene glycol through a succinate linker, and a TPGS dimer is made up of two vitamin E moieties, i.e., D-α-tocopherol, covalently joined to a polyethylene glycol through one or more succinate linkers (shown below). The esterification reaction between the vitamin E moiety, for example, D-α-tocopheryl succinate, and PEG results in a highly complex crude product that contains a mixture of TPGS monomer, unreacted PEG, unreacted vitamin E (e.g., D-α-tocopheryl succinate), catalyst, and TPGS dimer, formed when a second molecule of the vitamin E moiety reacts with the terminal hydroxyl group of a PEG moiety already conjugated to TPGS monomer via a linker. For purposes herein, mixtures are prepared with the PEGylated derivative under conditions that result in higher amounts of the TPGS dimer produced as compared to prior art preparations. In addition, the TPGS dimer can be purified and the amounts increased. The water-soluble vitamin E derivative mixtures (compositions) where the vitamin E derivative is TPGS, described herein, contain a mixture of TPGS monomer and TPGS dimer, and contain more than 12%, but generally at least 20%, 25%, 29%, 35% and more, TPGS dimer, up to as much as 95% or about 95% TPGS dimer, but typically up to about 75%. The remainder of the composition contains the TPGS monomer, and can contain unreacted starting materials and catalyst. Similarly, water-soluble vitamin E derivative mixtures (compositions) containing vitamin E derivatives other than TPGS contain mixtures of dimer and monomer.

As used herein, a concentrate is a composition that contains the water-soluble high dimer vitamin E derivative mixture and/or the active compound or non-polar compound(s) in higher than single dosage concentrations so that the concentrate compositions are diluted for ingestion.

As used herein, "colloid" refers to a mixture containing two phases, a dispersed phase and a continuous phase, the dispersed phase containing particles (droplets) distributed throughout the continuous phase. Colloidal mixtures include aerosols, foams and dispersions, for example, emulsions, for example, nanoemulsions. A liquid colloid, for example, a nanoemulsion, can have a similar appearance, for example, clarity, to a solution in which there is no dispersed phase.

As used herein, "emulsion" refers to a colloidal dispersion of two immiscible liquids, for example, an oil and water (or other aqueous liquid, e.g., a polar solvent), one of which is part of a continuous phase and the other of which is part of a dispersed phase. The provided liquid dilution compositions include emulsions, typically oil-in-water nanoemulsions (which include any oil soluble phase dispersed in any aqueous phase, also called the water phase), in which the oil phase is the dispersed phase and the water phase is the continuous phase. Emulsions typically are stabilized by one or more surfactants and/or co-surfactants and/or emulsion stabilizers. Surfactants form an interfacial film between the oil and water phase of the emulsion, providing stability. Typically, the nanoemulsions of the provided liquid dilution compositions contain micelles that contain one or more surfactants surrounding a non-polar active ingredient, which are dispersed in the water phase. Exemplary of the provided emulsions are the provided liquid nanoemulsion concentrates, liquid dilution compositions and flavored shots made by diluting the concentrates, typically in an aqueous medium. In general, emulsions (e.g., oil-in-water emulsions) are colloidal dispersions of two immiscible liquids (e.g., oil and an aqueous liquid, such as water), containing a continuous and a dispersed phase. Emulsions can be used to disperse non-polar compounds in aqueous liquids. In an oil-in-water emulsion, the dispersed phase is an oil phase and the continuous phase is an aqueous (e.g., water) phase.

As used herein, a "nanoemulsion" is an emulsion in which the dispersed droplets, for example, the micelles, have a diameter (particle size) less than 1000 nm or less than about 1000 nm, typically, less than 500 nm or less than about 500 nm, typically less than 300 nm or about 300 nm, for example, less than 250 nm or about 250 nm, for example, less than or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm. Exemplary of nanoemulsions are the provided liquid nanoemulsion concentrates and the liquid dilution compositions, for example, the aqueous liquid dilution compositions containing the diluted concentrates.

As used herein, "surfactant" refers to synthetic and naturally occurring amphiphilic molecules that have hydrophobic portion(s) and hydrophilic portion(s). Due to their amphiphilic (amphipathic) nature, surfactants typically can reduce the surface tension between two immiscible liquids, for example, the oil and water phases in an emulsion, stabilizing the emulsion. Surfactants can be characterized based on their relative hydrophobicity and/or hydrophilicity. For example, relatively lipophilic surfactants are more soluble in fats, oils and waxes, and typically have HLB values less than or about 10, while relatively hydrophilic surfactants are more soluble in aqueous compositions, for example, water, and typically have HLB values greater than or about 10. Relatively amphiphilic surfactants are soluble in oil- and water-based liquids and typically have HLB values close to 10 or about 10.

As used herein, "co-surfactant" is used to refer to a surfactant that is used in the provided compositions in combination with the primary surfactant, for example, the water-soluble vitamin E derivative mixtures (compositions) described herein, for example, to improve the emulsification of the provided compositions and/or compounds, for example, to emulsify the ingredients. In one example, the provided compositions can contain at least one surfactant and at least one co-surfactant. Typically, the co-surfactant represents a lower percent, by weight (w/w), of the provided compositions, compared to the surfactant. Thus, the provided compositions typically have a lower concentration of the co-surfactant(s) than of the surfactant.

As used herein, "HLB" refers to a value that is used to index and describe a surfactant according to its relative hydrophobicity/hydrophilicity, relative to other surfactants. A surfactant's HLB value is an indication of the molecular balance of the hydrophobic and lipophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactant form and the solubility of the surfactant. See, for example, Griffin (1949) J. Soc. Cos. Chem. 1:311. Surfactant HLB values range from 1-45, while the range for non-ionic surfactants typically is from 1-20. The more lipophilic a surfactant is, the lower its HLB value. Conversely, the more hydrophilic a surfactant is, the higher its HLB value.

As used herein, "micelle" refers to aggregates formed by surfactants that typically form when the surfactant is present in an aqueous composition, typically when the surfactant is used at a concentration above the critical micelle concentration (CMC). In micelles, the hydrophilic portions of the surfactant molecules contact the aqueous or the water phase, while the hydrophobic portions form the core of the micelle, which can encapsulate non-polar ingredient(s), for example, the non-polar compounds in the provided concentrates. Typically, the surfactants in the provided concentrates form micelles containing the non-polar ingredient at their center in aqueous liquid dilution compositions. Typically, the micelles in the provided concentrates have a particle size of about 1000 nm, typically, less than or less than about 500 nm, typically less than 300 or about 300 nm, for example, less than 250 nm or about 250 nm, for example, less than 200 nm or less than about 200 nm, for example, less than or less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190 or 200 nm.

As used herein, "analog" refers to a chemical compound that is structurally similar to another compound (referred to as a parent compound), but differs slightly in composition, for example, due to the variation, addition or removal of an atom, one or more units (e.g., methylene units, —($CH_2$)—) or one or more functional groups. The analog can have different chemical or physical properties compared with the original compound and/or can have improved biological and/or chemical activity. Alternatively, the analog can have similar or identical chemical or physical properties compared with the original compound and/or can have similar or identical biological and/or chemical activity. For example, the analog can be more hydrophilic or it can have altered reactivity as compared to the parent compound. The analog can mimic the chemical and/or biological activity of the parent compound (i.e., it can have similar or identical activity), or, in some cases, can have increased or decreased activity. The analog can be a naturally or non-naturally occurring (e.g., synthetic) variant of the original compound. Other types of analogs include isomers (e.g., enantiomers, diastereomers) and other types of chiral variants of a compound, as well as structural isomers. The analog can be a branched or cyclic variant of a linear compound. For example, a linear compound can have an analog that is branched or otherwise substituted to impart certain desirable properties (e.g., improved hydrophobicity or bioavailability). Exemplary of the analogs used in the provided compositions and methods are TPGS analogs, which can be formed using the methods provided herein and can be used in place of TPGS in the provided compositions.

As used herein, "tocopheryl polyethylene glycol succinate analog" or "TPGS analog" refer to compounds, other than TPGS, that are similar to a parent TPGS compound, but differ slightly in composition, for example, by the variation, addition or removal of an atom, one or more units (e.g., methylene units, —$(CH_2)_n$—) or one or more functional groups. TPGS analogs include vitamin E-derived surfactants, e.g., tocopheryls and tocotrienols, including PEG derivatives of vitamin E, including vitamin E PEG monomers and dimers, such as, but not limited to, tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz), and polyoxyethanyl tocotrienyl sebacate (PTrienS) as well as other PEG derivatives of vitamin E. The water-soluble vitamin E derivative compositions provided herein include at least 13%, typically more than 29%, such as 29%-55% dimer form in the composition, with the rest of the composition in the monomer form or small amounts of other forms and trace contaminants.

Exemplary of TPGS analogs are compounds having the formula shown in Formula II:

lar chemical and physical properties as the parent compound. Exemplary of the homologs used in the provided compositions and methods are TPGS homologs.

As used herein, "TPGS homologs" are analogs of TPGS that differ from a TPGS parent compound only by the presence or absence of a simple unit, such as a methylene unit, or some multiple of such units, e.g., —$(CH_2)_n$—. Typically, suitable TPGS homologs have similar surfactant properties compared to the parent compound (TPGS), for example, similar HLB values, for example, HLB values between 12 or about 12 or 13, or 14, and 20 or about 20. Exemplary of TPGS homologs are tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz). Exemplary of TPGS homologs are compounds having the formula in For- Formula II

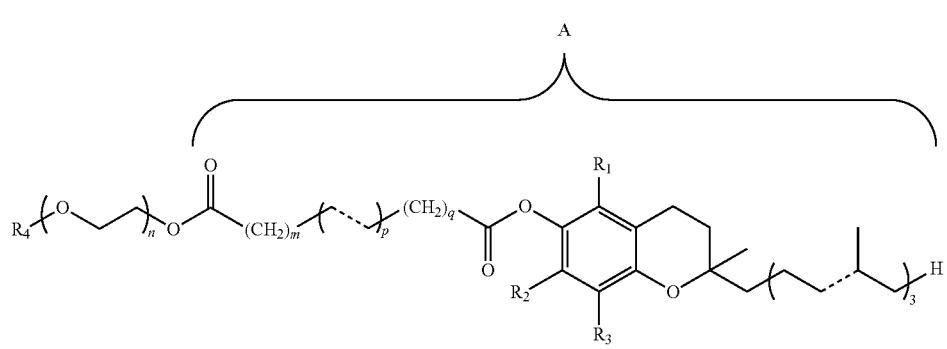

where $R_1$, $R_2$ and $R_3$ each independently is hydrogen (H) or methyl ($CH_3$); $R_4$ is H, $CH_3$ or the portion marked "A"; each dashed line (- - -) is independently a single or double bond; n is an integer from 1 to 5000; m and q each independently are 0 or 1; and p is an integer from 1 to 20.

As used herein, "TPGS 1000 analogs" are compounds other than TPGS 1000 that are similar to a parent TPGS 1000 compound by addition or removal of an atom, one or more units (e.g., methylene units —$(CH_2)_n$—) or one or more functional groups. TPGS 1000 analogs include, but are not limited to, TPGS compounds having one or more PEG moieties that vary in chain length and molecular weight compared to TPGS 1000, including, for example, TPGS compounds having PEG moieties having a molecular weight between or about between 200 Da to 20,000 Da or about 20,000 Da, for example, PEG moieties having a molecular weight of or about 200, 300, 400, 500, 600, 800, 1000, 3000, 5000, 6000, 8000, 10,000, 20,000 Da or more. Also exemplary of TPGS 1000 analogs are TPGS compounds including PEG analogs, e.g., PEG-NHS, PEG-aldehyde, PEG-SH, PEG-$NH_2$, PEG-$CO_2H$, and branched PEGs. Also exemplary of TPGS 1000 analogs are any TPGS analogs, e.g., vitamin E-derived surfactants, including PEG derivatives of vitamin E, including, but not limited to, tocopheryl polyethylene glycol sebacate (PTS), tocopheryl polyethylene glycol dodecanodioate (PTD), tocopheryl polyethylene glycol suberate (PTSr), tocopheryl polyethylene glycol azelaate (PTAz) and polyoxyethanyl tocotrienyl sebacate (PTrienS) as well as other PEG derivatives of vitamin E.

As used herein, "homolog" refers to an analog that differs from the parent compound only by the presence or absence of a simple unit, such as a methylene unit, or some multiple of such units, e.g., —$(CH_2)_n$—. Typically, a homolog has simimula I (above), where neither of the dashed lines represent a double bond and where, when m and q both are 0, and p is greater than 1.

As used herein, "TPGS 1000 homologs" are analogs of TPGS 1000 that differ from a TPGS 1000 parent compound only by the presence or absence of a simple unit, such as a methylene unit, or some multiple of such units, e.g., —$(CH_2)_n$—. Suitable TPGS 1000 homologs have similar surfactant properties compared to the parent compound (TPGS 1000), for example, similar HLB values, for example, HLB values between 12 or about 12 and 20 or about 20, such as 13-18. TPGS 1000 homologs include TPGS 1000 homologs with slight variations in the length of the PEG chain moiety.

As used herein, "TPGS monomer" refers to a single TPGS molecule covalently joined to a water-soluble moiety, such as a polyethylene glycol, through a linker. "TPGS monomer" can also refer to TPGS analogs, homologs or derivatives, including any other water-soluble vitamin E derivatives described herein.

As used herein, "TPGS dimer" refers to two TPGS molecules covalently joined to a water-soluble moiety, such as a polyethylene glycol, through one or more linkers. "TPGS dimer" can also refer to TPGS analogs, homologs or derivatives, including any other water-soluble vitamin E derivatives described herein.

As used herein, "organoleptic properties" refers to sensory attributes of a food or beverage, in particular the beverage compositions provided herein. Those of skill in the art understand such properties and they can be quantitated if needed. Organoleptic properties include, but are not limited to, taste, odor and/or appearance. "Desirable" organoleptic properties include those organoleptic properties that make a food or beverage composition desirable for consumption by an average human subject, such as a desirable odor, taste and/or appearance, or the lack of an undesirable odor, taste and/or appearance. Undesirable organoleptic properties include the presence of, for example, an undesirable taste, odor or appearance attribute, such as the presence of an "off-taste" or "off-odor," for example a fishy, grassy, metal or iron, sharp or tingling taste or odor, or the presence of an undesirable appearance attribute, such as separation or precipitation. In one example, the provided beverage compositions retain the same or about the same taste, odor and/or appearance as the same beverage composition that does not contain the provided concentrates, that is, the provided beverage compositions retain organoleptic properties desirable for consumption by an average human subject. Desirable and undesirable organoleptic properties can be measured by a variety of methods known to those skilled in the art, including, for example, organoleptic evaluation methods by which undesirable properties are detectable by sight, taste and/or smell and chemical tests, as well as by chemical analytical methods. For example, the provided beverage compositions retain the same or about the same organoleptic properties as the same beverage composition that does not contain the provided concentrates over a period of time, for example, at least or over 1, 2, 3, 4, 5, 6, or more days, at least or over 1, 2, 3, 4, or more weeks, at least or over 1, 2, 3, 4, 5, 6, 7, 8, 9, 10, 11, 12, or more months, or at least or over 1, 2, 3, 4, or more years.

In one example, the provided beverage compositions retain the same or about the same taste as the same beverage composition that does not contain the provided concentrates. In one example, the provided beverage compositions retain the same or about the same odor as the same beverage composition that does not contain the provided concentrates. In one example, the provided beverage compositions retain the same or about the same appearance as the same beverage composition that does not contain the provided concentrates. In one example, the beverage compositions retain the same organoleptic properties at room temperature, for example, at 25° C. or at about 25° C. In another example, the compositions retain the same organoleptic properties at between 19° C. or about 19° C. and 25° C. or about 25° C. In another example, the beverage compositions retain the same organoleptic properties at elevated temperatures, for example, at 40° C. or at about 40° C. In another example, the compositions retain the same organoleptic properties at refrigerated temperatures, for example, at 4° C. or at about 4° C., or at frozen temperatures, for example, at −20° C. or at about −20° C. Typically, retaining the same or about the same organoleptic properties means that the shelf life of beverage compositions that contain the provided concentrates is the same or about the same or longer than the beverage compositions not containing the provided concentrates. Any or all of the above organoleptic properties, particularly the desirable organoleptic properties, are retained for the shelf life of the beverage composition that does not contain the provided concentrates under conditions in which the beverage composition is normally stored. Generally, beverage compositions remain free from organoleptic changes for at least 6 months, unless the beverage composition that does not contain the provided concentrates has a shorter shelf life. The beverage composition retains its desired organoleptic properties for this period of time.

As used herein, "retaining the organoleptic properties" refers to retention of these properties upon storage for a recited period of time, typically at room temperature.

As used herein, "shelf life" refers to a time period within which the provided compositions retain desirable organoleptic properties, for example, the ability of the provided compositions to retain desirable organoleptic properties for a period of time, for example, for at least or more than 1, 2, 3, 4, or more weeks, typically at least or more than 1, 2, 3, 4, 5, 6, 7, 8, 9, 10, 11, 12 or more months, or at least or more than 1, 2, 3, 4 or more years. In one example, the compositions retain desirable organoleptic properties if they exhibit one or more of these described characteristics, over time, when kept at a particular temperature. In one example, the compositions retain desirable organoleptic properties at room temperature, for example, 25° C. or about 25° C. In another example, the compositions retain desirable organoleptic properties at between 19° C. and 25° C. In another example, the compositions retain desirable organoleptic properties at refrigerated temperatures, for example, 4° C. or about 4° C., or at frozen temperatures, for example, at −20° C. or about −20° C. In another example, the compositions retain desirable organoleptic properties at elevated temperatures, for example, at 40° C. or at about 40° C.

As used herein, "particle size" and "average particle size" refer synonymously to the average diameter of particles in a provided liquid, for example, the droplet diameter or micelle diameter in an emulsion. Particle size diameter can be expressed in terms of a unit of length, for example, nanometers (nm). Alternatively, information about particles in concentrates and liquid dilution compositions can be expressed in terms of particle density, for example, ppm (parts per million), or percent solids, in the compositions.

As used herein, "visible particles" are particles, for example, in a liquid, such as an emulsion, that are visible when viewing the liquid with the naked eye (i.e., without magnification). For example, the visible particles can be particles that are observed by the artisan formulating the compositions, for example, the concentrates or the aqueous liquid dilution compositions containing the diluted concentrates. In one example, the provided compositions contain no visible particles. In another example, the compositions contain few visible particles, for example, no more visible particles than another liquid, for example, a beverage. The presence of visible particles and the number of visible particles is determined by empirical observation.

As used herein, "turbidity" is a measure of the cloudiness or haziness of a liquid, caused by particles in suspension in the liquid. Turbidity can be measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light passes through a sample with low turbidity with little disturbance. Other methods for measuring turbidity are well known and can be used with the provided methods and compositions. The units of a turbidity value measured with a nephelometer are Nephelometric Turbidity Units (NTU). For purposes herein, the compositions provided herein typically have low turbidity, for example, a turbidity value (NTU) of less than or about 80. For example, the compositions provided herein can have a turbidity value (NTU) of less than or about 30.

As used herein, a "turbid liquid" is one that is thick or opaque with visible particles in suspension, for example, a liquid that is cloudy or muddy in appearance.

As used herein, "clear" can be used to describe the compositions provided herein, for example, the aqueous liquid dilution compositions containing the diluted nanoemulsion concentrates and/or the nanoemulsion concentrates themselves. In one example, a clear liquid is one that does not appear cloudy by empirical observation, such as to the naked eye, and/or does not contain particles or crystals that are visible to the naked eye, or that does not exhibit "ringing." In another example, a clear liquid is one that has a low or relatively low turbidity value, for example an NTU value, that is less than or equal to a desired NTU value. For example, a liquid is described as clear that has an NTU value of less than or about 80. For example, a liquid can be clear and have an NTU value of less than or about 30. In another example, a clear liquid is one that has a small or relatively small average particle size, for example, less than or about 1000 nm. For example, a liquid can be described as clear and have an average particle size of less than or about 200 nm. In another example, clarity is expressed relatively. For example, it can be desired that a particular composition is equally as clear, about as clear, or more clear than another liquid (as measured empirically, or by measuring turbidity value or particle size). For example, clarity can be assessed relative to another aqueous liquid dilution composition, for example, a beverage. In one example, a liquid is clear if it is similar in appearance to another clear liquid, for example, a beverage, for example, water. In another example, it can be desired that a composition has a particle size that is less than or equal to another liquid, for example, a beverage. In another example, it can be desired that a composition has a turbidity value that is less than or equal to another liquid, for example, a beverage. In another example, it can be desired that a composition appears more clear or as clear as another liquid, for example, a beverage, for example, by having no more visible particles, no more crystal formation and/or no more cloudiness than the other liquid. In one example, the provided compositions are clear. In another example, they are relatively clear or as clear as or about as clear as another liquid, for example, a beverage that does not contain the non-polar compound or liquid nanoemulsion composition.

As used herein, "ringing" refers to the formation of a whitish or opaque ring around a container containing a liquid, for example, an aqueous liquid, for example a beverage, for example, a liquid dilution composition containing an emulsion or nanoemulsion. Typically, the ring forms around the perimeter of the container, typically at the surface level of the liquid in the container, for example, at the neck of the container. Ringing can occur over time and, if it occurs over a short period of time, can be a sign of instability. Ringing typically is undesirable, particularly in the case of a liquid for human consumption, for example, a beverage. Typically, the provided concentrates and liquid dilution compositions do not exhibit ringing or are stable, without ringing, for a period of time, for example, days, weeks, months or years.

As used herein, "stability" refers to a desirable property of the provided concentrates and liquid dilution compositions, for example, the ability of the provided concentrates and liquid dilution compositions to remain free from one or more changes over a period of time, for example, at least or longer than 1 day, 1 week, 1 month, 1 year, or more. For example, a concentrate or liquid dilution composition can be described as stable if it is formulated such that it remains free from oxidation or substantial oxidation over time, remains clear over time, remains safe and/or desirable for human consumption over time, has a lack of precipitates forming over time, has a lack of ringing over time, and/or does not exhibit any visible phase separation over a period of time. For example, the concentrates and liquid dilution compositions can be described as stable if they exhibit one or more of these described characteristics, over time, when kept at a particular temperature, for example, room temperature, e.g., at or about 25° C., slightly below room temperature, e.g., between or between about 19° C. and 25° C., at refrigerated temperatures, e.g., at or about 4° C., or at frozen temperatures, e.g., at or about −20° C. or lower.

As used herein, "phase separation" refers to the physical separation of a homogenous emulsion, for example, the separation of the oil and water phases of an emulsion, into two separate visible heterogeneous layers.

As used herein, "stabilize" means to increase the stability of one of the provided compositions.

As used herein, "room temperature" and "ambient temperature" are used to describe a temperature that is common in one or more enclosed spaces in which human beings typically are or reside. Room temperature can vary, but generally refers to temperatures between or between about 19° C. and 25° C. When a composition is stored at room temperature, it should be understood it is generally kept at a temperature within this range or about within this range.

As used herein, "refrigerated temperature" refers to a temperature that is common in a refrigerator, for example, a household or restaurant refrigerator, for example, a temperature that is cooler than room temperature, but typically a few degrees above the freezing point of water. Typically, refrigerated temperatures are between or between about 0° C. and 10° C., for example, at or about 4° C. When a composition is stored at a refrigerated temperature, it should be understood that it is kept at a temperature common to household or industrial refrigerators.

As used herein, "frozen temperature" refers to a temperature around or below the freezing point of water, e.g., a temperature commonly used in a household freezer, for example, 0° F. or about 0° F., or −19° C. or about −19° C. or −20° C. or about −20° C., or colder.

As used herein, "hydrophilic" and "polar" refer synonymously to ingredients and/or compounds having greater solubility in aqueous liquids, for example, water, than in fats, oils and/or organic solvents (e.g., methanol ethanol, ethyl ether, acetone and benzene).

As used herein, a "solvent" is an ingredient that can be used to dissolve another ingredient. Solvents include polar and non-polar solvents. Non-polar solvents include oils and other non-polar ingredients that dissolve non-polar compounds. Typically, the non-polar solvent is an oil that is included in the concentrate or liquid dilution compositions provided herein in addition to the non-polar compound. The non-polar solvent typically is not the non-polar compound itself, i.e., is distinct from the non-polar compound. More than one non-polar solvent can be used. Certain compounds, for example, flaxseed oil and safflower oil, can be non-polar solvents and non-polar active ingredients. Typically, the non-polar solvent contains one or more oils, typically oils other than the non-polar active ingredient or oil(s) not contained in the active ingredient. Exemplary non-polar solvents include, but are not limited to, oils (in addition to the non-polar active ingredient), for example, vitamin E oil, flaxseed oil, CLA, borage oil, rice bran oil, D-limonene, canola oil, corn oil, MCT oil and oat oil. Other oils also can be used.

As used herein, "polar solvent" refers to a solvent that is readily miscible with water and other polar solvents. Polar solvents are well-known and can be assessed by measuring any parameter known to those of skill in the art, including dielectric constant, polarity index and dipole moment (see, e.g., Przybitek (1980) "High Purity Solvent Guide," Burdick and Jackson Laboratories, Inc.). For example, polar solvents generally have high dielectric constants, such as greater than or about 15, generally have high polarity indices, typically greater than or about 3, and generally large dipole moments, for example, greater than or about 1.4 Debye. Polar solvents include polar protic solvents and polar aprotic solvents.

As used herein, a "polar protic solvent" is a polar solvent containing a hydrogen atom attached to an electronegative atom, such that the hydrogen has a proton-like character and/or the bond between the hydrogen and electronegative atom is polarized. Exemplary polar protic solvents include, but are not limited to, water, alcohols, including monohydric, dihydric and trihydric alcohols, including, but not limited to, methanol, ethanol, glycerin and propylene glycol.

As used herein, "monohydric alcohols" are alcohols that contain a single hydroxyl group including, but not limited to, methanol, ethanol, propanol, isopropanol, n-butanol and t-butanol.

As used herein, "dihydric alcohols" are alcohols that contain two hydroxyl groups. Exemplary dihydric alcohols include, but are not limited to, glycols, e.g., propylene glycol, ethylene glycol, tetraethylene glycol, triethylene glycol and trimethylene glycol.

As used herein, "trihydric alcohols" are alcohols that contain three hydroxyl groups. Exemplary trihydric alcohols include, but are not limited to, glycerin, butane-1,2,3-triol, pentane-1,3,5-triol and 2-amino-2-hydroxymethyl-propane-1,3-diol.

As used herein, "non-polar," "lipophilic" and "lipid-soluble" synonymously refer to compounds and/or ingredients, for example, non-polar compounds and non-polar active ingredients, which have greater solubility in organic solvents (e.g., ethanol, methanol, ethyl ether, acetone and benzene), fats and oils than in aqueous liquids, for example, water. Non-polar compounds include drugs, hormones, vitamins, nutrients and other lipophilic compounds. Typically, non-polar compounds are poorly water-soluble, for example, water insoluble or compounds having low water solubility. Exemplary non-polar compounds include compounds that contain one or more non-polar active ingredients, for example, lipid-soluble drugs, hormones, essential fatty acids, for example, polyunsaturated fatty acids (PUFA), for example, omega-3 and omega-6 fatty acids, vitamins, nutrients, nutraceuticals, minerals and other compounds. Additional exemplary non-polar compounds are described herein. The provided compositions can be formulated with any non-polar compound, for example, any non-polar compound that is or contains a non-polar active ingredient.

As used herein, "non-polar compound" refers to a compound that is a non-polar active ingredient or contains one or more non-polar active ingredients. In some examples, the non-polar compound contains non-polar active ingredients. For example, the non-polar compound algae oil contains polyunsaturated fatty acid non-polar active ingredients, for example, the omega-3 polyunsaturated fatty acid DHA. In other examples, the non-polar compound is the non-polar active ingredient. For example, the non-polar compound coenzyme Q10 is the non-polar active ingredient coenzyme Q10.

As used herein, "non-polar active ingredient" refers to an ingredient that, when administered to a subject, for example, a human, induces or is proposed to induce a desired response, such as altering body function at the cellular, tissue, organ or other level, and/or altering the cosmetic appearance or other property, or an ingredient that is ingested in order to achieve a desired effect. Non-polar active ingredients can be any synthetic or natural non-polar ingredient or compound, including a pharmaceutical, drug, therapeutic, nutritional supplement, herb, hormone or other ingredient. Non-polar active ingredients can include the non-polar active ingredients listed herein, as well as other pharmaceutically acceptable or food-grade active derivatives of the active ingredients, for example, salts, esters, amides, prodrugs, active metabolites, isomers, fragments and analogs. Active ingredients can include compounds proven to have a desired effect and also compounds thought to produce such effects, for example, compounds typically ingested for nutritional supplementation purposes. The non-polar active ingredient can be contained in a non-polar compound or the non-polar active ingredient can be the non-polar compound.

As used herein, a "subject" includes an animal, typically a mammal, typically a human.

As used herein, an "additive" includes anything that one can add to a food, beverage, or other human consumable to enhance one or more of its nutritional, pharmaceutical, dietary, health, nutraceutical, health benefit, energy-providing, treating, holistic, or other properties. For example, the additives can be oil-based additives (e.g., non-polar compounds), such as nutraceuticals; pharmaceuticals; vitamins, for example, oil-soluble vitamins, e.g., vitamin D, vitamin E and vitamin A; minerals; fatty acids, such as essential fatty acids, for example, polyunsaturated fatty acids, e.g., omega-3 fatty acids and omega-6 fatty acids, such as alpha-linolenic acid (ALA), docosahexaenoic acid (DHA), eicosapentaenoic acid (EPA), gamma-linolenic acid GLA, CLA, saw palmetto extract, flaxseed oil, fish oil and algae oil; phytosterols; coenzymes, such as coenzyme Q10; and any other oil-based additives.

As used herein, "water insoluble" refers to a compound that does not dissolve when the compound is mixed with water, for example, when mixed with water at room temperature, for example, between or between about 25° C. and 50° C.

As used herein, "low water solubility" refers to a compound that has a solubility in water of less than or about 30 mg/mL, for example, when mixed with water at room temperature, such as between or between about 25 and 50° C. As used herein, "poorly water-soluble" can be used to refer to compounds, for example, non-polar compounds, that are water insoluble or have low water solubility.

As used herein, "pre-emulsion concentrate" is used to refer to the provided compositions that contain the water-soluble vitamin E derivative mixtures (compositions) described herein, i.e., water-soluble vitamin E derivative mixtures (compositions) that contain a mixture of monomers and dimers of the water-soluble vitamin E derivatives, and contain a substantial amount (compared to prior art preparations), i.e., 13% to 95%, inclusive, such as least 13%, 20%, 25%, 29%, up to as much as 75%, 80%, 85%, 90%, 95%, by weight, of the dimer form and generally less than 70%, 65%, 63%, 62%, 61% or 60% or less of the monomer form; and one or more non-polar compounds that contain non-polar active ingredients and can be diluted in aqueous media, for example, in water, to form the provided aqueous liquid dilution compositions. The pre-emulsion concentrates can additionally include other ingredients, such as preservatives or non-polar solvents. The pre-emulsion concentrates typically do not contain any polar solvent, such as water. Typically, the pre-emulsion concentrates are semi-solid compositions, which typically have a waxy consistency, for example, the consistency of a substance such as wax, for example, a lip balm, at room temperature, for example, at 25° C. or about 25° C., and become liquid at higher temperatures, for example when heated to higher temperatures, such as to 125° F. or about 125° F., or to 50° C. or about 50° C. or to 60° C. or about 60° C.

As used herein, "waxy" is used to describe compositions and materials, typically oil-soluble compositions or materials, that are similar in consistency to one or more waxes. Pre-emulsion concentrates, particularly those with higher concentrations (greater than 25% or 30%) of the water-soluble vitamin E derivative composition described herein have a waxy consistency at room temperature. Compositions and compounds having waxy consistencies typically have melting points or melting ranges above ambient temperature (e.g., above room temperature, for example, above 25° C. or about 25° C.), meaning they are either solid or semi-solid (i.e., not liquid) at room temperature. Typically, waxy compositions are of relatively low viscosity a little above their liquefying point. Exemplary of waxes that have waxy consistencies, are natural waxes, including waxes of vegetal origin, such as purcellin, shea butter, cocoa butter, Japan wax, esparto grass wax, cork wax, Guaruma wax, rice shoot wax, Ouricury wax, montan wax, sunflower wax, sugar cane wax, carnauba wax, candelilla wax, lanolin, fruit-derived waxes, such as orange wax, lemon wax, grapefruit wax and bayberry wax, and the like; waxes of animal origin, such as beeswax, woolwax, spermateci and bear fat, shellac wax, and the like; mineral waxes such as ceresine and ozokerite waxes; and synthetic waxes, including petroleum-based waxes such as paraffin, petrolatum, micro wax, polyalkylene and polyethyleneglycol waxes, e.g. polyethylene wax; waxes based on chlorinated naphthalenes such as 'Halowax', synthetic hydrocarbon waxes, and the like.

As used herein, "liquid concentrate" and "liquid nanoemulsion concentrate" are used synonymously to refer to the provided compositions that contain the water-soluble vitamin E derivative mixtures (compositions) described herein, i.e., water-soluble vitamin E derivative mixtures (compositions) that contain a mixture of monomers and dimers of the water-soluble vitamin E derivatives, and contain a substantial amount (compared to prior art preparations), i.e., 13% to 95%, inclusive, such as least 13%, 20%, 25%, 29%, up to as much as 75%, 80%, 85%, 90%, 95%, by weight, of the dimer form and generally less than 70%, 65%, 63%, 62%, 61% or 60% or less of the monomer form; one or more non-polar compounds that contain one or more non-polar active ingredients; a polar solvent; and optionally, additional ingredients. The liquid concentrates are liquid at room temperature, for example, at a temperature of at or about 25° C. or between or between about 25° C. and 50° C., and can be diluted in aqueous media, for example, in water, to form the provided aqueous liquid dilution compositions. Typically, the liquid concentrate is an emulsion that has a particle (droplet) size (or can be diluted to form an aqueous liquid dilution composition having a particle size) that is less than or about 1000 nm. For example, the particle size can be less than or about 200 nm.

As used herein, "aqueous liquid dilution composition," "liquid dilution composition," "dilution composition" and "liquid dilution" are used synonymously to refer to a composition that contains one or more of the provided concentrates (i.e., the pre-emulsion concentrates or liquid nanoemulsion concentrates provided herein) diluted in a liquid, for example, an aqueous medium, e.g., water. For example, the concentrate forms the dispersion phase within the aqueous liquid, which is an emulsion (e.g., nanoemulsion). The liquid dilution compositions are typically beverages suitable for human consumption. Exemplary of liquid dilution compositions are aqueous compositions that contain the concentrates provided herein, for example, waters, sauces, soups, syrups, soda, juice, e.g., fruit juice, milk, coffee, tea, nutritional beverages, sports drinks, energy drinks, vitamin-fortified beverages, flavored waters and any other beverage containing the diluted concentrates. It is not necessary that the aqueous liquid dilution compositions be completely aqueous. For example, the aqueous liquid dilution compositions can be primarily aqueous and can contain an aqueous portion, for example, an aqueous continuous phase, as well as an additional portion, for example, a dispersion phase, such as a lipophilic dispersion phase. Typically, the lipophilic dispersion phase contains one or more lipophilic substances, for example, the water-soluble vitamin E derivative mixtures (compositions) described herein and one or more non-polar compounds, for example, non-polar compounds that contain non-polar active ingredients.

As used herein, a "beverage composition" or "beverage product" refers to a composition, typically an aqueous ingestible composition, that contains one or more of the provided concentrates, one or more stabilizers and a beverage base that contains a polar solvent, such as water, a juice, a juice concentrate, a fruit juice extract or a fruit flavor. Typically, beverage compositions provided herein are provided for direct ingestion, that is they are directly consumed by a subject, e.g., a human. Beverage compositions can be formed by dissolving the pre-emulsion concentrates and liquid nanoemulsion concentrates provided herein in an aqueous liquid, e.g., water, to form an aqueous liquid dilution composition.

As used herein, "food and beverage product" refers to a product that is suitable for human consumption. For example, "food and beverage product" can refer to a pre-emulsion concentrate or liquid nanoemulsion concentrate that is dissolved in a solvent, typically an aqueous solvent, e.g., water, to form a liquid dilution composition, i.e., beverage composition or beverage product. "Food and beverage product" can also refer to the final product that is suitable for human consumption, such as the liquid dilution composition, i.e., beverage composition or beverage product.

As used herein, a "beverage base" refers to an aqueous composition to which one or more non-polar compounds can be added. A beverage base includes, but is not limited to, an aqueous composition that contains one or more of a polar solvent, typically water, a juice, such as a fruit juice, a fruit juice concentrate, a fruit juice extract, a fruit flavor, a soda, a flavored soda, a carbonated water, a carbonated juice and any combination thereof.

As used herein, a "fruit juice," "fruit juice concentrate," "fruit juice extract" or "fruit flavor" refer to fruit-based juices and flavors that impart taste or smell to the provided beverage compositions (products). Any juice or fruit flavor can be added to the provided beverage compositions, including, but not limited to, plum, prune, date, currant, fig, grape, raisin, cranberry, pineapple, peach, nectarine, banana, apple, pear, guava, apricot, Saskatoon berry, blueberry, plains berry, prairie berry, mulberry, elderberry, Barbados cherry (acerola cherry), choke cherry, chocolate, vanilla, caramel, coconut, olive, raspberry, strawberry, huckleberry, loganberry, dewberry, boysenberry, kiwi, cherry, blackberry, honey dew, green tea, cucumber, quince, buckthorn, passion fruit, sloe, rowan, gooseberry, pomegranate, persimmon, mango, rhubarb, papaya, litchi, lemon, orange, lime, tangerine, mandarin and grapefruit juices, or any combination thereof. Exemplary beverage compositions provided herein include combinations of juices or flavors that impart peach mango, peach, citrus, pomegranate blueberry, tropical berry, cherry chocolate, vanilla, cherry vanilla, chocolate blueberry, chocolate caramel, cucumber, green tea, honey-dew melon, pineapple papaya, peach nectarine, raspberry lemonade, grape, orange tangerine, orange, lime and mixed berry flavors.

As used herein, "oil phase" refers to the portion (or phase) of a composition, such as the concentrates and liquid dilution compositions provided herein, that contains one or more lipophilic ingredients and/or amphiphilic ingredients (oil phase ingredients) and is, in general, the lipid-soluble phase. In the provided emulsion compositions (e.g., the nanoemulsion concentrates and the dilution compositions), the oil phase typically represents the dispersion phase. "Oil phase" also can be used to refer to the liquid containing the oil phase ingredients that is generated, typically in an oil phase vessel, while carrying out the methods for making the liquid nanoemulsion concentrates. For example, "oil phase" can refer to the mixture of the components (oil phase ingredients) that are combined, mixed and heated, for example, in the oil phase vessel (e.g., tank), prior to mixing with the water phase. "Oil phase" can refer to the oil phase mixture that is formed after all the ingredients are dissolved; alternatively, it can refer to the forming mixture, for example, as it is being mixed/heated.

As used herein, "oil phase ingredient(s)" refers to the components of the provided concentrates and liquid dilution compositions that are included in the oil phase in the provided methods for making the concentrates and liquid dilution compositions. Typical oil phase ingredients include the water-soluble vitamin E derivative mixtures (compositions); non-polar compounds, e.g., non-polar active ingredients; co-surfactants; oils, such as non-polar solvents; preservatives; and emulsion stabilizers. Other lipophilic and/or amphiphilic ingredients can be included in the oil phase.

As used herein, "water phase" is used to refer to the portion (or phase) of a composition, such as the concentrates and liquid dilution compositions provided herein, that contains one or more hydrophilic ingredients and/or amphiphilic ingredients (water phase ingredients) and is, in general, the water-soluble phase. Typically, in the provided emulsion compositions, for example, the nanoemulsion concentrates and the dilution compositions, the water phase is the continuous phase. "Water phase" also is used to refer to the liquid containing the water phase ingredients that is generated while carrying out the methods for making the liquid nanoemulsion concentrates. For example, "water phase" can refer to the mixture of the components (water phase ingredients) that are combined, mixed and heated, for example, in the water phase tank, prior to mixing with the oil phase. "Water phase" can refer to the water phase mixture that is formed after all the ingredients are dissolved; alternatively, "water phase" can refer to the forming mixture, for example, as it is being mixed/heated.

As used herein, "water phase ingredient(s)" refers to the components of the provided concentrates and liquid dilution compositions that are included in the water phase (e.g., added to the water phase vessel) in the provided methods for making the concentrates and liquid dilution compositions. Typical water phase ingredients include, but are not limited to, polar solvents, typically polar protic solvents, such as water and alcohols, typically alcohols having more than one hydroxy group such as dihydroxy and trihydroxy alcohols, e.g., glycerol and propylene glycol; co-surfactants; preservatives; and emulsion stabilizers. Other hydrophilic and/or amphiphilic ingredients can be included in the water phase.

As used herein, an "initial concentrate" is a concentrate (e.g., pre-emulsion concentrate and/or liquid nanoemulsion concentrate) that is made in the provided methods of formulating the provided concentrates, typically by selecting ingredients, for example, the water-soluble vitamin E derivatives provided herein, non-polar compound(s), polar solvent, and, optionally, other ingredients, and selecting starting concentrations of the ingredients from an appropriate concentration range as described herein.

As used herein, "fatty acid" refers to straight-chain hydrocarbon molecules with a carboxyl (—COOH) group at one end of the chain.

As used herein, "polyunsaturated fatty acid" and "PUFA" are used synonymously to refer to fatty acids that contain more than one carbon-carbon double bonds in the carbon chain of the fatty acid. PUFAs, particularly essential fatty acids, are useful as dietary supplements.

As used herein, "essential fatty acids" are PUFAs that mammals, including humans, cannot synthesize using any known chemical pathway. Thus, essential fatty acids must be obtained from diet or by supplementation. Exemplary of essential PUFA fatty acids are omega-3 (ω3; n-3) fatty acids and the omega-6 (ω-6; n-6) fatty acids.

As used herein, "omega-3 (ω3; n-3) fatty acids" and "omega-3 fatty acids" are used synonymously to describe methylene-interrupted polyenes, which have two or more cis double bonds, separated by a single methylene group, in which the first double bond appears at the third carbon from the last (ω) carbon. Omega-3 fatty acids are used as dietary supplements, for example, for disease treatment and prevention. The provided concentrates and liquid dilution compositions can contain non-polar active ingredients that include at least one omega-3 fatty acid. Exemplary of omega-3 fatty acids are alpha-linolenic acid (α-linolenic acid; ALA) (18:3ω3) (a short-chain fatty acid); stearidonic acid (18:4ω3) (a short-chain fatty acid); eicosapentaenoic acid (EPA) (20:5ω3); docosahexaenoic acid (DHA) (22:6ω3); eicosatetraenoic acid (24:4ω3); docosapentaenoic acid (DPA, clupanodonic acid) (22:5ω3); 16:3ω3; 24:5ω3 and nisinic acid (24:6ω3). Longer chain omega-3 fatty acids can be synthesized from ALA (the short-chain omega-3 fatty acid). Exemplary of non-polar active ingredients containing omega-3 fatty acids are non-polar active ingredients containing DHA and/or EPA, for example, containing fish oil, krill oil and/or algae oil, for example, microalgae oil, non-polar active ingredients containing alpha-linolenic acid (ALA), for example, containing flaxseed oil.

As used herein, "omega-6 (ω-6; n-6) fatty acids" and "omega-6 fatty acids" are used synonymously to describe methylene-interrupted polyenes which have two or more cis double bonds, separated by a single methylene group, in which the first double bond appears at the sixth carbon from the last (ω) carbon. The provided concentrates and liquid dilution compositions can contain non-polar active ingredients that include at least one omega-3 fatty acid. Exemplary of omega-6 fatty acids are linoleic acid (18:2ω6) (a short-chain fatty acid); gamma-linolenic acid (GLA) (18:3ω6); dihomo gamma linolenic acid (DGLA) (20:3ω6); eicosadienoic acid (20:2ω6); arachidonic acid (AA) (20:4ω6); docosadienoic acid (22:2ω6); adrenic acid (22:4ω6); and docosapentaenoic acid (22:5ω6). Exemplary of non-polar active ingredients containing omega-6 fatty acids are ingredients containing GLA, for example, borage oil. Also exemplary of PUFA-containing non-polar active ingredients are compounds containing conjugated fatty acids, for example, conjugated linoleic acid (CLA) and compounds containing saw palmetto extract.

As used herein, "algae oil" refers to any oil derived from marine dinoflagellates in, for example, microalgae, for example, *Crypthecodinium* sp, particularly, *Crypthecodinium cohnii*. Algae oil can be used as a non-polar compound, for example, as an active ingredient, in the provided concentrates and liquid dilution compositions. The algae oil typically contains DHA. The algae oil can be a source of EPA.

As used herein, "fish oil" refers to any oil derived from any fish, typically a cold water fish, for example, from fish tissue, such as from frozen fish tissue, for example, from cod liver. Fish oil can be used as a non-polar compound, for example, an active ingredient, in the provided concentrates and liquid dilution compositions. The fish oil typically contains DHA. The fish oil can also contain EPA.

As used herein, "preservative" and "preservativer" are used synonymously to refer to ingredients that can improve the stability of the provided concentrates and liquid dilution compositions. Preservatives, particularly food and beverage preservatives, are well known. Any known preservative can be used in the provided concentrates and liquid dilution compositions. Exemplary of the preservatives that can be used in the provided concentrates and liquid dilution compositions are oil-soluble preservatives, such as benzyl alcohol, benzyl benzoate, methyl paraben, propyl paraben, antioxidants, for example, vitamin E, vitamin A palmitate and beta carotene. Typically, a preservative is selected that is safe for human consumption, for example, in foods and beverages, for example, a GRAS certified and/or Kosher-certified preservative, for example, benzyl alcohol.

As used herein, an "antioxidant" refers to a stabilizer or one component of a stabilizing system that acts as an antioxidant, and that, when added to a beverage composition in combination with the other required components (i.e., acid and/or bicarbonate or carbonate) yields beverage compositions that retain one or more desired organoleptic properties, such as, but not limited to, the taste, smell, odor and/or appearance, of the beverage composition over time. Typically, antioxidants are food-approved, e.g., edible antioxidants, for example, antioxidants that are safe and/or approved for human consumption. Exemplary antioxidants include, but are not limited to, ascorbic acid, vitamin C, ascorbate and coenzyme Q-containing compounds, including, but not limited to, coenzyme Q10.

As used herein, an "acid" or "ingestible acid" refers to a stabilizer or one component of a stabilizing system that, when added to a beverage composition in combination with the other components (i.e., antioxidant and/or bicarbonate or carbonate), yields beverage compositions that retain one or more desired organoleptic properties, such as, but not limited to, the taste, smell, odor and/or appearance, of the beverage composition over time. Typically, the acids are food-approved, e.g., edible acids or ingestible acids, for example, acids that are safe and/or approved for human consumption. Exemplary acids include, but are not limited to, citric acid, phosphoric acid, adipic acid, ascorbic acid, lactic acid, malic acid, fumaric acid, gluconic acid, succinic acid, tartaric acid and maleic acid.

As used herein, a "bicarbonate" or "carbonate" refers to a stabilizer or one component of a stabilizing system that, when added to a beverage composition in combination with the other components (i.e., the acid and/or antioxidant) yields beverage compositions that retain one or more desired organoleptic properties, such as, but not limited to, the taste, smell, odor and/or appearance, of the beverage composition over time. Typically, bicarbonates or carbonates are food-approved, e.g., edible bicarbonates or carbonates, for example, bicarbonates or carbonates that are safe and/or approved for human consumption. Exemplary bicarbonates include, but are not limited to, potassium bicarbonate and sodium bicarbonate. Exemplary carbonates include, but are not limited to, potassium carbonate, sodium carbonate, calcium carbonate, magnesium carbonate and zinc carbonate.

As used herein, "carbonation" or "carbonated" refers to carbon dioxide dissolved in liquid, such as a beverage base, including water. A liquid, or beverage, can be carbonated by direct addition of carbon dioxide to the liquid or beverage.

As used herein, "emulsion stabilizer" refers to compounds that can be used to stabilize and/or emulsify and/or change the viscosity of the provided concentrates and aqueous compositions containing the diluted concentrates. For example, the emulsion stabilizer can increase the viscosity of the liquid concentrate. One or more emulsion stabilizers can be added, for example, during formulation after evaluation of an initial concentrate, particularly if the oil and water phases of the initial concentrate (or the aqueous liquid dilution composition resulting from dilution of the initial concentrate) appear to be separating. Addition of the emulsion stabilizer can prevent separation of the oil and water phases.

As used herein, a "pH adjuster" is any compound, typically an acid or a base, that is capable of changing the pH of the provided concentrates and liquid dilution compositions, for example, to reduce the pH of the concentrates or liquid dilution composition or to increase the pH of the concentrates or liquid dilution composition, typically without altering other properties of the concentrates and liquid dilution composition, or without substantially altering other properties. pH adjusters are well known. Exemplary of the pH adjusters are acids, for example, citric acid and phosphoric acid, and bases.

As used herein, "flavor" is any ingredient that changes, typically improves, the taste and/or smell of the provided concentrates and liquid dilution compositions, for example, the beverages.

As used herein, "natural" is used to refer to a composition, concentrate or liquid dilution composition, and/or ingredients in the composition, concentrate or liquid dilution composition, that can be found in nature and is not solely man-made. For example, benzyl alcohol is a natural preservative. Similarly, tocopheryl polyethylene glycol is a natural surfactant. The natural composition/ingredient can be GRAS and/or Kosher-certified. Typically, the provided compositions, concentrates and liquid dilution compositions are natural, semi-natural and/or contain one or more natural ingredients.

As used herein, "G.R.A.S." and "GRAS" are used synonymously to refer to compounds, compositions and ingredients that are "Generally Regarded as Safe" by the USDA and FDA for use as additives, for example, in foods, beverages and/or other substance for human consumption, such as any substance that meets the criteria of sections 201(s) and 409 of the U.S. Federal Food, Drug and Cosmetic Act. Typically, the compositions, concentrates and liquid dilution compositions provided herein are GRAS certified.

As used herein, "kosher" is used to refer to substances that conform to Jewish Kosher dietary laws, for example, substances that do not contain ingredients derived from non-kosher animals or ingredients that were not made following kosher procedures. Typically, the compositions, concentrates and liquid dilution compositions provided herein are Kosher certified.

As used herein, "vessel" refers to any container, for example, any tank, pot, vial, flask, cylinder or beaker that can be used to contain the ingredients and/or phases of the provided concentrates and liquid dilution compositions during the methods for making the concentrates and liquid dilution compositions. The vessel can be a tank that is used to mix and/or heat one or more ingredients and/or phases of the composition, for example, the water phase tanks and oil phase tanks, such as during the provided scaled-up methods. The oil and the water phases can be mixed and heated in separate tanks before combining the phases to form an emulsion. The tank can be a packaging or holding tank, which holds the provided compositions after forming the compositions, for example, the emulsions. A number of tanks are available for mixing ingredients. Typically, the tanks are cleaned, for example, rinsed, soaped and/or sanitized according to known procedures prior to use and between uses. The tanks can be equipped with one or more mixers, for example, a standard mixer and/or homogenizer, which are used to mix the ingredients added to the tank. The tank can be equipped with a heating and/or cooling device. For example, the tank can be a water-jacketed tank. The temperature of the water-jacketed tank is controlled through the water-jacket, for example, to heat the contents, for example, while mixing.

As used herein, a "water phase vessel" refers to a vessel used to mix and/or heat the water phase ingredients to generate the water phase of the provided compositions. The water phase vessel can be a tank. The tank can be a water-jacketed tank, which is a tank equipped with a water jacket that can be used to heat the contents of the tank.

As used herein, an "oil phase vessel" refers to a vessel used to mix and/or heat the oil phase ingredients to generate the oil phase of the provided compositions. The oil phase vessel can be an oil phase tank. The tank can be a water-jacketed tank.

As used herein, "transfer device" refers to any equipment, combination of equipment and/or system that can be used to transfer liquid, for example, from one tank to another tank, in the provided methods for making the concentrates and liquid dilution compositions. Exemplary of the transfer devices is a transfer pump and appropriate fittings, for example, sanitary fittings, ball valves and transfer hoses, for example, food grade hoses.

As used herein a "mixer" is any piece of equipment or combination of equipment that can be used to mix ingredients in the provided methods for making the concentrates and liquid dilution compositions, for example, standard mixers and homogenizers (shears). For example, mixers can be used to mix the ingredients of the water phase and the oil phase and/or to mix the additional ingredients.

As used herein, "standard mixers" are mixers that are used to combine a group of ingredients, for example, the oil phase ingredients or the water phase ingredients, or to mix one or more ingredients with a liquid, for example, with an emulsion, for example, to mix additional ingredients with the emulsion. Standard mixers can be any mixers that move the material, for example, the ingredients, during heating, for example, to promote dissolving of the ingredients.

As used herein, "homogenizer" and "shear" are used to refer to mixers that typically have high shear, which can be used, for example, to form an emulsion, for example, to emulsify the water phase and the oil phase, in the provided methods. The homogenizers typically are capable of high-shear mixing, which emulsifies the phases.

As used herein, a "cooling apparatus" is any piece of equipment or combination of equipment that can be used with the provided methods to cool the compositions and phases and ingredients thereof, for example, during mixing and/or homogenizing, for example, to chill the mixture while emulsifying the oil and water phases. Exemplary of the cooling apparatuses are coolers (chillers), for example, recirculating coolers which can be attached, for example, to the tanks used in the provided methods, for example, remotely or by a tank mounted in the cooler, to recirculate fluid from the tank, through the chiller and back to the tank, in order to rapidly cool and maintain the temperature of the mixture during mixing. Typically, the cooling apparatus can be used to cool the liquid to between or about between 25° C. and 45° C., for example, to at or about 25, 26, 27, 28, 29, 30, 31, 32, 33, 34, 35, 36, 37, 38, 39, 40, 41, 42, 43, 44 or 45° C.

As used herein, "rapid cooling" refers to a process by which a composition, for example, a liquid composition, for example, a forming emulsion, is cooled to a desired temperature, for example, between or about between 25° C. and 45° C., in less than or about 2 hours, typically less than or less than about 1 hour, for example, less than or less than about 30 minutes, such as 15 minutes.

As used herein, "w/w," "by weight," "% by weight," "wt %" and "weight percent" are used synonymously to express the ratio of the mass of one component of a composition compared to the mass of the entire composition. For example, when the amount of a particular ingredient represents 1%, by weight (w/w), of a concentrate, the mass of that ingredient is 1% of the mass of the entire concentrate. Similarly, when the amount of an ingredient is 50% (w/w) of the concentrate, the mass of that ingredient is 50% of the entire mass of the concentrate. Similarly, when a composition and/or a compound contains 10%, by weight, of an ingredient, the mass of the ingredient is 10% of the total mass of the composition or compound. When a composition contains 10 wt % of an ingredient, the mass of that ingredient is 10% of the mass of the entire composition. When only a concentration, amount, or percentage (without units) is listed, it is to be understood that the concentration or percentage is a concentration or percentage by weight.

Similarly, as used herein "v/v" and "volume percent" are used synonymously to express the ratio of the volume of one component of a composition to the volume of the entire composition.

As used herein, "not more than" and "NMT" refer to a quantity that is less than or equal to the listed quantity. Similarly, "not less than" and "NLT" refer to a quantity that is greater than or equal to the listed quantity.

As used herein, the singular forms "a," "an" and "the" include plural referents unless the context clearly dictates otherwise. Thus, for example, reference to a composition containing "a non-polar ingredient" includes compositions with one or more non-polar ingredients.

As used herein, ranges and amounts can be expressed as "about" a particular value or range. About also includes the exact amount. Hence "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.72, 8.5 and 11.95 grams.

As used herein, "optional" or "optionally" means that the subsequently described element, event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

As used herein, "consisting essentially of" means containing the following list of ingredient(s), and not including any additional non-polar ingredient other than those listed.

B. Water-Soluble Vitamin E Derivatives

Provided herein are concentrates, compositions and beverage compositions, such as liquid dilution compositions and aqueous beverages, that contain water-soluble vitamin E derivative mixtures (compositions), such as water-soluble tocopherol-derived compositions and tocotrienol-derived compositions. The water-soluble vitamin E derivative mixtures (compositions) contain a relatively high concentration, as described herein, of the dimer form of the water-soluble vitamin E derivative. This composition is employed in the preparation of beverage compositions and concentrates that contain non-polar ingredients, such as nutritional supplements, including water-insoluble vitamins, fatty acids, phytosterols, coenzyme Q and other such compounds, and for addition to foods, particularly aqueous beverages. Also provided are compositions that contain the water-soluble vitamin E derivative mixtures (compositions) with an active ingredient and other optional ingredients for direct consumption without dilution.

Water-soluble vitamin E derivatives can be formed by covalently attaching the vitamin E moiety, a hydrophobic moiety, to another moiety, such as a hydrophilic moiety, for example, a polyalkylene glycol moiety, e.g., a polyethylene glycol (PEG) moiety, via a linker. For example, the vitamin E derivative compositions can include, but are not limited to, polyalkylene glycol derivatives of tocopherol, e.g., polyethylene glycol (PEG) derivatives of tocopherol, and polyalkylene glycol derivatives of tocotrienol, e.g., polyethylene glycol (PEG) derivatives of tocotrienol, and any other derivatized water-soluble form of vitamin E that is capable of forming a dimer, such as those described in U.S. Pub. No. 2011-0184194. The water-soluble vitamin E derivatives include, for example, vitamin E TPGS (D-α-tocopheryl polyethylene glycol succinate), TPGS analogs, TPGS homologs and TPGS derivatives.

Polyethylene glycol derivatives of vitamin E, such as vitamin E TPGS (D-α-tocopheryl polyethylene glycol succinate), are known. Compositions of PEG derivatives of vitamin E, for example, TPGS compositions, typically contain a mixture of monomers and dimers, where a monomer is a single vitamin E molecule covalently joined to a water-soluble moiety, such as a polyethylene glycol, through a linker, where the water-soluble moiety, e.g., PEG, has a free, unreacted, terminal reactive group, e.g., a free terminal hydroxyl group. A dimer is made up of two vitamin E molecules covalently joined to a water-soluble moiety, such as a polyethylene glycol, through one or more linkers, where both ends of the water-soluble moiety, e.g., both terminal hydroxyl groups of a PEG moiety, have reacted with a linker that is joined to a vitamin E molecule so that there are no free terminal reactive groups, e.g., hydroxyl groups. For example, the monomer and dimer are formed during the esterification reaction between the acid moiety of vitamin E succinate and the terminal hydroxyl groups of a polyethylene glycol to produce TPGS. Known TPGS compositions contain primarily TPGS monomer, e.g., between 70 wt % and 87 wt %, or higher TPGS monomer. The monomer has been considered the effective component and the dimer considered to be a byproduct, thus the amounts of dimer are minimal, e.g., less than 12 wt %.

In contrast, the water-soluble vitamin E derivative mixtures (compositions) employed in the concentrates and compositions provided herein are prepared so that they contain significantly more dimer, i.e., more than 12%, particularly at least 20%, 25%, 29% or more, generally between about 29-55%, or 35%-55%, or more, such as up to 75%, 80%, 85%, 90% or 95% dimer, and contain some monomer, i.e., less than 70 wt % monomer. For example, described herein are TPGS compositions that contain less TPGS monomer, i.e., less than 70 wt % TPGS monomer, and more TPGS dimer, i.e., more than 12 wt % TPGS dimer, such as at least 20%, 25%, 29% or more, up to 75%, 80%, 85%, 90% or 95% dimer. PEG derivatives of tocopherols or tocotrienols, e.g., TPGS, are water-soluble and can be added to products formulated for human consumption, such as food and beverage products, in particular aqueous food and beverage products. They have been used, for example, to increase bioavailability of vitamin E and/or to act as a surfactant for other water-insoluble compounds, for example, non-polar compounds.

The concentrates and foods and beverages provided herein contain the water-soluble vitamin E derivative mixtures (compositions) that have the higher concentrations of dimer, such as TPGS compositions containing, for example, less monomer, i.e., less than 70 wt %, and more dimer, i.e., more than 12 wt %.

It is shown herein that the water-soluble vitamin E derivative mixtures (compositions) described herein have advantageous properties compared to vitamin E derivative compositions that contain higher concentrations (i.e., greater than 70%) monomer. In particular, the vitamin E derivative compositions provided herein contain at least about 13%, typically more, dimer form of the vitamin E derivative than previous preparations, in which the amount of monomer form is maximized. It is shown herein, that the vitamin E derivative compositions that contain more dimer form are more effective in solubilizing non-polar additives (non-polar compounds) in aqueous compositions than compositions that contain the monomer form and very little dimer form, and result in compositions, and concentrates that produce liquid dilution compositions, such as aqueous beverages, that are more clear and stable than comparable compositions produced from concentrates that contain low amounts of dimer and higher amounts of monomer. In addition, the higher dimer-containing water-soluble vitamin E derivative mixtures (compositions) described herein permit dissolution of higher concentrations of non-polar ingredients while retaining the clarity and stability of the resulting foods and beverages. As shown herein, higher concentration of non-polar compounds can be dissolved, and result in beverages of greater clarity than those containing water-soluble vitamin E derivative mixtures (compositions) that contain lower concentrations of dimer. In addition, across all ranges of concentrations of non-polar compounds, the resulting beverages are significantly more clear (see Examples below). Thus, provided herein are products formulated for human consumption, for example, food and beverage products, such as aqueous food and beverage products, that contain the water-soluble vitamin E derivative mixtures (compositions) described herein and one or more non-polar compounds that contain one or more non-polar active ingredients, and methods for producing such products.

The concentrates containing the water-soluble vitamin E derivative mixtures (compositions) described herein can be used in aqueous compositions, for example, aqueous food and beverage products for human consumption. In some instances, the so-called concentrates can be formulated for direct administration or direct consumption so that they are not concentrates per se, but contain amounts of active compounds, such as the nutraceuticals, that are for direct consumption. Those compositions contain lower amounts of the vitamin E derivative composition compared to concentrates intended for dilution into beverages, as well as amounts of the active ingredient to provide a dosage or effective amount upon consumption of a single serving, such as 1-10 mL, thereof.

The food and beverage products provided herein that contain the water-soluble vitamin E derivative mixtures with concentrations of dimer that are greater than 12%, particularly at least 20%, 25%, 29% and higher, contain non-polar compounds, for example, non-polar compounds that are poorly water-soluble (e.g., have low water solubility or are water-insoluble), that contain one or more non-polar active ingredients. The use of the water-soluble vitamin E derivative mixtures (compositions) that contain less monomer, i.e., less than 70 wt % monomer, and more dimer, i.e., more than 12 wt % dimer, than known water-soluble vitamin E derivative mixtures with higher concentrations of monomer and lower concentrations of dimer, in aqueous food and beverage products allows for the addition of higher amounts (i.e., concentrations) of non-polar compounds as compared to available food and beverage products without sacrificing clarity and stability of the resulting product. Thus, described herein are water-soluble vitamin E derivative mixtures (compositions), such as TPGS compositions, that can be added to food and beverage products that allow for the addition of higher concentrations of non-polar compounds that result in food and beverage products that retain desirable organoleptic properties.

1. Vitamin E

Vitamin E refers to a group of eight water-insoluble compounds that include tocopherols and tocotrienols. Both structures are similar, containing a chromal ring and a 16-carbon side chain. The 16-carbon side chain of the tocopherols is saturated, while the side chain of the tocotrienols is unsaturated, with double bonds at the 3', 7' and 11' positions. Each tocopherol and tocotrienol exists in the α, β, γ and δ forms, differentiated by the number and position of methyl groups on the ring (labeled $R_1$, $R_2$ and $R_3$), as shown below.

vitamin E, for example, PEG derivatives of tocopherols or tocotrienols. Suitable PEG derivatives of vitamin E can contain one or more tocopherol or tocotrienol, attached to one or more PEG moiety via a linker, for example, a dicarboxylic acid linker. Exemplary dicarboxylic acid linkers include succinic acid and succinic anhydride. An exemplary water-soluble vitamin E derivative is shown schematically below:

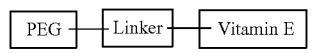

where the line between the PEG and the linker, and the line between the linker and the vitamin E moiety, each independently represent a covalent bond, for example, a covalent bond that forms an ester, ether, amide or thioester.

Typically, the vitamin E-PEG derivatives are made by covalently attaching the PEG moiety, such as by esterification, to a vitamin E-linker conjugate (e.g., a tocopherol-linker conjugate). The vitamin E-linker conjugate can be formed through esterification of the hydroxyl group of the vitamin E

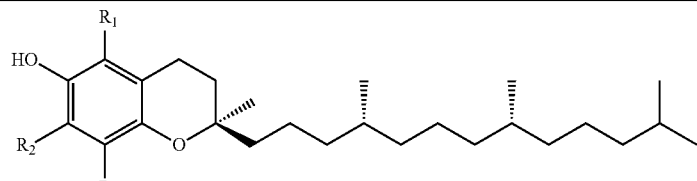

Tocopherol

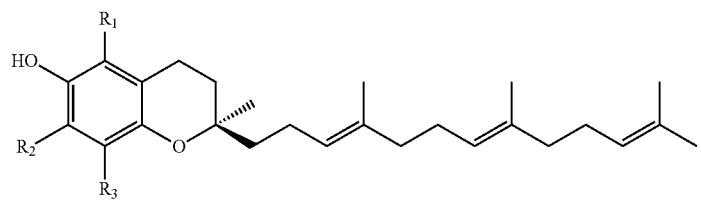

Tocotrienol

| Form | $R_1$ | $R_2$ | $R_3$ |
|---|---|---|---|
| α | Me | Me | Me |
| β | Me | H  | Me |
| γ | H  | Me | Me |
| δ | H  | H  | Me |

Vitamin E is an important natural antioxidant and has been shown to have anti-inflammatory and anti-carcinogenic activity (Yang et al. (2010) Ann. N.Y. Acad. Sci. 1203:29-34; Ju et al. (2010) Carcinogenesis 31(4):533-542; Li et al. (2011) Cancer Prev. Res. (Phila.) 4(3):404-413). The most common and biologically active form of vitamin E is α-tocopherol, and is the form often referred to as vitamin E. Since tocopherols, including α-tocopherol, cannot be synthesized in humans and animals, they must be obtained from dietary sources. Alpha-tocopherol, the main component of vitamin E in the American diet, is most commonly found in wheat germ, nuts and vegetable and plant oils, such as oils from soybean, corn, sesame, cottonseed, sunflower and almond.

2. Polyalkylene Glycol Derivatives of Vitamin E

The water-soluble vitamin E derivatives described herein (e.g., water-soluble tocopherols or water-soluble tocotrienols) can include polyalkylene glycol derivatives of vitamin E, such as polyethylene glycol (PEG) derivatives of moiety with a carboxylic acid group of a linker, such as a dicarboxylic acid linker. In one example, the vitamin E-linker conjugate can be a tocopherol-linker conjugate, such as a tocopherol ester, for example, tocopherol succinate. The esterification reaction can be performed by any of a number of known methods, including those described in U.S. Pat. Nos. 2,680,749; 4,665,204; 3,538,119; and 6,632,443. The resulting vitamin E-linker conjugate can then be attached to a PEG moiety by another esterification reaction, for example, between a carboxylic acid group of the vitamin E-linker conjugate and a hydroxyl group of the PEG moiety, to form a vitamin E-PEG derivative.

PEG derivatives of a tocopherol-linker or tocotrienol-linker conjugate can be made by any other method known to those of skill in the art. Various methods known in the art for producing PEG derivatives can be used to attach a PEG molecule to tocopherol-linker or tocotrienol-linker compounds. For example, a tocopherol-linker conjugate can form a covalent bond to the PEG molecule via an amide, ether or thioether bond. For example, a tocopherol-linker conjugate that contains an amine group can be reacted with a PEG-NHS (N-hydroxysuccinimide) derivative to form an amide bond between the tocopherol-linker conjugate and the PEG molecule. A tocopherol-linker conjugate that contains an amine group can be reacted with a PEG-aldehyde derivative to form an amide bond between the tocopherol-linker conjugate and the PEG molecule. In another example, a tocopherol-linker conjugate that contains an carboxylic acid can be activated to the corresponding acid halide and reacted with a PEG-SH derivative to form a thioester bond between the tocopherol-linker conjugate and the PEG molecule.

a. Tocopherols and Tocotrienols

The tocopherols used to make the water-soluble vitamin E derivative mixtures described herein can be any natural or synthetic vitamin E tocopherol, including, but not limited to, alpha-tocopherols, beta-tocopherols, gamma-tocopherols and delta tocopherols, either in pure form or in a heterogeneous mixture of more than one form. Exemplary tocopherols are d-α-tocopherols and dl-α-tocopherols. To make the vitamin E-PEG derivative, the tocopherol typically is esterified with a linker, for example, a dicarboxylic acid, to form a tocopherol ester, which then is joined to a PEG moiety.

The tocotrienols used to make the water-soluble vitamin E derivative mixtures described herein can be any natural or synthetic vitamin E tocotrienol, including, but not limited to, alpha-tocotrienols, beta-tocotrienols, gamma-tocotrienols and delta tocotrienols, either in pure form or in a heterogeneous mixture of more than one form. Mixtures of tocopherols and tocotrienols are contemplated for use in the described methods and compositions. A tocotrienol can be esterified with a linker, such as a dicarboxylic acid, before joining with a PEG moiety to form a vitamin E-PEG derivative.

b. Linkers

Typically, the water-soluble vitamin E derivatives described herein include a vitamin E moiety, e.g., a tocopherol or tocotrienol, attached to a PEG moiety through a linker. The linker can be any linker that is capable of forming a covalent bond with both the vitamin E moiety and the PEG moiety. For example, the linker can be any linker capable of forming more than one covalent bond such as an ester bond, an amide bond, an ether bond, a thioether bond, or any combination thereof. In some embodiments, the linker is capable of forming more than one ester bond, for example, the linker can be a dicarboxylic acid or dicarboxylic acid derivative. Exemplary dicarboxylic acids and derivatives useful as linkers in the water-soluble vitamin E derivatives described herein include succinic acid, succinic anhydride, sebacic acid, dodecanedioic acid, suberic acid (i.e., octanedioic acid), azelaic acid, citraconic acid, methylcitraconic acid, itaconic acid, maleic acid, glutaric acid, glutaconic acid, fumaric acid and phthalic acid. Accordingly, exemplary of the vitamin E-linker conjugates (i.e., tocopherol or tocotrienol attached to a linker through an ester bond) that can be further esterified to form the vitamin E-PEG derivatives (i.e., water-soluble vitamin E derivatives) described herein are tocopheryl succinate, tocopheryl sebacate, tocopheryl dodecanodioate, tocopheryl suberate, tocopheryl azelaate, tocopheryl citraconate, tocopheryl methylcitraconate, tocopheryl itaconate, tocopheryl maleate, tocopheryl glutarate, tocopheryl glutaconate, tocopheryl fumarate, tocopheryl phthalate, tocotrienol succinate, tocotrienol sebacate, tocotrienol dodecanodioate, tocotrienol suberate, tocotrienol azelaate, tocotrienol citraconate, tocotrienol methylcitraconate, tocotrienol itaconate, tocotrienol maleate, tocotrienol glutarate, tocotrienol glutaconate, tocotrienol fumarate and tocotrienol phthalate.

In other embodiments the linker can be any compound capable of forming more than one covalent bond, for example, a succinate ester, such as N-hydroxysuccinimide; an amino acid, such as glycine, alanine, 5-aminopentanoic acid or 8-aminooctanoic acid; or an amino alcohol, such as ethanolamine.

c. PEG Moieties

The polyalkylene moiety used to produce the water-soluble vitamin E derivatives described herein can be any polyalkylene moiety. Exemplary of a polyalkylene moiety is a polyethylene glycol (PEG) moiety. The PEG moiety used in the vitamin E derivatives described herein can be any of a plurality of known PEG moieties. Exemplary of suitable PEG moieties are PEG moieties having varying chain lengths and varying molecular weights, such as, for example, PEG 200, PEG 500, PEG 1000 and PEG 20,000, where the molecular weight of the PEG moiety is 200 Da, 500 Da, 1000 Da and 20,000 Da, respectively. Typically, the number following "PEG" indicates the molecular weight, in daltons (Da), of the PEG moiety. The PEG moiety of the water-soluble vitamin E derivatives described herein typically has a molecular weight of between or about between 200 Da to 20,000 Da, for example, between or about between 200 Da to 20,000 Da, 200 Da to 10,000 Da, 200 Da to 8000 Da, 200 Da to 6000 Da, 200 Da to 5000 Da, 200 Da to 3000 Da, 200 Da to 1000 Da, 200 Da to 800 Da, 200 Da to 600 Da, 200 Da to 400 Da, 400 Da to 20,000 Da, 400 Da to 10,000 Da, 400 Da to 8000 Da, 400 Da to 6000 Da, 400 Da to 5000 Da, 400 Da to 3000 Da, 400 Da to 1000 Da, 400 Da to 800 Da, 400 Da to 600 Da, 600 Da to 20,000 Da, 600 Da to 10,000 Da, 600 Da to 8000 Da, 600 Da to 6000 Da, 600 Da to 5000 Da, 600 Da to 3000 Da, 600 Da to 1000 Da, 600 Da to 800 Da, 800 Da to 20,000 Da, 800 Da to 10,000 Da, 800 Da to 8000 Da, 800 Da to 6000 Da, 800 Da to 5000 Da, 800 Da to 3000 Da, 800 Da to 1000 Da, 1000 Da to 20,000 Da, 1000 Da to 10,000 Da, 1000 Da to 8000 Da, 1000 Da to 6000 Da, 1000 Da to 5000 Da, 1000 Da to 3000 Da, 3000 Da to 20,000 Da, 3000 Da to 10,000 Da, 3000 Da to 8000 Da, 3000 Da to 6000 Da, 3000 Da to 5000 Da, 5000 Da to 20,000 Da, 5000 Da to 10,000 Da, 5000 Da to 8000 Da, 5000 Da to 6000 Da, 6000 Da to 20,000 Da, 6000 Da to 10,000 Da, 6000 Da to 8000 Da, 8000 Da to 20,000 Da, 8000 Da to 10,000 Da, or 10000 Da to 20,000 Da. For example, the PEG moiety of the water-soluble vitamin E derivatives described herein can have a molecular weight of 200, 300, 400, 500, 600, 800, 1000, 3000, 5000, 6000, 8000, 10,000, 20,000 Da or more.

Other known PEG analogs also can be used in the water-soluble vitamin E derivatives described herein. The PEG moieties can be selected from among any reactive PEG moiety, including, but not limited to, PEG-OH, PEG-NHS, PEG-aldehyde, PEG-SH, PEG-NH$_2$, PEG-CO$_2$H, and branched PEG moieties.

Exemplary of a water-soluble vitamin E derivative having a PEG moiety with a molecular weight of 1000 Da is TPGS 1000 (i.e., D-α-tocopheryl polyethylene glycol succinate 1000).

d. Surfactant Properties

The water-soluble vitamin E derivative mixtures (compositions) described herein, for example, the polyalkylene glycol derivatives of vitamin E described herein, are surfactants. Surfactants are molecules that contain hydrophobic and hydrophilic portions. For example, the hydrophobic portion can be a hydrophobic tail and the hydrophilic portion can be a hydrophilic head of the surfactant molecule. The water-soluble vitamin E derivatives described herein can be natural surfactants, for example, surfactants that are G.R.A.S. certified (generally recognized as safe) by the FDA and/or Kosher certified.

Typically, surfactants aggregate in aqueous liquids, such as water, to form micelles. The hydrophilic portion(s) of the surfactant molecules are oriented toward the outside of the micelle, in contact with the aqueous medium, while the hydrophobic portion(s) of the surfactant molecules are oriented toward the center of the micelle. Surfactants also are capable of forming "inverse micelles," which form in lipophilic medium, the hydrophobic tails being in contact with the lipophilic medium and the hydrophilic heads facing the center of the inverse micelle. Typically, however, the water-soluble vitamin E derivatives described herein are surfactants that form micelles in aqueous medium, for example, in aqueous liquids, such as water.

The water-soluble vitamin E derivatives described herein can be represented by an HLB (hydrophobic-lipophilic balance) value. Generally, HLB is a value, derived from a semi-empirical formula, which is used to index surfactants according to their relative hydrophobicity/hydrophilicity. An HLB value is a numerical representation of the relative representation of hydrophilic groups and hydrophobic groups in a surfactant or mixture of surfactants. The weight percent of these respective groups indicates properties of the molecular structure. See, for example, Griffin (1949) J. Soc. Cos. Chem. 1:311. Surfactant HLB values range from 1-45, while the range for non-ionic surfactants typically is from 1-20. The more lipophilic a surfactant is, the lower its HLB value. Conversely, the more hydrophilic a surfactant is, the higher its HLB value. Lipophilic surfactants have greater solubility in oil and lipophilic substances, while hydrophilic surfactants dissolve more easily in aqueous liquids. In general, surfactants with HLB values greater than 10 or greater than about 10 are called "hydrophilic surfactants," while surfactants having HLB values less than 10 or less than about 10 are referred to as "hydrophobic surfactants." It should be appreciated that HLB values for a given surfactant can vary, depending upon the empirical method used to determine the value. Thus, HLB values of surfactants provide a rough guide for formulating compositions based on relative hydrophobicity/hydrophilicity. For example, a surfactant typically is selected from among surfactants having HLB values within a particular range of the surfactant or co-surfactant that can be used to guide formulations. The water-soluble vitamin E derivatives described herein, such as the polyalkylene glycol derivatives of vitamin E with greater than 12%, 20%, 25%, or 29% dimer, are surfactants in which the vitamin E moiety represents the hydrophobic region of the surfactant and is attached, via a linker, to a polyalkylene glycol moiety, such as a polyethylene glycol (PEG) moiety, that provides the hydrophilic portion of the surfactant. The water-soluble vitamin E derivative mixtures (compositions) described herein contain more than 12%, such as at least 20%, 25% and 29%, up to 95%, 90%, 85%, 80%, or 75% of dimers of the water-soluble vitamin E derivative, such as PEG-derivatives of vitamin E. Exemplary of the water-soluble vitamin E derivatives that can be used as surfactants are tocopherol-derived surfactants, including polyalkylene glycol derivatives of tocopherol, typically polyethylene glycol (PEG) derivatives of tocopherol, such as tocopheryl polyethylene glycol succinate (TPGS), TPGS analogs, TPGS homologs and TPGS derivatives and tocotrienol-derived surfactants, including polyalkylene glycol derivatives of tocotrienol, typically polyethylene glycol (PEG) derivatives of tocotrienol. These are prepared as compositions containing the higher levels of dimers as described herein.

Exemplary of vitamin E derivatives that can be prepared for use herein are tocopheryl polyalkylene glycol derivatives, such as tocopheryl polyethylene glycol derivatives. These include tocopheryl polyethylene glycol succinate (TPGS), tocopheryl sebacate polyethylene glycol, tocopheryl dodecanodioate polyethylene glycol, tocopheryl suberate polyethylene glycol, tocopheryl azelaate polyethylene glycol, tocopheryl citraconate polyethylene glycol, tocopheryl methylcitraconate polyethylene glycol, tocopheryl itaconate polyethylene glycol, tocopheryl maleate polyethylene glycol, tocopheryl glutarate polyethylene glycol, tocopheryl glutaconate polyethylene glycol and tocopheryl phthalate polyethylene glycol, TPGS analogs and TPGS homologs. Other tocopheryl polyethylene glycol derivatives, such as those prepared as described in U.S. Pub. No. 2011-0184194 can be used in the concentrates and food and beverage compositions described herein. These derivatives are prepared as described herein or other methods such that the resulting compositions contain greater than 12%, such as at least 20%, 25% and 29%, up to 95%, 90%, 85%, 80%, 75% of the dimer form of the vitamin E derivative. Concentrates and beverage compositions containing such compounds have advantageous properties shown herein.

The water-soluble vitamin E derivatives described herein typically have an HLB value between or about between 12 and about 20, for example, 12, 13, 14, 15, 16, 17, 18, 19, 20, or about 12, about 13, about 14, about 15, about 16, about 17, about 18, about 19 or about 20. Exemplary of water-soluble vitamin E derivatives that can be used as surfactants are the water-soluble vitamin E derivatives described herein. For example, the water-soluble vitamin E derivatives described herein, such as polyalkylene glycol derivatives of vitamin E, have an HLB value of between or about between 12 and about 20. Exemplary of a water-soluble vitamin E derivate having an HLB value between or about between 12 and about 20 is tocopheryl polyethylene glycol succinate (TPGS), such as the TPGS compositions described herein. TPGS typically has an HLB value of between or about between 12 and 14 or about 13.

The following discussion describes properties and preparations of the vitamin E derivative D-α-tocopheryl polyethylene glycol succinate (TPGS) as exemplary of the water-soluble vitamin E derivatives that can be prepared in compositions with the higher levels of dimer as described herein.

3. Tocopheryl Polyalkylene Glycol Derivatives

In its natural water-insoluble state, vitamin E, e.g., tocopherol or tocotrienol, is easily absorbed and used in humans and animals. Processing of foods and feeds by industry for long-term storage can promote accelerated degradation of the effective vitamin E content. To compensate for the loss of natural vitamin E from food sources, nutritional supplements of natural or synthetic fat-soluble vitamin E have been developed. Not all humans and animals can sufficiently absorb the supplements though. To address this problem, water-soluble vitamin E derivatives have been developed that are an excellent source of vitamin E (i.e., maintain a high degree of vitamin E biological activity) in humans with impaired vitamin E absorption, for example, in humans with malabsorption syndromes (Traber et al. (1986) Am. J. Clin. Nutr. 44:914-923). Water-soluble vitamin E derivatives have been developed for this purpose. Tocopheryl polyethylene glycol derivatives, such as those listed above, are employed to produce the water-soluble vitamin E derivative mixtures (compositions) with higher levels of dimer as described herein. The water-soluble vitamin E derivative D-α-tocopheryl polyethylene glycol succinate (TPGS) is exemplary of the tocopheryl polyethylene glycol derivatives.

TPGS contains a hydrophilic (i.e., water-soluble) polyethylene glycol (PEG) chain and a lipophilic (i.e., water-insoluble) α-tocopherol head. The amphiphilic structure of TPGS, shown below, renders it much more water-soluble than traditional vitamin E, allowing TPGS to form a micellar solution at low concentrations (0.04-0.06 mmol/L) that can be absorbed by humans and animals in the absence of bile salts.

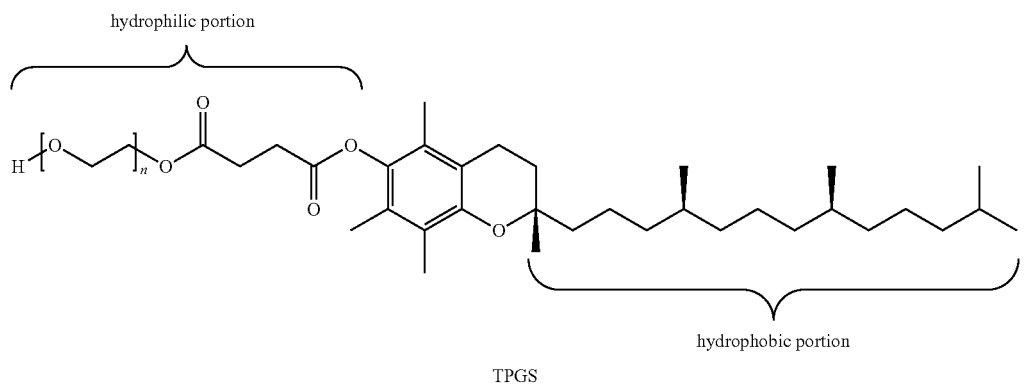

TPGS a. Uses i. Nutritional Supplement

TPGS has been approved by the FDA as a water-soluble vitamin E nutritional supplement. It is a GRAS (Generally Regarded As Safe)-listed supplement that can be taken orally at long-term doses of 13.4-16.8 mg/kg/day or up to 100 mg/kg/day for people with impaired uptake. In the body, TPGS undergoes enzymatic cleavage to deliver the lipophilic antioxidant α-tocopherol (vitamin E) to cell membranes. Cellular enzymatic hydrolysis by cytoplasmic esterases liberates free α-tocopherol, which then localizes in the cell membrane, and through free radical quenching, protects the membrane from lipid peroxidation and damage.

ii. Surfactant

TPGS also is used as a non-ionic surfactant and emulsifier. Non-ionic surface-active agents are used in oral formulations to enhance the bioavailability of water-insoluble pharmaceuticals, such as drugs, vitamins, or other biologically active compounds. TPGS has is an effective absorption and bioavailability enhancer, and has been approved for use as a drug solubilizer in oral, parenteral, topical, nasal, and rectal/vaginal therapies (see, e.g., Constantinides et al. (2006) Pharm. Res. 23(2):243-255; Varma et al. (2005) Eur. J. Pharm. Sci. 25(4-5):445-453) and as a solubilizer for inhalation drug delivery (Fulzele et al. (2006) 23(9):2094-2106). TPGS improves the bioavailability of such water-insoluble drugs as the HIV protease inhibitor amprenavir (Yu et al. (1999) Pharm. Res. 16:1812-1817; Brouwers et al. (2006) J. Pharm. Sci. 95:372-383), the non-nucleoside reverse transcriptase inhibitor UC 781 (Goddeeris et al. (2008) Eur. J. Pharm. Sci. 35:104-113), cyclosporin (Sokol et al. (1991) Lancet 338: 212-215), paclitaxel (Zhao et al. (2010) J. Pharm. Sci. 99(8): 3552-3560), estradiol (Sheu et al. (2003) J. Controlled Release 88:355-368), and fat-soluble vitamins such as vitamin D (Argao et al. (1992) Ped. Res. 31(2):146-150).

TPGS acts as a surfactant due to its hydrophilic polyethylene glycol (PEG) chain and its hydrophobic α-tocopherol portion. Surfactants aggregate and form micelles in aqueous mediums such that the hydrophilic portion(s) of the surfactant molecules are oriented toward the outside of the micelle, in contact with the aqueous medium, while the hydrophobic portion(s) of the surfactant molecules are oriented toward the center of the micelle. In the food and beverage products provided herein, TPGS can act as a surfactant by forming micelles in an aqueous medium, such as water, where the hydrophilic portion of TPGS, i.e., the polyethylene glycol (PEG) moiety, is oriented toward the outside of the micelle, in contact with the aqueous medium, while the hydrophobic portion of TPGS, i.e., the vitamin E moiety, is oriented toward the center of the micelle, in contact with the non-polar compound(s), which are thus contained in the center of the micelle.

The hydrophobic/hydrophilic character of a surfactant can be described in terms of an HLB, or hydrophilic-lipophilic balance, value. The HLB value is a numerical representation of the molecular balance of the hydrophobic and hydrophilic portions of the surfactant, relative to other surfactants. HLB values are derived from a semi-empirical formula, where the relative weight percentages of the hydrophobic and hydrophilic groups are indicative of surfactant properties, such as the types of aggregates the surfactant form, and the solubility of the surfactant (Griffin (1949) J. Soc. Cosmet. Chem. 1:311-326). Surfactant HLB values range from 1-45, where the range for non-ionic surfactants typically is from 1-20. The more lipophilic a surfactant is, the lower its HLB value. Conversely, the more hydrophilic a surfactant is, the higher its HLB value. The exact HLB value for a given surfactant can vary, however, depending on the empirical method used to determine the value. Values have been determined for a number of surfactants (see, e.g., U.S. Pat. No. 6,267,985). TPGS a non-ionic surfactant, as reported, has an HLB value of approximately 13.

4. Synthesis

Scheme 1 shows the synthesis of an exemplary water-soluble vitamin E derivative, TPGS, but any vitamin E moiety, i.e., any tocopherol or tocotrienol, can be used as the starting material, and reacted with any linker, such as those described herein, that is capable of reacting with a polyalkylene glycol moiety to form a monomer form and dimer form of a water-soluble vitamin E derivative. As shown in Scheme 1 below, TPGS can be prepared by reacting vitamin E with succinic anhydride or succinic acid to obtain vitamin E succinate, i.e., D-α-tocopheryl succinate, followed by esterification with a polyethylene glycol molecule, to obtain TPGS (see U.S. Pat. No. 2,680,749). TPGS analogs varying in PEG chain length (e.g., TPGS 200, 238, 400, 600, 2000, 3400, 3500, 4000 and 6000) have been synthesized, but the most widely used form of TPGS is TPGS 1000 which incorporates PEG 1000, a polyethylene glycol molecule with a molecular weight of approximately 1,000 Daltons (Collnot et al. (2006) J. Controlled Release 111:35-40). TPGS 1000 is a pale yellow, waxy solid substance that is amphipathic and hydrophilic, with a molecular weight of approximately 1,513 Daltons.
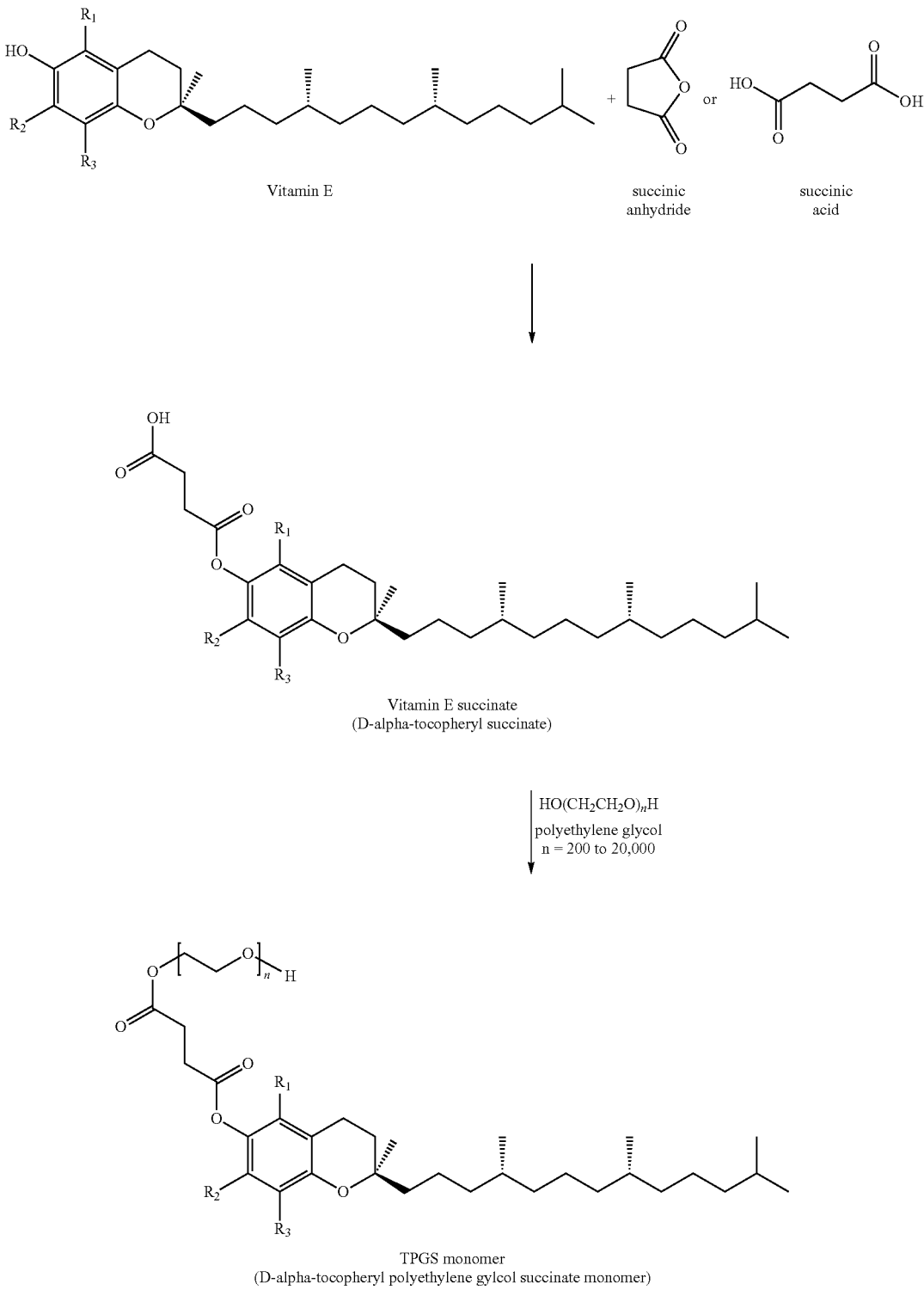

-continued

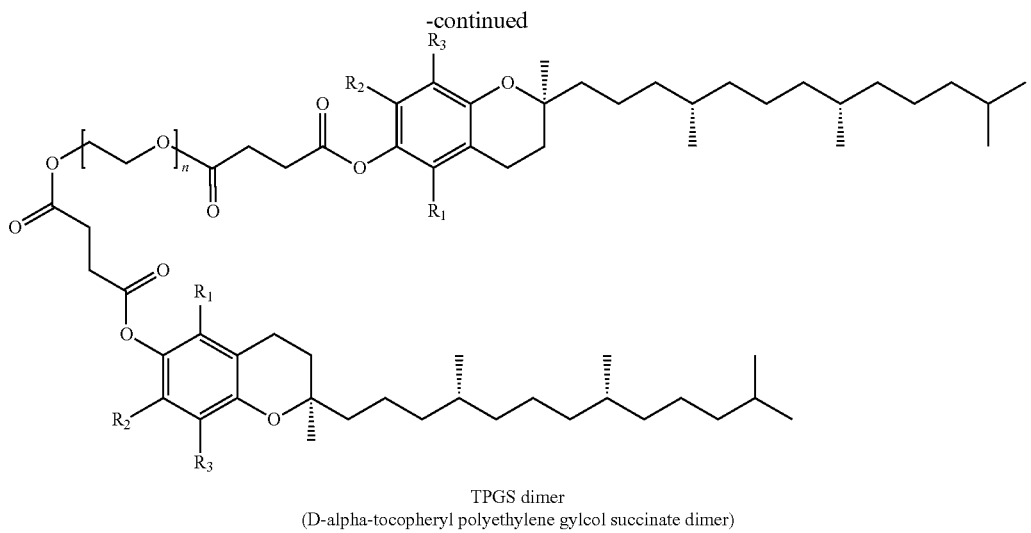

TPGS dimer
(D-alpha-tocopheryl polyethylene gylcol succinate dimer)

TPGS compositions, as generally prepared, such as commercially available TPGS 1000, are mixtures that contain primarily TPGS monomer (between 70% and 87% or more) and a lesser amount of TPGS dimer (less than 12%). The monomer is considered the effective component in TPGS, while the dimer is viewed as a byproduct of the esterification reaction between polyethylene glycol and vitamin E succinate. For example, commercially available TPGS, such as TPGS 1000 available from Eastman Chemical Company (Kingsport, Tenn.), contains primarily TPGS monomer (~86% or more) and a small amount of TPGS dimer (~11% or less) (Christiansen et al. (2011) J. Pharm. Sci. 100(5):1773-1782). TPGS synthesized according to standard methods, for example, the method described in U.S. Pat. No. 2,680,749, results in a TPGS composition that is composed primarily of TPGS monomer (70-87%) and a small amount of TPGS dimer (<12%) (US Pharmacopeia 23 (1998) Supp. 9:4712; Scientific Panel of the European Food Safety Authority (2007) EFSA J. 490:1-20). Because the separation of TPGS monomer and TPGS dimer is difficult and because TPGS monomer is considered the effective component in TPGS, TPGS compositions containing primarily TPGS dimer have not been developed (Kong et al. (2011) J. Chromatography A 1218:8664-8671). TPGS dimer, shown below, is usually considered an unwanted byproduct of the esterification reaction between PEG and vitamin E succinate, formed due to the equal reactivity of both terminal hydroxyl groups of PEG.

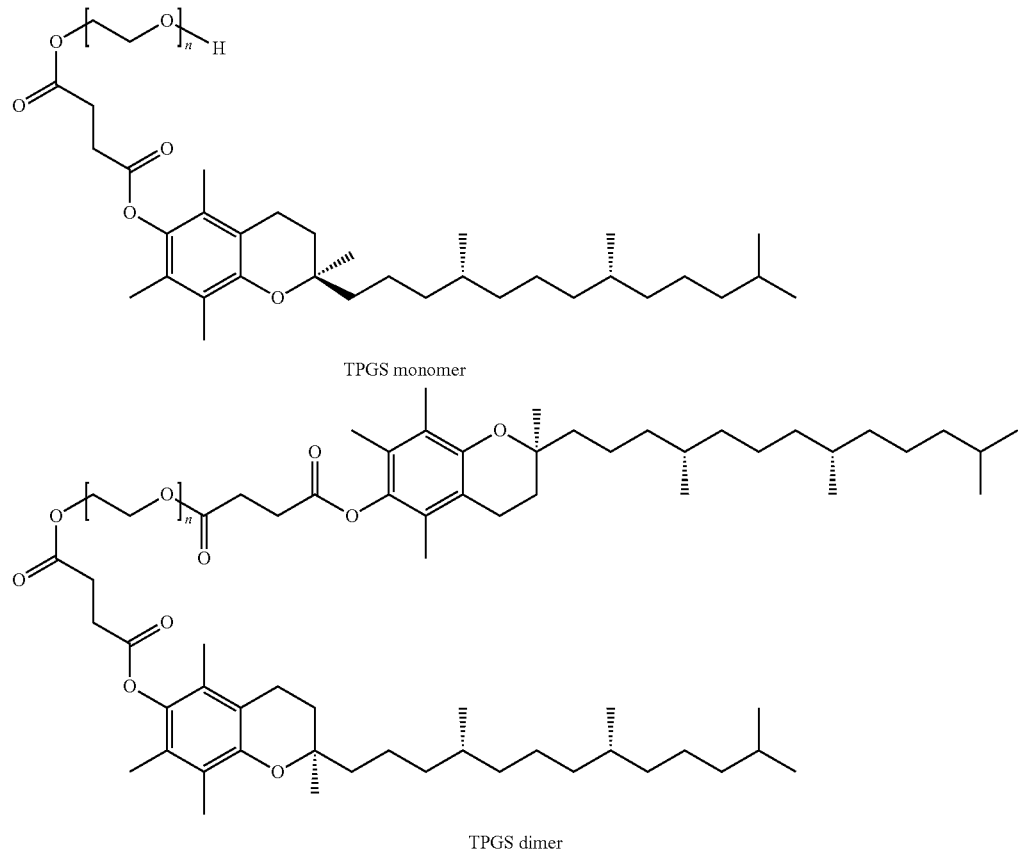

TPGS monomer

TPGS dimer

5. Water-Soluble Vitamin E Derivative Mixtures (Compositions)

Described herein are water-soluble vitamin E derivative mixtures (compositions), for example, TPGS compositions, that contain varying amounts of monomer and dimer, particularly compositions that contain less monomer than is found in typical known water-soluble vitamin E derivative mixtures (compositions), for example, less than 70 wt % monomer, and more dimer, i.e., greater than 12 wt % dimer, than in typical known water-soluble vitamin E derivative mixtures (compositions), for example, known TPGS compositions. For example, the water-soluble vitamin E derivative mixtures (compositions) described herein can contain between or between about 25 wt % and 69 wt % monomer and between or between about 13 wt % and 95 wt % dimer, such as water-soluble vitamin E derivative mixtures (compositions) containing between or about between 40 wt % and 60 wt % monomer and between or about between 25 wt % to 60 wt % dimer, such as 29% to 55%, 35% to 50% or 30% to 45%, dimer. Advantageous properties are exhibited by compositions that contain at least these amounts.

In the water-soluble vitamin E derivative mixtures (compositions) described herein, the total amount of monomer as a percentage (%), by weight, of the composition (wt %) can be, e.g., between or between about 25 wt % and 69 wt % monomer, inclusive, such as between or between about 25% and 30%, 25% and 35%, 25% and 40%, 25% and 45%, 25% and 50%, 25% and 55%, 25% and 60%, 25% and 65%, 25% and 69%, 30% and 35%, 30% and 40%, 30% and 45%, 30% and 50%, 30% and 55%, 30% and 60%, 30% and 65%, 30% and 69%, 35% and 40%, 35% and 45%, 35% and 50%, 35% and 55%, 35% and 60%, 35% and 65%, 35% and 69%, 40% and 45%, 40% and 50%, 40% and 55%, 40% and 60%, 40% and 65%, 40% and 69%, 45% and 50%, 45% and 55%, 45% and 60%, 45% and 65%, 45% and 69%, 50% and 55%, 50% and 60%, 50% and 65%, 50% and 69%, 55% and 60%, 55% and 65%, 55% and 69%, 60% and 65%, 60% and 69%, and 65% and 69% monomer, by weight, of the composition. Generally, the compositions contain less than 69 wt % monomer. For example, the water-soluble vitamin E derivative mixtures (compositions) described herein contain at least or about at least 25%, 30%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, but less than 69% (wt %) total monomer.

In the water-soluble vitamin E derivative mixtures (compositions) described herein, the total amount of dimer as a percentage (%), by weight, of the composition (wt %) can be, e.g., between or between about 13 wt % and 95 wt % dimer, inclusive, such as between or between about 13% and 20%, 13% and 25%, 13% and 30%, 13% and 35%, 13% and 40%, 13% and 45%, 13% and 50%, 13% and 55%, 13% and 60%, 13% and 65%, 13% and 70%, 13% and 75%, 13% and 80%, 13% and 85%, 13% and 90%, 13% and 95%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 20% and 80%, 20% and 85%, 20% and 90%, 20% and 95%, 25% and 30%, 25% and 35%, 25% and 40%, 25% and 45%, 25% and 50%, 25% and 55%, 25% and 60%, 25% and 65%, 25% and 70%, 25% and 75%, 25% and 80%, 25% and 85%, 25% and 90%, 25% and 95%, 30% and 35%, 30% and 40%, 30% and 45%, 30% and 50%, 30% and 55%, 30% and 60%, 30% and 65%, 30% and 70%, 30% and 75%, 30% and 80%, 30% and 85%, 30% and 90%, 30% and 95%, 35% and 40%, 35% and 45%, 35% and 50%, 35% and 55%, 35% and 60%, 35% and 65%, 35% and 70%, 35% and 75%, 35% and 80%, 35% and 85%, 35% and 90%, 35% and 95%, 40% and 45%, 40% and 50%, 40% and 55%, 40% and 60%, 40% and 65%, 40% and 70%, 40% and 75%, 40% and 80%, 40% and 85%, 40% and 90%, 40% and 95%, 45% and 50%, 45% and 55%, 45% and 60%, 45% and 65%, 45% and 70%, 45% and 75%, 45% and 80%, 45% and 85%, 45% and 90%, 45% and 95%, 50% and 55%, 50% and 60%, 50% and 65%, 50% and 70%, 50% and 75%, 50% and 80%, 50% and 85%, 50% and 90%, 50% and 95%, 55% and 60%, 55% and 65%, 55% and 70%, 55% and 75%, 55% and 80%, 55% and 85%, 55% and 90%, 55% and 95%, 60% and 65%, 60% and 70%, 60% and 75%, 60% and 80%, 60% and 85%, 60% and 90%, 60% and 95%, 65% and 70%, 65% and 75%, 65% and 80%, 65% and 85%, 65% and 90%, 65% and 95%, 70% and 75%, 70% and 80%, 70% and 85%, 70% and 90%, 70% and 95%, 75% and 80%, 75% and 85%, 75% and 90%, 75% and 95%, 80% and 85%, 80% and 90%, 80% and 95%, 85% and 90%, 85% and 95% and 90% and 95% dimer, by weight, of the composition. Generally, the compositions contain less than 95 wt % dimer, such as less than 65% with the rest of the composition monomer and up to about 5%, generally 1-3%, contaminants as described above. For example, the water-soluble vitamin E derivative mixtures (compositions) described herein contain at least or about at least 13%, 15%, 20%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, but less than 95% (wt %) total dimer.

The compositions described herein containing less than 70 wt % monomer and greater than 12 wt % dimer exhibit decreased turbidity values when dissolved in an aqueous solution, for example, when dissolved in water, as compared to typical known water-soluble vitamin E derivative mixtures (compositions), i.e., water-soluble vitamin E derivative mixtures (compositions) that contain more than 70 wt % monomer and less than 12 wt % dimer. The compositions described herein containing less than 70 wt % monomer and greater than 12 wt % dimer allow for the addition of a higher concentration of non-polar compounds when used in aqueous food and beverage products as compared to available aqueous food and beverage products, while maintaining clarity and stability, for example, exhibiting decreased turbidity values.

Exemplary of the compositions described herein are TPGS compositions containing less than 70 wt % TPGS monomer and more than 12 wt % TPGS dimer, such as compositions containing between or about between 25 wt % and 69 wt % TPGS monomer and between or about between 13 wt % and 95 wt % TPGS dimer, such as TPGS compositions containing between or about between 40 wt % and 60 wt % TPGS monomer and between or about between 25 wt % to 60 wt % TPGS dimer, are described herein. The compositions described herein containing less than 70 wt % TPGS monomer and greater than 12 wt % TPGS dimer exhibit decreased turbidity values when dissolved, for example, when dissolved in water, as compared to typical known TPGS compositions, i.e., TPGS compositions that contain more than 70 wt % TPGS monomer and less than 12 wt % TPGS dimer. The TPGS compositions described herein allow for the addition of a higher concentration of non-polar compounds when used in aqueous food and beverage products as compared to available aqueous food and beverage products, while maintaining clarity and stability, for example, exhibiting decreased turbidity values.

The water-soluble vitamin E derivative mixtures (compositions), e.g., TPGS compositions, described herein contain a mixture of monomer and dimer, e.g., a mixture of TPGS monomer and TPGS dimer. The monomer, for example, a TPGS monomer, can be present in an amount that is less than what is typically found in known water-soluble vitamin E derivative mixtures (compositions), e.g., known TPGS compositions, i.e., less than 70 wt % monomer. The dimer, for example, a TPGS dimer, can be present in an amount that is greater than what is typically found in known water-soluble vitamin E derivative mixtures (compositions), e.g., known TPGS compositions, i.e., greater than 12 wt % dimer. The water-soluble vitamin E derivative mixtures (compositions), such as the TPGS compositions, described herein can also contain other components, such as, for example, unreacted PEG, unreacted vitamin E, e.g., D-α-tocopheryl succinate, and one or more catalysts.

Methods for preparing the water-soluble vitamin E derivative mixtures (compositions), such as the TPGS compositions described herein, are described herein, for example, methods of preparing water-soluble vitamin E derivative composition, such as TPGS compositions, that contain less than 70 wt % TPGS monomer and more than 12 wt % TPGS dimer. Any known method for preparing derivatives of vitamin E can be employed, except that the methods are modified to produce higher concentrations of dimer by modifying reaction conditions. Such modifications can be determined empirically if needed, such as by varying reaction parameters, such as time, temperature and reactant concentrations to identify conditions that favor higher levels of dimer production.

The water-soluble vitamin E derivative mixtures e.g., TPGS monomer-dimer mixtures, prepared according to the methods can contain between or about between 25 wt % and 69 wt % monomer, for example, at or about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 or 69 wt % monomer and between or about between 13 wt % and 95 wt % dimer, for example, at or about 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 89, 80, 81, 82, 83, 84, 85, 86, 87, 88, 89, 90, 91, 92, 93, 94 or 95 wt % dimer.

Exemplary of the water-soluble vitamin E derivative mixtures (compositions) described herein that contain a mixture of monomer and dimer, for example, TPGS compositions that contain a mixture of TPGS monomer and TPGS dimer, are compositions that contain between or about between 25 wt % and 69 wt % monomer and between or about between 13 wt % and 95 wt %, such as 29% to 55%, dimer. For example, the water-soluble vitamin E derivative mixtures can contain at or about at least 39.35 wt % monomer and at or about at least 35.56 wt % dimer; at or about 40.39 wt % monomer and at or about 54.90 wt % dimer; at or about 40.95 wt % monomer and at or about 53.15 wt % dimer; at or about 42.76 wt % monomer and at or about 51.10 wt % dimer; at or about 43.52 wt % monomer and at or about 49.80 wt % dimer; at or about 43.90 wt % monomer and at or about 53.90 wt % dimer; at or about 52.92 wt % monomer and at or about 33.70 wt % dimer; at or about 55.88 wt % monomer and at or about 29.27 wt % dimer; at or about 57.70 wt % monomer and at or about 40.40 wt % dimer; at or about 60.00 wt % monomer and at or about 38.10 wt % dimer; and at or about 70.90 wt % monomer and at or about 28.65 wt % dimer. Thus, described herein are water-soluble vitamin E derivative mixtures (compositions), such as TPGS compositions, that contain less monomer, i.e., less than 70 wt % monomer, such as between 25 wt % and 69 wt % monomer, and more dimer, i.e., more than 12 wt % dimer, such as between 13 wt % and 95% dimer, than typical commercial TPGS compositions, which are prepared to have mostly (greater than 87%) monomer.

The concentrates containing water-soluble vitamin E derivative mixtures, such as tocopheryl polyalkylene glycol derivative compositions, including TPGS compositions, described herein, allow for the solubilization of higher amounts of non-polar compounds, such as non-polar compounds containing non-polar active ingredients, in foods and beverages, particularly aqueous beverages to which the concentrate is added. Provided herein are pre-emulsion concentrates or liquid nanoemulsion concentrates and liquid dilution compositions and beverage compositions that contain the high dimer-containing water-soluble vitamin E derivative mixtures (compositions) described herein.

For example, these concentrates allow for the addition of non-polar compounds containing non-polar active ingredients to products suitable for human consumption in amounts between or between about 1 wt % and 75 wt %, such as between or between about 1% and 5%, 1% and 10%, 1% and 15%, 1% and 20%, 1% and 25%, 1% and 30%, 1% and 35%, 1% and 40%, 1% and 45%, 1% and 50%, 1% and 55%, 1% and 60%, 1% and 65%, 1% and 70%, 1% and 75%, 5% and 10%, 5% and 15%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 15%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 15% and 20%, 15% and25%, 15% and 30%, 15% and 35%, 15% and 40%, 15% and 45%, 15% and 50%, 15% and 55%, 15% and 60%, 15% and 65%, 15% and 70%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 25% and 30%, 25% and 35%, 25% and 40%, 25% and 45%, 25% and 50%, 25% and 55%, 25% and 60%, 25% and 65%, 25% and 70%, 25% and 75%, 30% and 35%, 30% and 40%, 30% and 45%, 30% and 50%, 30% and 55%, 30% and 60%, 30% and 65%, 30% and 70%, 30% and 75%, 35% and 40%, 35% and 45%, 35% and 50%, 35% and 55%, 35% and 60%, 35% and 65%, 35% and 70%, 35% and 75%, 40% and 45%, 40% and 50%, 40% and 55%, 40% and 60%, 40% and 65%, 40% and 70%, 40% and 75%, 45% and 50%, 45% and 55%, 45% and 60%, 45% and 65%, 45% and 70%, 45% and 75%, 50% and 55%, 50% and 60%, 50% and 65%, 50% and 69%, 55% and 60%, 55% and 65%, 55% and 70%, 55% and 75%, 60% and 65%, 60% and 70%, 60% and 75%, 65% and 70%, 65% and 75% and 70% and 75% non-polar compound, by weight, of the food or beverage product. Generally, the products contain less than 75 wt % non-polar compound. For example, the food and beverage products containing the water-soluble vitamin E derivative mixture, including the concentrates, provided herein contain at least or about at least 1%, 5%, 10%, 15%, 20%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, but less than 75% (wt %) total non-polar compound.

C. Methods For Making Water-Soluble Vitamin E Derivatives

The water-soluble vitamin E derivative mixtures (compositions) with higher amounts of dimer can be prepared by modification of methods that compositions with higher amounts of monomer and lower amounts of dimer are prepared by, appropriately varying reaction conditions to favor increased dimer formation. Alternatively, standard known methods can be employed and the dimers purified or partially purified and added to compositions to increase the percentage of dimer to a desired level.

For example, for production of compositions with higher amounts of TPGS dimer, the methods employ the use of vitamin E succinate, e.g., D-α-tocopheryl succinate, as a starting material. Methods that use vitamin E, e.g., tocopherol or tocotrienol, and succinic acid or succinic anhydride as the starting materials (to synthesize vitamin E succinate) also can be used to prepare the water-soluble vitamin E derivative mixtures (compositions) described herein. The methods can be adapted for production of any desired water-soluble vitamin E derivative composition that contains the higher amounts of dimer.

As noted, these water-soluble vitamin E derivative mixtures (compositions) exhibit decreased turbidity values as compared to known water-soluble vitamin E derivative mixtures (compositions), such as known TPGS compositions, when dissolved, such as, for example, when dissolved in water or other aqueous beverage. Thus, the described methods are advantageous over existing prior art methods of preparing TPGS compositions that exhibit high turbidity values, e.g., higher than 80 NTUs, when dissolved, such as when dissolved in water.

Water-soluble vitamin E derivatives, such as TPGS, can be prepared by esterifying vitamin E succinate, for example, D-α-tocopheryl acid succinate, with polyethylene glycol. The resulting vitamin E TPGS has a chemical formula of $C_{33}O_5H_{54}(CH_2CH_2O)_n$, where "n" represents the number of polyethylene oxide moieties attached to the acid group of the vitamin E succinate. In an exemplary embodiment, the method includes preparing a crude water-soluble vitamin E, e.g., TPGS, composition by first preparing a reaction mixture containing vitamin E succinate, a polyethylene glycol (PEG) and optionally, a catalyst, in a solvent and heating the reaction mixture to an elevated temperature to produce a crude water-soluble vitamin E, e.g., TPGS, composition containing less TPGS monomer and more TPGS dimer than what is typically found in known TPGS compositions, i.e., less than 70 wt % TPGS monomer and more than 12 wt % TPGS dimer. The crude water-soluble vitamin E, e.g., TPGS, composition then can be purified and concentrated to obtain a purified water-soluble vitamin E, e.g., TPGS, composition containing less TPGS monomer and more TPGS dimer than what is typically found in known TPGS compositions, i.e., less than 70 wt % TPGS monomer and more than 12 wt % TPGS dimer. Any purification process known in the art can be used to purify the reaction product.

1. Reaction Mixture

The methods include preparing a crude water-soluble vitamin E derivative mixture, such as a crude TPGS composition, by esterifying vitamin E succinate with polyethylene glycol in a solvent. The esterification procedure can be promoted by a catalyst, for example, an esterification catalyst. In the methods, the crude composition can be prepared from a reaction mixture containing vitamin E succinate, a polyethylene glycol (PEG), a solvent and optionally, a catalyst. The components of the reaction mixture can be added in any order. In an exemplary embodiment, the polyethylene glycol is dissolved in the solvent before the addition of vitamin E succinate and the catalyst.

The methods produce a crude water-soluble vitamin E derivative mixture, such as a crude TPGS composition, that contains less TPGS monomer and more TPGS dimer than what is typically found in known TPGS compositions, i.e., less than 70 wt % TPGS monomer and more than 12 wt % TPGS dimer. In some instances the crude TPGS composition contains between or about between 25 wt % and 69 wt % TPGS monomer and between or about between 13 wt % and 95 wt % TPGS dimer, such as between or about between 40 wt % and 60 wt % TPGS monomer and between or about between 25 wt % to 60 wt % TPGS dimer.

a. Vitamin E Succinate

The reaction mixtures of the methods contain vitamin E succinate, for example, D-α-tocopheryl succinate. Vitamin E succinate can be purchased from suppliers such as Sigma-Aldrich (St. Louis, Mo.), Parchem (New Rochelle, N.Y.), Fisher Scientific (Fair Lawn, N.J.), and VWR International (Radnor, Pa.) or can be synthesized according to methods known to those of skill in the art. Typically, vitamin E succinate can be synthesized by reacting vitamin E (i.e., D-α-tocopherol) with succinic anhydride in a solvent (e.g., toluene) in the presence of a base (e.g., triethylamine) (see, for example, U.S. Patent Pub. Nos. 2011/0130562 and 2011/0184194; Lipshutz et al. (2011) J. Org. Chem. 76(11):4379-4391; Gelo-Pujic et al. (2008) Int. J. Cosmet. Sci. 30(3):195-204; and Vraka et al. (2006) Bioorg. Med. Chem. 14(8):2684-2696).

In the methods, the total amount of vitamin E succinate in the reaction mixture as a percentage (%), by weight, of the reaction mixture (wt %) can be, e.g., from at or about 0.1% to at or about 15%, such as 0.1% to 1%, 0.1% to 3%, 0.1% to 5%, 0.1% to 10%, 0.1% to 15%, 0.5% to 1%, 0.5% to 3%, 0.5% to 5%, 0.5% to 10%, 0.5% to 15%, 1% to 3%, 1% to 5%, 1% to 10%, 1% to 15%, 3% to 5%, 3% to 10%, 3% to 15%, 5% to 10%, 5% to 15%, or 10% to 15%, by weight, of the reaction mixture. Generally, the reaction mixtures contain less than 15 wt % vitamin E succinate. For example, the reaction mixtures described herein contain up to at or about 1%, 2%, 3%, 4%, 5%, 6%, 7%, 8%, 9%, 10%, 11%, 12%, 13%, 14% or 15% vitamin E succinate. Generally, the reaction mixtures described herein contain less than 15% (wt %) total vitamin E succinate.

b. Polyethylene Glycol

In the methods, the reaction mixtures include any polyethylene glycol that can react with the acid moiety of vitamin E succinate to form an ester. The polyethylene glycol can include, for example, any polyethylene glycol that gives the desired molecular weight of the water-soluble vitamin E compound, the desired polyethylene glycol chain length of the water-soluble vitamin E compound or the desired amount of water-soluble vitamin E water-solubility. The polyethylene glycol in the reaction mixtures of the methods can include, for example, any polyethylene glycol that is capable of forming an ester when reacted with vitamin E succinate to produce a vitamin E derivative that is water-soluble. For example, the polyethylene glycol can include PEG-OH, PEG-SH, PEG-$NH_2$ and branched PEGs. Typically, the polyethylene glycol is PEG-OH. The resulting water-soluble vitamin E product, for example, TPGS, formed by the reaction between vitamin E succinate and a polyethylene glycol contains at least polyethylene glycol esters of vitamin E succinate. The esters can be a mixture of esters, such as a mixture of TPGS monomer and TPGS dimer.

The polyethylene glycols in the reaction mixtures of the methods can be any molecular weight, for example, any molecular weight that renders vitamin E succinate water-soluble after esterification with the polyethylene glycol (i.e., the resulting TPGS is water-soluble). Such polyethylene glycols are known in the art and can be purchased from suppliers such as Sigma-Aldrich (St. Louis, Mo.), Fisher Scientific (Fair Lawn, N.J.), and VWR International (Radnor, Pa.). The polyethylene glycol can be added to the reaction mixture by any method suitable for transferring the PEG to the reaction mixture. For example, the PEG can be transferred to the reaction mixture in molten form.

Suitable polyethylene glycols for use in the methods include polyethylene glycols having an average molecular weight ranging from between or between about 100 Daltons (Da) and 20,000 Da. For example, the average molecular weight can be between or between about 200 Da and 10,000 Da, or 400 Da and 5,000 Da, or 500 Da and 1500 Da, or 750 Da and 1200 Da, or 1000 Da and 2,500 Da. Generally, the molecular weight of the polyethylene glycol is less than 20,000 Da. For example, the average molecular weight of the polyethylene glycol used in the reaction mixtures described herein can be or can be about 100, 200, 238, 300, 400, 500, 600, 750, 800, 1000, 1200, 1500, 2000, 2500, 3000, 3400, 3500, 4000, 6000, 8000, 10,000, or 12,000 Da, but less than 20,000 Da.

Exemplary polyethylene glycols include PEG 100 (where 100 represents the PEG chain molecular weight), PEG 200, PEG 238, PEG 300, PEG 400, PEG 500, PEG 600, PEG 750, PEG 800, PEG 1000, PEG 1200, PEG 1500, PEG 2000, PEG 2500, PEG 3000, PEG 3400, PEG 3500, PEG 4000, PEG 6000, PEG 8000, PEG 10,000, PEG 12,000 or PEG 20,000. Any other suitable polyethylene glycol known to those of skill in the art also can be used in the methods. In some embodiments described herein, the polyethylene glycol is PEG 1000.

In the methods, the total amount of PEG in the reaction mixture as a percentage (%), by weight, of the reaction mixture (wt %) can be, e.g., from at or about 1% to at or about 50%, such as 1% to 5%, 5% to 10%, 5% to 15%, 5% to 20%, 5% to 25%, 5% to 30%, 5% to 35%, 5% to 40%, 5% to 45%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 40%, 20% to 50%, 25% to 50%, or 30% to 50%, by weight, of the reaction mixture. Generally, the reaction mixtures contain less than 50 wt % PEG. For example, the reaction mixtures described herein contain at least or about at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, but less than 50% (wt %) total PEG.

c. Catalyst

The reaction mixtures of the methods can optionally contain a catalyst. Suitable catalysts include those catalysts that can be used to promote the esterification reaction between the PEG and the acid moiety of vitamin E succinate. Exemplary catalysts include acidic catalysts, such as p-toluenesulfonic acid, oxalic acid, hydrochloric acid, trichloroacetic acid, and any other known catalyst that can promote esterification.

In the reaction mixtures of the methods, the total amount of catalyst, as a percentage (%), by weight, of the reaction mixture (wt %) can be, e.g., from at or about 0% to at or about 15%, such as 0.01% to 0.05%, 0.01% to 0.1%, 0.01% to 0.5%, 0.01% to 0.75%, 0.01% to 1%, 0.01% to 3%, 0.01% to 5%, 0.01% to 10%, 0.01% to 15%, 0.01% to 0.5%, 0.01% to 0.75%, 0.01% to 1%, 0.01% to 3%, 0.01% to 5%, 0.01% to 10%, 0.01% to 15%, 0.05% to 0.1%, 0.05% to 0.5%, 0.05% to 0.75%, 0.05% to 1%, 0.05% to 3%, 0.05% to 5%, 0.05% to 10%, 0.05% to 15%, 0.05% to 0.5%, 0.05% to 0.75%, 0.05% to 1%, 0.05% to 3%, 0.05% to 5%, 0.05% to 10%, 0.05% to 15%, 0.1% to 0.5%, 0.1% to 0.75%, 0.1% to 1%, 0.1% to 3%, 0.1% to 5%, 0.1% to 10%, 0.1% to 15%, 0.5% to 0.75%, 0.5% to 1%, 0.5% to 3%, 0.5% to 5%, 0.5% to 10%, 0.5% to 15%, 1% to 3%, 1% to 5%, 1% to 10%, 1% to 15%, 3% to 5%, 3% to 10%, 3% to 15%, 5% to 10%, 5% to 15%, 10% to 15%, by weight, of the reaction mixture. Generally, the reaction mixtures contain less than 15 wt % catalyst. For example, the reaction mixtures described herein can contain up to at or about 1%, 2%, 3%, 4%, 5%, 6%, 7%, 8%, 9%, 10%, 11%, 12%, 13%, 14% or 15% catalyst, based on the weight of the reaction mixture.

d. Solvent

The reaction mixtures of the methods include a solvent or combination of solvents. Suitable solvents include those that do not prevent the esterification reaction between the PEG and acid moiety of vitamin E succinate from taking place. For example, the solvent or combination of solvents can be aprotic solvents.

Suitable solvents used in the methods include solvents that are inert to the reaction and are aprotic, for example, solvents that lack an acidic hydrogen, such as toluene, xylenes, ethers such as tetrahydrofuran (THF), diethyl ether and dioxane, ethyl acetate, acetone, dimethylformamide (DMF), N,N-dimethylacetamide, acetonitrile, methyl ethyl ketone (MEK), methyl isobutyl ketone (MIBK), dimethyl sulfoxide (DMSO), ethyleneglycol dimethylether, hexanes, cyclohexane, pentane, cyclopentane and any combination thereof. An exemplary solvent used in the reaction mixtures of the methods is toluene.

In the reaction mixtures of the methods, the total amount of solvent as a percentage (%), by weight, of the reaction mixture (wt %) can be, e.g., from at or about 60% to at or about 95%, such as 60% to 65%, 60% to 70%, 60% to 75%, 60% to 80%, 60% to 85%, 60% to 90%, 60% to 95%, 65% to 70%, 65% to 75%, 65% to 80%, 65% to 85%, 65% to 90%, 65% to 95%, 70% to 75%, 70% to 80%, 70% to 85%, 70% to 90%, 70% to 95%, 75% to 80%, 75% to 85%, 75% to 90%, 75% to 95%, 80% to 85%, 80% to 90%, 80% to 95%, 85% to 90%, 85% to 95% and 90% to 95%, by weight, of the reaction mixture. Generally, the reaction mixtures contain less than 95 wt % solvent. For example, the reaction mixtures can contain at least or about at least 60%, 65%, 70%, 75%, 80%, 85%, 90%, but less than 95% (wt %) total solvent.

e. Exemplary Reaction Mixtures

Exemplary reaction mixtures that can be used in the methods to ultimately produce a water-soluble vitamin E derivative mixture, for example, a TPGS composition, that contains less TPGS monomer and more TPGS dimer than what is typically manufactured, i.e., less than 70 wt % TPGS monomer and more than 12 wt % TPGS dimer are described. They are exemplified with TPGS, but similar reaction mixtures can be prepared and reactions performed to produce tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol and tocopherol phthalate polyethylene glycol, TPGS analogs and TPGS homologs.

The reaction mixtures exemplified herein include vitamin E succinate, a polyethylene glycol, a solvent, and optionally, a catalyst. Exemplary of such reaction mixtures contain from at or about 0.1 wt % to at or about 15 wt % of vitamin E succinate; a polyethylene glycol, in an amount from at or about 1 wt % to at or about 50 wt %; a catalyst, in an amount from at or about 0.01 wt % to at or about 15 wt %; and from at or about 60% to at or about 95% of a solvent.

In some embodiments, the polyethylene glycol can be a polyethylene glycol with a molecular weight of around 1000 Da, for example, PEG 1000. For example, the exemplary reaction mixtures described herein can contain from at or about 0.1 wt % to at or about 15 wt % of vitamin E succinate; from at or about 1 wt % to at or about 50 wt % of a polyethylene glycol, for example, PEG 1000; from at or about 0.01 wt % to at or about 15 wt % of a catalyst, for example, p-toluenesulfonic acid; and from at or about 60% to at or about 95% of a solvent, for example, toluene.

2. Exemplary Methods

The methods include preparing a reaction mixture containing vitamin E succinate, a polyethylene glycol and optionally, a catalyst, in a solvent; heating the reaction mixture to a temperature equal to or higher than the boiling point of the solvent to form a crude water-soluble vitamin E derivative mixture; processing the reaction mixture to obtain the crude water-soluble vitamin E derivative mixture; and purifying the crude water-soluble vitamin E derivative mixture to obtain a purified water-soluble vitamin E derivative mixture. In particular, the methods use the exemplary reaction mixtures described above. The methods to synthesize water-soluble vitamin E derivative mixtures described herein result in water-soluble vitamin E derivative mixtures, such as TPGS compositions, that are less turbid than known water-soluble vitamin E derivative mixtures, i.e., known compositions that contain more than 70% TPGS monomer and less than 12% TPGS dimer, when diluted in an aqueous medium, e.g., water.

The following methods are exemplary only and provide a platform from which adjustments can be made. It is understood that changes can be made to the steps of the method and to the reaction components while retaining some if not all of the desirable properties of the method. Further changes can be made by adding or altering steps or components of each step. For example, the order in which the steps are performed can be changed.

a. Preparation of Crude Water-Soluble Vitamin E Derivative Mixtures (Compositions)

Exemplary of the methods is preparation of a high dimer-containing mixture of TPGS. The methods can be employed to produce high dimer mixtures of any vitamin E derivative, including PEG derivatives of vitamin E. Exemplary of the methods is a method of preparing a crude water-soluble vitamin E derivative mixture, for example, a crude TPGS composition, by providing a reaction mixture containing vitamin E succinate, e.g. D-α-tocopheryl succinate, a polyethylene glycol, e.g., PEG 1000, a catalyst, e.g., p-toluenesulfonic acid, and a solvent, e.g., toluene, heating the reaction mixture to a temperature of at least or about at least 110° C. and maintaining the elevated temperature for a period of up to at or about 6.5 hours before cooling, for example, to room temperature, i.e., at or about 20° C., and washing the reaction mixture with an aqueous solution of a weak base, e.g., a 10% aqueous solution of sodium bicarbonate.

A crude water-soluble vitamin E derivative mixture is prepared by providing a reaction mixture containing vitamin E succinate, a polyethylene glycol and optionally, a catalyst, in a solvent and heating the reaction mixture from room temperature, i.e., at or about 20° C., to an elevated temperature, and maintaining the elevated temperature for a period of time until a crude water-soluble vitamin E derivative mixture, for example, a crude TPGS composition, is formed that contains the desired amounts of TPGS monomer and TPGS dimer. The elevated temperature can be any temperature in the range of from 30° C. to about 300° C., generally between 80° C. and 250° C., such as between 100° C. and 200° C. The elevated temperature can be, for example, the boiling point of the solvent in the reaction mixture. A typical heating schedule can be heating the reaction mixture to a temperature of at least or about at least 110° C. with stirring, and once achieved, the elevated temperature, e.g., at least or about at least 110° C., is maintained for a total time of up to at or about 6.5 hours with stirring. Other heating temperatures and times can be used depending on the substrates, solvent and formation of the desired crude water-soluble vitamin E derivative mixture. For example, the total time the elevated temperature is maintained can be at least at or about 1 hour, at least at or about 1.5 hours, at least at or about 2 hours, at least at or about 2.5 hours, at least at or about 3 hours, at least at or about 3.5 hours, at least at or about 4 hours, at least at or about 4.5 hours, at least at or about 5 hours, at least at or about 5.5 hours, at least at or about 6 hours, or at least at or about 6.5 hours or longer, before cooling.

After the elevated temperature has been maintained for the desired amount of time, e.g., the amount of time required to produce the desired amounts of TPGS monomer and TPGS dimer, the reaction mixture can be cooled to a temperature lower than the elevated temperature. For example, the reaction mixture can be cooled to room temperature, i.e., at or about 20° C., after heating at an elevated temperature for the desired amount of time. The reaction mixture can be heated to at least or about at least 110° C. for a total time of about 6.5 hours before cooling, e.g., to room temperature (i.e., at or about 20° C.), depending on the substrates, solvent and formation of the crude water-soluble vitamin E derivative mixture, for example, a crude TPGS composition, resulting in the desired amounts of TPGS monomer and TPGS dimer. One of skill in the art can perform the methods and, if necessary, empirically determine the appropriate reaction duration to produce the desired ratio of dimer to monomer based on the formation of the desired amounts of TPGS monomer and TPGS dimer.

In the methods, the reaction mixture can be heated from room temperature (i.e., at or about 20° C.) to an elevated temperature of at least at or about 30° C., 40° C., 50° C., 60° C., 70° C., 80° C., 90° C., 100° C., 105° C., 110° C., 115° C., 120° C., 125° C., 130° C., 140° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., or higher. The reaction mixture can be maintained at a temperature elevated from room temperature for at least at or about 1 hour, 1.5 hours, 2 hours, 2.5 hours, 3 hours, 3.5 hours, 4 hours, 4.5 hours, 5 hours, 5.5 hours, 6 hours, 6.5 hours, or longer before cooling. In an exemplary method, the reaction mixture can be maintained at an elevated temperature for up to at or about 6.5 hours before cooling, e.g., to room temperature, i.e., at or about 20° C. The particular conditions depend upon the particular vitamin E derivative and the amount of monomer and dimer desired.

The amount of time that the reaction mixture is maintained at the temperature elevated from room temperature, for example, between or about between 30° C. and 300° C., such as the boiling point of the solvent in the reaction mixture, can be determined by monitoring the progress of reaction during heating. For example, the reaction mixture can be monitored during heating to determine the amounts of TPGS monomer and TPGS dimer present in the reaction mixture. The heating can then be terminated when the desired amounts of TPGS monomer and TPGS dimer are formed. The monitoring can be done by any method of monitoring a reaction known to those of skill in the art, such as by chromatography, spectroscopy or spectrometry. For example, the reaction can be monitored by thin layer chromatography (TLC), high performance liquid chromatography (HPLC), infrared spectroscopy (IR), Fourier transform infrared spectroscopy (FTIR), mass spectrometry (MS), nuclear magnetic resonance (NMR) spectroscopy, or any combination thereof. In some embodiments of the methods, the reaction progress is monitored by TLC. In other embodiments, the reaction progress is monitored by HPLC. In yet other embodiments, the reaction progress is monitored by both TLC and HPLC. One of skill in the art can, if necessary, determine particular parameters empirically, such as appropriate reaction duration based on monitoring the formation of the desired amounts of vitamin E derivative monomer and dimer, such as TPGS monomer and TPGS dimer.

The reaction mixture of the methods can be heated to an elevated temperature under an inert gas atmosphere, such as a nitrogen gas or argon gas atmosphere, or under air. The reaction mixture of the methods can be heated to an elevated temperature at atmospheric pressure or at an elevated pressure, i.e., a pressure higher than atmospheric pressure. The elevated pressure can be achieved, e.g., by performing the reaction in a closed vessel or in a vented vessel.

The progress of the reaction can be terminated after heating for the desired amount of time, for example, up to at or about 6.5 hours, by cooling the reaction mixture, for example, to room temperature, i.e., at or about 20° C. After cooling, such as cooling to room temperature, i.e., at or about 20° C., the reaction mixture can be washed with an aqueous solution. The aqueous solution can be an aqueous solution of base, such as a weak base, i.e., bases that do not fully ionize in an aqueous solution. Suitable weak bases include, for example, carbonates or bicarbonates, e.g., sodium carbonate, sodium bicarbonate, potassium carbonate and potassium bicarbonate; amines, ammonias or ammoniums, e.g., methyl amine, methyl ethyl amine, dimethyl amine, aniline, ammonia, trimethyl ammonia and ammonium hydroxide; and pyridine. For example, the aqueous solution of base can be an aqueous solution of sodium bicarbonate. Suitable aqueous solutions of the weak base include solutions that contain, e.g., 1% to 20% weak base, such as at least or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, or more weak base. For example, the aqueous solution can be an aqueous solution containing at or about 10% sodium bicarbonate. After the aqueous solution of a weak base has been added to the reaction mixture, the aqueous solution can be separated from the reaction mixture, such as by allowing the reaction mixture and aqueous solution of weak base to separate into layers, and removed. In some embodiments, the reaction mixture and aqueous solution of weak base can be stirred for a period of time before separating. For example, the reaction mixture and aqueous solution can be stirred for 1 minute, 2 minutes, 3 minutes, 4 minutes, 5 minutes, 6 minutes, 7 minutes, 8 minutes, 9 minutes, 10 minutes, 15 minutes, 20 minutes, or more, before allowing the reaction mixture and aqueous solution of weak base to separate into layers.

b. Processing the Reaction Mixture to Obtain a Crude Water-Soluble Vitamin E Derivative Mixture After preparing the reaction mixture, the reaction mixture can be further processed in order to obtain a crude water-soluble vitamin E mixture, for example, a crude TPGS composition that contains less TPGS monomer, i.e., less than 70 wt %, and more TPGS dimer, i.e., more than 12 wt %, than known water-soluble vitamin E derivative mixtures. The further processing can be performed to remove impurities from the reaction mixture before obtaining the crude water-soluble vitamin E derivative mixture. The further processing can be performed in order to isolate the crude water-soluble vitamin E derivative mixture from the reaction mixture. For example, the reaction mixture can be further processed by treating the reaction mixture with an adsorbent, such as activated charcoal (i.e., activated carbon). Activated charcoal can be used as a decolorizer and to remove impurities by chemical adsorption. Any activated charcoal known to those of skill in the art can be used to treat the reaction mixture. Such activated charcoal is available from commercial sources under such trade names as Calgon-Type CPG®, Type PCB®, Type SGL®, Type CAL®, and Type OL®.

Further processing of the reaction mixture, for example, treating the reaction mixture with activated charcoal, can take place for a period of time of from at or about 0.5 hours to at or about 5 hours, or longer if required. For example, treating the reaction mixture with activated charcoal can take place for at least or about at least 0.5 hours, 1 hour, 1.5 hours, 2 hours, 3 hours, 4 hours, 5 hours, or longer. The further processing, for example, treating the reaction mixture with activated charcoal, can be done at any temperature of from at or about room temperature, i.e., at or about 20° C., to a temperature elevated from room temperature. For example, the temperature of the process, e.g., activated charcoal treatment, can be at or about 20° C., 30° C., 40° C., 50° C., 55° C., 60° C., 70° C., 80° C., 90° C., or 100° C., or any temperature between 20° C. and 100° C., such as between or about between 55° C. and 60° C. The treatment temperatures and times can be varied depending on the reaction mixture, the solvent, and the impurities present in the reaction mixture. In an exemplary process, such as an activated charcoal treatment process, the reaction mixture can be treated, e.g., with activate charcoal, for at least or about at least 1 hour at a temperature of between or about between 55° C. and 60° C., before cooling.

In the methods, the reaction mixture can be filtered and washed after cooling, such as cooling to room temperature, i.e., at or about 20° C., after further processing, such as after treating the reaction mixture with activated charcoal. The reaction mixture can be filtered and washed, for example, to remove the activated charcoal from the reaction mixture. For example, the reaction mixture can be filtered through a filter aid, such as diatomaceous earth. Suitable filter aids for use in the methods include, for example, those sold under the trademark Celite®, such as those sold under the trademark Hyflo®. After filtering through a filter aid, such as diatomaceous earth, the reaction mixture can be washed, for example, with the same solvent used in the reaction mixture. In an exemplary embodiment, after further processing, e.g., treatment with activated charcoal, and cooling, e.g., to room temperature, i.e., at or about 20° C., the reaction mixture is filtered through diatomaceous earth, e.g., Hyflo® filter aid, and washed with solvent, e.g., toluene.

In the methods, the reaction mixture can be further processed in order to isolate the crude water-soluble vitamin E derivative mixture from the reaction mixture. For example, the reaction mixture can be further processed by removing the solvent from the reaction mixture, i.e., concentrating the reaction mixture, in order to obtain a crude water-soluble vitamin E derivative mixture. Any method of removing a solvent from a reaction mixture known to those of skill in the art can be used, including, for example, vacuum distillation, rotary evaporation and filtration. Removing the solvent from the reaction mixture can be done at any temperature, for example at room temperature, i.e., 20° C., or at a temperature elevated from room temperature. For example, the solvent can be removed at a temperature of at or about 20° C., 30° C., 40° C., 50° C., 55° C., 60° C., 70° C., 80° C., or 90° C., but below or about below 100° C., such as below or about below 60° C. In an exemplary embodiment, the solvent can be removed from the reaction mixture by distillation, e.g., vacuum distillation, at a temperature elevated from room temperature, i.e., at or about 20° C., but below or about below 60° C.

Further processing of the reaction mixture of the methods can include further processing by treating the reaction mixture to remove impurities from the reaction mixture, such as by treating the reaction mixture with activated charcoal. Further processing of the reaction mixture of the methods can include further processing by removing the solvent from the reaction mixture, such as by removing the solvent by vacuum distillation. The further processing can include treating the reaction mixture with activated charcoal or removing the solvent from the reaction mixture or both. In an exemplary method, the further processing of the reaction mixture includes removing the impurities from the reaction mixture, e.g., treating the reaction mixture with activated charcoal, and removing the solvent from the reaction mixture, e.g., removing the solvent by vacuum distillation, in order to obtain a crude water-soluble vitamin E derivative mixture, for example, a crude TPGS composition, containing less TPGS monomer, i.e., less than 70 wt %, and more TPGS dimer, i.e., more than 12 wt %, than in known TPGS compositions.

c. Purification of the Crude Water-Soluble Vitamin E Derivative Mixture to Obtain a Purified High Dimer Water-Soluble Vitamin E Derivative Mixture The crude water-soluble vitamin E derivative mixture obtained after further processing can be further purified in order to obtain a purified high dimer water-soluble vitamin E derivative mixture. For example, the purified water-soluble vitamin E derivative mixture can be a PEG-derivative of vitamin E, such as TPGS, PTS, PTD and other TPGS analogs and PEG-derivatives of vitamin E, mixture. The mixture contains less TPGS monomer, i.e., less than 70 wt %, and more TPGS dimer, i.e., more than 12, 19, 24, or 29 wt % dimer. The purification process removes impurities from the crude water-soluble vitamin E derivative mixture, such as impurities that were not removed by further processing of the reaction mixture. For example, the crude water-soluble vitamin E derivative mixture can be purified by performing one or more wash, i.e., extraction, steps. The wash can be performed using more than one solvent, such as more than one organic solvent, for example, two organic solvents that are not miscible with each other. For example, in the methods, the crude water-soluble vitamin E derivative mixture can be dissolved in a first solvent, for example, a polar solvent, such as an alcohol, and can be washed with a second solvent, for example, a non-polar solvent, such as a hydrocarbon solvent that is not miscible with the first solvent. The purification process, e.g., the wash, can be performed one time, two times, three times, four times, or more, depending on the desired purity level of the water-soluble vitamin E derivative mixture and the amount of impurities present. For example, the purification process, e.g., the wash, can be performed one or more times on the crude water-soluble vitamin E derivative mixture, e.g., after the crude water-soluble vitamin E derivative mixture is obtained after processing. In an exemplary method, the purification process can be performed three or more times on the crude water-soluble vitamin E derivative mixture after the further processing is complete.

The purification process, i.e., the wash, can be performed by dissolving the crude water-soluble vitamin E derivative mixture in a first solvent, for example, an organic solvent, such as a polar organic solvent. The polar organic solvent can be any solvent that can dissolve the crude water-soluble vitamin E derivative mixture, such as a polar protic solvent, for example, an alcohol, e.g., methanol, ethanol, propanol or butanol. In the methods, the amount of first solvent, e.g., polar organic solvent, used to dissolve the crude water-soluble vitamin E derivative mixture can be based on the ratio of the volume of the first solvent to the volume of the crude water-soluble vitamin E derivative mixture. The ratio of the volume of the first solvent to the volume of the crude water-soluble vitamin E derivative mixture can range from 0.1:1 to 10:1. In some embodiments, the ratio of the volume of the first solvent to the volume of the crude TPGS composition is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the volume of the first solvent to the volume of the crude water-soluble vitamin E derivative mixture can be 2:1.

The wash can be performed using a second solvent, for example, an organic solvent, that is not miscible with the first solvent, i.e., the solvent used to dissolve the crude water-soluble vitamin E derivative mixture. The second solvent can be any solvent that is not miscible with the first solvent, for example, any solvent that is not miscible with a polar protic solvent such as an alcohol. Suitable organic solvents that can be used as a second solvent include non-polar organic solvents, such as hydrocarbons, e.g., alkanes and cycloalkanes, such as hexane and cyclohexane; halogenated hydrocarbons, e.g., chloroform and dichloromethane; ethers, e.g., diethyl ether; and aromatics, e.g., benzene and toluene. In the methods, the amount of second solvent, e.g., a non-polar organic solvent immiscible with the first solvent, used to wash the crude water-soluble vitamin E derivative mixture dissolved in the first solvent can be based on the ratio of the volume of the second solvent to the volume of the crude water-soluble vitamin E derivative mixture. The ratio of the volume of the second solvent to the volume of the crude water-soluble vitamin E derivative mixture can range from 0.1:1 to 10:1. In some embodiments, the ratio of the volume of second solvent to the volume of crude water-soluble vitamin E derivative mixture is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the volume of the second solvent to the volume of the crude water-soluble vitamin E derivative mixture can be 3:1.

The purification process of the methods, for example, a wash with organic solvent, can be performed one or more times on the crude water-soluble vitamin E derivative mixture, for example, two times, three times, four times, or more. The wash can be performed while stirring. In an exemplary method, the crude water-soluble vitamin E derivative mixture can be dissolved in a first solvent, for example, a protic polar organic solvent, e.g., an alcohol, and washed three or more times with a second solvent, for example, a non-polar organic solvent not miscible in the first solvent, e.g., a hydrocarbon.

Exemplary of the methods is a method of purifying a crude water-soluble vitamin E derivative mixture by performing a purification process, such as a wash with an organic solvent, e.g., by dissolving the crude water-soluble vitamin E derivative mixture in methanol and washing with cyclohexane, and repeating the wash with the cyclohexane three or more times.

The crude water-soluble vitamin E derivative mixture can be further purified in order to obtain a purified water-soluble vitamin E derivative mixture, for example, a purified TPGS composition. The purified water-soluble vitamin E derivative mixture can be a purified TPGS composition that contains less TPGS monomer, i.e., less than 70 wt %, and more TPGS dimer, i.e., more than 12 wt %, than known TPGS compositions. The further purification can be performed to remove impurities from the crude water-soluble vitamin E derivative mixture. The further purification can be performed in order to isolate the purified water-soluble vitamin E derivative mixture from the first solvent. For example, the crude water-soluble vitamin E derivative mixture can be further purified by treating the crude water-soluble vitamin E derivative mixture with an adsorbent, such as activated charcoal (i.e., activated carbon). Activated charcoal can be used as a decolorizer and to remove impurities by chemical adsorption. Any activated charcoal known to those of skill in the art can be used to treat the crude water-soluble vitamin E derivative mixture. Such activated charcoal is available from commercial sources under such trade names as Calgon-Type CPG®, Type PCB®, Type SGL®, Type CAL®, and Type OL®.

Further purification of the crude water-soluble vitamin E derivative mixture, for example, treating the crude water-soluble vitamin E derivative mixture with activated charcoal, can take place for a period of time of from at or about 0.5 hours to at or about 5 hours, or longer if required. The crude water-soluble vitamin E derivative mixture to be treated can be dissolved in a solvent, for example, the first solvent used in the wash described above. Additional solvent can be added, for example, the same solvent used to dissolve the crude water-soluble vitamin E derivative mixture during the wash, e.g., a polar protic organic solvent. In the methods, the amount of additional solvent, e.g., polar protic organic solvent, added to the crude water-soluble vitamin E derivative mixture can be based on the ratio of the total volume of the solvent, e.g., the first solvent, such as a polar protic organic solvent, plus the additional solvent, to the volume of the crude water-soluble vitamin E derivative mixture. The ratio of the total volume of the first solvent plus the additional solvent to the volume of the crude TPGS composition can range from 0.1:1 to 10:1. In some embodiments, the ratio of the volume of total solvent to the volume of crude water-soluble vitamin E derivative mixture is or is about 0.1:1, 0.2:1, 0.25:1, 0.3:1, 0.4:1, 0.45:1, 0.5:1, 0.6:1, 0.7:1, 0.75:1, 0.8:1, 0.9:1, 1:1, 1.2:1, 1.25:1, 1.3:1, 1.4:1, 1.5:1, 1.6:1, 1.7:1, 1.75:1, 1.8:1, 1.9:1, 2:1, 2.5:1, 3:1, 3.5:1, 3.6:1, 4:1, 4.5:1, 5:1, 5.5:1, 6:1, 6.5:1, 7:1, 7.5:1, 8:1, 8.5:1, 9:1, 9.5:1, or 10:1 or more. For example, the ratio of the total volume of the first solvent plus additional solvent to the volume of the crude water-soluble vitamin E derivative mixture can be 5:1.

In the methods, further purification, such as treating the reaction mixture with, for example, activated charcoal, can take place for at least or about at least 0.5 hours, 1 hour, 1.5 hours, 2 hours, 3 hours, 4 hours, 5 hours, or longer. The further purification, for example, treating the reaction mixture with activated charcoal, can be done at any temperature of from at or about room temperature, i.e., at or about 20° C., to a temperature elevated from room temperature. For example, the temperature of the purification process, e.g., activated charcoal treatment, can be at or about 20° C., 30° C., 40° C., 50° C., 55° C., 60° C., 70° C., 80° C., 90° C., or 100° C., or any temperature between 20° C. and 100° C., such as between or about between 55° C. and 60° C. The treatment temperatures and times can be varied depending on the nature of the crude water-soluble vitamin E derivative mixture, the solvent, and the impurities present in the crude water-soluble vitamin E derivative mixture. In an exemplary purification process, such as an activated charcoal treatment process, the crude water-soluble vitamin E derivative mixture can be treated, e.g., with activate charcoal, for at least or about at least 1 hour at a temperature of between or about between 55° C. and 60° C., before cooling.

In the methods, the crude water-soluble vitamin E derivative mixture can be filtered and washed after cooling, such as cooling to room temperature, i.e., at or about 20° C., after further purification, such as after treating the crude water-soluble vitamin E derivative mixture with activated charcoal. The crude water-soluble vitamin E derivative mixture, for example, the crude water-soluble vitamin E derivative mixture dissolved in a solvent, can be filtered and washed, for example, to remove the activated charcoal from the crude water-soluble vitamin E derivative mixture. For example, the crude water-soluble vitamin E derivative mixture, for example, the crude water-soluble vitamin E derivative mixture dissolved in a solvent, can be filtered through a filter aid, such as diatomaceous earth. Suitable filter aids for use in the methods include, for example, those sold under the trademarks Celite® and Hyflo®. After filtering through a filter aid, such as diatomaceous earth, the crude TPGS composition can be washed, for example, with the same solvent used to dissolve the crude water-soluble vitamin E derivative mixture, e.g., the first solvent. In an exemplary embodiment, after further purification, e.g., treatment with activated charcoal, and cooling, e.g., to room temperature, i.e., at or about 20° C., the crude water-soluble vitamin E derivative mixture is filtered through diatomaceous earth, e.g., Hyflo® filter aid and washed with solvent, e.g., methanol.

In the methods, the crude water-soluble vitamin E derivative mixture can be further purified in order to isolate the purified water-soluble vitamin E derivative mixture from the solvent, e.g., the first solvent. For example, the crude water-soluble vitamin E derivative mixture can be further purified by removing the solvent from the water-soluble vitamin E derivative mixture dissolved in solvent, i.e., concentrating the crude water-soluble vitamin E derivative mixture, in order to obtain a purified water-soluble vitamin E derivative mixture. Any method of removing a solvent from a composition known to those of skill in the art can be used, including, for example, vacuum distillation, rotary evaporation and filtration. Removing the solvent from the water-soluble vitamin E derivative mixture can be done at any temperature, for example at room temperature, i.e., 20° C., or at a temperature elevated from room temperature. For example, the solvent can be removed at a temperature of at or about 20° C., 30° C., 40° C., 50° C., 55° C., 60° C., 70° C., 80° C., or 90° C., but below or about below 100° C., such as below or about below 60° C. In an exemplary embodiment, the solvent can be removed from the crude water-soluble vitamin E derivative mixture by distillation, e.g., vacuum distillation, at a temperature elevated from room temperature, i.e., at or about 20° C., but below or about below 60° C. After removing the solvent, the purified water-soluble vitamin E derivative mixture can be dried by any method of drying known to those of skill in the art. Suitable methods of drying include drying under an inert gas, for example, nitrogen or argon, or drying under vacuum, or any combination thereof.

In exemplary embodiments of the methods, further purification of the crude water-soluble vitamin E derivative mixture produced by the methods can include further purification by treating the crude water-soluble vitamin E derivative mixture to remove impurities from the reaction mixture, such as by treating the crude water-soluble vitamin E derivative mixture with activated charcoal. Further purification of the crude water-soluble vitamin E derivative mixture produced by the methods can include further purification by removing the solvent from the crude water-soluble vitamin E derivative mixture, for example, a crude water-soluble vitamin E derivative mixture dissolved in a solvent, such as by removing the solvent by vacuum distillation. The further purification can include treating the crude water-soluble vitamin E derivative mixture with activated charcoal or removing the solvent from the crude water-soluble vitamin E derivative mixture or both. In an exemplary method, the further purification of the crude water-soluble vitamin E derivative mixture includes removing the impurities from the crude water-soluble vitamin E derivative mixture, e.g., treating the crude water-soluble vitamin E derivative mixture with activated charcoal, and removing the solvent from the crude water-soluble vitamin E derivative mixture, e.g., removing the solvent by vacuum distillation, in order to obtain a purified water-soluble vitamin E derivative mixture, for example, a purified TPGS composition. The purified TPGS composition can contain less TPGS monomer, i.e., less than 70 wt %, and more TPGS dimer, i.e., more than 12 wt %, than in known TPGS compositions.

The methods yield a purified water-soluble vitamin E derivative mixture, such as a purified TPGS composition, with the desired amount of dimer (greater than 12%) that can be used in any application where water-soluble vitamin E derivative mixtures are used, such as in food, beverage, pharmaceutical or nutraceutical products for human consumption, and particularly to prepare concentrates that contain the water-soluble vitamin E derivative composition and a non-polar ingredient(s) and other optional ingredients. For example, the methods produce a purified water-soluble vitamin E derivative mixture, such as a purified TPGS composition, for example, a TPGS composition that contains less TPGS monomer, i.e., less than 70 wt %, and more TPGS dimer, i.e., more than 12 wt %, than in known TPGS compositions, that can be used in products for human consumption, for example, food and beverage products, particularly aqueous food and beverage products, and any other application in which a water-soluble vitamin E derivative mixture can be added. Exemplary purified water-soluble vitamin E derivative mixtures (compositions) that can be prepared following the methods are those that contain less than 70 wt % monomer and more than 12 wt % dimer, such as such as compositions containing between or about between 25 wt % and 69 wt % monomer and between or about between 13 wt % and 95 wt % dimer, such as compositions containing between or about 40 wt % and 60 wt % monomer and between or about between 25 wt % to 60 wt % dimer. For example, the methods can be followed to obtain water-soluble vitamin E derivative mixtures (compositions) that contain between or about between 25 wt % and 69 wt % monomer, for example, at or about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 or 69 wt % monomer and between or about between 13 wt % and 95 wt % dimer, for example, at or about 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 wt % dimer.

These methods are described with reference to TPGS and can be adapted to produce any higher dimer-containing water-soluble vitamin E derivative composition. Other methods to produce compositions with the desired dimer concentration or dimer and monomer concentrations can be employed, including purifying the dimer from standard preparations and adding the dimer back to a standard preparation to increase its concentration. The resulting compositions are employed in the concentrates and dilution compositions described herein.

D. Products Containing High Dimer-Containing Water-Soluble Vitamin E Derivative Mixtures (Compositions)

Provided herein are products containing the high dimer-containing water-soluble vitamin E mixtures. These include, for example, products for human consumption, such as food and beverage products, in particular aqueous food and beverage products, and methods for making the products. In particular, provided are pre-emulsion concentrates, liquid nanoemulsion concentrates and liquid dilution (beverage) compositions containing the concentrates and other beverage compositions that contain the water-soluble vitamin E derivative mixtures (compositions) as described herein. Also provided are compositions for direct consumption in that the water-soluble vitamin E derivative mixture and other ingredients are present in amounts for direct ingestion. The water-soluble vitamin E derivative mixture is typically present in an amount less than 10%, generally in an amount of about 1% to 5%.

The compositions provided herein that contain the water-soluble vitamin E derivative mixtures described herein can contain non-polar compounds. Non-polar compounds are poorly water-soluble (e.g., have low water solubility or are water-insoluble). Thus, it generally can be difficult to formulate non-polar compounds into products for human consumption, particularly aqueous products, for example, food and beverage compositions. Poor water solubility of non-polar compounds also can contribute to their poor bioavailability. Improved methods and compositions for formulating food and beverage products containing non-polar compounds are provided herein. The products containing the water-soluble vitamin E derivative mixtures described herein can contain higher concentrations of non-polar compounds as compared to available food and beverage products. The products containing the water-soluble vitamin E derivative mixtures (compositions) can solubilize higher amounts of non-polar compounds than in products containing such water-soluble vitamin E with lower concentrations (i.e., less than 13%, 29%, 35%, 52%) of dimers. These resulting products retain desirable organoleptic properties, such as clarity (i.e., low turbidity). The products provided herein can contain high amounts of non-polar compounds, such as non-polar compounds that contain non-polar active ingredients, for example, between or between about 1 wt % and 75 wt % non-polar compound, such as between or between about 1% and 5%, 1% and 10%, 1% and 15%, 1% and 20%, 1% and 25%, 1% and 30%, 1% and 35%, 1% and 40%, 1% and 45%, 1% and 50%, 1% and 55%, 1% and 60%, 1% and 65%, 1% and 70%, 1% and 75%, 5% and 10%, 5% and 15%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 15%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 15% and 20%, 15% and 25%, 15% and 30%, 15% and 35%, 15% and 40%, 15% and 45%, 15% and 50%, 15% and 55%, 15% and 60%, 15% and 65%, 15% and 70%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 25% and 30%, 25% and 35%, 25% and 40%, 25% and 45%, 25% and 50%, 25% and 55%, 25% and 60%, 25% and 65%, 25% and 70%, 25% and 75%, 30% and 35%, 30% and 40%, 30% and 45%, 30% and 50%, 30% and 55%, 30% and 60%, 30% and 65%, 30% and 70%, 30% and 75%, 35% and 40%, 35% and 45%, 35% and 50%, 35% and 55%, 35% and 60%, 35% and 65%, 35% and 70%, 35% and 75%, 40% and 45%, 40% and 50%, 40% and 55%, 40% and 60%, 40% and 65%, 40% and 70%, 40% and 75%, 45% and 50%, 45% and 55%, 45% and 60%, 45% and 65%, 45% and 70%, 45% and 75%, 50% and 55%, 50% and 60%, 50% and 65%, 50% and 69%, 55% and 60%, 55% and 65%, 55% and 70%, 55% and 75%, 60% and 65%, 60% and 70%, 60% and 75%, 65% and 70%, 65% and 75% and 70% and 75%, by weight, of the food or beverage product. The products that contain the water-soluble vitamin E derivative mixtures and high amounts of non-polar compound retain desirable organoleptic properties, such as remaining free from turbidity. For example, the products provided herein can contain up to twice the amount of non-polar compound as available products that contain known TPGS compositions and retain the same level of turbidity. Products that contain known TPGS compositions, such as products that contain TPGS compositions made up of mostly monomer (e.g., 70% or greater) and a small amount of dimer (e.g., 12% or less), and a high amount of non-polar compound, e.g., up to 75 wt % non-polar compound, exhibit higher turbidity levels, for example, a two-fold higher turbidity level, as compared to the products provided herein that contain the TPGS compositions provided herein and the same amount of non-polar compound, e.g., up to 75 wt % non-polar compound.

The water-soluble vitamin E derivative mixtures (compositions) provided herein can be formulated with non-polar compounds that contain non-polar active ingredients to form a pre-emulsion concentrate. The water-soluble vitamin E derivate compositions described herein can be formulated with non-polar compounds that contain non-polar active ingredients and additional ingredients, such as a polar solvent, to form liquid nanoemulsion concentrates. The liquid nanoemulsion concentrates that contain the water-soluble vitamin E derivative mixtures (compositions) described herein and the non-polar compounds can be diluted to form liquid dilution compositions that contain the water-soluble vitamin E derivative mixtures (compositions) described herein and non-polar compounds that contain non-polar active ingredients. The liquid dilution compositions that are produced are clear or remain clear.

The water-soluble vitamin E derivative mixtures (compositions) provided herein can be formulated with non-polar compounds that contain non-polar active ingredients or other active ingredients to form a composition for direct consumption, such as beverage composition. These compositions can be formulated in a variety of volumes and sizes, including, but not limited to, a single-serving shot and a multi-serving composition. The beverage compositions that are produced are clear and typically remain clear.

Concentrates and compositions for direct consumption that contain the water-soluble vitamin E derivative mixtures (compositions) described herein and a non-polar component are provided. The concentrates contain from 99% or more of the water-soluble vitamin E derivative composition with the remainder as a non-polar ingredient, to as little as 1%, typically 5%, of the water-soluble vitamin E derivative composition. The compositions for direct consumption contain from 50% or more of the water-soluble vitamin E derivative composition to as little as 0.1%, typically 1.5%, of the water-soluble vitamin E derivative composition. Further description and examples are provided below. The concentrates and compositions for direct consumption can contain additional optional ingredients, including polar solvents, such as water and/or alcohol.

Depending upon the amount of the vitamin E derivative, the concentrates are waxy or creamy (semi-solids) or liquids, including emulsions, depending upon the particular components and amounts thereof. The concentrates are added to foods, particularly beverages, including aqueous beverages, that contain desired amounts of the non-polar ingredients by adding an appropriate amount of an appropriate concentrate to the beverage. For example, the concentrate can be dissolved and diluted to form a liquid dilution composition. Alternatively, the water-soluble vitamin E derivative mixtures (compositions) can be formulated directly into a beverage composition. For example, the water-soluble vitamin E derivative mixtures (compositions) can be added to the beverage composition without formulating a concentrate. The resulting food/beverage compositions retain desirable organoleptic properties, such as improved clarity (e.g., small particle size, low turbidity), stability (e.g., lack of separation), taste and smell are needed. The emulsions provided herein address those needs among others.

Among the compositions for direct consumption and concentrates described herein are concentrates that are semi-solid waxes and emulsions where the concentrates and compositions for direct consumption also contain a polar solvent, such as water or alcohol. The emulsions provided herein contain the water-soluble vitamin E derivative mixtures described herein.

It is shown herein that the water-soluble vitamin E derivative mixtures (high dimer) described herein permit higher amounts of non-polar compounds to be dispersed in an aqueous liquid than compositions containing water-soluble vitamin E derivative mixtures with low dimer amounts. For example, oil-in-water emulsions are provided that contain water-soluble vitamin E derivative mixtures and non-polar compounds dispersed in an aqueous liquid that have desirable properties, including improved clarity, stability, smell and taste. The provided emulsions (and methods for making the emulsions) can be used to formulate any non-polar compound in an aqueous composition, including the non-polar compounds (e.g., non-polar active ingredients) described herein and other known non-polar compounds and active ingredients. Typically, the provided compositions containing the water-soluble vitamin E derivatives are emulsions. Typically, the provided emulsion compositions are oil-in-water nanoemulsions that contain the non-polar compounds dispersed in aqueous liquid.

The provided emulsion compositions can be further stabilized by inclusion of one or more co-surfactants and/or emulsion stabilizers in addition to the water-soluble vitamin E derivatives described herein. Surfactants form an interfacial film in the emulsion, between the oil and water phase, providing stability. Typically, the nanoemulsions of the provided compositions contain micelles, in which one or more surfactants surround the non-polar active compound. The micelles are dispersed in the water phase.

The provided emulsion compositions include liquid nanoemulsion concentrates containing the water-soluble vitamin E derivatives described herein and non-polar compounds, which can be diluted to provide non-polar compounds in aqueous compositions, such as beverage products. The liquid nanoemulsion concentrates can be diluted into a medium, for example, an aqueous medium, to form a liquid dilution composition (e.g., an aqueous liquid dilution composition) containing the non-polar compounds. Also exemplary of the provided compositions are the liquid dilution compositions (e.g., aqueous liquid dilution compositions) made by diluting the liquid nanoemulsion concentrates in the medium, that remain clear.

The emulsion compositions and food and beverage products provided herein can contain any non-polar compound or active ingredient. The non-polar compounds typically are non-polar active ingredients, for example, pharmaceuticals, nutraceuticals, vitamins and minerals. The non-polar active ingredients include, but are not limited to, polyunsaturated fatty acid (PUFA)-containing compounds, such as omega-3-containing active ingredients, for example, compounds containing ALA, DHA and/or EPA, e.g., oils derived from fish and microalgae, krill and/or flaxseed extract, and omega-6-containing non-polar active ingredients, for example, gamma-linolenic acid (GLA)-containing compounds, e.g., borage oil; saw palmetto oil-containing compounds; conjugated fatty acid containing-ingredients, for example, conjugated linoleic acid (CLA)-containing compounds; coenzyme Q-containing active ingredients, for example, coenzyme Q10 (coQ10), e.g., oxidized coQ10 (ubidecarenone)-containing compounds; and compounds containing phytosterols (plant sterols). Additional exemplary non-polar active ingredients and other active ingredients are described herein. Any non-polar compound or active ingredient can be used in the provided emulsion compositions and food and beverage products provided herein.

1. Concentrates a. Pre-Emulsion Concentrates

Exemplary of the provided compositions are pre-emulsion concentrates containing one or more non-polar compounds that are to be diluted into a food or, typically, an aqueous beverage, for direct consumption. The pre-emulsion concentrates can be semi-solid compositions, typically having a waxy or creamy consistency, for example, the consistency of a substance such as wax, for example, a lip balm, at room temperature, for example, at 25° C. or about 25° C., and become liquid at higher temperatures, for example, when heated to higher temperatures, such as to 125° F. or about 125° F., or to 50° C. or about 50° C. or to 60° C. or about 60° C.

The pre-emulsion concentrates can be diluted into aqueous media, using the provided methods, to form the provided liquid dilution compositions containing the water-soluble vitamin E derivative mixtures (compositions) and non-polar compounds. The pre-emulsion concentrates are formulated such that dilution of the concentrates, for example, in aqueous media, yields a composition having one or more desirable properties, for example, clarity; safety; taste; smell; stability, for example, lack of phase separation, "ringing" and/or precipitation over time; and/or bioavailability. In one example, the desirable property is the ability of the provided pre-emulsion concentrates to yield a clear or partially clear aqueous liquid dilution composition when it is diluted into aqueous medium, for example, a beverage such as water. In another example, the desirable property relates to the safety of the pre-emulsion concentrates and/or the desirability of the pre-emulsion concentrates for human consumption, for example, in foods and beverages. In another example, it can be desirable that the pre-emulsion concentrate contains less than or equal to a particular concentration of one or more ingredients. In another example, it can be desirable that the pre-emulsion concentrate contains greater than or equal to a particular concentration of one or more ingredients.

In addition to the non-polar compounds, the pre-emulsion concentrates contain at least one surfactant, such as the water-soluble vitamin E derivative mixtures (compositions) described herein. Typically, the surfactant has an HLB value between 12 or about 12 and 20 or about 20, for example, 12, 13, 14, 15, 16, 17, 18, 19, 20, about 12, about 13, about 14, about 15, about 16, about 17, about 18, about 19 or about 20. Exemplary of suitable surfactants are tocopherol polyethylene glycol succinate (TPGS), such as the TPGS, TPGS analogs, TPGS homologs and TPGS derivatives described herein, and other surfactants having similar properties to TPGS, for example, other surfactants having HLB values between 12 or about 12 and 20 or about 20. Typically, the surfactant is a natural surfactant, for example, a surfactant that is GRAS (generally recognized as safe)-certified by the FDA and/or Kosher certified, for example, TPGS.

Typically, the pre-emulsion concentrates further contain one or more additional ingredients. Exemplary of additional ingredients that can be included in the pre-emulsion compositions are preservatives, solvents, co-surfactants, emulsion-stabilizers, additional active ingredients and flavoring agents, as described herein.

Typically, the pre-emulsion concentrates are formulated such that, when diluted into an aqueous medium (e.g., water), they yield a dilution composition that is a nanoemulsion, in which the non-polar compound(s) are present in micelles. These micelles, containing the non-polar compound surrounded by the one or more surfactants, facilitate the dispersion of the non-polar compound among the polar solvent(s) of the aqueous medium in the dilution compositions. Typically, the pre-emulsion concentrates are formulated such that the micelles in the dilution composition have a small or relatively small particle size, for example, less than 1000 or about 1000 nm, less than 500 or about 500 nm, typically less than 300 or about 300 nm, typically less than 250 or about 250 nm, typically less than 200 or about 200 nm, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with increased clarity of the dilution compositions that results from diluting the pre-emulsion concentrates. For example, a liquid with a smaller particle size can be more clear than a liquid with a larger particle size. Small particle size also can contribute to other desirable properties, for example, stability.

A number of parameters of the pre-emulsion concentrates, including ingredients, their relative concentrations, and methods for making the pre-emulsion concentrates, affect the particle size of the liquid dilution compositions made by diluting the pre-emulsion concentrates. By extension, these parameters of the pre-emulsion concentrates also affect the desirable properties of the dilution compositions, for example, the clarity of the dilution compositions. In particular, the nature of the surfactant, particularly the HLB of the surfactant, and the relative concentrations of the surfactant and the non-polar compound in the pre-emulsion concentrates, contribute to small particle size and clarity of the dilution compositions. Typically, several of these parameters and properties relate to one another. For example, several of the parameters contribute to the particle size, typically small particle size. Particle size contributes directly to clarity of the aqueous liquid dilution compositions containing the pre-emulsion concentrates. Particle size also can relate to other properties, for example, stability, lack of "ringing" and/or precipitate formation of the aqueous liquid dilution compositions containing the pre-emulsion concentrates.

Accordingly, properties of the ingredients and their relative concentrations in the pre-emulsion concentrates are important for the ability of the pre-emulsion concentrate to yield desirable dilution compositions. Determining the appropriate ingredients, and relative concentrations thereof, that yield dilution compositions having desirable properties is carried out using the provided methods for formulating the pre-emulsion concentrates.

ii. Formulating the Pre-emulsion Concentrates

Using the provided formulation methods, the pre-emulsion concentrates are formulated by selecting ingredients and concentration ratios of the ingredients that yield compositions having one or more desired properties. When formulating the pre-emulsion concentrates, selected ingredients and starting concentrations are used to make initial pre-emulsion concentrates, which typically are diluted, evaluated and modified, if necessary.

As a first step in formulating the provided pre-emulsion concentrates, one or more initial pre-emulsion concentrates are made and evaluated for desired properties. For this step, ingredients are selected, for example, from one or more of the lists of ingredients provided below. A starting concentration (weight percentage) of each selected ingredient is selected from within an appropriate concentration range for that ingredient or category of ingredient. For example, a starting surfactant concentration, such as a water-soluble vitamin E derivative composition, e.g., TPGS, is selected from within an appropriate surfactant concentration range. In some cases, the initial pre-emulsion concentrate is formulated based on the ingredients, and concentrations thereof, of an existing pre-emulsion concentrate having one or more desired properties.

The initial pre-emulsion concentrate(s) is then made, using the methods for making the pre-emulsion concentrates provided below, adding each ingredient at its starting concentration at the appropriate step. In one example, more than one initial pre-emulsion concentrate is made. For example, multiple initial pre-emulsion concentrates, each having a different concentration of one or more ingredients, can be made and compared. For example, multiple initial pre-emulsion concentrates can be made in order to test various representative concentrations within an appropriate concentration range for one or more particular ingredients.

In a typical example, the initial pre-emulsion concentrate is made by including at least one surfactant, such as the water-soluble vitamin E derivative mixtures (compositions) described herein, having an HLB value between 12 or about 12 and 20 or about 20, typically a tocopherol polyethylene glycol succinate (TPGS) surfactant.

In one example, the starting concentration of the surfactant, for example, a water-soluble vitamin E derivative composition described herein, e.g., TPGS, is greater than 50% or about 50%, typically greater than 60% or about 60%, typically greater than 65% or about 65%, for example, greater than 70% or about 70%, for example, a starting concentration within the concentration range of between 50% or about 50% and 95% or about 95%, between 60% or about 60% and 95% or about 95%, typically between 65% or about 65% and 90% or about 90%, for example, between 69% or about 69% and 90% or about 90%, for example, between 69% or about 69% and 89% or about 89%, for example, 65, 66, 67, 68, 69, 69.5, 69.9, 70, 71, 72, 73, 74, 75, 76, 77, 78, 79, 79.5, 79.9, 80, 81, 82, 83, 84, 85, 86, 87, 88, 89, 89.5, 89.9 or 90%, by weight, of the pre-emulsion concentrate.

In another example, the starting concentration of the surfactant, for example, a water-soluble vitamin E derivative composition described herein, e.g., TPGS, is greater than 20% or about 20%, typically greater than 30% or about 30%, for example, between 30% or about 30% and 55% or about 55%, for example, between 30% or about 30% and 50% or about 50%, for example, between 30% or about 30% and 45% or about 45%, for example, 30, 31, 32, 33, 34, 35, 36, 37, 38, 39, 40, 41, 42, 43, 44, 45, 46, 47, 48, 49, 50, 51, 52, 53, 54 or 55%, by weight, of the pre-emulsion concentrate. This example is typically used for pre-emulsion concentrates where the non-polar active ingredient includes a phytosterol.

Also in this typical example, the initial pre-emulsion concentrate further includes at least one non-polar compound (e.g., non-polar active ingredient). In one example, the starting concentration of the non-polar compound (e.g., non-polar active ingredient), or the total of all of the one or more non-polar compounds, is chosen from within a concentration range of between 5% or about 5% and 35% or about 35%, typically between 10% or about 10% and 30% or about 30%, for example, between 10% or about 10% and 20% or about 20%, or between 20% or about 20% and 30% or about 30%, for example, 5, 6, 7, 8, 9, 10, 11, 12, 13, 14, 15, 16, 17, 18, 19, 20, 21, 22, 23, 24, 25, 26, 27, 28, 29 or 30%, by weight, of the pre-emulsion concentrate.

In another example, the starting concentration of the non-polar compound (e.g., non-polar active ingredient), or the total of all of the one or more non-polar compounds, is chosen from within a concentration range of between 1% or about 1% and 50% or about 50%. In this example, which typically is used when using more than one non-polar active ingredient, the total concentration of the non-polar compounds is chosen from within a concentration range of between 30% or about 30% and 55% or about 55%, for example between 40% or about 40% and 50% or about 50%, by weight, of the composition. Exemplary of starting concentrations for individual non-polar active ingredients used in this example are between 1% and 50%, for example, 1%, 10.5%, 34% or 45%, by weight, of the pre-emulsion concentrate, and other concentrations within the range.

In one example, the initial pre-emulsion concentrate further includes other ingredients, for example, preservative(s), for example, benzyl alcohol; co-surfactant(s), for example, a phospholipid, for example, phosphatidylcholine; a non-polar solvent, for example, an oil, and/or an emulsion stabilizer. Typically, a polar solvent, e.g., water, is not added as an ingredient to the pre-emulsion concentrate.

After making the initial pre-emulsion concentrate(s), the pre-emulsion concentrate(s) is evaluated for one or more desired properties, for example, the ability to form dilution compositions (e.g., clear dilution compositions or dilution compositions having a particular turbidity value, particle size or other property). The ability to form dilution compositions having one or more properties is assessed by diluting the pre-emulsion concentrate in aqueous medium, for example, diluting the pre-emulsion composition in the aqueous medium at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In one example, the dilution is carried out by including one or more drops of the heated pre-emulsion concentrate in the aqueous medium, for example, in 25 mL or more of the aqueous medium.

After evaluation, the ingredients, and/or concentrations thereof, can be adjusted in order to generate the desired properties in the final pre-emulsion concentrate. Typically, the concentration of the non-polar compound and/or the surfactant, for example, a water-soluble vitamin E derivative composition, e.g., TPGS, is the concentration that is adjusted after evaluating the initial pre-emulsion concentrate. Similarly, when formulating multiple initial pre-emulsion concentrates, one or more of the non-polar compound and the surfactant is/are varied among the multiple initial pre-emulsion concentrates. In some cases, following evaluation, it can be determined that additional ingredients (not included in the initial formulation) are needed or desirable for achieving the desired properties of a particular pre-emulsion concentrate. This process can be repeated until a pre-emulsion concentrate having the desired property or properties is generated.

ii. Exemplary Ingredients and Typical Concentration Ranges

Each of the provided pre-emulsion concentrates and other compositions contains at least one non-polar compound, for example, a non-polar compound that contains one or more non-polar active ingredients, and a surfactant, for example, the water-soluble vitamin E derivative mixtures (compositions) described herein, e.g., mixtures of monomers and dimers of TPGS. Any non-polar compound that contains one or more non-polar active ingredient can be formulated with the provided methods and pre-emulsion concentrates. Several exemplary non-polar compounds that can be incorporated into the provided concentrates are described herein below. Typically, the non-polar compound is or contains a non-polar active ingredient, for example, an oil-based active ingredient, for example, a polyunsaturated fatty acid (PUFA), a coenzyme Q or a phytochemical.

In one example, for formulating the initial pre-emulsion concentrates, the starting concentration of the non-polar compound, or the total of all the one or more non-polar compounds, typically is chosen from within a concentration range of between 5% or about 5% and 35% or about 35%, typically between 10% or about 10% and 30% or about 30%, for example, between 10% or about 10% and 20% or about 20%, or between 20% or about 20% and 30% or about 30%, for example, 5, 6, 7, 8, 9, 10, 11, 12, 13, 14, 15, 16, 17, 18, 19, 20, 21, 22, 23, 24, 25, 26, 27, 28, 29 or 30%, by weight, of the pre-emulsion concentrate. In another example, the starting concentration of the non-polar compound (e.g., non-polar active ingredient), or the total of all the one or more non-polar compounds, is chosen from within a concentration range of between 1% or about 1% and 50% or about 50%. In this example, which typically is used when using more than one non-polar active ingredient, the total concentration of the non-polar compounds is chosen from within a concentration range of between 30% or about 30% and 55% or about 55%, for example between 40% or about 40% and 50% or about 50%, by weight, of the concentrate. Exemplary of starting concentrations for individual non-polar active ingredients used in this example are between 1% and 50%, for example, 1%, 10.5%, 34% or 45%, by weight, of the concentrate, and other concentrations within the range.

In addition to the non-polar compound, the pre-emulsion concentrates contain at least one surfactant that is the water-soluble vitamin E derivative mixture described herein, such as TPGS. The surfactant has an HLB value of between 12 or about 12 and 20 or about 20, for example, 12, 13, 14, 15, 16, 17, 18, 19 or 20. Exemplary of suitable surfactants are the water-soluble vitamin E derivative mixtures (compositions) described herein, such as TPGS, TPGS analogs, TPGS homologs and TPGS derivatives and other surfactants having similar properties, for example, any surfactant having an HLB value between 12 or about 12 and 20 or about 20, where the vitamin E derivative is provided as a mixture of dimer and monomer with at least 13% percent dimer, typically at least 29%, 35%, or 50% dimer, and the remainder monomer and about or no more than 10%, 5%, 4%, 3%, 2%, or 1% other minor contaminants, impurities or higher forms of polymer. Surfactants, HLB values and methods for determining HLB values are well known.

In one example, the starting concentration of the water-soluble vitamin E derivative mixtures (compositions) described herein, e.g., TPGS, is greater than 50% or about 50%, typically greater than 60% or about 60%, typically greater than 65% or about 65%, for example, greater than 70% or about 70%, for example, a starting concentration within the concentration range of between 50% or about 50% and 95% or about 95%, between 60% or about 60% and 95% or about 95%, typically between 65% or about 65% and 90% or about 90%, for example, between 69% or about 69% and 90% or about 90%, for example, between 69% or about 69% and 89% or about 89%, for example, 65, 66, 67, 68, 69, 69.5, 69.9, 70, 71, 72, 73, 74, 75, 76, 77, 78, 79, 79.5, 79.9, 80, 81, 82, 83, 84, 85, 86, 87, 88, 89, 89.5, 89.9 or 90%, by weight, of the pre-emulsion concentrate.

In another example, the starting concentration of the surfactant, for example, the water-soluble vitamin E derivative mixtures (compositions) described herein, e.g., TPGS, is greater than 20% or about 20%, typically greater than 30% or about 30%, for example, between 30% or about 30% and 55% or about 55%, for example, between 30% or about 30% and 50% or about 50%, for example, between 30% or about 30% and 45% or about 45%, for example, 30, 31, 32, 33, 34, 35, 36, 37, 38, 39, 40, 41, 42, 43, 44, 45, 46, 47, 48, 49, 50, 51, 52, 53, 54 or 55%, by weight, of the pre-emulsion concentrate. This example is typically used for pre-emulsion concentrates where the non-polar active ingredient includes a phytosterol.

One or more, typically more than one, additional ingredients can be added to the initial pre-emulsion concentrate. For example, the pre-emulsion concentrates typically contain at least one preservative, typically a natural preservative, for example, benzyl alcohol. Exemplary of other additional ingredients that can be added to the pre-emulsion concentrates, including the initial pre-emulsion concentrates, are emulsion stabilizers, for example, a blend of gums; a non-polar solvent for the non-polar compound, for example, an oil other than the non-polar compound, for example, vitamin E oil or flax seed oil; a pH adjuster, for example, citric acid or phosphoric acid; one or more flavoring agents, for example, D-limonene or lemon oil; a co-surfactant, for example, a phospholipid, e.g., phosphatidylcholine.

The appropriate concentration ranges for the additional ingredients are described in individual sections below. Typically, the concentration of the additional ingredients depends, in part, on the concentrations of the non-polar active ingredient and/or of the surfactant. Typically, the concentrations of these three ingredients are the focus of the formulating methods. For example, when it is determined that modifications to ingredient concentrations in the initial pre-emulsion concentrate should be made, it typically is the concentration of one or more of these two ingredients, i.e., the non-polar active ingredient and/or surfactant, that is/are adjusted.

In one example, it can be desirable to add one or more of the additional ingredients after evaluation of the initial pre-emulsion concentrate, for example, in order to improve the pre-emulsion concentrate with respect to one or more desired properties.

b. Liquid Nanoemulsion Concentrates

Provided herein are liquid nanoemulsion concentrates (also called "liquid concentrates") containing the water-soluble vitamin E derivative mixtures described herein, one or more non-polar compounds that contain one or more active ingredients and a polar solvent. The liquid concentrates, which include emulsions, can be diluted into aqueous medium to form aqueous liquid dilution compositions containing the water-soluble vitamin E derivative mixtures described herein and non-polar compounds that contain non-polar active ingredients. The liquid concentrates are formulated based on one or more desirable properties, such as clarity; safety; taste; smell; stability, for example, lack of phase separation, "ringing" and/or precipitation over time; and/or bioavailability of the concentrate and/or the aqueous liquid dilution compositions containing the concentrate. In one example, the desirable property is the ability of the provided concentrate to yield a clear or partially clear aqueous liquid dilution composition when it is diluted into aqueous medium, e.g., water, such as in a beverage product. In another example, the desirable property relates to the safety of the concentrates and/or the desirability of the liquid concentrates for human consumption, for example, in food and beverage products. In another example, it can be desirable that the liquid concentrate contains less than or equal to a particular concentration of one or more ingredients. In another example, it can be desirable that the liquid concentrate contains greater than or equal to a particular concentration of one or more ingredients.

In addition to the water-soluble vitamin E derivatives described herein and non-polar compounds, the liquid concentrates further contain a polar solvent, such as water (e.g., filtered water), or any other edible aqueous liquid (e.g., propylene glycol or glycerin), or combination thereof. Typically, the liquid concentrates contain a high amount of the polar solvent, for example, between or between about 50% and about 80%, by weight (w/w), of the liquid concentrate, typically between or between about 50% and about 79%, by weight, of the liquid concentrate.

Typically, the liquid concentrates further contain one or more additional ingredients. Exemplary of additional ingredients that can be included in the liquid concentrates are preservatives, non-polar solvents, co-surfactants, emulsion stabilizers, pH adjusters, additional active ingredients and flavoring agents.

The non-polar compounds in the liquid concentrates and dilution compositions provided herein are contained in micelles. These micelles, containing the non-polar compounds surrounded by the one or more surfactants, allow dispersion of the non-polar compounds among polar solvents, for example, when the liquid concentrates are diluted to form aqueous liquid dilution compositions. The micelles containing the non-polar compounds typically have a small or relatively small particle size, for example, less than or less than about 1000 nm, less than or less than about 500 nm, less than or less than about 300 nm, less than or less than about 200 nm, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150 or 200 nm. Smaller particle size correlates with clarity of the aqueous liquid dilution compositions containing the diluted liquid concentrates. For example, a liquid with a smaller particle size can be more clear than a liquid with a larger particle size. Small particle size also can contribute to other desirable properties, for example, stability.

A number of factors, including ingredients, their relative concentrations, and methods for making the liquid concentrates, affect the particle size of the compositions, and other desirable properties of the compositions, such as clarity. In particular, the nature of the surfactant, particularly the HLB of the surfactant, and the relative concentrations of polar solvent (e.g., water), surfactant and the non-polar compound, contribute to small particle size, and the clarity of the aqueous liquid dilution compositions. Typically, several of these parameters and properties are related to one another. For example, several of the parameters contribute to the particle size, typically small particle size, of the compositions. Particle size contributes directly to clarity of the aqueous liquid dilution compositions containing the liquid concentrates. Particle size also can relate to other properties, for example, stability, lack of "ringing" and/or precipitate formation of the aqueous liquid dilution compositions containing the liquid concentrates.

Accordingly, properties of the ingredients and their relative concentrations in the liquid concentrates are important for the ability of the concentrate to yield desirable dilution compositions. Provided are methods for formulating the liquid nanoemulsion concentrates. Determining the appropriate ingredients, and relative concentrations thereof, that yield dilution compositions having desirable properties is performed using provided methods for formulating the liquid concentrates.

i. Formulating the Liquid Nanoemulsion Concentrates

In the provided formulation methods, the liquid concentrates are formulated by selecting ingredients and amounts of the ingredients that yield compositions having one or more desired properties. When formulating the liquid concentrates, selected ingredients and starting amounts (concentrations) are used to make initial liquid concentrates, which are evaluated and modified, if necessary.

As a first step in formulating the provided liquid concentrates, one or more initial concentrates are made and evaluated for desired properties. For this step, ingredients are selected, for example, from among the ingredients described herein. The ingredients generally include surfactants, for example, the water-soluble vitamin E derivatives described herein, e.g., TPGS, polar solvents, non-polar active ingredients, and other ingredients. A starting concentration (weight percentage) of each selected ingredient is selected from within the appropriate range for that ingredient or category of ingredient, for example, the appropriate concentration range for the surfactant. In some cases, the initial liquid concentrate is formulated based on the ingredients, and amounts (concentration) thereof, of an existing liquid concentrate having one or more desired properties.

The initial liquid concentrate is made, for example, using the methods for making the liquid concentrates, provided below, adding each ingredient at its starting concentration at the appropriate step. More than one initial liquid concentrate, e.g., multiple initial liquid concentrates, each having a different concentration of one or more ingredients, can be made and compared. For example, multiple initial liquid concentrates can be produced to test various representative concentrations within an appropriate concentration range for one or more particular ingredient.

In a typical example, the initial liquid concentrate is made by including at least one surfactant, for example, a water-soluble vitamin E derivative described herein, e.g., TPGS, that has an HLB value of between or about between 12 and 20, at a starting concentration within the concentration range of between or about between 5 wt % and 35 wt % of the liquid concentrate; at least one non-polar compound, at a starting concentration within the concentration range of between or about between 1 wt % and 30 wt % of the liquid concentrate; and a polar solvent, at a starting concentration of between or about between 40 wt % and 85 wt % of the liquid concentrate. In one example, the initial liquid concentrate further includes other ingredients, for example, preservatives, co-emulsifiers, pH adjusters and/or other ingredients as described herein.

After making an initial liquid concentrate, the liquid concentrate can be evaluated for one or more desired properties, for example, the ability to form dilution compositions (e.g., clear dilution compositions or dilution compositions having a particular turbidity value, particle size or other property). The ability to form dilution compositions having one or more properties can be assessed by diluting the liquid concentrate in an aqueous medium, such as water. For example, the liquid concentrate can be diluted in an aqueous medium at a dilution factor of between or about between 1:10 and 1:1000 or more, typically between or about between 1:10 and 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more, or according to other dilutions provided herein.

After evaluation, the ingredients and/or amounts (concentrations) thereof can be adjusted in order to generate the desired properties in the final liquid concentrate. Typically, the concentrations of the non-polar compound, the surfactant, e.g., water-soluble vitamin E derivative, and/or the polar solvent are the concentrations that are adjusted after evaluating the initial liquid concentrate. Similarly, when formulating multiple initial liquid concentrates, one or more of the non-polar compounds, surfactant, e.g., water-soluble vitamin E derivative, and polar solvent concentrations are varied among the multiple initial liquid concentrates. In some cases, following evaluation, it can be determined that additional ingredients (not included in the initial formulation) are needed or desirable for achieving the desired properties of a particular concentrate. This process can be repeated until a liquid concentrate having the desired property or properties is generated.

c. Liquid Dilution Compositions Containing the Concentrates

Among the products provided herein are liquid dilution compositions, typically aqueous liquid dilution compositions (i.e., beverages), containing the described concentrates containing the water-soluble vitamin E derivative mixtures (compositions) described herein and non-polar compounds. The aqueous liquid dilution compositions are made by diluting the provided liquid nanoemulsion concentrates into aqueous media, for example, beverages, for example, water, flavored water, soda, milk, juices, including fruit juices, sauces, syrups, soups, sports drinks, nutritional beverages, energy drinks, vitamin-fortified beverages, or any beverage. Any beverage can be prepared or modified using the water-soluble vitamin E derivative mixtures (compositions) described herein and other water-soluble vitamin E derivative mixtures (compositions), for example, see U.S. Pub. No. 2008-0254188 and U.S. Pat. No. 6,045,826.

In one example, the aqueous liquid dilution composition contains between 0.05 grams (g) or about 0.05 g and 10 g or about 10 g, typically between 0.05 g and 5 g, of the concentrate per 8 fluid ounces or about 8 fluid ounces, at least 8 fluid ounces or at least about 8 fluid ounces, or less than 8 fluid ounces or less than about 8 fluid ounces, or per serving size, of the aqueous medium, for example, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g, or 10 g of the concentrate per 8 fluid ounces, about 8 fluid ounces, or at least 8 fluid ounces or at least about 8 fluid ounces of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains between 1 mL or about 1 mL and 10 mL or about 10 mL of the concentrate, for example, 1 mL, 2 mL, 3 mL, 4 mL, 5 mL, 6 mL, 7 mL, 8 mL, 9 mL or 10 mL of the concentrate, per 8 fluid ounces, about 8 fluid ounces, at least 8 fluid ounces or at least about 8 fluid ounces, or less than 8 fluid ounces or less than about 8 fluid ounces, or per serving size, of the aqueous medium, for example 8, 9, 10, 11, 12, 13, 14, 15, 16, 17, 18, 19, 20, 25, 30, 35, 40, 45, 50, 100, 200 or more fluid ounces, of aqueous medium.

In another example, the aqueous liquid dilution composition contains at least 10 mg or about 10 mg, typically at least 25 mg or about 25 mg, typically at least 35 mg, of the non-polar compound, for example, the non-polar active ingredient, per 8 fluid ounces or about 8 fluid ounces, at least 8 fluid ounces or at least about 8 fluid ounces of the aqueous medium, or less than 8 ounces or less than about 8 ounces, or per serving size, of the aqueous medium; for example, 10, 11, 12, 13, 14, 15, 16, 17, 18, 19, 20, 21, 22, 23, 25, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 700, 800, 900, 1000, 1500, 2000 mg, or more, of the non-polar compound per at least 8 fluid ounces or at least about 8 fluid ounces of aqueous medium. In another example, the aqueous liquid dilution composition contains the concentrate diluted at a dilution factor of between 1:10 or about 1:10 and 1:1000 or about 1:1000 or more, typically between 1:10 or about 1:10 and 1:500 or about 1:500 or more, for example, diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. In another example, the aqueous liquid dilution compositions contain the liquid concentrate diluted to any amount. In another example the dilution is less than 1:10 or about 1:10.

Properties of the provided concentrates that are diluted into the aqueous medium contribute to various properties of the provided resulting aqueous liquid dilution compositions, for example, clarity; desirability for human consumption, for example, pleasant taste, and/or smell, for example, lack of "fishy" taste/smell, lack of "ringing" and lack of crystal formation; stability, for example, lack of oxidation, "ringing" and/or precipitation over time; and safety for human consumption. As described herein, the liquid concentrates are formulated according to the desired properties of the aqueous liquid dilution compositions containing the concentrates.

d. Evaluation of the Concentrates and Liquid Dilution Compositions

The formulation methods can further include analysis of the initial concentrates, e.g., the pre-emulsion concentrates and/or the liquid nanoemulsion concentrates, based on one or more desired properties, for example, properties of an aqueous liquid dilution composition containing the diluted concentrate such as clarity, color, smell, taste, safety, stability, "ringing" or forming of precipitates and/or the presence of crystals. For example, the methods typically include analyzing the ability of the initial concentrate to form a clear liquid upon dilution in an aqueous medium, such as by analysis of the clarity/turbidity of the resulting aqueous liquid dilution composition containing the initial concentrate.

For evaluation of properties of the initial concentrates in an aqueous liquid dilution composition, the initial concentrates, e.g., the pre-emulsion concentrates and/or the liquid nanoemulsion concentrates, can be diluted into an aqueous medium, for example, water or another polar solvent, at a dilution factor of between or about between 1:10 and 1:1000, typically between or about between 1:10 and 1:500, for example, diluted at least or about 1:10, at least or about 1:20, at least or about 1:25, at least or about 1:50, at least or about 1:100, at least or about 1:200, at least or about 1:250, at least or about 1:300, at least or about 1:400 or at least or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or any other dilution, such as others provided herein. Typically, clarity of the resulting aqueous liquid dilution composition containing the diluted initial concentrate is evaluated using one or more approaches. Additionally, other properties can be evaluated, for example, smell and/or taste properties of the liquid. For example, when the non-polar compound is a polyunsaturated fatty acid (PUFA), particularly fish oil or algae oil, the aqueous liquid dilution composition can be evaluated empirically for a "fishy" smell.

i. Clarity

Dilution of the provided concentrates, e.g., the pre-emulsion concentrates and/or the liquid nanoemulsion concentrates, in aqueous media can yield clear liquids. The clarity of the resulting aqueous liquid dilution composition containing the initial concentrate can be evaluated by one or more of a plurality of approaches, such as by empirical observation, by measuring particle size and/or by measuring the turbidity value of the liquid.

For example, the concentrates, e.g., the pre-emulsion concentrates and/or the liquid nanoemulsion concentrates, can be diluted to form clear liquids (or liquids that are equal in clarity to known liquids), by adding between or about between 0.05 grams (g) and 10 g of the concentrate, such as between or about between 0.05 g and 5 g, for example, about 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1 g, 2 g, 3 g, 4 g, 5 g, 6 g, 7 g, 8 g, 9 g or 10 g of the concentrate, to aqueous medium, for example, to at least or about at least 8 fluid ounces, such as at least or about at least 8, 9, 10, 11, 12, 13, 14, 15, 16, 17, 18, 19, 20, 25, 30, 35, 40, 45, 50, 100, 200 or more fluid ounces of aqueous medium, e.g., water, to form a clear aqueous liquid dilution composition that contains the concentrate that contains the water-soluble vitamin E derivative composition and non-polar compound. The concentrates can be diluted to form clear aqueous liquid dilution compositions by adding between or about between 1 mL and 10 mL of the concentrate, for example, about 1 mL, 2 mL, 3 mL, 4 mL, 5 mL, 6 mL, 7 mL, 8 mL, 9 mL or 10 mL of the concentrate to at least or about at least 8 fluid ounces of aqueous medium, for example at least or about at least 8, 9, 10, 11, 12, 13, 14, 15, 16, 17, 18, 19, 20, 25, 30, 35, 40, 45, 50, 100, 200 or more fluid ounces of aqueous medium, e.g., water, to form a clear aqueous liquid dilution composition that contains the concentrate that contains the water-soluble vitamin E derivative composition and non-polar compound.

The provided concentrates, e.g., the pre-emulsion concentrates and/or the liquid nanoemulsion concentrates, can be formulated using any non-polar compound for dilution in an aqueous medium. The concentrate can be diluted in an aqueous medium, such as water, to form a clear aqueous liquid dilution composition at a dilution factor of between or about between 1:10 and 1:1000, such as between or about between 1:10 and 1:500, for example, when diluted not more than 1:10 or about 1:10, 1:20 or about 1:20, 1:25 or about 1:25, 1:50 or about 1:50, 1:100 or about 1:100, 1:200 or about 1:200, 1:250 or about 1:250, 1:300 or about 1:300, 1:400 or about 1:400, 1:500 or about 1:500, for example, 1:10, 1:20, 1:25, 1:30, 1:35, 1:40, 1:50, 1:55, 1:60, 1:65, 1:70, 1:75, 1:80, 1:90, 1:100, 1:110, 1:120, 1:130, 1:140, 1:150, 1:160, 1:170, 1:180, 1:190, 1:200, 1:210, 1:220, 1:230, 1:235, 1:240, 1:250, 1:260, 1:270, 1:280, 1:290, 1:300, 1:350, 1:400, 1:450, 1:500 or more. The clear liquid can be formed at dilutions less dilute than 1:10 of the concentrate. Typically, the clarity of the liquid is maintained with increasing dilutions, for example, to infinity.

Clarity of the aqueous liquid dilution composition containing the diluted concentrate, e.g., the pre-emulsion concentrates and/or the liquid nanoemulsion concentrates, can be evaluated using one or more of a plurality of approaches, for example, qualitatively, such as by empirical evaluation, or quantitatively, such as by measuring particle size and/or by measuring the turbidity value of the liquid. In one example, the aqueous liquid dilution compositions are clear aqueous liquid dilution compositions or non-turbid aqueous liquid dilution compositions, for example, as determined, as described below, empirically or by measuring turbidity and/or particle size. In another example, the aqueous liquid dilution compositions are not clear, or not completely clear. The liquid dilution compositions can be more or less clear, or have the same clarity as another liquid, for example, an aqueous liquid dilution composition made according to the provided methods or a beverage, for example, a beverage that does not contain the diluted concentrate.

For example, a particular quantitative or qualitative clarity value can be desired. It may be desirable that the aqueous liquid dilution composition is as clear as, less clear or more clear than another liquid, for example, an aqueous liquid dilution composition made according to the provided methods, or a beverage product, for example, a beverage product or other aqueous medium that does not contain the concentrate. For example, an aqueous liquid dilution composition containing the concentrate diluted in a beverage product, can be as clear or about as clear as the same beverage containing no concentrate. The evaluation can be done qualitatively, for example by empirical observation, or quantitatively, for example, by calculating particle size and/or turbidity value (NTU) for the liquid(s).

Properties of the liquid concentrates can affect the clarity of the liquid. A number of parameters can vary the clarity of the liquids, for example, the relative concentration of surfactant, non-polar compound and/or water; the type of non-polar ingredient; the concentration of excipient(s) in the particular non-polar compound; and the purity of the non-polar compound, for example, whether it has been standardized to a high purity, or whether it is an extract or a filtered extract. For example, an aqueous liquid dilution composition made by diluting a concentrate containing a non-polar active ingredient that contains lecithin, for example a high amount of lecithin, can be less clear than one made with a concentrate containing a non-polar compound that does not contain lecithin. In another example, a liquid concentrate containing a non-polar compound that is a filtered extract can produce a clearer aqueous liquid dilution composition when diluted than a concentrate containing a crude extract.

(a) Empirical Evaluation

The relative clarity/turbidity of the aqueous liquid dilution composition containing the diluted concentrate, e.g., the pre-emulsion concentrates and/or the liquid nanoemulsion concentrates, can be assessed qualitatively by observation. For example, a liquid can be considered clear if it does not have a cloudy appearance and/or if no particles are visible when looking at the liquid with the naked eye. Clarity can be assessed empirically by comparison to other liquids, for example, water, fruit juice, soda and/or milk. For example, it can be desirable that the liquid is as clear or about as clear as water or another liquid, for example a beverage. For example, the liquid (containing the concentrate diluted in an aqueous medium, for example, a beverage product) can be as clear or about as clear as the same aqueous medium not containing the concentrate. In some cases, the aqueous liquid dilution composition is as clear or about as clear as water or another liquid, for example a beverage. In some examples, there is no substantial difference, for example, no observable difference, between the aqueous liquid dilution composition containing the concentrate and the same aqueous medium without the concentrate. A clear liquid is not necessarily colorless, for example, a yellow liquid that contains no visible particles or cloudiness can be considered clear. In another example, the liquid is clear or partially clear or substantially clear if no crystals are visible and/or if no "ringing" is observed on the container containing the liquid.

(b) Particle Size or Number of Particles

Alternatively, the clarity of the aqueous liquid dilution composition containing the diluted concentrate, e.g., the pre-emulsion concentrates and/or the liquid nanoemulsion concentrates, can be assessed by measuring the particle size and/or number of particles of the liquid. Methods for measuring particle size are known and any method for measuring particle size that can measure particle sizes in the appropriate ranges as described below, can be used.

Particle size can be analyzed by commercial services, for example, from Delta Analytical Instruments, Inc., such as by using a light-scattering analyzer, for example, a dynamic light scattering analyzer, e.g., the Horiba® LB-550, which can measure particle sizes within a range of 0.001 microns to 6 microns and uses a Fourier-transform/iterative deconvolution technique for reporting data and can measure sample concentrations from ppm to 40% solids; the Horiba® LA-920, which is a laser light-scattering instrument having an He—Ne laser and a tungsten lamp and can determine particle sizes from 0.02 microns to 2000 microns using Mie theory; or other analyzers known to those of skill in the art, for example, analyzers available from Delta Analytical Instruments, Inc.

Alternatively, the particle size can be measured microscopically, for example, by viewing the liquid under a microscope, for example, at 640× magnification. With this method, particle size can be quantified by comparing to a measuring device, for example, a ruler, which is visible when viewing the liquid under the microscope. If any particles are observable at this magnification, they are measured by comparison to the measuring device. At a magnification of 640×, for example, any particle that is about or greater than 25 nm is visible, while particle sizes smaller than 25 nm typically are not visible.

Typically, it is desired that the aqueous liquid dilution compositions have a particle size less than or about less than 200 nm, for example, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190 or 200 nm. Typically, it is desired that the aqueous liquid dilution compositions have a particle size less than or about less than 100 nm, less than or about less than 50 nm, or less than or about less than 25 nm. Typically, the particle size of the aqueous liquid dilution composition containing the concentrate is between or about between 5 nm and 200 nm, or between 5 nm or about 5 nm and 50 nm or about 50 nm.

Typically, the particle size of the provided aqueous liquid dilution composition containing the liquid concentrate, which contains the non-polar compound, is smaller than the particle size of a liquid containing the non-polar compound (not formulated in a liquid concentrate).

(c) Turbidity Measurement

Clarity of the liquid dilution composition can be analyzed by taking optical turbidity measurements, which indicate the level of cloudiness or haziness of a liquid, correlating to the size and number of particles in suspension in a liquid. For example, turbidity can be measured optically, to get a value indicating the cloudiness or haziness of the liquid, which correlates with particles in suspension in the liquid. The units of a turbidity value measured with a nephelometer are expressed as Nephelometric Turbidity Units (NTU). The more clear a particular liquid, the lower its turbidity (i.e., NTU) value.

Turbidity can be measured optically, for example, using a nephelometer, an instrument with a light and a detector. The nephelometer measures turbidity by detecting scattered light resulting from exposure of the liquid to an incident light. The amount of scattered light correlates to the amount of particulate matter in the liquid. For example, a beam of light passes through a sample with low turbidity with little disturbance. Other methods for measuring turbidity are well known and can be used with the provided methods and compositions.

The concentrates and the resulting compositions provided herein have greater clarity than the same concentrates/compositions that contain the higher monomer/lower dimer water-soluble vitamin E derivative compositions. To measure the turbidity of the concentrates, it generally is necessary to dilute the concentrate so that the turbidity of the resulting composition can be read by the instrument. As long as all compositions are treated the same, turbidity can be compared. Among the concentrates prepared herein are those that produce resulting aqueous compositions containing the diluted concentrates, e.g., the pre-emulsion concentrates and/or the liquid nanoemulsion concentrates, that have low turbidity, for example, a turbidity value (NTU) less than or about 80, such as less than or about 70, less than or about 60, less than or about 50, less than or about 40, less than or about 30, less than or about 29, less than or about 28, less than or about 27, less than or about 26, less than or about 25, less than or about 24, less than or about 23, less than or about 22, less than or about 21, less than or about 20, less than or about 19, less than or about 18, less than or about 17, less than or about 16, less than or about 15, less than or about 14, less than or about 13, less than or about 12, less than or about 11, less than or about 10, less than or about 9, less than or about 8, less than or about 7, less than or about 6, less than or about 5, less than or about 4, less than or about 3, less than or about 2, less than or about 1, or 0 or about 0 when diluted as described above. For example, the turbidity value of the aqueous liquid dilution compositions when, for example, 1 gram is diluted into 8 oz of water, can be less than or about 80, for example, 80, 70, 60, 50, 40, 30, 25, 20, 15, 10, 5, 4, 3, 2, 1 or less. For purposes herein, the high dimer-containing compositions produce concentrates and dilution compositions that are less turbid (more clear) than the same compositions with low dimer water-soluble vitamin E derivatives.

In one example, the clear aqueous liquid dilution composition has a turbidity value (NTU) less than or about 80, such as less than or about 70, less than or about 60, less than or about 50, less than or about 40, less than or about 30, less than or about 29, less than or about 28, less than or about 27, less than or about 26, less than or about 25, less than or about 24, less than or about 23, less than or about 22, less than or about 21, less than or about 20, less than or about 19, less than or about 18, less than or about 17, less than or about 16, less than or about 15, less than or about 14, less than or about 13, less than or about 12, less than or about 11, less than or about 10, less than or about 9, less than or about 8, less than or about 7, less than or about 6, less than or about 5, less than or about 4, less than or about 3, less than or about 2, less than or about 1, or 0 or about 0.

In another example, the turbidity value of the aqueous liquid dilution composition is less than or about 80, for example, 80, 70, 60, 50, 40, 30, 25, 20, 15, 10 or less.

It may be desirable that the aqueous liquid dilution composition possess a turbidity value that is comparable, for example, about the same as, the same as, or less than, or greater than, the turbidity value of another liquid, for example, a beverage not containing the concentrate, e.g., the pre-emulsion concentrates and/or the liquid nanoemulsion concentrates, or an aqueous liquid dilution composition made by the provided methods.

ii. Stability

Typically, the provided aqueous liquid dilution compositions containing the concentrates are stable, for example, free from one or more changes over a period of time, for example, 1 or more days, 1 or more weeks, 1 or more months, or one or more years, for example, 1, 2, 3, 4, 5, 6, 7 or more days, 1, 2, 3, 4, 5, 6, 7, 8, 9, 10 or more weeks, 1, 2, 3, 4, 5, 6, 7, 8, 9, 10, 11, 12 or more months or 1, 2, 3, 4 or more years.

In one example, the liquid dilution compositions are stable because they are free from oxidation or substantial oxidation over time. In another example, they are stable because they remain clear over time. In another example, the stable compositions remain safe and/or desirable for human consumption over time. In one example, stability refers to the lack of precipitates forming in the compositions over the period of time. In a related example, the compositions are stable because they do not exhibit "ringing," formation of a whitish or opaque ring around the perimeter of the container holding the liquid, typically at the surface of the liquid. Ringing typically is undesirable, particularly in the case of a liquid for human consumption, for example, a beverage.

In another example, the liquid dilution composition is stable if it does not exhibit any visible phase separation over a period of time, for example, after 24 hours, after one week or after one month. In one example, the compositions are stable if they exhibit one or more of these described characteristics, over time, when kept at a particular temperature. In one example, the liquid dilution compositions remain stable at room temperature, for example, 25° C. or about 25° C. In another example, the liquid dilution compositions remain stable at between 19° C. and 25° C. In another example, the liquid dilution compositions remain stable at refrigerated temperatures, for example, 4° C. or about 4° C., or at frozen temperatures, for example, at −20° C. or about −20° C.

Stability refers to a desirable property of the provided liquid dilution compositions, for example, the ability of the provided liquid dilution compositions to remain free from one or more changes over a period of time, for example, 1 or more days, 1 or more weeks, 1 or more months, or one or more years, for example, 1, 2, 3, 4, 5, 6, 7 or more days, 1, 2, 3, 4, 5, 6, 7, 8, 9, 10 or more weeks, 1, 2, 3, 4, 5, 6, 7, 8, 9, 10, 11, 12 or more months or 1, 2, 3, 4 or more years. In one example, the liquid dilution composition is stable if it is formulated such that it remains free from oxidation or substantial oxidation over time. In another example, the stable liquid dilution compositions remain clear over time. In another example, the stable liquid dilution compositions remain safe and/or desirable for human consumption over time. In one example, stability refers to the lack of precipitates forming in the liquid dilution compositions over the period of time. In a related example, stability refers to the lack of "ringing" over the period of time. In another example, the liquid dilution composition is stable if it does not exhibit any visible phase separation over a period of time, for example, after 24 hours, after one week or after one month. In one example, the liquid dilution compositions are stable if they exhibit one or more of these described characteristics, over time, when kept at a particular temperature.

In one example, the liquid dilution compositions are stable at room temperature, for example, 25° C. or about 25° C. In another example, the liquid dilution compositions remain stable at between 19° C. and 25° C. In another example, the liquid dilution compositions remain stable at refrigerated temperatures, for example, 4° C. or about 4° C., or at frozen temperature, for example, at −20° C. or about −20° C.

iii. Desirable Characteristics for Human Consumption

A variety of properties of the concentrates and liquid dilution compositions can contribute to its desirability as a consumable product. For example, taste, smell, clarity, color, crystal formation, precipitation and "ringing," are properties of interest. In one example, the liquid dilution composition has a pleasant taste and/or smell, for example, due to one or more flavors added to the concentrate and/or to the aqueous medium. In another example, the liquid dilution composition containing the concentrate is free from an unpleasant taste or smell, for example, a "fishy" taste or smell. In one example, the liquid dilution composition smells or tastes less unpleasant, for example, less fishy, compared to another aqueous liquid dilution composition. In another example, the aqueous liquid dilution composition does not have crystals or has fewer crystals compared with another aqueous liquid dilution composition. In another example, the aqueous liquid dilution composition is desirable because it does not exhibit ringing.

iv. Safety

Typically, the aqueous liquid dilution compositions containing the concentrates are safe for human consumption, for example, containing only ingredients approved by the FDA for human consumption, for example GRAS-certified ingredients. In one example, one or more of the ingredients, for example, all the ingredients, are Kosher-certified. Safety of the liquid dilution compositions also relates to stability over time. Lack of or minimum oxidation of the liquid dilution compositions over time can contribute to the safety of the compositions.

v. Oral Bioavailability

In one example, the non-polar compounds, for example, the non-polar active ingredients, contained in the aqueous liquid dilution compositions exhibit a high or relatively high bioavailability, for example, a bioavailability that is higher than a liquid containing the non-polar active ingredient alone (i.e., not formulated in the liquid concentrate). Bioavailability relates to the ability of the body to absorb the non-polar active ingredient into a particular space, tissue cell and/or cellular compartment. Typically, non-polar active ingredients in liquids having small particle sizes are better absorbed than those with larger particle sizes.

e. Selecting a Formulation and Modifying Formulations

After evaluating a concentrate, e.g., a pre-emulsion concentrate and/or a liquid nanoemulsion concentrate, or a liquid dilution composition, either a particular formula can be chosen or one or more modifications can be made to the initial concentrate formula based on the results of the evaluation. When an initial concentrate does not display one or more desired properties, e.g., to the desired extent, based on the evaluation, the concentration of one or more ingredients can be adjusted and another initial concentrate made. The process can be repeated until a concentrate with the desired properties is made. For modification of the initial concentrate, the amount of the polar solvent (in the liquid nanoemulsion concentrates), surfactant, e.g., water-soluble vitamin E derivative, and/or non-polar active ingredient can be adjusted, for example, by adjusting the concentration within the appropriate concentration range. Additional ingredients also can be chosen. For example, modification of the initial concentrates can involve the addition of one or more additional ingredients. For example, if evaluation reveals that the oil and water phases of the concentrate or aqueous liquid dilution composition containing the diluted concentrate are separating, an emulsion stabilizer can be added to the formulation. In another example, a co-surfactant can be added to help emulsify the components of the concentrate. In another example, the phase (oil phase or water phase), to which a particular ingredient is added, can be modified. For example, the formulation can be modified to change whether an ingredient is added to the oil phase or the water phase.

When evaluation of the initial concentrate, e.g., the pre-emulsion concentrates and/or the liquid nanoemulsion concentrates, reveals that it has the desired properties, no modifications are made. In this example, the formula of the initial concentrate is used for making the concentrate. When two or more initial concentrates are made, for example, with increasing concentrations of an ingredient, the formula of one of the initial concentrates can be chosen. Which formula is chosen can be based on which formula has the most desirable properties. Alternatively, desirable properties can be balanced with relative amounts of ingredients. For example, it may be desirable to choose a formulation that uses the lowest or the highest concentration of a particular ingredient but still provides a concentrate that yields a clear liquid upon dilution in an aqueous medium, for example, when formulating a liquid dilution composition. The desired formulation may be the formulation that has the lowest concentration of the surfactant, e.g., the water-soluble vitamin E derivates described herein, while still providing a concentrate that yields a clear liquid upon dilution in an aqueous medium, for example, when formulating a liquid dilution composition. Or the desired formulation may be the formulation that has the highest concentration of the non-polar active ingredient, while still providing a concentrate that yields a clear liquid upon dilution into an aqueous medium, for example, when formulating a liquid dilution composition. In some examples, the formulation that yields the clearest liquid is desired.

Modifications can be made to the formula even if the initial concentrate, e.g., the pre-emulsion concentrates and/or the liquid nanoemulsion concentrates, possess the desired properties. For example, upon determining that a particular concentrate formulation results in desired properties, it can be desirable to modify the concentration of one or more ingredients to determine whether the same desired properties can be achieved if a higher or lower concentration of the ingredient is used. For example, it can be desirable to determine the lowest concentration of surfactant that can be used, while still generating a concentrate with a desired property, for example, the ability to form a clear liquid upon dilution in an aqueous medium. In another example, it can be desirable to determine the highest concentration of the non-polar ingredient that can be incorporated into a concentrate, while still maintaining the desired property, for example, the ability of the concentrate to form a clear liquid upon dilution in an aqueous medium. In another example, one or more additional ingredients can be added after making an initial concentrate with desirable properties, for example, flavoring agents and/or pH adjusting agents.

2. Compositions for Direct Consumption

Among the products provided herein are compositions that can be directly consumed without dilution. As such, they typically provide a single dosage or effective amount of an active compound, typically a non-polar compound, in an aqueous-based composition that contains 0.1-25%, generally 0.1-10%, 0.1-5%, 1%-5%, 1%-2% of the soluble vitamin E derivative with high dimer concentration (13%-29%) and any other ingredients of interest, including flavorings to render the composition palatable.

The compositions for direct consumption include any described above as concentrates, where the amount of active ingredient is suitable for direct consumption. Also included are the dilution compositions. All of the compositions for direct consumption can include the ingredients described in sections 1 and 2, above. In particular, compositions for direct consumption include flavorings or other ingredients, such as sweeteners, that render them palatable. The compositions for direct consumption can be formulated for single serving (single shot) ingestion or multiple servings. A single serving size depends upon the purpose of the composition as well as size, (and appetite) of the consumer. For example, a single serving can be at least 1 mL, 10 mL, 100 mL, 200 mL or more. The compositions can be provided in sealed containers, such as bottles and ampoules, and can contain other components to preserve freshness, such as bicarbonate, liquid nitrogen and other such components.

The compositions for direct consumption provided herein can be formulated in a variety of volumes and sizes, including, but not limited to, a single-serving shot or beverage. The composition is intended for consumption as a single serving, typically 1-200 mL, particularly smaller amounts, such as 1-10 mL, such as 4-5 mL. The compositions can be packaged in an ampoule or other sealed container. Thus, the compositions are single-serving beverage compositions, e.g., single-serving shots, that contain the water-soluble vitamin E derivative mixtures (compositions) provided herein and non-polar compounds and/or other active ingredients. Also provided herein are methods for formulating the compositions for direct consumption.

The compositions for direct consumption provided herein can be formulated for a single serving, for example, a single-serving shot. Typically, the compositions for direct consumption are formulated by diluting the non-polar compound or other active ingredient into an aqueous media, for example, a beverage, for example, water, flavored water, soda, milk, juice, including fruit juice, sauce, syrup, soup, a sports drink, a nutritional beverage, an energy drink, a vitamin-fortified beverage, or any beverage. Any beverage and concentration can be prepared or modified using the water-soluble vitamin E derivative mixtures (compositions) described herein and other water-soluble vitamin E derivative mixtures (compositions), for example, see U.S. Pub. No. 2008-0254188 and U.S. Pat. No. 6,045,826.

The provided beverage compositions include compositions for direct consumption, e.g., single-serving beverage compositions, such as single-serving shots. The compositions for direct consumption contain effective amounts of the non-polar active ingredient or other active ingredient, e.g., any of the non-polar ingredients described herein, including but not limited to, an alkaloid active ingredient, a vitamin, a γ-aminobutyric acid (GABA) derivative active ingredient, in relatively low volumes of liquid, for example, relatively low volumes of aqueous solvent for direct consumption without dilution. For example, the compositions for direct consumption, e.g., single-serving beverage compositions, include beverage compositions having a total volume of at or about, or less than at or about 400 mL, 350 mL, 300 mL, 250 mL, 200 mL, 150 mL, 100 mL, 75 mL, 50 mL, 40 mL, 30 mL, 20 mL, 19 mL, 18 mL, 17 mL, 16 mL, 15 mL, 14 mL, 13 mL, 12 mL, 11 mL, 10 mL, 9 mL, 8 mL, 7 mL, 6 mL, 5 mL, 4 mL, 3 mL, 2 mL, 1 mL, or less, that contain an effective amount of the non-polar active ingredient or other active ingredient. Typically, the amount of non-polar active ingredient or other active ingredient as a percentage (%), by weight, of the compositions for direct consumption, e.g., single-serving beverage compositions, can be, e.g., between 0.1% or about 0.1% and 30% or about 30%, by weight, of the beverage composition, and typically is between at or about 0.1% and at or about 20%, such as at or about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, by weight, of the beverage composition.

In one example, the composition for direct consumption has a serving size of between 1 mL or about 1 mL and 10 mL or about 10 mL, inclusive, for example, 1 mL, 2 mL, 3 mL, 4 mL, 5 mL, 6 mL, 7 mL, 8 mL, 9 mL or 10 mL. In some examples, the beverage composition contains between at or about 1 mg and at or about 1000 mg non-polar active ingredient or other active ingredient per mL or per serving, such as a 4 mL serving of the beverage composition. For example, the compositions for direct consumption can contain, e.g., at or about 1000 mg, 800 mg, 600 mg, 500 mg, 400 mg, 300 mg, 200 mg, 180 mg, 150 mg, 125 mg, 100 mg, 80 mg, 75 mg, 50 mg or 25 mg or less non-polar active ingredient or other active ingredient per serving of the beverage composition, e.g., per 4 mL of the beverage composition. Exemplary of the compositions are those described in co-pending Publication No. US-2010-0041622-A1. The active ingredient therein is an aminoalkane and/or aminoalkane derivative compounds of formula I:

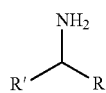

and biocompatible derivatives thereof, where one of R and R' is an alkyl containing from 2 to 20 carbons, such as 2-10, 2-8, 2-7, 2-6, 2-5, 2-4 and 2-3 carbons and the other is a hydrogen or an alkyl containing from 1 to 20 carbons, such as 1-10, 1-8, 1-7, 1-6, 1-5, 1-4, 1-3 and 1 or 2 carbons, such as 2-amino-4-methylhexane HCl and its derivatives. For example, an aminoalkane and/or aminoalkane derivative compound can replace any desired additive, nutraceutical, vitamin, drug or other compound, for which direct administration intended. The compositions contain taste-modifying agents to render the compositions palatable, e.g. increase or enhance palatability compared to the composition in the absence of the taste-modifying agents, for oral ingestion by a subject. Exemplary compositions are provided in Example 10.

3. Exemplary Ingredients and Concentration Ranges

The following sections describe ingredients used in the provided pre-emulsion concentrates and liquid nanoemulsion concentrates or other forms of concentrates and beverage compositions. As noted, the form of the resulting composition containing the high dimer water-soluble vitamin E derivative mixture depends upon the concentration ranges and types of ingredients. Concentrates typically are intended for dilution prior to consumption, and, thus, contain active ingredients in higher than single dosage concentrations. Where high concentration of the water-soluble vitamin E derivative composition are employed (typically greater than 25% or about 25%), particularly without any liquid components, the compositions are waxy. Where lower concentrations are used, the compositions can be more liquid; where polar solvents and or other polar ingredients are included the concentrates are emulsions. All can be used as vehicles for solubilizing desired non-polar ingredients in food and beverages.

Each of the provided concentrates, e.g., pre-emulsion concentrates and liquid nanoemulsion concentrates and semi-solids, and beverage compositions, e.g., liquid dilution compositions and single-serving shots, contains at least one surfactant that is a water-soluble vitamin E derivative composition described herein, for example, the TPGS, TPGS analogs, TPGS homologs and TPGS derivatives described herein. The surfactant typically has an HLB value of between 12 or about 12 and 20 or about 20, for example, 12, 13, 14, 15, 16, 17, 18, 19 or 20, or about 12, about 13, about 14, about 15, about 16, about 17, about 18, about 19 or about 20, typically between at or about 12 and at or about 14. For example, TPGS, such as the TPGS described herein has an HLB value of about 12 to 14, generally about 13.

For compositions that are to be diluted, the water-soluble vitamin E derivative mixture (composition), e.g., TPGS, is present in an amount as a percentage (%), by weight, of the concentrate (wt %), e.g., from at or about 20% to at or about 90%, such as 20% to 25%, 20% to 30%, 20% to 35%, 20% to 40%, 20% to 45%, 20% to 50%, 20% to 55%, 20% to 60%, 20% to 65%, 20% to 70%, 20% to 75%, 20% to 80%, 20% to 85%, 20% to 90%, 25% to 30%, 25% to 35%, 25% to 40%, 25% to 45%, 25% to 50%, 25% to 55%, 25% to 60%, 25% to 65%, 25% to 70%, 25% to 75%, 25% to 80%, 25% to 85%, 25% to 90%, 30% to 35%, 30% to 40%, 30% to 45%, 30% to 50%, 30% to 55%, 30% to 60%, 30% to 65%, 30% to 70%, 30% to 75%, 30% to 80%, 30% to 85%, 30% to 90%, 35% to 40%, 35% to 45%, 35% to 50%, 35% to 55%, 35% to 60%, 35% to 65%, 35% to 70%, 35% to 75%, 35% to 80%, 35% to 85%, 35% to 90%, 40% to 45%, 40% to 50%, 40% to 55%, 40% to 60%, 40% to 65%, 40% to 70%, 40% to 75%, 40% to 80%, 40% to 85%, 40% to 90%, 45% to 50%, 45% to 55%, 45% to 60%, 45% to 65%, 45% to 70%, 45% to 75%, 45% to 80%, 45% to 85%, 45% to 90%, 50% to 55%, 50% to 60%, 50% to 65%, 50% to 70%, 50% to 75%, 50% to 80%, 50% to 85%, 50% to 90%, 55% to 60%, 55% to 65%, 55% to 70%, 55% to 75%, 55% to 80%, 55% to 85%, 55% to 90%, 60% to 65%, 60% to 70%, 60% to 75%, 60% to 80%, 60% to 85%, 60% to 90%, 65% to 70%, 65% to 75%, 65% to 80%, 65% to 85%, 65% to 90%, 70% to 75%, 70% to 80%, 75% to 85%, 75% to 90%, 80% to 85%, 80% to 90% and 85% to 90%, by weight, of the concentrate. For direct consumption, the water-soluble vitamin E derivative composition, such as TPGS, is present in amounts well below 15%, such as for example, equal to or less than 5%, 4%, 3%, 2%, 1%, 0.5%, or 0.1%.

Exemplary concentrations of the water-soluble vitamin E derivative, e.g., TPGS, in the pre-emulsion concentrate are at or about 15%, 16%, 18%. 20%, 25%, 30%, 35%, 40%, 45%, 49.5%, 50%, 55%, 60%, 65%, 68%, 69.5%, 70%, 75%, 79.5%, 80%, 85%, 89.5% and 90% (wt %) of the concentrate. The concentrates can contain lower amounts of the water-soluble vitamin E derivative mixture, and the compositions for direct consumption contain lower amounts, such as 0.1%-15%, generally 1%-5%.

Each of the provided compositions, e.g., pre-emulsion concentrates and liquid nanoemulsion concentrates, further contains a non-polar compound including, but not limited to, the exemplary non-polar compounds described herein below. Typically, the non-polar compound is or has one or more non-polar active ingredients, for example, an oil-based active ingredient such as a polyunsaturated fatty acid (PUFA), a coenzyme Q or a phytochemical. The concentrates provided herein can contain one non-polar compound or more than one non-polar compound, such as two, three, four, five or more non-polar compounds. The concentrates provided herein can contain higher amounts (i.e., concentrations) of non-polar compounds than can available concentrates, such as up to at or about 75 wt % non-polar compound For formulating the concentrates, the total amount of non-polar compound(s) that contains one or more non-polar active ingredients, is typically present in a total amount as a percentage (%), by weight, of the concentrate (wt %), e.g., from at or about 1% to at or about 75 wt %, such as between or between about 1% and 5%, 1% and 10%, 1% and 15%, 1% and 20%, 1% and 25%, 1% and 30%, 1% and 35%, 1% and 40%, 1% and 45%, 1% and 50%, 1% and 55%, 1% and 60%, 1% and 65%, 1% and 70%, 1% and 75%, 5% and 10%, 5% and 15%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 15%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 15% and 20%, 15% and 25%, 15% and 30%, 15% and 35%, 15% and 40%, 15% and 45%, 15% and 50%, 15% and 55%, 15% and 60%, 15% and 65%, 15% and 70%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, 25% and 30%, 25% and 35%, 25% and 40%, 25% and 45%, 25% and 50%, 25% and 55%, 25% and 60%, 25% and 65%, 25% and 70%, 25% and 75%, 30% and 35%, 30% and 40%, 30% and 45%, 30% and 50%, 30% and 55%, 30% and 60%, 30% and 65%, 30% and 70%, 30% and 75%, 35% and 40%, 35% and 45%, 35% and 50%, 35% and 55%, 35% and 60%, 35% and 65%, 35% and 70%, 35% and 75%, 40% and 45%, 40% and 50%, 40% and 55%, 40% and 60%, 40% and 65%, 40% and 70%, 40% and 75%, 45% and 50%, 45% and 55%, 45% and 60%, 45% and 65%, 45% and 70%, 45% and 75%, 50% and 55%, 50% and 60%, 50% and 65%, 50% and 69%, 55% and 60%, 55% and 65%, 55% and 70%, 55% and 75%, 60% and 65%, 60% and 70%, 60% and 75%, 65% and 70%, 65% and 75% and 70% and 75% non-polar compound, by weight, of the concentrate. Exemplary concentrations of the total amount of non-polar compound(s) in the concentrate is at or about 5%, 10%, 12.5%, 15%, 15.5%, 16.7%, 20%, 22%, 25%, 30%, 31.5%, 35%, 40%, 45.5% and 50% (wt %) of the concentrate.

The concentrates, e.g., the pre-emulsion concentrates and liquid nanoemulsion concentrates, can further contain additional ingredients, for example, preservatives and/or non-polar solvents. In some examples, the preservative is a natural preservative, such as benzyl alcohol. In some examples, the non-polar solvent is an oil, other than the non-polar compound, for example, vitamin E oil, flaxseed oil or rice bran oil.

The liquid nanoemulsion concentrates additionally contain at least one polar solvent. Exemplary polar solvents include water, propylene glycol and glycerin (glycerol). One or more, typically more than one, additional ingredients can be added to the liquid nanoemulsion concentrate. Exemplary of other additional ingredients that can be added to the liquid concentrates include emulsion stabilizers, for example, a blend of gums; a pH adjuster, for example, citric acid, phosphoric acid; one or more flavoring agents, for example, D-limonene or lemon oil; a co-surfactant, for example, a phospholipid, for example, phosphatidylcholine, or a sucrose fatty acid ester surfactant.

The appropriate concentration ranges for the additional ingredients are described in individual sections below. Typically, the concentration of the additional ingredients depends, in part, on the concentrations of the non-polar active ingredient and the water-soluble vitamin E derivative surfactant. Typically, the concentrations of these ingredients (surfactant and non-polar compound) are the focus of the formulating methods. For example, when it is determined that modifications to ingredient concentrations in the initial concentrate should be made, it typically is the concentrations of one or more of these ingredients that are adjusted.

In one example, it can be desirable to add one or more of the additional ingredients after evaluation of the initial concentrate, for example, in order to improve the concentrate with respect to one or more desired properties.

a. Water-Soluble Vitamin E Derivatives

The compositions for direct consumption, the pre-emulsion concentrates and liquid nanoemulsion concentrates provided herein contain the water-soluble vitamin E derivatives described herein, for example, the TPGS compounds noted above, including TPGS, TPGS homologs, TPGS analogs and TPGS derivatives and other vitamin E derivatives. The water-soluble vitamin E derivatives can act as surfactants. The water-soluble vitamin E derivatives can be any water-soluble vitamin E derivative composition described herein and prepared according to the methods described herein, for example, tocopherol-derived compositions and tocotrienol-derived compositions, including, but not limited to, polyalkylene glycol derivatives of tocopherol, e.g., polyethylene glycol (PEG) derivatives of tocopherol, such as vitamin E TPGS (D-α-tocopheryl polyethylene glycol succinate), and polyalkylene glycol derivatives of tocotrienol, e.g., polyethylene glycol (PEG) derivatives of tocotrienol. The water-soluble vitamin E derivative mixtures (compositions), e.g., compositions of TPGS, TPGS analogs, TPGS homologs or TPGS derivatives, contain less water-soluble vitamin E derivative monomer, i.e., less than 70 wt %, and more water-soluble vitamin E derivative dimer, i.e., more than 12 wt %, than in known water-soluble vitamin E derivative mixtures (compositions).

In the concentrates provided herein, e.g., the pre-emulsion concentrates and liquid nanoemulsion concentrates, the water-soluble vitamin E derivatives can act as surfactants by aggregating in aqueous liquids, such as water, to form micelles, which contain the non-polar compound(s). The hydrophilic portion(s) of the surfactant molecules are oriented toward the outside of the micelle, in contact with the aqueous medium, while the hydrophobic portion(s) of the surfactant molecules are oriented toward the center of the micelle, in contact with the non-polar compound(s), which is contained in the center of the micelle. Properties of the provided food and beverage products, for example, the particle size of the concentrates and desirable properties related to the particle size, are influenced by the choice of surfactant(s) and the relative amount (concentration) of surfactant. For example, the HLB of the surfactant(s) can affect particle size, clarity, taste, smell, crystal formation and other properties of the provided food and beverage products. Similarly, the concentration of the surfactant compared with the concentration(s) of other ingredients, particularly compared with the concentration of the polar solvent(s) and the concentration of the non-polar compound(s), can affect various desirable properties, for example, the ability to disperse or dissolve in aqueous media, e.g., to form a clear aqueous liquid dilution composition or pleasant taste and/or smell. The water-soluble vitamin E derivative mixtures (compositions) described herein can be used to increase the amount of non-polar compound that can be added to a concentrate, such as the concentrates provided herein, without sacrificing the various desirable properties of the food and beverage products containing the concentrate, such as particle size, clarity, taste, smell, crystal formation and other desirable properties of food and beverage products.

The water-soluble vitamin E derivatives described herein and others known to those of skill in the art and used in the concentrates provided herein, e.g., the pre-emulsion concentrates and liquid nanoemulsion concentrates, typically have an HLB value between or about between 12 and 20, for example, at least 12, 13, 14, 15, 16, 17, 18, 19, up to 20, about 12, about 13, about 14, about 15, about 16, about 17, about 18, about 19 or about 20. Typically, the water-soluble vitamin E derivative is a natural surfactant, for example, a surfactant that is GRAS (generally recognized as safe) certified by the FDA and/or Kosher certified, for example, TPGS, such as the TPGS compositions described herein. In one example, the water-soluble vitamin E derivative composition used in the provided concentrates is a polyalkylene glycol derivative of vitamin E, for example, a polyethylene glycol derivative of vitamin E, e.g., TPGS. TPGS has an HLB value of or about 13.

At room temperature, TPGS typically is a waxy low-melting solid. TPGS can be heated prior to use, for example, to at least the melting temperature, such as between or about between 37° C. and 41° C. or about 41° C. and the desired amount is poured out. Alternatively, TPGS can be added as a waxy solid to a vessel and heated with the heating apparatus.

b. Non-Polar Compounds Containing Non-Polar Active Ingredients

The concentrates, e.g., the pre-emulsion concentrates and liquid nanoemulsion concentrates, contain one or more non-polar compounds that contain one or more non-polar active ingredients. Non-polar compounds include any lipophilic or lipid-soluble compound that has greater solubility in organic solvents (e.g., ethanol, methanol, ethyl ether, acetone, and benzene) and in fats and oils, than in polar solvents, for example, water. Typically, the non-polar compounds are poorly water-soluble, for example, water insoluble or are compounds that have low water solubility. The non-polar compounds include, but are not limited to, drugs, hormones, vitamins, nutrients and other lipophilic compounds. Exemplary non-polar compounds are listed herein below. The provided methods and compositions can be used to dilute (e.g., dissolve/disperse) any non-polar compound in aqueous medium, such as water. The non-polar compound can differ from the surfactant, e.g., water-soluble vitamin E derivative, for example, the non-polar compound is not a water-soluble vitamin E derivative. Exemplary of non-polar compounds that can be used in the provided pre-emulsion concentrates and liquid nanoemulsion concentrates are:

Non-polar ingredients containing essential fatty acids, such as polyunsaturated fatty acids (PUFAs), for example, gamma-linolenic acid (GLA), e.g., borage oil and evening primrose (Oenothera biennis) oil, blackcurrant seed oil, hemp seed oil and spirulina extract; compounds containing omega-3 fatty acids, such as natural and synthetic omega-3 fatty acids, for example, compounds containing omega-3 polyunsaturated long-chain fatty acids, including eicosapentaenoic acid (EPA) (20:5ω3); docosahexaenoic acid (DHA) (22:6ω3); eicosatetraenoic acid (24:4ω3); docosapentaenoic acid (DPA, clupanodonic acid) (22:5ω3); 16:3ω3; 24:5ω3and/or nisinic acid (24:6ω3), e.g., fish oil, algae oil, krill oil, canola oil, flaxseed oil, soybean oil and walnut oil; compounds containing short-chain omega-3 fatty acids, for example, alpha-linolenic acid (α-linolenic acid; ALA;18:3ω3) and stearidonic acid (18:4ω3), esters of an omega-3 fatty acid and glycerol, for example, monoglycerides, diglycerides and triglycerides, esters of omega-3 fatty acid and a primary alcohol, for example, fatty acid methyl esters and fatty acid esters, precursors of omega-3 fatty acid oils, for example, EPA precursor, DHA precursor, derivatives such as polyglycolized derivatives or polyoxyethylene derivatives, oils containing the omega-3 fatty acids, for example, fish oil (marine oil), e.g., highly purified fish oil concentrates, perilla oil, krill oil, and algae oil, e.g., microalgae oil; compounds containing omega-6 fatty acids, such as compounds containing linoleic acid (18:2ω6) (a short-chain fatty acid); gamma-linolenic acid (GLA; 18:3ω6); dihomo gamma linolenic acid (DGLA; 20:ω6); eicosadienoic acid (20:2ω6); arachidonic acid (AA; 20:4 6); docosadienoic acid (22:2ω6); adrenic acid (22:4ω6); and/or docosapentaenoic acid (22:5ω6), for example, borage oil, corn oil, cottonseed oil, grapeseed oil, peanut oil, primrose oil, e.g., evening primrose (Oenothera biennis) oil, blackcurrant seed oil, hemp seed oil, spirulina extract, safflower oil, sesame oil, coconut oil and soybean oil;

other fatty acids, such as triglycerides, including medium chain triglycerides, polar lipids, for example, ether lipids, phosphoric acid, choline, fatty acids, glycerol, glycolipids, triglycerides, and phospholipids (e.g., phosphatidylcholine (lecithin), phosphatidylethanolamine, and phosphatidylinositol); saw palmetto extract; ethyl linoleate; herb oils, for example, garlic oils and scordinin; short-chain saturated fatty acids (4:0-10:0), lauric acid (12:0), myristic acid (14:0), pentadecanoic acid (15:0), palmitic acid (16:0), palmitoleic acid (16:1ω7), heptadecanoic acid (17:0), stearic acid (18:0), oleic acid (18:1ω9), and arachidic acid (20:0);

micronutrients, such as vitamins, minerals, co-factors, for example, coenzyme Q10 (coQ10, also called ubiquinone), ubiquinol, tumeric extract (cucuminoids), saw palmetto lipid extract (saw palmetto oil), echinacea extract, hawthorn berry extract, ginseng extract, lipoic acid (thioctic acid), ascorbyl palmitate, kava extract, St. John's Wort (hypericum, Klamath weed, goat weed), extract of quercitin, dihydroepiandrosterone, and indol-3-carbinol;

carotenoids, including hydrocarbons and oxygenated, alcoholic derivatives of hydrocarbons, for example, beta carotene, mixed carotenoid complex, lutein, lycopene, zeaxanthin, cryptoxanthin, for example, beta-crytoxanthin, beta carotene, astaxanthin, bixin, canthaxanthin, capsanthin, capsorubin, apo-carotenal, beta-12'-apo-carotenal, "Carotene" (mixture of alpha- and beta-carotene), gamma carotene, ciolerythrin, and esters of hydroxyl- or carboxyl-containing members thereof;

fat-soluble vitamins, for example, vitamins A, D, E and K, and corresponding pro-vitamins and vitamin derivatives, such as esters, with an action resembling that of vitamin A, D, E or K, for example; retinol (vitamin A) and pharmaceutically acceptable derivatives thereof, such as palmitate ester of retinol and other esters of retinol, calciferol (vitamin D) and its pharmaceutically acceptable derivatives thereof and precursors of vitamin D, d-alpha tocopherol (vitamin E) and derivatives thereof, including pharmaceutical derivatives thereof, for example, tocotrienols, d-alpha tocopherol acetate and other esters of d-alpha tocopherol, and ascorbyl palmitate, a fat-soluble version of vitamin C;

phytochemicals, including phytoestrogens, for example, genistein and daidzein, such as isoflavones, e.g., soy isoflavones, flavonoids, phytoalexins, for example, resveratrol (3,5,4'-trihydroxystilbene), red clover extract, and phytosterols;

lipid-soluble drugs, including natural and synthetic forms of immunosuppressive drugs, such as cyclosporin, protease inhibitors such as ritonavir, macrolide antibiotics and oil soluble anesthetics such as propofol, natural and synthetic forms of steroidal hormones, for example, estrogens, estradiols, progesterone, testosterone, cortisone, phytoestrogens, dehydroepiandrosterone (DHEA), growth hormones and other hormones; and oil-soluble acids and alcohols, for example, tartaric acid, lactylic acid, butylated hydroxyanisole, butylated hydroxytoluene, lignin, sterols, polyphenolic compounds, oryzanol, cholesterol, phytosterols, flavonoids, such as quercetin and resveratrol, and diallyl disulfides.

i. Polyunsaturated Fatty Acid (PUFA)-Containing Active Ingredients

Exemplary of the non-polar compounds contained in the concentrates, e.g., pre-emulsion concentrates and liquid nanoemulsion concentrates, are compounds containing fatty acids, for example, non-polar ingredients containing the non-polar active ingredients polyunsaturated fatty acids (PUFAs). Fatty acids are straight-chain hydrocarbon molecules with a carboxyl (COOH) group at one end of the chain. PUFAs are fatty acids that contain more than one carbon-carbon double bonds in the carbon chain of the fatty acid. PUFAs, particularly essential fatty acids, are useful as dietary supplements.

Different nomenclature are used to describe fatty acid molecules. Lipid nomenclature, for example, 18:3ω3, indicates the carbon chain length, number of double bonds and the position along the carbon chain of the first carbon-carbon double bond in a fatty acid. Using this nomenclature, each carbon along the chain is labeled according to its position relative to one end of the chain. For example, the first carbon away from the carboxylate end is named α, the second is named β, and so forth. The last carbon in the molecule (furthest from the carboxy group) always is labeled ω (or omega, or n). The number of carbons and the number of double bonds are listed first in the lipid name of a fatty acid, separated by a colon. For example, the name "18:3" indicates that the molecule has eighteen (18) carbons and three (3) double bonds. Following these numbers, the position at which the first double bond appears, relative to the last (ω) carbon, is listed. For example, the nomenclature, 18:3ω3 (or 18:3 omega-3; or 18:3 n-3), describes a fatty acid with eighteen (18) carbons and three (3) double bonds, the first of which occurs at the third carbon away from the omega carbon.

Alternatively, chemical nomenclature can be used. The chemical name of a fatty acid describes the position of each double bond. In the chemical naming, the carbons are numbered, beginning with 1, starting with the carbon that is part of the carboxy (COOH) group. Thus, with this numbering system, the α carbon is labeled "2." The chemical name of the fatty acid lists the first carbon (from the COOH end) to participate in each double bond.

Certain PUFAs are called essential fatty acids because mammals, including humans, cannot synthesize them using any known chemical pathway, and must obtain them from diet or by supplementation (U.S. Pat. No. 6,870,077; Covington (2004) American Family Physician 70(1):133-140). The essential PUFAs are the omega-3 (ω3; n-3) fatty acids and the omega-6 (ω-6; n-6) fatty acids. Omega-3 and omega-6 fatty acids are methylene interrupted polyenes, which have two or more cis double bonds, separated by a single methylene group. Exemplary of omega-3 fatty acids are alpha-linolenic acid (α-linolenic acid; ALA; 18:3ω3) (a short-chain fatty acid); stearidonic acid (18:4ω3) (a short-chain fatty acid); eicosapentaenoic acid (EPA; 20:5ω3); docosahexaenoic acid (DHA; 22:6ω3); eicosatetraenoic acid (24:4ω3); docosapentaenoic acid (DPA; clupanodonic acid; 22:5ω3); 16:3ω3; 24:5ω3 and nisinic acid (24:6ω3). Longer chain omega-3 fatty acids can be synthesized from ALA (the short-chain omega-3 fatty acid). Exemplary of omega-6 fatty acids are linoleic acid (18:2ω6) (a short-chain fatty acid); gamma-linolenic acid (GLA; 18:3ω6); dihomo gamma linolenic acid (DGLA; 20:3ω6); eicosadienoic acid (20:2ω6); arachidonic acid (AA; 20:4ω6); docosadienoic acid (22:2ω6); adrenic acid (22:4ω6); and docosapentaenoic acid (22:5ω6).

While the longer chain omega-3 and omega-6 essential fatty acids can be synthesized from ALA (the short-chain omega-3 fatty acid) and linolenic acid (LA), respectively, evidence suggests that conversion of these short chain fatty acids in humans is slow. Thus, a major source of long chain essential PUFAs is dietary (see, e.g., Ross et al. (2007) Lipids in Health and Disease 6:21 and Lands (1992) FASEB J. 6(8):2530). Dietary supplements containing PUFAs, particularly essential PUFAs, are desirable for protection against cardiovascular disease, inflammation and mental illnesses (see, e.g., Ross et al. (2007) Lipids in Health and Disease 6:21; Lands (1992) FASEB J. 6(8):2530; and U.S. Pat. No. 6,870,077). Evidence suggests that essential fatty acids, particularly EPA and DHA, in the form of food and nutritional supplements, play a role in preventing a number of disease states, including cardiovascular diseases, inflammation, mental health and behavioral diseases and disorders (see, e.g., Ross et al. (2007) Lipids in Health and Disease 6:21; Lands (1992) FASEB J. 6(8):2530; U.S. Pat. No. 6,870,077; and Covington (2004) American Family Physician 70(1):133-140).

Omega-9 fatty acids are non-essential PUFAs. Exemplary of omega-9 fatty acids are oleic acid (which is monounsaturated) (18:1ω9); eicosenoic acid (20:1ω9); mead acid (20:3ω9); erucic acid (22:1ω9); and nervonic acid (24:1ω9).

Conjugated fatty acids are PUFAs with two or more conjugated double bonds. Conjugated fatty acids can be used as nutritional supplements. Exemplary of conjugated fatty acids are conjugated linoleic acid (CLA), for example, 18:2ω7, 18:2ω6; conjugated linolenic acid, for example, 18:3ω6, 18:3ω5; and other conjugated fatty acids, for example, 18:3ω3, 18:4ω3, and 20:5ω6.

(a) Omega-3 Fatty Acid Compounds

Exemplary of the PUFA-containing non-polar compounds that can be used in the provided concentrates, e.g., pre-emulsion concentrates and liquid nanoemulsion concentrates, are non-polar compounds that contain one or more of the non-polar active ingredient omega-3 (ω3; n-3) fatty acids, for example, compounds containing DHA and/or EPA fatty acids, for example, marine oils, e.g., fish oil, krill oil and algae oil; and compounds containing ALA fatty acids, for example, flax seed oil.

Typically, oils and aqueous compositions containing long-chain polyunsaturated fatty acids (PUFA) are susceptible to oxidation, making them unstable and giving them an unpleasant taste. The ingredients and relative concentrations thereof, as well as the methods for making the concentrates, contribute to desirable properties of DHA/EPA-containing concentrates. For example, the ingredients and methods used to make the concentrates provided herein minimize the "fishy" odor and/or taste of DHA/EPA compositions and increase their stability over time. For example, the compounds in the concentrates can have low oxidation, contributing to these desirable properties.

(1) DHA/EPA

Exemplary of non-polar compounds that contain one or more omega-3 fatty acids, which can be used in the provided concentrates, e.g., pre-emulsion concentrates and liquid nanoemulsion concentrates, are compounds containing DHA and/or EPA, for example, marine oil, e.g., fish oil, hill oil and algae oil. Any oil containing DHA and/or EPA can be used. In one example, the non-polar compound contains between 10% or about 10% and 40% or about 40% DHA. In another example, the non-polar compound contains between 25% or about 25% and 45% or about 45% DHA. In another example, the non-polar compound contains at least 60% or about 60%, by weight (w/w), DHA, for example, at least 65% or about 65%, at least 70% or about 70%, at least 75% or about 75%, at least 80% or about 80%, at least 85% or about 85%, or at least 90% or about 90%, by weight (w/w), DHA. In another example, the non-polar compound contains between 5% or about 5% and 15% or about 15% EPA, for example, 5, 6, 7, 8, 9, 10, 11, 12, 13, 14 or 15%, by weight (w/w), EPA. In another example, the non-polar compound comprises not more than 10% or about 10% EPA or less than 10% or about 10%, EPA. In another example, the non-polar compound contains DHA and EPA, for example, DHA representing at least 20% or about 20%, by weight, of the non-polar compound and EPA representing not more than 13% or about 13% of the non-polar compound, for example, not more than 10% or about 10%, by weight, of the non-polar compound. In another example, the non-polar compound contains DHA, representing at least 35% or about 35% of the non-polar compound and EPA representing not more than 13% or about 13% of the non-polar compound, for example, not more than 10% or about 10% of the non-polar compound. In another example, the non-polar compound contains DHA and EPA, for example, DHA representing at least 70% or about 70% of the non-polar compound and EPA representing not more than 13% or about 13% of the non-polar compound, for example, not more than 10% or about 10% of the non-polar compound. In one example, the non-polar compound contains DHA and EPA, for example, the total of DHA and EPA represents at least 30% or about 30% of the non-polar compound. In another example, the non-polar compound contains DHA and EPA, for example, the total of DHA and EPA represents at least 61% or about 61% of the non-polar compound.

(i) Fish Oils

Exemplary of the PUFA-containing non-polar compounds that can be used in the provided concentrates, e.g. pre-emulsion concentrates and liquid nanoemulsion concentrates, are oils derived from fish which contain DHA, EPA or both DHA and EPA. Particularly, cold water marine fish are a known source of omega-3 fatty acids (U.S. Pat. No. 4,670,285). Suitable fish oils containing DHA, EPA or both DHA and EPA can be obtained from any of a number of commercial sources, for example, fish oils available from Jedwards International, Inc., any of which can be used with the provided compositions.

Fish oils typically are extracted from fish tissue, for example, frozen fish tissue. For example, the fish oil can be a tasteless fish oil, for example, a cod liver oil, which has been isolated from fish, for example, from cod liver, and then refined and deodorized, or in some other way treated so its taste becomes, neutral, such as described in International Publication Nos. WO 00/23545 and WO 2004/098311. In one example, these fish oils are isolated from frozen fish tissue by a process that minimizes oxidation. Exemplary of such a tasteless fish oil is a fish oil sold under the trademark Denomega™ 100 (Borregaard Ingredients, Sarpsborg, Norway; distributed by Denomega Nutritional Oils AS, Boulder, Colo.). Typically, the tasteless fish oil, for example, cod liver oil, contains between or about between 25% and 35% omega-3 fatty acids, for example, 34% omega-3 fatty acids. In one example, the fish oil, for example, the Denomega™ 100 oil, contains 13% or about 13% DHA and 13% or about 13% EPA.

Also exemplary of the fish oils that can be included in the provided concentrates are fish oils containing high amounts of omega-3 fatty acids, for example, high amounts of DHA. One example of such a fish oil contains at least or about at least 85% DHA, typically greater than 85% DHA, and at least or about at least 90% omega-3 fatty acids, typically greater than 90% omega-3 fatty acids. In another example, the fish oil can contain 98% PUFA, 89% omega-3 fatty acids, about 70% DHA, about 10% EPA, 8.9% omega-6 fatty acids and 0.7% omega-9 fatty acids.

Exemplary of a fish oil containing high amounts of omega-3 fatty acids that can be used as the non-polar compound in the provided concentrates is an omega-3 fish oil EE (O3C Nutraceuticals; supplied by Jedwards International Inc., Quincy, Mass.), which contains 89% omega-3 fatty acids, 8.9% omega-6 fatty acids, 0.7% omega-9 fatty acids, 0.1% saturated fatty acids, 1.0% monounsaturated fatty acids, 74.5% docosahexanoic (DHA) fatty acids, 9.3% eicosapentaenoic (EPA) fatty acids and 98% polyunsaturated fatty acids (PUFA). This fish oil also contains 0.1% (16:0) palmitic acid, 0.1% (16:1ω7) palmitoleic acid, 0.1% (18:0) stearic acid, 0.6% (18:1ω9) oleic acid, 0.1% (18:1ω7) oleic acid, 0.3% (18:2ω6) linoleic acid, 0.2% (18:3ω3) linolenic acid, 0.2% (18:4ω3) octadecatetraenoic acid, 0.1% (20:1ω9) eicosanoic acid, 0.1% (20:2ω6) eicosadienoic acid, 0.2% (20:3ω6) eicosatrienoic acid, 2.4% (20:4ω6) arachidonic acid, 0.6% (20:4ω3) arachidonic acid, 0.1% (22:1ω11) erucic acid, 0.6% (21:5ω3) uncosapentaenoic acid, 0.5% (22:4ω6) docosatetraenoic acid, 5.4% (22:5ω6) docosapentaenoic acid, 3.6% (22:5ω3) docosapentaenoic acid and 0.9% other fatty acids.

Also exemplary of a fish oil containing high amounts of omega-3 fatty acids that can be used in the provided concentrates is Omega Concentrate 85 DHA TG Ultra (O3C Nutraceuticals AS, Oslo, Norway), which contains greater than 85% DHA (C22:6n-3) and greater than 90% total omega-3 fatty acids and is isolated from fatty fish species in the Eugraulidae, Clupeidae and Scombridae families. This fish oil is produced by purifying and concentrating the oils from these fish with gentle technologies to increase the concentration of omega-3 fatty acid DHA. Any fish oil containing DHA and/or EPA can be used as the non-polar compound in the provided compositions. Also exemplary of the fish oils are other fish oils made by O3C Nutraceuticals, AS and other fish oils supplied by Jedwards International, Inc.

Any fish oil containing DHA and/or EPA can be used as the non-polar compound in the provided concentrates. Exemplary of the fish oils that can be included in the provided compositions is Eterna™ Omegasource™ Oil (supplied by Hormel Foods Specialty Products Division, Austin, Minn.), which contains at least 30% omega-3 fatty acids (DHA, EPA and ALA), is odorless, virtually free of cholesterol and bland in flavor. This fish oil contains about 28% DHA and EPA, typically 17% EPA and 11% DHA, and additionally contains 4.5% omega-6 fatty acids. Also exemplary of the fish oils that can be included in the provided compositions are Omega 30 TG Food Grade (Non-GMO) MEG-3™ Fish Oil (supplied by Ocean Nutrition Canada, Dartmouth, Nova Scotia, Canada), a kosher fish oil which contains about 30% DHA/EPA and Marinol C-38 (supplied by Lipid Nutrition B.V., Channahon, Ill.), which contains about 52% omega-3 fatty acids, including at least 38% DHA/EPA, more specifically includes about 22% EPA and 14% DHA. Also exemplary of fish oils are Marinol D-40 (supplied by Lipid Nutrition B.V., Channahon, Ill.), which contains about 40% DHA and 7% EPA; omega-3 fish oil 70TG that is 61%, by weight, DHA/EPA; fish oils sold by GC Rieber Oils (Kristiansund, Norway) that contain 30% or 65% DHA; ONC TG fish oil sold by Ocean Nutrition Canada (Dartmouth, Nova Scotia); Omevital™ 30% MP Gold, a fish oil that contains 30% DHA/EPA (Cognis, Monheim am Rhein, North Rhine-Westphalia, Germany); and a fish oil containing 60% DHA (sold by FINA LLC, Cincinnati, OH). Also exemplary of the fish oils are krill oils, such as those made according to International Publication No. WO 2007/080515.

(ii) Algae Oil

Also exemplary of non-polar compounds containing omega-3 PUFAs, particularly DHA (and optionally EPA), that can be used as the non-polar compound in the provided concentrates, e.g., pre-emulsion concentrates and liquid nanoemulsion concentrates, are oils derived from microorganisms, for example, oils derived from marine dinoflagellates, such as microalgae, e.g., *Crypthecodinium* sp, particularly *Crypthecodinium cohnii*. Microalgae oils, like fish oils, are an excellent source of omega-3 fatty acids, particularly DHA (U.S. Pat. Nos. 5,397,591; 5,407,957; 5,492,938; and 5,711,983). Exemplary of oils derived from microalgae are the oils disclosed in (and oils made according to the methods described in) U.S. Pat. Nos. 5,397,591; 5,407,957; 5,492,938; and 5,711,983 and U.S. Publication No. 2007/0166411, including DHASCO® and DHASCO-S® (Martek Biosciences Corporation).

For example, U.S. Pat. No. 5,397,591 describes, inter alia, single cell edible oils (algae oils) (and methods for making the oils), which contain at least 70% triglycerides, which contain about 20-35% DHA and lack EPA, isolated from *Crypthecodinium cohnii*, preferably containing more than 70% triglycerides, having 15-20% myristic acid; 20-2 5% palmitic acid; 10-15% oleic acid; 30-40% DHA; and 0-10% other triglycerides. U.S. Pat. No. 5,407,957 describes, inter alia, algae oils (and methods for making the oils) derived from *Crypthecodinium cohnii*, preferably containing greater than about 90% triglycerides, at least 35% DHA, by weight (w/w), in one example, having 15-20% myristic acid; 20-25% palmitic acid; 10-15% oleic acid; 40-45% DHA; and 0-5% other oils. U.S. Pat. No. 5,492,938 describes, inter alia, single cell edible oils (and methods for making the oils) containing at least 70% triglycerides, which contain about 20-35% DHA and lack EPA, isolated from *Crypthecodinium cohnii*, in one example containing more than 70% triglycerides, having 15-20% myristic acid; 20-25% palmitic acid; 10-15% oleic acid; 30-40% DHA; and 0-10% other triglycerides. U.S. Pat. No. 5,711,983 describes, inter alia, single cell edible oils (and methods for making the oils) containing at least 70% triglycerides, which contain about 20-35% DHA and lack EPA, isolated from *Crypthecodinium cohnii*, in one example, containing more than 70% triglycerides, having 15-20% myristic acid; 20-25% palmitic acid; 10-15% oleic acid; 30-40% DHA; and 0-10% other triglycerides.

Also exemplary of suitable microalgae oils are those disclosed, for example, in U.S. Pat. No. 6,977,166 and U.S. Publication No. US 2004/0072330. Any oil derived from dinoflagellate, for example, microalgae, which contains DHA, and optionally EPA, is suitable as an algae oil for use with the provided compositions, for example, V-Pure algae oil (Water4Life, Switzerland), which contains EPA and DHA, and Martek DHA™-S (supplied by Martek Biosciences Corporation, Columbia, Md.), derived from the marine alga *Schizochytrium* sp., containing not less than 35% DHA and 16.1% (22:5ω6) docosapentaenoic acid, 1.3% (20:5ω3) eicosapentaenoic acid, 0.6% (20:4ω6) arachidonic acid, 1.6% (18:2ω6) linoleic acid, 16.9% (18:1ω9) oleic acid and 19.8% other fatty acids.

(2) Flax Seed Oil—Omega 3 (ALA)

Also exemplary of the omega-3 containing non-polar compounds used in the provided concentrates, e.g., pre-emulsion concentrates and liquid nanoemulsion concentrates, is flaxseed oil (linseed oil). Flaxseed oils, which are good sources of omega-3 fatty acids, particularly alpha-linolenic acid, have been used as nutritional supplements. Flaxseed oils are produced by pressing the flax seed and refining the oil from the flax seeds. Exemplary of flaxseed oil that can be used as the non-polar compound in the provided compositions is flaxseed oil derived from *Linum usitatissimum*L. Exemplary of flaxseed oils suitable for use in the concentrates provided herein include flaxseed oil supplied by Sanmark LLC (Greensboro, N.C.; Sanmark Limited, Dalian, Liaoning Province, China), which contains not less than (NLT) 50% C18:3 alpha-linolenic acid, and further contains other fatty acids, for example, 3-8% C16:0 palmitic acid, 2-8% C18:0 stearic acid, 11-24% C18:1 oleic acid, 11-24% C18:2 linoleic acid and 0-3% other fatty acids. Also exemplary of suitable flaxseed oil is a flaxseed oil containing 6% palmitic acid, 2.5% stearic acid, 0.5% arachidic acid, 19% oleic acid, 24.1% linoleic acid, 47.4% linolenic acid, and 0.5% other fatty acids. The fatty acid composition of flaxseed oil can vary. Any flaxseed oil can be used as the non-polar compound in the provided compositions. For example, the flaxseed oil can contain at least or about at least 50%, at least or about at least 65%, or at least or about at least 70% alpha-linolenic acid. Exemplary of a flaxseed containing greater than 65% linolenic acid content (of total fatty acid content), for example, 70-80% or 70-75%, is the flaxseed described in U.S. Pat. No. 6,870,077.

(b) Omega-6 Compounds

Also exemplary of the non-polar compounds used in the provided concentrates, e.g., pre-emulsion concentrates and liquid nanoemulsion concentrates, are compounds containing omega-6 PUFAs, for example, gamma-linolenic acid (GLA), for example, borage oil and evening primrose (*Oenothera biennis*) oil, blackcurrant seed oil, hemp seed oil, fungal oil and spirulina extract. Any oil containing omega-6 fatty acids can be used in the provided compositions.

Exemplary of the omega-6 containing non-polar compounds are compounds containing GLA, for example, borage oil. GLA is an omega-6 PUFA, which primarily is derived from vegetable oils, for example, evening primrose (*Oenothera biennis*) oil, blackcurrant seed oil, hemp seed oil, and spirulina extract. GLA has been used as a nutritional supplement. It has been proposed that GLA has a role in treating various chronic diseases and in particular that it has anti-inflammatory effects (Fan and Chapkin (1998) J. Nutr. 128(9):1411-1414). In one example, the non-polar compound contains at least or about at least 22 wt % of GLA, for example, 22, 23, 24, 25, 26, 27, 28, 29, 30, 31, 32, 33, 34, 35, 36, 37, 38, 39, 40, 50, 60 wt % or more, by weight of GLA.

Borage (*Borago offcinalis*), also known as "starflower," is an herb with seeds containing high amounts of GLA. Exemplary of borage oils that can be used as a non-polar active ingredient in the provided compositions are borage oils supplied by Sanmark LLC (Greensboro, N.C.; Sanmark Limited, Dalian, Liaoning Province, China), derived by pressing and isolating oil from the seeds of *Borago officinalis*L. This oil contains not less than (NLT) 22% C18:3 gamma-linolenic acid (GLA), between 9 and 12% C16:0 palmitic acid, between 3% and 5% C18:0 stearic acid, between 15% and 20% C18:1 oleic acid, between 35% and 42% C18:2 linoleic acid, between 3% and 5% C20:1 ocosenoic acid, between 1% and 4% C22:1 docosenoic acid and between 0% and 4% other fatty acids. Other borage oils can be used. Other GLA-containing oils also can be used as the non-polar compound.

(c) Saw Palmetto Extract

Also exemplary of the non-polar compounds used in the provided concentrates, e.g., pre-emulsion concentrates and liquid nanoemulsion concentrates, is saw palmetto extract, a lipophilic extract of the ripe berries of the American dwarf palm (also called *Serenoa repens* or *Sabal serrulata*), which has been used to treat genitourinary and other diseases and to enhance sperm production, breast size and libido, as a mild diuretic, a nerve sedative, an expectorant and a digestive tract tonic, and particularly to treat benign prostate hyperplasia (BHP) (Ernst (2002) Acad. Clin. 136:42-53; and Gordon and Shaughnessy (2003) Comp. Alt. Med. 76(6):1281-1283). Saw palmetto extract is commercially available from a number of sources. Any saw palmetto lipid extract can be used in the provided concentrates. Exemplary of the saw palmetto extract that can be used in the provided concentrates is Saw Palmetto, Lipophilic Extract, commercially available from Natural Medicinals, Inc. (Felda, Fla.). This saw palmetto lipophilic extract is carbon dioxide extracted and, in one example, contains 85.9% total fatty acids, including 0.8% caproic acid, 2% caprylic acid, 2.4% capric acid, 27.% lauric acid, 10.3% myristic acid, 8.1% palmitic acid, 0.2% palmitoleic acid, 2% stearic acid, 26.7% oleic acid, 4.9% linoleic acid, 0.7% linolenic acid, 0.42% phytosterols, including 0.42% beta sitosterol, 0.09% campesterol, 0.03% stigmasterol; and 0.2% moisture. Other sources of saw palmetto extract can be used.

(d) Conjugated Linoleic Acid (CLA)

Also exemplary of the PUFA non-polar compounds that can be used in the provided concentrates, e.g., pre-emulsion concentrates and liquid nanoemulsion concentrates, are non-polar compounds containing conjugated fatty acids. Conjugated fatty acids are PUFAs with two or more conjugated double bonds. Conjugated fatty acids can be used as nutritional supplements. Exemplary of the active ingredients containing conjugated fatty acids are compounds containing conjugated linoleic acid (CLA), for example, 18:2ω7 and 18:2ω6; conjugated linolenic acid, for example, 18:3ω6 and 18:3ω5; and other conjugated fatty acids, for example, 18:3ω3, 18:4ω3 and 20:5ω6. CLA refers to a family of linoleic acid isomers found primarily in meat and dairy products of ruminants. Typically, the CLA compounds contain a mixture of different CLA isomers, for example, C18:2 CLA c9, t11, CLA t10, c12 and other CLA isomers. Exemplary of the CLA that can be used as an active ingredient in the provided compositions is CLA (70%) commercially available from Sanmark, LTD (Dalian, Liaoning Province, China; product code 01057-A80). This CLA is a clear white to pale yellow oil and has the following fatty acid composition: NMT (not more than) 9.0% C16:0 palmitic acid, NMT 4.0% stearic acid, NMT 15.0% C18:1 oleic acid, NMT 3.0% C18:2 linoleic acid, NLT (not less than) 80% C18:2 CLA (including the following isomers: NLT 37.5% C18:2 CLA c9, t11, 37.5% C18:2 CLA t10, c12, and NMT 5.0% other CLA isomers); and NMT 5.0% other fatty acids. Another exemplary CLA compound is a CLA that contains 74.5% CLA (Clarinol® CLA, Stepan Lipid Nutrition, Maywood, N.J.). Other CLA-containing compounds can be used.

ii. Coenzyme Q Compounds

Exemplary of the non-polar active compounds are compounds containing the non-polar active ingredient coenzyme Q, for example, coenzyme Q10 (also called coQ10, ubiquinone, ubidecarenone, ubiquinol and vitamin Q10). Coenzyme Q compounds are benzoquinone compounds containing isoprenyl units. The number of isoprenyl units in each of the different CoQ species is indicated with a number following CoQ. For example, coQ10 contains 10 isoprenyl units. Coenzyme Q10 is a predominant coenzyme Q species.

Coenzyme Q can exist in two different forms: an oxidized form and a reduced form. When the oxidized form of a coenzyme Q species is reduced by one equivalent, it becomes a ubisemiquinone, denoted QH, which contains a free radical on one of the oxygens in the benzene ring of the benzoquinone. Both oxidized and reduced coenzyme Q-containing compounds can be used as active ingredients in the provided compositions.

Exemplary of the coenzyme Q-containing non-polar compounds that can be used in the provided concentrates, e.g., pre-emulsion concentrates and liquid nanoemulsion concentrates, are non-polar compounds containing coenzyme Q10 (also called coQ10, ubiquinone, ubidecarenone, ubiquinol and vitamin Q10), a benzoquinone compound that contains 10 isoprenoid units. The "Q" in the name refers to quinone and the 10 refers to the number of isoprenoid units. CoQ10 typically refers to the oxidized form of coQ10, which also is referred to as ubidecarenone, as opposed to the reduced form of coQ10. Both the reduced and oxidized forms of coQ10 are exemplary of the coenzyme Q species that can be used as active ingredients in the provided concentrates.

CoQ10 has electron-transfer ability and is present in cellular membranes, such as those of the endoplasmic reticulum, peroxisomes, lysosomes, vesicles and the mitochondria. A decrease in natural coQ10 synthesis has been observed in sick and elderly people. Because of this observation and its potent antioxidant properties, coQ10 is used as a dietary supplement and a treatment for diseases such as cancer and heart disease. CoQ10, however, exhibits relatively poor bioavailability.

CoQ10 containing compounds are available commercially. Any coQ10 compound or reduced coQ10 compound can be used with the provided concentrates, e.g., pre-emulsion concentrates and liquid nanoemulsion concentrates. Exemplary of the coQ10 compounds that can be used are coenzyme Q10 compounds containing greater than 98% or greater than about 98% ubidecarenone, for example, the compound sold under the name Kaneka Q10™ (USP Ubidecarenone) by Kaneka Nutrients, L.P. (Pasadena, Tex.). The compound sold under the name Kaneka Q10™ is fermented entirely from yeast and is identical to the body's own coQ10 and free from the cis isomer found in some synthetically produced coQ10 compounds. Any coQ10 compound can be used in the provided concentrates.

iii. Phytochemical-Containing Non-Polar Compounds

Exemplary of the non-polar compounds that contain non-polar active ingredients in the provided compositions are phytochemical-containing compounds, for example, phytosterols (plant sterols), phytoestrogens, for example, genistein and daidzein, flavonoids, for example, isoflavones, for example, soy isoflavones, phytoalexins, for example, resveratrol (trans-3,5,4'-trihydroxystilbene) and red clover extract.

Typically, phytochemical-containing compounds are added to the compositions in amounts such that when diluted in a beverage, one serving of the beverage provides between at or about 0.5 and at or about 10 mg, typically, between at or about 1 and at or about 10 mg, between at or about 1 and at or about 5 mg, for example, at or about 0.5, at or about 1, at or about 2, at or about 3, at or about 4, at or about 5 mg, at or about 6 mg, at or about 7 mg, at or about 8 mg, at or about 9 mg or at or about 10 mg phytochemical-containing compound, for example phytochemical-containing compound, per serving of the beverage, such as for example, 8 ounces of a beverage.

(a) Phytosterols

Exemplary of the phytochemical-containing compounds that contain active ingredients in the provided compositions are phytosterols (plant sterols). Plant sterols are structurally similar to cholesterol and have been found to reduce the absorption of dietary cholesterol, which can affect the levels of serum cholesterol. According to the U.S. Food and Drug Administration (FDA), two servings per day, each containing 0.4 grams of plant sterols, for a total daily intake of at least 0.8 grams, as part of a diet low in saturated fat and cholesterol, is reported to reduce the risk of heart disease. Thus, plant sterols are used in nutritional supplements.

Phytosterol non-polar compounds are typically added to the compositions in amounts such that when diluted in a beverage, one serving of the beverage provides between at or about 100 and at or about 1000 mg, typically between at or about 100 and at or about 500 mg, between at or about 100 and at or about 800 mg, between at or about 300 and at or about 500 mg, between at or about 300 and at or about 800 mg, between at or about 500 and at or about 1000 mg, for example, at or about 100, at or about 200, at or about 300, at or about 400, at or about 500, at or about 600, at or about 700, at or about 800, at or about 900 or at or about 1000 mg phytosterols, per serving of the beverage, such as for example, 8 ounces of a beverage.

Any phytosterol-containing compound can be used as an active ingredient in the provided compositions. Exemplary of the phytosterol-containing compounds that can be used as active ingredients in the provided compositions are compounds containing plant sterols, for example, the compound sold under the name CardioAid™, distributed by B&D Nutrition and manufactured by ADM Natural Health and Nutrition, Decatur, Ill. This compound contains kosher, pareve, and halal plant sterols that are produced under current food GMPs. The sterols are PCR negative and the material is derived from genetically modified organisms (GMOs). This phytosterol compound contains a minimum of 95% plant sterols, which can include up to 5 plant sterols. The compound can contain, for example, 40-58% beta sitosterol, 20-30% campesterol, 14-22% stigmasterol, 0-6% brassicasterol and 0 5% sitostanol. The compound further can contain tocopherols, for example, 0-15 mg/g tocopherols. The compound is tested and is negative for microorganisms, such as *Salmonella, E. coli* and *Staphylococcus aureus*.

(b) Resveratrol

Exemplary of the phytochemical-containing compounds used as active ingredients in the provided compositions is resveratrol. Resveratrol, or trans-resveratrol (trans-3,5,4'-trihydroxystilbene), is a phytoalexin that is naturally produced by several plants, such as the Japanese knotweed, and also is found in the skin and seeds of grapes, numerous berries, including mulberry, blueberries, bilberries and cranberries, and in peanuts. This polyphenolic compound can act as an antioxidant and additionally aid in cancer prevention and reduction of cardiovascular disease.

Any resveratrol-containing compound can be used as an active ingredient in the provided compositions. Exemplary of the resveratrol-containing compounds that can be used as active ingredients in the provided compositions are compounds containing trans-resveratrol, for example the compounds sold under the name ReserveNature™, sold by Jiaherb, Shaanxi, China. This compound contains trans-resveratrol from the botanical source *Polygonum cuspidatum* (Japanese knotweed). This resveratrol compound contains a minimum of 98.5% trans resveratrol and does not contain emodin. The compound is tested and is negative for microorganisms, such as *Salmonella, E. coli*, yeast and mold.

iv. Carotenoid-Containing Compounds

Exemplary of the non-polar compounds used as active ingredients in the provided compositions are carotenoid-containing compounds, for example, carotenoids, including hydrocarbons (carotenes) and oxygenated, alcoholic derivatives of hydrocarbons (xanthophylls), for example, beta carotene, mixed carotenoids complex, lutein, zeaxanthin, cryptoxanthin, for example, beta-crytoxanthin, lycopene, beta carotene, mixed carotenoids complex, astaxanthin, bixin, canthaxanthin, capsanthin, capsorubin, apo-carotenal, beta-12'-apo-carotenal, "carotene" (mixture of alpha and beta-carotene), gamma carotene, ciolerythrin and esters of hydroxyl- or carboxyl-containing members thereof. Carotenoids are efficient free-radical scavengers, or anti-oxidants, and are capable of enhancing the vertebrate immune system.

Typically, carotenoid-containing compounds are used in the provided compositions within a concentration range of between 0% or about 0% and 10% or about 10%, typically between 0% or about 0% and 5% or about 5%, for example, at or about 1%, 2%, 3%, 4%, 5%, 6%, 7%, 8%, 9% or 10%, w/w, of the beverage composition.

(a) Carotenes

Exemplary of the carotenoid-containing compounds used as active ingredients in the provided beverage compositions are carotenes, for example, alpha-carotene, beta-carotene and lycopene. Any carotene-containing compound can be used as an active ingredient in the provided compositions. Exemplary of the carotene-containing compounds that can be used as active ingredients in the provided compositions is lycopene, sold by Zhejiang Medicine CO., LTD, Xinchang Pharmaceutical Factory, Xinchang, China, a purple or red crystalline powder containing not less than 70% all E-lycopene, not more than 23% 5-Z-lycopene and not more than 9% related substances.

(b) Xanthophylls

Exemplary of the carotenoid-containing compounds used as active ingredients in the provided compositions are xanthophylls, for example, neoxanthin, violaxanthin, α- and β-cryptoxanthins, lutein and zeaxanthin. Xanthophylls, or phylloxanthins, are oxygen containing carotenoids that are typically yellow pigments. Any carotene-containing compound can be used as an active ingredient in the provided compositions. Exemplary of the carotene-containing compounds that can be used as active ingredients in the provided compositions are lutein and zeaxanthin, sold under the name Xanmax®-80 (Lutein crystals), by Katra Phytochem (India) Private Limited, Bangalore, India, containing 80% lutein and 4.5% zeaxanthin.

v. Micronutrient-Containing Compounds

Exemplary of the non-polar compounds used as active ingredients in the provided compositions are micronutrient-containing compounds, for example, vitamins, including vitamins A, B, C, D, E and K, and corresponding provitamins and vitamin derivatives with an action resembling that of vitamin A, B, C, D, E or K, and alpha lipoic acid (thioctic acid), yerba mate, ginseng and *ginkgo biloba*.

(a) Vitamins

Exemplary of the vitamins used as active ingredients in the provided compositions are fat-soluble vitamins, for example, vitamins A, B, C, D, E and K, and corresponding provitamins and vitamin derivatives, such as esters with an action resembling that of vitamin A, B, C, D, E or K, for example, retinol (vitamin A) and pharmaceutically acceptable derivatives thereof, for example, palmitate ester of retinol and other esters of retinol, for example, vitamin A palmitate; B vitamins, for example, thiamin (vitamin B1), riboflavin (vitamin B2), niacin (vitamin B3), pantothenic acid (vitamin B5), pyridoxine (vitamin B6), biotin (vitamin B7), folic acid or folate (vitamin B9), and cyanocobalamin, cobalamin, or reduced forms of cobalamin (vitamin B12); calciferol (vitamin D) and its pharmaceutically acceptable derivatives thereof, for example, for example, cholecalciferol (vitamin D3), and precursors of vitamin D; d-alpha tocopherol (vitamin E) and derivatives thereof, including pharmaceutical derivatives thereof, for example, tocotrienols, d-alpha tocopherol acetate and other esters of d-alpha tocopherol; and ascorbyl palmitate, a fat-soluble version of vitamin C.

Any vitamin can be used as an active ingredient in the provided compositions. Exemplary of the vitamins that can be used as active ingredients in the provided compositions are vitamin A palmitate, for example, vitamin A palmitate containing 1.7 mIU/g, produced by DSM Nutritional Products, Inc., Belvidere, N.J., and distributed through Stauber Performance Ingredients, Inc., Fullerton, Calif.; vitamin D3, for example, vitamin D3 in corn oil, containing about 1 mIU/g, produced by DSM Nutritional Products, Inc., Belvidere, N.J., and distributed through Stauber Performance Ingredients, Inc., Fullerton, Calif.; vitamin B12; vitamin B1; vitamin B3; vitamin B5; and vitamin B6.

Typically, vitamin non-polar active ingredients are included in the provided compositions within a concentration range of between 0.0001% or about 0.0001% and 1% or about 1%, more typically between at or about 0.001% and at or about 0.1%, for example, at or about 0.0001%, 0.0005%, 0.0008%, 0.0009%, 0.001%, 0.002%, 0.003%, 0.004%, 0.005%, 0.01%, 0.02%, 0.03%, 0.04%, 0.05%, 0.1%, 0.5% or 1%, w/w, of the beverage composition. Vitamin non-polar active ingredients are typically added to the beverage compositions in amounts such that one serving of the beverage provides an amount of the vitamin that corresponds to the dietary reference intakes. For example, vitamin A is added such that a serving of the beverage provides between at or about 10 to at or about 2000 micrograms (mcg), for example, between at or about 20 to at or about 900 mcg, more typically between at or about 40 to at or about 400 mcg of vitamin A per serving, for example, between at or about 40 and at or about 200 mcg, or between at or about 100 and at or about 400 mcg, or between at or about 100 and at or about 300 mcg per serving. For example, the beverage composition can contain 40 or about 40, 50 or about 50, 60 or about 60, 70 or about 70, 80 or about 80, 90 or about 90, 100 or about 100, 110 or about 110, 120 or about 120, 130 or about 130, 140 or about 140, 150 or about 150, 200 or about 200, 250 or about 250, 300 or about 300, 350 or about 350, or 400 or about 400 mcg vitamin A per serving. In another example, vitamin D3 is added such that a serving of the beverage composition provides between at or about 100 to at or about 2000 International Units (IU), for example, between at or about 100 to at or about 1000 IU, more typically, between at or about 400 and at or about 800 IU, per serving, for example between at or about 400 and at or about 600 or between at or about 500 and at or about 800, or between at or about 600 and at or about 800 IU per serving. For example, the beverage composition can contain 400 or about 400, 450 or about 450, 500 or about 500, 550 or about 550, 600 or about 600, 650 or about 650, 700 or about 700, 750 or about 750 or 800 or about 800 IU vitamin D3 per serving. In another example, vitamin B12 is added such that a serving of the beverage composition provides between at or about 1 and 12 mcg, such as 1 or about 1, 2 or about 2, 2.4 or about 2.4, 3 or about 3, 4 or about 4, 5 or about 5, 6 or about 6, 8 or about 8, 10 or about 10 or 12 or about 12 mcg vitamin B12 per serving. In another example, vitamin B1 is added such that a serving of the beverage composition provides between at or about 0.2 and 1.4 mg, such as 0.2 or about 0.2, 0.3 or about 0.3, 0.4 or about 0.4, 0.5 or about 0.5, 0.6 or about 0.6, 0.7 or about 0.7, 0.8 or about 0.8, 0.9 or about 0.9, 1.0 or about 1.0, 1.1 or about 1.1, 1.2 or about 1.2, 1.3 or about 1.3 or 1.4 or about 1.4 mg vitamin B1 per serving. In another example, vitamin B3 is added such that a serving of the beverage composition provides between at or about 2 and 18 mg, such as 2 or about 2, 3 or about 3, 4 or about 4, 5 or about 5, 6 or about 6, 7 or about 7, 8 or about 8, 9 or about 9, 10 or about 10, 11 or about 11, 12 or about 12, 13 or about 13, 14 or about 14, 15 or about 15, 16 or about 16, 17 or about 17 or 18 or about 18 mg vitamin B3 per serving. In another example, vitamin B5 is added such that a serving of the beverage composition provides between at or about 1.7 and 7 mg, such as 1.7 or about 1.7, 1.8 or about 1.8, 1.9 or about 1.9, 2 or about 2, 3 or about 3, 4 or about 4, 5 or about 5, 6 or about 6 or 7 or about 7 mg vitamin B5 per serving. In another example, vitamin B6 is added such that a serving of the beverage composition provides between at or about 0.1 and 2.0 mg, such as 0.1 or about 0.1, 0.2 or about 0.2, 0.3 or about 0.3, 0.4 or about 0.4, 0.5 or about 0.5, 0.6 or about 0.6, 0.7 or about 0.7, 0.8 or about 0.8, 0.9 or about 0.9, 1.0 or about 1.0, 1.1 or about 1.1, 1.2 or about 1.2, 1.3 or about 1.3, 1.4 or about 1.4, 1.5 or about 1.5, 1.6 or about 1.6, 1.7 or about 1.7, 1.8 or about 1.8, 1.9 or about 1.9 or 2.0 or about 2.0 mg vitamin B6 per serving.

(b) Alpha-Lipoic Acid (Thioctic Acid)

The alpha lipoic acid active ingredients include the alpha-lipoic acids sold by NutriChem Resources Company (Walnut, Calif.) and Zhejiang Medicines & Health Products Import & Export Co., Ltd (Hangzhou, China) and other alpha-lipoic acids. Typically, alpha-lipoic acid is used in the provided compositions within a concentration range of between 0% or about 0% and 10% or about 10%, typically between 0% or about 0% and 5% or about 5%, for example, at or about 1%, 2%, 3%, 4%, 5%, 6%, 7%, 8%, 9% or 10%, w/w, of the beverage composition.

c. Non-Polar Solvents

The pre-emulsion concentrates and liquid nanoemulsion concentrates provided herein can further contain a non-polar solvent, for example, an oil. The non-polar solvent can be included in the composition in addition to the non-polar active ingredient and can be used to dissolve the non-polar active ingredient. For example, the solvent can be an oil that does not contain the non-polar active ingredient. When a non-polar solvent is included in the concentrates, it typically is used to dissolve the non-polar compound before mixing with the other ingredients, for example, before mixing with the other oil phase ingredients. For example, use of a non-polar solvent can reduce the crystal size and/or increase the clarity of the aqueous liquid dilution composition containing the diluted concentrate. Exemplary of non-polar solvents that can be used in the provided concentrates are oils (in addition to the non-polar compounds that contain non-polar active ingredients) such as vitamin E oil, flaxseed oil, CLA, borage oil, rice bran oil, D-limonene, canola oil, corn oil, MCT oil and oat oil. Other oils also can be used. Exemplary of a non-polar solvent suitable for use in the concentrates provided herein includes vitamin E oil, such as the vitamin E oil sold by ADM Natural Health and Nutrition under the name Novatol™ 5-67 Vitamin E (D-alpha-tocopherol; product code 410217; Decatur, Ill.), which contains at least 67.2% tocopherol and approximately 32.8% soybean oil. Another exemplary oil includes a flaxseed oil solvent, such as the flaxseed oil from Sanmark LLC (Greensboro, N.C.; Sanmark Limited, Dalian, Liaoning Province, China), which contains not less than (NLT) 50% C18:3 alpha-linolenic acid.

When present in the pre-emulsion concentrates provided herein, the non-polar solvent typically represents less than or about 50%, by weight (w/w), of the pre-emulsion concentrate, for example, less than or about 45%, 40%, 35%, 30%, 25%, 20%, 15%, 10%, 5% or less, by weight (w/w), of the concentrate.

When present in the liquid nanoemulsion concentrates provided herein, the non-polar solvent typically represents less than or about 15%, by weight (w/w), of the pre-emulsion concentrate, for example, less than or about 15%, 14%, 13%, 12%, 11%, 10%, 9%, 8%, 7%, 6%, 5%, 4%, 3%, 2%, 1% or less, by weight (w/w), of the concentrate.

d. Preservatives and Sterilizers

The concentrates, e.g., pre-emulsion concentrates or liquid nanoemulsion concentrates, provided herein can further contain one or more preservatives (or preservativers) and/or sterilizers. The preservative or sterilizer can be included to improve the stability of the concentrate and the compositions made by diluting the concentrate, over time. Preservatives can be added to preserve the ingredients, for example, in order to prevent oxidation of the ingredients, for example, the non-polar active ingredients, for example, the omega-3 containing compounds, for example, the DHA. Preservatives, particularly food and beverage preservatives, are well known. Any known preservative can be used in the provided concentrates. Exemplary of the preservatives that can be used in the provided concentrates are oil soluble preservatives, for example, benzyl alcohol, benzyl benzoate, methyl paraben, propyl paraben, and antioxidants, for example, vitamin E, vitamin A palmitate and beta carotene. Typically, a preservative is selected that is safe for human consumption, for example, in foods and beverages, for example, a GRAS certified and/or Kosher-certified preservative, for example, benzyl alcohol.

The preservative typically represents less than 1%, less than about 1%, 1% or about 1%, by weight (w/w), of the pre-emulsion concentrate or liquid concentrate or between 0.1% or about 0.1% and 1% or about 1%, by weight (w/w), of the concentrate, for example, 0.1%, 0.2%, 0.3%, 0.4%, 0.5%, 0.6%, 0.7%, 0.725%, 0.75%, 0.8%, 0.9%, 1%, about 0.1%, about 0.2%, about 0.3%, about 0.4%, about 0.5%, about 0.6%, about 0.7%, about 0.8%, about 0.9%, about 1%, by weight (w/w), of the concentrate.

e. Polar Solvents

The liquid nanoemulsion concentrates and the liquid dilution compositions (i.e., beverages), further include polar solvents. Polar solvents are well known in the art. The polarity of a solvent generally indicates which compounds are soluble in the solvent, and with which other solvents/liquids the solvent is miscible. Generally speaking, polar compounds are more readily solubilized in water and other polar solvents than are non-polar compounds. Polar solvents are more likely to be miscible with water and other polar solvents and liquids.

The polarity of a solvent can be assessed by measuring a number of different parameters according to well known methods (see, e.g., Przybitek, "High Purity Solvent Guide," Burdick and Jackson Laboratories, Inc., 1980), such as by determining a property of the solvent, such as the dielectric constant, the dipole moment or the polarity index. For example, polar solvents generally have high dielectric constants, typically dielectric constants greater than at or about 15 (see, e.g., Lowery et al., "Mechanism and Theory in Organic Chemistry," Harper Collins Publishers, 3rd ed., 1987, p. 177), such as at or about 15, 16, 17, 18, 19, 20, 21, 22, 23, 24, 25, 26, 27, 28, 29, 30, 31, 32, 33, 34, 35, 40, 45, 50, 55, 60, 65, 70, 75, 80 85, 90 or greater than 90. For example, the dielectric constant of water is at or about 80.10 at 20° C. Polar solvents generally have high polarity indices, typically greater than at or about 3 (see, e.g., Snyder, "Classification of the solvent properties of common liquids" (1974) J. Chromatog. A 92:223-230), such as at or about 3, 4, 5, 6, 7, 8 or 9 or greater than 9. Polar solvents generally have large dipole moments, typically greater than at or about 1.4 Debye, such as at or about 1.4, 1.5, 1.6, 1.7, 1.8, 1.9, 2.0, 2.1, 2.2, 2.3, 2.4, 2.5, 2.6, 3.0, 3.5, 4 or greater than 4 Debye (see, e.g., "CRC Handbook of Chemistry and Physics," Lide, ed., 82nd edition, CRC Press, 2001, p. 15(14)-15(18)). Other methods of assessing solvent polarity are known in the art, including, but not limited to, the Kosower Z scale (Kosower, "An introduction to physical organic chemistry," Wiley, 1969, p. 293), the donor number and donor acceptor scale (Gutmann, "Solvent effects on the reactivities of organometallic compounds" (1976) Coord. Chem. Rev. 18:225-255), and the Hildebrand solubility parameters (see, e.g., Giddings et al., "High pressure gas chromatography of nonvolatile species. Compressed gas is used to cause migration of intractable solutes" (1968) Science 162:67-73).

Polar solvents include polar protic solvents and polar aprotic solvents. A polar protic solvent (e.g., water, methanol, ethanol) contains a hydrogen atom attached to an electronegative atom, such that the hydrogen has a proton-like character and/or the bond between the hydrogen and electronegative atom is polarized. Polar aprotic solvents, on the other hand (e.g., acetone, acetonitrile), generally do not contain positively polarized hydrogen atoms.

The polar solvents in the provided compositions typically are polar protic solvents, including, but not limited to, water; alcohols, such as dihydric alcohols which contain two hydroxyl groups (for example, glycols, e.g., propylene glycol, ethylene glycol, tetraethylene glycol, triethylene glycol, trimethylene glycol), trihydric alcohols which contain three hydroxyl groups (e.g., glycerin, butane-1,2,3-triol, pentane-1,3,5-triol, 2-amino-2-hydroxymethyl-propane-1,3-diol), monohydric alcohols (e.g., methanol, ethanol, propanol, isopropanol, n-butanol and t-butanol) and other alcohols; and acids, such as acetic acid and formic acid. Other polar solvents include, but are not limited to, acetone, acetonitrile, butyl acetate, dimethylformamide, dimethyl sulfoxide, dioxane, ethyl acetate, tetrahydrofuran and hexamethylphosphoric triamide. Typically, the polar solvent is water, or is an alcohol that typically contains two or more hydroxyl groups, such as a trihydric or dihydric alcohol, such as, but not limited to, glycerol and propylene glycol. The polar solvents further include low molecular weight polyethylene glycols (PEGs), such as PEGs having a molecular weight not more than at or about 600 kDa, such as between or about between 200 kDa and 600 kDa, typically not more than at or about 400 kDa, for example, not more than 200 kDa.

In one example, the polar solvent has a dielectric constant greater than at or about 15, and typically between at or about 20 and at or about 80, such as at or about 80.1. In another example, the polar solvent has a polarity index between at or about 3 and at or about 9. In another example, the dipole moment of the polar solvent is between 1.5 and 3, and typically between at or about 1.8 and 2.8, such as 1.85 (for dielectric constants of solvents, see, for example, Landolt-Bornstein, New Series IV/17, "Static Dielectric Constants of Pure Liquids and Binary Liquid Mixtures," Springer, 2008; and "CRC Handbook of Chemistry and Physics," Lide, ed., 82nd edition, CRC Press, 2001; for dipole moment of solvents, see, for example, "CRC Handbook of Chemistry and Physics," Lide, ed., 82nd edition, CRC Press, 2001; and for polarity indices of solvents, see, for example, Snyder, "Classification of the solvent properties of common liquids," J. Chromatography A, 92:223-230, 1974).

When present, such as in the liquid nanoemulsion concentrates, the amount of the polar solvent typically is present in a high concentration, for example, the total amount of polar solvent as a percentage (%), by weight, of the liquid concentrate (wt %) can be, e.g., from at or about 45% to at or about 80%, such as 45% to 50%, 45% to 55%, 45% to 60%, 45% to 65%, 45% to 70%, 45% to 75%, 50% to 55%, 50% to 60%, 50% to 65%, 50% to 70%, 50% to 75%, 50% to 80%, 55% to 60%, 55% to 65%, 55% to 70%, 55% to 75%, 55% to 80%, 60% to 65%, 60% to 70%, 60% to 75%, 60% to 80%, 65% to 70%, 65% to 75%, 65% to 80%, 70% to 75%, 70% to 80% and 75% to 80%, by weight, of the liquid concentrate. Exemplary concentrations of the polar solvent in the liquid nanoemulsion concentrate are at or about 50%, 52%, 55%, 58%, 60%, 62%, 65%, 68%, 70%, 72% and 76% (w/w) of the concentrate.

In the provided methods for making the liquid nanoemulsion concentrates, the polar solvent is added to the water phase. In one example, the polar solvent is water, e.g., purified water, such as water that is purified prior to adding it to the concentrate formula, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the concentrates.

f. Co-Surfactants (Emulsifiers)

The concentrates, e.g., pre-emulsion concentrates and liquid nanoemulsion concentrates, can further contain one or more co-surfactants (emulsifiers). For example, a co-surfactant can be included to improve emulsification of the active ingredient and/or the stability of the composition, for example, by preventing or slowing oxidation of the non-polar compound. Exemplary of a co-surfactant that can be used in the provided concentrates is a phospholipid, for example, phosphatidylcholine. Other exemplary co-surfactants include non-ionic surfactants, such as sugar-derived surfactants, including fatty acid esters of sugars and sugar derivatives, and PEG-derived surfactants, such as PEG derivatives of sterols, PEG derivatives of fat-soluble vitamins and PEG-sorbitan fatty acid esters.

When present, such as in the liquid nanoemulsion concentrates, the amount of the co-surfactant typially is present in a concentration less than or less than about 10%, typically less than or less than about 5%, for example, the total amount of co-surfactant as a percentage (%), by weight, of the liquid concentrate (wt %) can be, e.g., less than or less than about 10%, such as less than or about 5%, 4.5%, 4%, 3.5%, 3.15%, 3%, 2.5%, 2%, 1.75%, 1.5%, 1.25%, 1%, 0.75%, 0.5%, 0.25%, 0.15% or less, by weight, of the liquid concentrate.

i. Phospholipids

Exemplary of the co-surfactants that can be used in the provided compositions are phospholipids. Phospholipids are amphipathic lipid-like molecules, typically containing a hydrophobic portion at one end of the molecule and a hydrophilic portion at the other end of the molecule. A number of phospholipids can be used as ingredients in the provided compositions, for example, lecithin, including phosphatidylcholine (PC), phosphatidylethanolamine (PE), distearoylphosphatidylcholine (DSPC), phosphatidylserine (PS), phosphatidylglycerol (PG), phosphatidic acid (PA), phosphatidylinositol (PI), sphingomyelin (SPM) or a combination thereof. Typically, the phospholipid is phosphatidylcholine (PC), which sometimes is referred to by the general name "lecithin." Exemplary of the phospholipids that can be used as co-surfactants in the provided compositions are the phospholipids sold by Lipoid, LLC (Newark, N.J.), for example, Purified Egg Lecithins, Purified Soybean Lecithins, Hydrogenated Egg and Soybean Lecithins, Egg Phospholipids, Soybean Phospholipids, Hydrogenated Egg and Soybean Phospholipids, Synthetic Phospholipids, PEG-ylated Phospholipids and phospholipid blends. Exemplary of the phosphatidylcholine that can be used as a co-surfactant in the provided compositions is the phosphatidylcholine composition sold by Lipoid, LLC, under the name Lipoid S100, which is derived from soy extract and contains greater than or greater than about 95% phosphatidylcholine.

ii. Sugar-Derived Surfactants

Exemplary sugar-derived surfactants include, but are not limited to, sugar fatty acid esters including fatty acid esters of sucrose, glucose, maltose and other sugars, esterified to fatty acids of varying lengths (e.g., containing a varying numbers of carbons). The fatty acids typically have carbon chains between 8 and 28 carbons in length, and typically between 8 and 20, or between 8 and 18 or between 12 and 18, such as, but not limited to, stearic acid (18 carbons), oleic acid (18 carbons), palmitic acid (16 carbons), myristic acid (14 carbons) and lauric acid (12 carbons). Typically, the sugar ester surfactants are sucrose ester surfactants, typically sucrose fatty acid ester surfactants.

iii. PEG-Derived Surfactants

Exemplary PEG-derived surfactants include, but are not limited to, PEG derivatives of sterols, e.g., a cholesterol or a sitosterol (including, for example, any of the PEG derivatives disclosed in U.S. Pat. No. 6,632,443); PEG derivatives of fat-soluble vitamins, for example, some forms of vitamin A (e.g., retinol) or vitamin D (e.g., Vitamin D1-D5); and PEG-sorbitan fatty acid esters, such as polysorbates, including polyoxyethylene (20) sorbitan monooleate (also called polysorbate 80) and analogs (e.g., homologs) of polysorbate 80, such as, for example, polysorbate 20 (polyoxyethylene (20) sorbitan monolaurate), polysorbate 40 (polyoxyethylene (20) sorbitan monopalmitate) and polysorbate 60 (polyoxyethylene (20) sorbitan monostearate); and stearic acid derivatives, including, for example, polyethylene glycol 400 distearate (PEG 400 DS), such as the PEG 400 DS sold by Stepan Lipid Nutrition (Maywood, N.J.).

iv. Sucrose Fatty Acid Ester Surfactants

Sucrose fatty acid ester (SFAE) surfactants contain one or more sucrose fatty acid esters, which are non-ionic surfactants that contain sucrose in the hydrophilic portions and fatty acids in the hydrophobic portions. The sucrose fatty acid esters can be made by well-known methods (see, for example, U.S. Pat. Nos. 3,480,616; 3,644,333; 3,714,144; 4,710,567; 4,898,935; 4,996,309; 4,995,911; 5,011,922 and 5,017,697 and International Patent Pub. No. WO 2007/082149), typically in an esterification reaction as described in U.S. Pub. No. 2012-0016026.

Because sucrose contains eight hydroxy (OH) groups, the esterification reaction can join the sucrose molecule to one fatty acid molecule, or can join it to a plurality of fatty acid molecules, producing different degrees of esterification, e.g., mono-, di-, tri- and poly- (up to octa-) fatty acid esters, but primarily mono-, di- and/or tri-esters. The degree of esterification can depend on conditions of esterification. The esterification reaction can be carried out with a single type of fatty acid, or a plurality of fatty acids, such as fatty acids with varying carbon chain lengths, branched and linear fatty acids, and/or saturated or unsaturated fatty acids. The esterification reaction with a single fatty acid can produce a single ester, and typically forms more than one ester, such as mono- di-, tri- and/or poly-esters, formed from one reaction. The relative amounts of mono- di- tri- and/or poly-esters can depend on reaction conditions.

The fatty acid in the sucrose fatty acid ester can be any fatty acid, and can contain between 4 and 28 carbon atoms, typically between 8 and 28 carbon atoms, and typically between 8 and 25 carbon atoms, such as between 8 and 18 carbon atoms, such as 8, 9, 10, 11, 12, 13, 14, 15, 16, 17 and 18 carbon atoms. The fatty acid can be synthetic or naturally occurring, and include linear and branched fatty acids. The fatty acids include, but are not limited to, myristic acid, palmitic acid, stearic acid, oleic acid, caproic acid, capric (or decanoic) acid, lauric acid, caprylic acid and pelargonic (or nonanoic) acid.

Thus, the sucrose fatty acid ester surfactants include sucrose monoesters, diesters, triesters and polyesters, and mixtures thereof, and typically contain sucrose monoesters. The sucrose fatty acid ester surfactants include single fatty acid esters and also include homogeneous mixtures of sucrose esters, containing members with different lengths of fatty acid carbon chain and/or members with different degrees of esterification. For example, the sucrose fatty acid ester surfactants include mixtures of monoesters, diesters, triesters, and/or polyesters. The sugar ester surfactants further include sucrose fatty acid ester analogs and homologs and mixtures thereof.

In general, sucrose fatty acid esters, including mixtures of sucrose fatty acid esters, can have varying HLB values, such as HLB values ranging from at or about 1 to at or about 20. The HLB value of the sucrose fatty acid ester generally depends on the degree of esterification (e.g., the average degree of esterification in a mixture of different esters). Typically, the lower the degree of esterification (e.g., average degree), the higher the HLB value of the sucrose fatty acid ester or mixture thereof. Exemplary sucrose esters include sucrose distearate (HLB=3), sucrose distearate/monostearate (HLB 12), sucrose dipalmitate (HLB=7.4), sucrose monostearate (HLB=15), sucrose monopalmitate (HLB>10), sucrose monolaurate (HLB 15). Typically, the sucrose fatty acid ester surfactants in the provided concentrates have an HLB value of between at or about 13 and at or about 20, such as at or about 13, 14, 15, 16, 17, 18, 19, or 20, and typically between at or about 13 and at or about 18, such as, but not limited to, HLB values of at or about 15, 16 and 17, such as, for example, sucrose ester surfactants including sucrose monopalmitate, sucrose monolaurate and sucrose monostearate.

The sugar ester surfactants include sucrose ester blends, for example, sucrose ester mixtures containing a specified amount (e.g., percent, by weight) of sucrose monoesters. Exemplary surfactants include sucrose ester mixtures having at least at or about 50%, by weight (w/w), monoester, such as at least or about at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, by weight (w/w), sucrose monoesters, and typically at least at or about 60%, by weight, or at least at or about 70%, by weight (w/w), monoesters.

The sucrose fatty acid ester surfactants include sucrose fatty acid monoesters, such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanoate, sucrose monopentadecanoate and sucrose monoheptadecanoate. The sucrose fatty acid esters further include mixtures containing varying percentages of monoesters, diesters, triesters and polyesters, such as, but not limited to, a mixture having at or about 72% monoesters, 23% diesters, 5% triesters and 0 polyesters; a mixture having at or about 61% monoesters, 30% diesters, 7% triesters, and 2% polyesters; and a mixture having at or about 52% monoesters, 36% diesters, 10% triesters and 2% polyesters.

The sucrose fatty acid ester surfactants include sucrose fatty acid esters sold under the trade name DK Ester®, produced by Dai-Ichi Kogyo Seiyaku Co., Ltd of Japan (which, in some examples, can be produced according to the methods described in U.S. Pat. Nos. 4,898,935; 4,996,309; 4,995,911; 5,011,922 and 5,017,697), and distributed through Montello Inc., Tulsa, Okla., such as the F-160 and F-140 grade esters sold under the trade name DK Ester®, and sucrose esters sold under the trade name SURFHOPE® SE PHARMA, by Mitsubishi-Kagaku Foods Corporation, distributed by Mitsubishi Chemical Performance Polymers, Inc. These sucrose fatty acid esters are mixtures of esters with different degrees of esterification. The sucrose fatty acid esters further include Ryoto sugar esters, which are food-grade esters sold by Mitsubishi-Kagaku Foods Corporation, distributed by Mitsubishi Chemical Performance Polymers, Inc. Other exemplary sucrose fatty acid ester surfactants are described in Youan et al. (2003) AAPS PharmaSci 5(2):Article 22 (1-9) and in Okamoto et al. (2005) Biol. Pharm. Bull. 28(9):1689-1694.

g. Emulsion Stabilizers (Co-Emulsifiers)

The provided liquid concentrates can further contain one or more emulsion stabilizers (co-emulsifiers), which can be used to stabilize the liquid nanoemulsion concentrate and/or the aqueous compositions containing the diluted concentrates. For example, the emulsion stabilizer can increase the viscosity of the liquid concentrate. One or more emulsion stabilizers can be added, for example, during formulation after evaluation of an initial concentrate, particularly if the oil and water phases of the initial concentrate (or the aqueous liquid dilution composition resulting from dilution of the initial concentrate) appear to be separating. Addition of the emulsion stabilizer can prevent separation of the oil and water phases.

Exemplary of an emulsion stabilizer that can be used in the provided compositions is a composition containing a blend of gums, for example, gums used as emulsifying agents, for example, a blend containing one or more of xanthan gum, guar gum and sodium alginate. Exemplary of such an emulsion stabilizer includes the emulsion stabilizer sold under the brand name SALADIZER® available from TIC Gums, Inc. (Belcamp, Md.). Other gums can be included in the emulsion stabilizer, for example, gum acacia, ester gums and sugar beet pectin. An exemplary emulsion stabilizer includes modified food starches. These include the modified gum acacia sold under the name Tic Pretested® Ticamulsion A-2010 Powder, available from TIC Gums, Inc. (Belcamp, Md.). Other exemplary emulsion stabilizers containing an ester gum are, for example, the emulsion stabilizer sold under the name Tic Pretested® Ester Gum 8BG, available from TIC Gums, Inc. (Belcamp, Md.) or Ester Gum 8BG, available from Hercules/Pinova (Brunswick, Ga.). Others sold by Ingredion, Inc. (Westchester, Ill.) under the trademarks CAPSUL®, FIRMTEX®, THERMFLO®, THERMTEX®, TEXTRA® and others can be included in the compositions provided herein. Other blends of similar gums can also be used as emulsion stabilizers.

The emulsion stabilizer can be added to the water phase, the oil phase, or both the water and the oil phase, during formation of the liquid concentrates and compositions. In one example, the emulsion stabilizer is added to the water phase at a concentration, such that it represents less than 1% or about 1% w/w of the liquid concentrate. In another example, the emulsion stabilizer is added for a final concentration of greater than 1%, such as at or about 1.5% w/w of the liquid concentrate. In one example, the emulsion stabilizer is added to the water phase for a final concentration of between 0.1% or about 0.1% and 1% or about 1%, for example, 0.1%, 0.12%, 0.13%, 0.14%, 0.15%, 0.16%, 0.17%, 0.18%, 0.19%, 0.2%, 0.25%, 0.3%, 0.31%, 0.32%, 0.33%, 0.34%, 0.35%, 0.36%, 0.37%, 0.38%, 0.39%, 0.4%, 0.5%, 0.6%, 0.7%, 0.8%, 0.9% or 1% w/w of the liquid concentrate. In one example, the emulsion stabilizer is added to the oil phase such that it represents less than 0.1% or about 0.1%, for example, between 0.01% or about 0.01% and 0.1% or about 0.1%, for example, 0.01%, 0.02%, 0.03%, 0.04%, 0.05%, 0.06%, 0.061%, 0.062%, 0.063%, 0.0635%, 0.07%, 0.08%, 0.09% or 0.1%, by weight (w/w), of the concentrate. In one example, the emulsion stabilizer is added to the water phase and the oil phase, for example, at a concentration within the oil and water phase concentration ranges listed above. In one such example, the emulsion stabilizer represents less than 1%, for example, between 0.01% or about 0.01% and 1% or about 1% (w/w), emulsion stabilizer, for example, 0.01%, 0.02%, 0.03%, 0.04%, 0.05%, 0.06%, 0.061%, 0.062%, 0.063%, 0.0635%, 0.07%, 0.08%, 0.09%, 0.1%, 0.12%, 0.13%, 0.14%, 0.15%, 0.16%, 0.17%, 0.18%, 0.19%, 0.2%, 0.25%, 0.3%, 0.31%, 0.32%, 0.33%, 0.34%, 0.35%, 0.36%, 0.37%, 0.38%, 0.39%, 0.4%, 0.5%, 0.6%, 0.7%, 0.8%, 0.9% or 1%, by weight (w/w), of the liquid concentrate. The emulsion stabilizer, such as the Ticamulsion, can be added in higher concentrations, including 5, 10, 15, 18, 20, or 25%, by weight, or more.

h. Flavors

The liquid nanoemulsion concentrates and compositions provided herein can further contain one or more flavors or flavoring agents, for example, any compound that can add flavor to the concentrate and/or to the aqueous liquid dilution composition containing the diluted concentrate, for example, the food or beverage product containing the concentrate. Several flavors are well known. Any flavor can be added to the concentrates, for example, any flavor sold by Mission Flavors (Foothill Ranch, Calif.). Exemplary of flavors that can be used are fruit flavors, such as guava, kiwi, peach, mango, papaya, pineapple, banana, strawberry, raspberry, blueberry, orange, grapefruit, tangerine, lemon, lime and lemon-lime; cola flavors, tea flavors, coffee flavors, chocolate flavors, dairy flavors, root beer and birch beer flavors, methyl salicylate (wintergreen oil, sweet birch oil), citrus oils and other flavors. Typically, the flavors are safe and/or desirable for human consumption, for example, GRAS or Kosher-certified flavors. An exemplary flavoring agent that can be used in the concentrates and compositions provided herein are lemon oil, for example lemon oil sold by Mission Flavors (Foothill Ranch, Calif.), and D-limonene, for example, 99% GRAS certified D-Limonene, sold by Florida Chemical (Winter Haven, Fla.). The flavor can be added, using the provided methods, to the nanoemulsion concentrates after combining the oil and water phases. Alternatively, flavor(s) can be added to the water and/or oil phase directly.

i. pH Adjusters

One or more pH adjusters can be added to the provided liquid nanoemulsion concentrates, typically to the emulsion that is formed after combining the water and oil phases according to the provided methods. In particular, the pH adjuster can be used in compositions containing water. Alternatively, the pH adjuster can be added, at an appropriate concentration to achieve a desired pH, to the oil phase and/or the water phase. Typically, the pH adjuster is added to adjust the pH of the concentrate to within a range of 2.0 or about 2.0 to 4.0 or about 4.0. One or more of a plurality of pH adjusting agents can be used. Typically, the pH adjusting agent is safe for human consumption, for example, GRAS certified. The pH adjuster can be citric acid. An exemplary pH adjuster suitable for use with the concentrates provided herein includes the citric acid sold by Mitsubishi Chemical (Dublin, Ohio). Another exemplary pH adjuster is phosphoric acid, such as Food Grade 80% Phosphoric Acid, sold by Univar.

Typically, the concentration of pH adjuster added to the provided liquid concentrates is less than 5% or about 5%, for example, less than or about 4%, 3.5%, 3%, 2.5%, 2%, 1.5%, 1%, 0.9%, 0.8%, 0.7%, 0.6%, 0.5%, 0.4%, 0.3%, 0.2%, 0.1% or less, by weight, of the liquid concentrate.

j. Soluble Fibers

The liquid nanoemulsion concentrates provided herein can contain soluble fiber. Soluble fibers include any soluble dietary fiber that can be readily fermented in the colon, typically a plant based dietary fiber, for example, a soluble fiber from legumes, vegetables, such as broccoli and carrots, root vegetables, such as potatoes, sweet potatoes and onions, oats, rye, chia, barley and fruits, such as prunes, plums, berries, bananas, apples and pears. Typically, soluble dietary fiber contains non-starch polysaccharides, such as arabinoxylans, cellulose, dextrans, inulin, beta-glucans, fructo-oligosaccharides, oligosaccharides and polysaccharides. Soluble fibers include, but are not limited to, fructo-oligosaccharides, for example, inulins, for example, inulins found in chicory, Jerusalem artichoke, dahlia, garlic, leeks and onions, fructans and water-soluble soybean fiber. Exemplary of a soluble fiber is an inulin, for example, Oliggo-Fiber Instant Inulin (Fibruline® Instant) (supplied by Cosucra-Groupe Warcoing SA, Belgium, sold by Gillco Products, San Marcos, Calif.), containing chicory inulin.

k. Additional Ingredients

The beverage compositions, e.g., liquid dilution compositions and compositions for direct consumption, e.g., single-serving shots, provided herein additionally can contain further ingredients. For example, the beverage compositions provided herein can contain one or more active ingredients. The beverage compositions can additionally contain stabilizers (i.e., stabilizing system) and a beverage base. The beverage compositions can additionally contain sweeteners.

i. Active Ingredients

The beverage compositions provided herein can contain one or more additional active ingredients. The beverage compositions, for example, the compositions for direct consumption, e.g., single-serving shots, can contain a non-polar compound containing active ingredients or can contain an additional active ingredient or can contain both. Active ingredients include any compound that can induce, promote or enhance one or more effects, such as upon delivery to a subject or upon administration to a sample, for example, sympathomimetic effects, stimulatory effects, vasoconstriction, decongestion (e.g., bronchial or nasal decongestion), increased energy, endurance, mood-enhancement, appetite suppression and/or weight loss. The additional active ingredients include, but are not limited to, alkaloids, e.g., caffeine and synephrine and γ-aminobutyric acid (GABA) derivatives, e.g., 4-amino-3-phenylbutyric acid (i.e., phenibut), plant extracts, particularly those with medicinal and herbal effects, and any combination thereof. Typically the additional active ingredients are food-approved, i.e., edible or ingestible, active ingredients, for example, active ingredients that are safe and/or approved for human consumption.

In general, the beverage compositions provided herein contain at least one active ingredient, i.e., at least one non-polar compound containing non-polar active ingredients or an additional active ingredient. Typically, when included in a beverage composition, the total amount of additional active ingredient included in the provided beverage compositions is less than 30% or about 30%, typically less than 20% or about 20%, for example, less than 30%, 25%, 20%, 15%, 10%, 5%, 4.5%, 4%, 3.5%, 3%, 2.5%, 2%, 1.5%, 1%, 0.5% or 0.1%, by weight, of the beverage composition.

(a) Alkaloids

Exemplary of an additional active ingredient used in the provided beverage compositions is an alkaloid, for example, any edible or food-approved alkaloid. Exemplary of a suitable alkaloid includes caffeine and synephrine. Suitable alkaloids for inclusion in the provided beverage compositions are a matter of design choice and well within the skill of the skilled artisan.

The amount of alkaloid depends upon the desired or intended dosage and the particular compound. Typically, the amount of alkaloid, e.g., caffeine, included in the provided beverage compositions is between or between about 0.01% and 10%, by weight, of the composition, for example, between at or about 0.01% and 9%, between at or about 0.01% and 8%, between at or about 0.01% and at or about 7%, between at or about 0.01% and at or about 6%, between at or about 0.01% and at or about 5% between at or about 0.01% and at or about 4%, between at or about 0.1% and at or about 3%, between at or about 0.1% and at or about 6%, between at or about 0.1% and at or about 5%, between at or about 0.1% and at or about 4%, between at or about 0.1% and at or about 3%, between at or about 0.1% and at or about 2%, between at or about 0.1% and at or about 1%, between at or about 0.5% and at or about 7%, between at or about 0.5% and at or about 6%, between at or about 0.5% and at or about 5%, between at or about 0.5% and at or about 4%, between at or about 0.5% and at or about 3%, between at or about 0.5% and at or about 2%, between at or about 0.5% and at or about 1%, between at or about 1% and at or about 7%, between at or about 1% and at or about 6%, between at or about 1% and at or about 5%, between at or about 1% and at or about 4%, between at or about 1% and at or about 3%, between at or about 1% and at or about 2%, between at or about 2% and at or about 7%, between at or about 2% and at or about 5%, between at or about 2% and at or about 4%, between at or about 3% and at or about 7%, between at or about 3% and at or about 5%, between at or about 4% and at or about 7%, between at or about 6% and at or about 7%, between at or about 5% and at or about 7%, or between at or about 5% and at or about 6%, by weight, of the beverage composition. In some examples, the amount of bicarbonate or carbonate used in the provided beverage compositions is less than 7% or about 7%, typically less than 5% or about 5%, for example at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.2%, 6.5%, 6.7%, or 7%, by weight, of the beverage composition.

The caffeine active ingredients include caffeine that is added in the form of caffeine anhydrous, such as the Caffeine Anhydrous powder (white, crystalline powder), sold by Pacific Rainbow International, Inc., City of Industry, CA, which is a white crystalline powder containing caffeine anhydrous. The amount of caffeine in the composition can be between at or about 0% and at or about 50%, by weight, of the composition, and typically is between at or about 0% and at or about 25%, and typically between at or about 0% and at or about 10%, or between at or about 0% and at or about 5%, e.g. at or about 0%, 0.01%, 0.015%, 0.02%, 0.025%, 0.03%, 0.035%, 0.04%, 0.05%, 0.06%, 0.07%, 0.08%, 0.09%, 0.1%, 0.15%, 0.2%, 0.3%, 0.4%, 0.5%, 0.6%, 0.7%, 0.8%, 0.9%, 1% 1.5%, 2%, 2.5%, 3%, 3.5%, 4%, 4.5%, 5%, 6%, 7%, 8%, 9%, 10%, such as between at or about 0% and at or about 3%, by weight, of the composition, e.g. between at or about 0% and 2%, e.g. at or about 2%, by weight, of the composition, or is less than 5%, by weight, of the composition, e.g. at or about 5, 4, 3, 2 or 1%, by weight, of the composition, or less. In one example, the composition contains at or about 2%, by weight, caffeine. In another example, the composition contains between at or about 1 and at or about 500 mg caffeine per mL or per serving, such as a 4 mL serving of the composition, e.g. at or about 200, 150, 125, 100, 80, 75, 50 or 25 milligrams (mg) caffeine per serving of the composition, e.g. per 4 mL of the composition.

Other exemplary ingredients include herbal extracts, medicinal extracts and compounds from plants and drugs. Example 10 below describes additional exemplary active ingredients.

ii. Stabilizers

The compositions provided herein contain one or more stabilizers, or a stabilizing system. Stabilizers include any compound used to stabilize the non-polar compounds in the beverage compositions. The stabilizer or stabilizing system can aid in retaining one or more desirable properties of the compositions, for example the appearance, taste or odor. The compositions provided herein containing non-polar compounds and a stabilizer or stabilizing system can retain one or more desirable properties of the beverage composition for a period of time after formulation, such as at or about 1, 2, 3, 4, 5, 6, or 7 days, at or about 1, 2, 3, 4, 5, 6, 8, 12, 18, 24, or 36 weeks, at or about 1, 2, 3, 4, 5, 6, 8, 12, 18, 24, or 36 months, or at or about 1, 2, 3, or 4 years. The stabilizers include, but are not limited to, carbonates and bicarbonates, acids, antioxidants, and any combination thereof. Typically the stabilizer or stabilizing system are food-approved, i.e., edible or ingestible, stabilizers, for example, stabilizers that are safe and/or approved for human consumption.

In general, the beverage compositions contain more than one stabilizer. Typically, the total amount of stabilizers included in the provided beverage compositions is less than 20% or about 20%, typically less than 10% or about 10%, for example, less than 20%, 15%, 10%, 5%, 4.5%, 4%, 3.5%, 3%, 2.5%, 2%, 1.5%, 1%, 0.5% or 0.1%, by weight, of the beverage composition.

(a) Bicarbonates or Carbonates

Exemplary of a stabilizer used in the provided beverage compositions is a bicarbonate or carbonate, for example, any edible or food-approved bicarbonate or carbonate. Examples of suitable bicarbonates and carbonates include sodium bicarbonate, potassium bicarbonate, sodium carbonate, potassium carbonate, calcium carbonate, magnesium carbonate, zinc carbonate, and any combination thereof. In some examples, the carbonate or bicarbonate is a carbonated beverage, such as a soda, flavored soda, carbonated water or carbonated juice. Alternatively, the beverage can be carbonated by the addition of carbon dioxide. Selection of suitable bicarbonates and carbonates for use in the provided beverage compositions is within the skill of the skilled artisan.

Typically, the amount of bicarbonate or carbonate used in the provided beverage compositions is between or between about 0.01% and 7%, by weight, of the composition, for example, between at or about 0.01% and at or about 6%, between at or about 0.01% and at or about 5%, between at or about 0.01% and at or about 4%, between at or about 0.01% and at or about 3%, between at or about 0.01% and at or about 2%, between at or about 0.01% and at or about 1%, between at or about 0.1% and at or about 7%, between at or about 0.1% and at or about 6%, between at or about 0.1% and at or about 5%, between at or about 0.1% and at or about 4%, between at or about 0.1% and at or about 3%, between at or about 0.1% and at or about 2%, between at or about 0.1% and at or about 1%, between at or about 0.5% and at or about 7%, between at or about 0.5% and at or about 6%, between at or about 0.5% and at or about 5%, between at or about 0.5% and at or about 4%, between at or about 0.5% and at or about 3%, between at or about 0.5% and at or about 2%, between at or about 0.5% and at or about 1%, between at or about 1% and at or about 7%, between at or about 1% and at or about 6%, between at or about 1% and at or about 5%, between at or about 1% and at or about 4%, between at or about 1% and at or about 3%, between at or about 1% and at or about 2%, between at or about 2% and at or about 7%, between at or about 2% and at or about 5%, between at or about 2% and at or about 4%, between at or about 3% and at or about 7%, between at or about 3% and at or about 5%, between at or about 4% and at or about 7%, or about 7%, between at or about 6% and at or about 7%, between at or about 5% and at or about 7%, or between at or about 5% and at or about 6%, by weight, of the beverage composition. In some examples, the amount of bicarbonate or carbonate used in the provided beverage compositions is less than 7% or about 7%, typically less than 5% or about 5%, for example at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.2%, 6.5%, 6.7%, or 7%, by weight, of the beverage composition.

(b) Acids

In one example, the stabilizer used in the beverage compositions contains one or more acids, for example, any compound added to the beverage composition that can lower the pH of the composition. The acid can be, for example, an edible, ingestible or food-approved acid. Exemplary of suitable acids for use in the provided beverage compositions are citric acid, phosphoric acid, adipic acid, ascorbic acid, lactic acid, malic acid, fumaric acid, gluconic acid, succinic acid, tartaric acid, maleic acid, and any combination thereof. In one example, the acid is citric acid.

Typically, the amount of acid added to the provided beverage compositions is between or between about 0.01% and 5%, by weight, of the composition, for example, between at or about 0.01% and at or about 4%, between at or about 0.01% and at or about 3%, between at or about 0.01% and at or about 2%, between at or about 0.01% and at or about 1%, between at or about 0.1% and at or about 5%, between at or about 0.1% and at or about 4%, between at or about 0.1% and at or about 3%, between at or about 0.1% and at or about 2%, between at or about 0.1% and at or about 1%, between at or about 0.5% and at or about 5%, between at or about 0.5% and at or about 4%, between at or about 0.5% and at or about 3%, between at or about 0.5% and at or about 2%, between at or about 0.5% and at or about 1%, between at or about 1% and at or about 5%, between at or about 1% and at or about 4%, between at or about 1% and at or about 3%, between at or about 1% and at or about 2%, between at or about 2% and at or about 5%, between at or about 2% and at or about 4%, between at or about 2% and at or about 3%, between at or about 3% and at or about 5%, between at or about 3% and at or about 4%, or between at or about 4% and at or about 5%, by weight, of the beverage composition. In some examples, the amount of acid added to the provided beverage compositions is less than 5% or about 5%, typically less than 4% or about 4%, for example, at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9% or 5%, by weight, of the beverage composition.

(c) Antioxidants

In one example, the stabilizer used in the beverage compositions contain an antioxidant, for example, a molecule that is capable of inhibiting the oxidation of other molecules. Antioxidants include molecules that scavenge free radicals. Suitable antioxidants include those that are used as ingredients in dietary supplements. The antioxidant can be a natural antioxidant or a synthetic antioxidant.

Examples of antioxidants include, but are not limited to hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavanoid phenolics, isothiocyanates, vitamins and vitamin cofactors, such as vitamin A, vitamin C, vitamin E, vitamin E phosphate and ubiquinone (ubidecarenone, coenzyme Q, coenzyme Q10), ascorbic acid, citric acid, rosemary oil, minerals, such as mineral selenium and manganese, melatonin, α-carotene, β-carotene, lycopene, lutein, zeanthin, crypoxanthin, resveratrol, eugenol, quercetin, catechin, gossypol, hesperetin, curcumin, ferulic acid, thymol, hydroxytyrosol, tumeric, thyme, olive oil, lipoic acid, glutathione, gulamine, oxalic acid, tocopherol-derived compounds, di-alpha-tocopheryl phosphate, tocotrienols, butylated hydroxyanisole, butylated hydroxytoluene, ethylenediaminetetraacetic acid, tert-butylhydroquinone, acetic acid, pectin, tocotrienol, tocopherol, coenzyme Q10 (coQ10), zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms theaflavin and its gallate forms, thearubigins, isotlavone phytoestrogens, genistein, daidzein, glycitein, anythocyanins, cyaniding, delphinidin, malvidin, pelargonidin and peonidin. In one example, the antioxidant is vitamin C. In another example, the antioxidant is a coenzyme Q-containing compounds, such as ubiquinone (ubidecarenone, coenzyme Q, coenzyme Q10).

Typically, the amount of antioxidant added to the provided beverage compositions is between at or about 0.01% and at or about 3%, for example, between at or about 0.01% and at or about 2.5%, between at or about 0.01% and at or about 2%, between at or about 0.01% and at or about 1.5%, between at or about 0.01% and at or about 1%, between at or about 0.01% and at or about 0.5%, between at or about 0.05% and at or about 3%, between at or about 0.05% and at or about 2.5%, between at or about 0.05% and at or about 2%, between at or about 0.05% and at or about 1.5%, between at or about 0.05% and at or about 1%, between at or about 0.05% and at or about 0.5%, between at or about 0.1% and at or about 3%, between at or about 0.1% and at or about 2.5%, between at or about 0.1% and at or about 2%, between at or about 0.1% and at or about 1.5%, between at or about 0.1% and at or about 1%, between at or about 0.1% and at or about 0.5%, between at or about 0.5% and at or about 3%, between at or about 0.5% and at or about 2.5%, between at or about 0.5% and at or about 2%, between at or about 0.5% and at or about 1.5%, between at or about 0.5% and at or about 1%, between at or about 1% and at or about 3%, between at or about 1% and at or about 2.5%, between at or about 1% and at or about 2%, between at or about 1% and at or about 1.5%, between at or about 1.5% and at or about 3%, between at or about 1.5% and at or about 2.5%, between at or about 1.5% and at or about 2%, between at or about 2% and at or about 3%, between at or about 2% and at or about 2.5%, between at or about 2.5% and at or about 3%, by weight, of the beverage composition. In some examples, the amount of antioxidant added to the provided beverage compositions is less than 5% or about 5%, typically less than 3% or about 2%, for example, at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9% or 3.0%, by weight, of the beverage composition.

iii. Beverage Base

The beverage compositions provided herein contain a beverage base. The beverage base can include, but is not limited to a polar solvent, for example water (e.g., filtered water); a juice, for example a fruit, vegetable or berry juice, such as a juice blend, a dried juice, a juice concentrate, a juice extract, a juice puree, a milk; a fruit flavor or flavoring agent, for example, natural and synthetic flavors, such as fruit flavors, botanical flavors, spice flavors, other flavors; a carbonated beverage, such as a soda, flavored soda, carbonated water, carbonated juice or other carbonated beverage; or any combination thereof.

In general, a high amount (i.e., a large wt %) of the beverage composition is a beverage base. Typically, the amount of beverage base included in the provided beverage compositions is more than 55% or about 55%, typically more than 75% or about 75%, for example, at or about 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9%, by weight, of the beverage composition.

(a) Water

Exemplary of a beverage base used in the provided beverage compositions is a polar solvent, for example, water. In one example, the water is a purified water, such as water that is purified prior to adding it to the beverage composition, for example, by charcoal filter, ion exchange, reverse osmosis, UV sterilization and/or filtering using a filter, for example, a 50-100 micron filter. Typically, when a filter is used, it is an end point of use filter, which filters the water before it reaches the tank in the provided process. Alternatively, previously filtered water can be added to the beverage compositions.

Generally, a high amount (i.e., a large wt %) of the beverage base of the beverage compositions provided herein is a polar solvent, such as water. Typically, the amount of water included in the provided beverage compositions is more than 55% or about 55%, typically more than 75% or about 75%, for example, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9%, by weight, of the beverage composition.

(b) Juices or Juice Concentrates

In one example, the beverage base included in the provided beverage compositions further contains one or more juices, such as a juice blend, a dried juice, a juice concentrate, a juice extract, a juice puree, a milk, or any combination thereof. Any juice or combination of juices can be added to the beverage compositions, for example, any fruit, vegetable, or berry juice. Multiple different fruit, vegetable and/or berry juices can be combined in the beverage compositions to generate a beverage composition having the desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, coconut, olive, raspberry, strawberry, huckleberry, loganberry, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, mandarin and grapefruit. Numerous additional and alternative juices suitable for inclusion in the provided beverage compositions are well within the skill of the skilled artisan.

Typically, the concentration of pH adjuster added to the provided beverage compositions, including the beverages and shots, is less than 3% or about 3%, typically less than 1.5% or about 1.5%, for example, at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.11%, 2.12%, 2.13%, 2.14%, 2.1415%, 2.15%, 2.16%, 2.17%, 2.18%, 2.19%, 2.2%, 2.3%, 2.4%, 2.5%, 2.6%, 2.7%, 2.8%, 2.9% or 3.0%, by weight, of the beverage composition.

(c) Flavors

In one example, the beverage base included in the provided beverage compositions further contains one or more flavors or flavoring agents, for example, any compound to add flavor to the beverage composition, including the beverages and shots. The flavor or flavoring agent can be, for example, natural and synthetic flavors, fruit flavors, botanical flavors, spice flavors, other flavor, and mixtures thereof. Several flavors are well known. Any flavor can be added to the beverage compositions, for example, any flavor sold by Mission Flavors (Foothill Ranch, Calif.) or Creative Flavor Concepts (Irvine, Calif.). Exemplary of flavors that can be used are fruit flavors, including citrus flavors and other fruit flavors, such as guava, kiwi, peach, mango, papaya, pineapple, banana, strawberry, raspberry, blueberry, orange, coconut, grapefruit, tangerine, mandarin orange, tangelo, pomelo, apple, grape, cherry, tomato, passion fruit, apricot, lemon, lime and lemon-lime; vegetable flavors, such as carrot; botanical flavors, such as cola flavors and tea flavors; spice flavors, such as *cassia*, clove, cinnamon, pepper, ginger, vanilla spice, cardamom, coriander, root beer, birch beer, sassafras, and ginseng; coffee flavors, such as coffee, latte, and cappuccino; mint flavors; chocolate flavors, such as chocolate and fudge; dairy flavors; vanilla flavors; butterscotch flavors; nut flavors, such as almond, peanut, and other nuts; methyl salicylate (wintergreen oil, sweet birch oil); citrus oils and other flavors.

Typically, the flavors are safe and/or desirable for human consumption, for example, GRAS or Kosher-certified flavors. Exemplary of flavoring agents that can be used in the compositions are pomegranate grape (Code F0233), mixed berry (Code F3090), peach mango (Code F0079) and citrus (Code F4721), all sold by Creative Flavor Concepts (Irvine, Calif.); peach (PH-147), vanilla (CA-158), cherry (CH-172) and mixed berry (MB-106), all sold by Mission Flavors and Fragrances, Inc. (Foothill Ranch, Calif.); blackberry (Code 125-00875) sold by Cargill; and any other suitable flavor or flavoring agent that is apparent to those skilled in the art.

Typically, the concentration of flavor or flavoring agent added to the provided beverage compositions is less than 5% or about 5%, typically less than 3% or about 3%, for example, at or about 0.0%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0%, by weight, of the beverage composition.

(d) Carbonated Beverages

In one example, the beverage base included in the provided beverage compositions further contains one or more carbonated beverages, such as a soda, carbonated water, carbonated juice, flavored soda, or any combination thereof. Any carbonated beverage can be added to the beverage compositions, for example, any soda, carbonated water or carbonated juice. Multiple different sodas, carbonated waters and carbonated juices can be combined in the beverage compositions to generate a beverage composition having the desired flavor. Numerous additional and alternative carbonated beverages suitable for use in the provided beverage compositions are well within the skill of the skilled artisan.

Generally, when the beverage base contains a carbonated beverage, such as a soda, flavored soda, carbonated water or carbonated juice, the carbonated beverage is used in place of the polar solvent. Thus, a high amount (i.e., a large wt %) of the beverage base of the beverage compositions provided herein is a carbonated beverage. Typically, the amount of carbonated beverage included in the provided beverage compositions is more than 55% or about 55%, typically more than 75% or about 75%, for example, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9%, by weight, of the beverage composition.

iv. Sweeteners

In one example, one or more sweeteners are added to the beverage compositions at an appropriate concentrate to achieve a desired level of sweetness. Sweeteners are well known. Typically, the sweeteners are safe and/or desirable for human consumption, for example, GRAS or Kosher-certified sweeteners. Exemplary sweeteners that can be used in the provided beverage compositions are sucralose, such as Sucralose FCC VI Grade, manufactured by Changzhou Tianhua Imports & Exports Co., Ltd, sold by Ausvita, stevia, such as Stevia Leaf Powder Extract, Product code STE091 sold by MiniStar International Inc., and Xylitol, sold by Nutra Food Ingredients. Additional sweeteners that can be used in the provided beverage compositions include, but are not limited to, sucrose, lactose, fructose, an acesulfame salt, aspartame, saccharin, stevia, stevioside, and combinations thereof.

v. pH Adjusters

In one example, one or more pH adjusters are added to the provided beverage compositions at an appropriate concentration to achieve a desired pH. Typically, the pH adjuster is added to adjust the pH of the beverage composition to within a range of 2.0 or about 2.0 to 4.0 or about 4.0, for example, to a pH of 3.8. One or more of a plurality of pH adjusting agents can be used. Typically, the pH adjusting agent is safe for human consumption, for example, GRAS certified. Exemplary of a pH adjuster is phosphoric acid, such as Food Grade 80% Phosphoric Acid, sold by Univar.

Typically, the concentration of pH adjuster added to the provided beverage compositions, including the beverages and shots, is less than 3% or about 3%, typically less than 1.5% or about 1.5%, for example, at or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.11%, 2.12%, 2.13%, 2.14%, 2.1415%, 2.15%, 2.16%, 2.17%, 2.18%, 2.19%, 2.2%, 2.3%, 2.4%, 2.5%, 2.6%, 2.7%, 2.8%, 2.9% or 3.0% by weight of the beverage composition.

vi. Antifoaming Agents

In one example, an antifoaming agent is added to the provided beverage compositions, typically when adding the stabilizer and/or stabilizing system, according to the provided methods. Typically the antifoaming agent is added dropwise to the provided beverage composition to prevent air bubbles from forming. Any antifoaming agent can be used in the provided concentrates. Exemplary of an antifoaming agent that can be added is Tramfloc 1147, sold by Tramfloc Inc, Formey, Tex., containing an emulsion of polydimethylsiloxane fluid and amorphous silica.

E. Exemplary Methods for Preparing Products Containing High Dimer-Containing Water-Soluble Vitamin E Derivative Mixtures Methods for preparing products containing the high dimer water-soluble vitamin E derivative mixtures, e.g., TPGS compositions, for example, products for human consumption, such as food and beverage products, in particular aqueous food and beverage products. For example, methods for preparing the concentrates provided herein are described. Equipment for use in the methods and general steps of the methods are described below. The methods include bench-top manufacturing processes, which are used to make small quantities of the products. The methods also include scaled-up manufacturing processes, which are used to make larger batches of the products. Any of the bench-top processes can be scaled up to perform the methods using the scaled-up processes. Any of the provided products can be made using either scaled-up or bench-top processes. The concentrates and liquid dilution compositions provided herein can be made following the methods provided in U.S. Pat. No. 8,282,977 and U.S. Pub. Nos. 2009-0297491 and 2012-0016026.

1. Equipment Employed in the Methods

Equipment used in various steps of the provided methods for making the products can include, for example, vessels, such as tanks, for mixing the water and oil phases and the product; scales; mixers, for example standard mixers and homogenizers; heating and cooling apparatuses, such as water-jacketed tanks, hot plates, water baths and chillers (coolers), including recirculating coolers; transfer apparatuses, for example, transfer devices, such as, pumps, hoses and sanitary fittings; ball valves; purifiers, for example, filters, such as carbon filters, ion exchange equipment, reverse osmosis equipment, end-point filters and end product filters; evaluation devices, for example, pH and temperature meters; and other equipment. The choice of equipment depends on a plurality of factors, including batch size and the manufacturing process.

a. Scales

One or more scales can be used to measure the amount of the ingredients before adding them to the appropriate vessel. Alternatively, the ingredients can be weighed in the vessel, for example, in a tank on top of a scale.

Any of a plurality of well-known, commercially sold scales can be used to weigh the ingredients. The choice of scale(s) can depend on a number of factors, including the mass of the product being made (e.g., the batch size) and the ingredient being weighed. In one example, multiple scales are used to weigh the various ingredients of the products. In general, relatively larger capacity (i.e., weight) scale(s) are used in making larger batches of the products while relatively smaller capacity scale(s) are used in making smaller batches.

Exemplary of the scales used to weigh the ingredients using the provided methods are a Toledo Scale (Model GD13x/USA); a Sartorius Basic Analytical Scale (Model BA110S), which is a basic series analytical scale with a 110 g capacity and a resolution of 0.1 mg; and an OHAUS Scale (Model CS2000), which is a compact portable digital scale having a 2000 g capacity and a resolution of 1 g.

b. Purifiers

Purifiers, such as filters, are used in the provided methods to remove impurities from the ingredients prior to their addition to and/or from the product or to and/or from a phase of the product. For example, the water added to the water phase typically is purified water. In one example, one or more purifiers, for example, carbon filters, ion exchange purifiers, reverse osmosis purifiers, and/or end point filters can be used to filter water, for example, city water, prior to its addition to the water phase. For example, the water can be filtered to remove impurities, such as sediment, from the water.

Purifiers that can be used with the provided methods include filters, for example, 100 micron filters and carbon filters, which are filters that use activated carbon to remove impurities by chemical adsorption. Carbon filtering typically is used for water purification and is particularly effective at filtering out chlorine, sediment, volatile organic compounds and other impurities. Typically, the particles removed by carbon filters are between about 0.5 microns and about 50 microns. Other filters are well known and can be used with the provided methods.

The purifiers also include reverse osmosis purifiers, which use mechanical pressure to purify liquids, for example, water. In one example, the pressure forces the water through a semipermeable membrane to remove impurities.

The purifiers also include exchange purifiers, for example, an ion exchange purifier. The ion exchange purifier can use a resin bed, such as a zeolite resin bed, to replace salts, such as cations, e.g., magnesium and calcium, with other cations, such as sodium and potassium cations. Such purifiers can be purchased, for example, from Aqua pure Filters (Clarkston, Mich.).

In one example, the purifier is an end product filter (e.g., a 100 micron filter; Product No. BPEM 100-5GP; FSI, Michigan City, Ind.). This filter is used to filter any impurities out of the final product (e.g., the final pre-emulsion composition). Other filters also are known and can be used with the provided methods.

c. Vessels

One or more, typically two or more, vessels, can be used in the methods to contain the ingredients of the provided products, for example, during mixing and/or heating or cooling. The vessels can be tanks, for example, water-jacketed tanks; pots; and/or beakers, for example, Pyrex® beakers. Separate vessels (e.g., an oil phase tank and a water phase tank) can be used for mixing and heating the ingredients of the oil phase and the water phase prior to combining the two phases. In some examples, an additional vessel, for example, a holding and/or packaging tank, can be used for holding and/or packaging the products and/or for addition/mixing of additional ingredients to the products.

A number of vessels are available for mixing ingredients. Typically, the vessels are cleaned, for example, rinsed, soaped and/or sanitized, according to known procedures prior to use and between uses, such as with the cleaning procedures described below.

In the bench-top process, the vessel can be a container, for example, a bench-top container, such as a flask, beaker (e.g., a Pyrex® beaker), vial, measuring container, bottle and/or other bench-top container.

In the scaled-up manufacturing process, the vessels can be tanks, for example, water phase tanks, oil phase tanks and holding/packaging tanks. Typically, the tanks are equipped with one or more mixers, for example, a standard mixer and/or homogenizer, which are used to mix the ingredients that are added to the tank. In one example, the tank is further equipped with a heating and/or cooling device. For example, the tank can be a water-jacketed tank. The temperature of the water-jacketed tank is controlled through the water jacket, for example, to heat the contents, such as during mixing.

Exemplary of the tanks that can be used with the provided methods are water-jacketed tanks, for example, the Overly 550 gallon water-jacketed tank (Model 10576501G), which has a 550 gallon capacity and typically is used as a water phase tank, the Schweitzer's 450 gallon tank (Model #5214-C), which has a 450 gallon capacity and typically is used as an oil phase tank and the Royal 190 gallon water-jacketed tank (Model 9977-5), which has a 190 gallon capacity and can be used as a water or oil phase tank when mixing smaller volumes. Other tanks are well known and can be used with the provided methods for mixing the products, for example, the phases of the product.

d. Mixers

Mixers are used in the methods to blend, mix and/or emulsify the products and ingredients, mixtures and phases of the products. In some examples, the mixers can be used to keep the ingredients and/or mixture circulating to maintain temperature, viscosity and/or other parameters of the mixture. Suitable mixers include, but are not limited to, standard mixers, for example, those that can be used to mix ingredients and maintain a homogeneous mixture, such as while heating a mixture of ingredients. Exemplary of the standard mixers are LIGHTNIN® mixers (LIGHTNIN, Rochester, N.Y.), for example, Model Numbers XJC117 and ND-2. In one example, the LIGHTNIN® mixers are fixed-mount, gear drive high-flow mixers, for use with closed tanks. Another example of a standard mixer is a mixer sold by IKA®, for example, overhead IKA® mixers. Exemplary IKA® mixers include Model Nos. RW-14 Basic and RE-16S, which are laboratory stirrers that can be used to mix ingredients. In some examples, the mixer can be attached to the vessel, e.g., the tank, such as by mounting or clamping onto the tank, such as at the top of the tank. In other examples, the mixer can be placed in the vessel for mixing.

The mixer can be a homogenizer which can be used, for example, to emulsify mixtures, i.e., form an emulsion. The homogenizer can be used to mix phases of the compositions, e.g., oil and water phases, after combining the phases, in order to form an emulsion. The homogenizer provides high-shear dispersion of solids and emulsification of immiscible liquids at high shear rates. Suitable homogenizers include, but are not limited to, high-shear homogenizers, for example, reversible homogenizers sold by Arde Barinco, Inc. (Norwood, N.J.).

Exemplary Arde Barinco, Inc. reversible homogenizers are Model CJ-50 (a 3600 rpm mixer having a 6-inch rotor diameter, tip speed of 5575 ft/minute, emersion depth of 33 inches, and six separate openings at the bottom and top, which concentrate the liquid into six chambers, reducing the surface volume and creating a shear effect); and Model CJ-4E (a 10,000 rpm mixer with fan-cooled motor, optimized for 1 to 5 gallon batch sizes, having a 1.875 inch rotor diameter, tip speed of 4920 rpm, and immersion depth of 16 inches). The homogenizers further include other homogenizers, for example, other reversible homogenizers sold by Arde Barinco, Inc.

In one example, the homogenizer is attached to the top of the vessel, for example, the tank, for example, by clamps or by channel locks and an electrical hoist. In another example, the homogenizer is placed in the vessel. The Arde Barinco reversible homogenizers contain axial flow impellers, which create two distinct mixing actions, depending on direction. Downward "vortex flow" pulls solids from the top and bottom of the mixture, while upward "umbrella flow" controls mixing at the highest shear and recirculation rates without splashing or incorporating air. The reversible homogenizers typically are equipped with an adjustable baffle plate, which can be adjusted to control the type of mixing, for example at different times during mixing, e.g., during emulsification.

A number of other mixers are well known and can be used with the provided methods. Exemplary of suitable mixers that can be used with the provided methods are homogenizers, inline mixers, ribbon mixers, plow mixers, paddle mixers, Forberg® mixers, conveyors, bag dumps and compactors, V-blenders, blade mixers, double cone mixers, continuous mixers, speedflow mixers, batch mixers, double ribbon blenders, paddle and ribbon mixers with choppers, plow blenders, turbulent mixers, fluidizing Forberg-type mixers, air mixers, active mixers, passive mixers, top-entry mixers, side-entry mixers, static mixers, fixed-entry mixers, portable mixers (e.g., direct and gear drive), sanitary mixers, drum mixers, bulk container (IBC) mixers, lab stirrers, variable speed mixers, dough mixer, vertical mixer, spiral mixer, twin arm mixer, fork mixer, double spiral mixer, all agitators, agitator mixers, Banbury® mixers, rubber mixers, Blondheim mixers, churn mixers, conical mixers, continuous mixers, disperser mixers, pan mixers, emulsifier mixers, Hobart® mixers, liquifier mixers, Littleford mixers, meat mixers, plow mixers, Mix-Muller® Mixers, vertical screw mixers (e.g., Nauta mixers), Oakes mixers, planetary mixers, pony mixers, pug mixers, Ross mixers, rotary mixers, Sigma mixers, single arm mixers, tote bin mixers, tumble mixers, vacuum mixers, Turbolizer mixers, twin shell mixers, V-type mixers, zigzag mixers, sidearm mixers, hand-held mixers, stir rods, stir bars, magnetic mixers, overhead mixers (e.g., mechanical and/or electric overhead mixers), and any mixer known to those of skill in the art.

e. Heating/Cooling Apparatuses

Equipment that can be used in the methods includes heating and cooling apparatuses. The heating and cooling apparatuses can be used to control the temperature of the ingredients and combinations thereof, such as while generating the products.

Heating apparatuses that can be used in the provided methods are those that are capable of heating the mixture to between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. Typically, the heating apparatus is used to heat the mixtures to a temperature of at or about 60° C.

The heating apparatus can be a water jacket, for example, a water jacket on a water-jacketed tank, which can be controlled, for example, by a control panel, such as to adjust the temperature of the contents of the tank. Other suitable heating apparatuses are immersible and/or submersible heaters, for example, 12 KW or 13 KW sanitary heaters, including food-grade heaters, that can be immersed into the tanks, typically while mixing and typically when higher temperatures are required, such as when temperatures greater than 60° C. or about 60° C., or greater than 80° C. or about 80° C. are required. The heating apparatuses also include stoves, for example, propane stoves, and hot plates, for example, Thermolyne® hot plates (e.g., Model Nos. 846925 and SP46615).

The cooling apparatus can be any apparatus that can cool the ingredients and combinations thereof, such as rapidly cooling and/or cooling while mixing the ingredients. Typically, the cooling apparatus is capable of cooling the mixtures to a temperature between at or about 25° C. and at or about 45° C., for example, to at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C. or 45° C. In some examples, the cooling apparatus can cool the mixture to a temperature between at or about 30° C. and at or about 35° C. Typically, the cooling is rapid cooling. For example, the products can be cooled to a temperature between at or about 30° C. and at or about 35° C. in at or about 15 minutes to at or about 2 hours, for example, in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In an exemplary method, the products can be cooled to a temperature between at or about 30° C. to at or about 35° C. in at or about 30 minutes to at or about 60 minutes.

Suitable cooling apparatuses for used in the methods include chillers, for example, recirculating coolers. The cooling apparatuses can be attached to the vessel, such as remotely or by a tank mounted in the cooler, to repeatedly circulate fluid from the tank, through the chiller and back to the vessel, to rapidly cool and maintain the temperature of the mixture during mixing. Exemplary of cooling apparatuses that can be attached to the tank and used with the provided methods are open-loop chillers and closed-loop chillers, for example, those sold by Turmoil (West Swanzey, N.H.), such as Model No. OC-1000 RO. Suitable cooling apparatuses also include water baths and ice baths, for example, water baths and/or ice baths in which the vessel is placed, for example, during homogenizing. Other cooling apparatuses are well known by those of skill in the art and can be used with the provided methods.

f. Transfer Devices

Transfer devices can be used with the provided methods to transfer liquid from one vessel to another vessel. Transfer devices can be used in the methods to combine the phases and form the emulsion. For example, transfer device can be used to transfer the water phase from the water phase vessel to the oil phase vessel or to transfer the oil phase from the oil phase vessel to the water phase vessel. Transfer devices include, for example, transfer pumps and associated accessories (e.g., fittings), including ball valves, sanitary fittings (for example, sanitary fittings sold by Granger, Inc. (Lake Forrest, Ill.)) and transfer hoses (for example, hoses sold by Sani-Tech West (Oxnard, Calif.)), such as food grade hoses attached to a transfer pump, for example, the food grade Sani-Tech® STHT-R-HD Braid-Reinforced Heavy Duty Silicone Hose. Suitable transfer pumps include the Teel Pump (Model 2P377B; Granger, Inc., Lake Forrest Ill.), a self-priming pump having a power rating of 2 HP, 60 Hz voltage, 208-230/460 AC, speed of 3450 rpm; and other pumps, such as self-priming pumps from Granger, Inc. The transfer device can also include equipment for manually transferring the liquid to another vessel, for example, by pouring, pipetting and/or other well-known methods of manually transferring liquids.

g. Evaluation Equipment

Evaluation equipment includes equipment that can be used to evaluate properties of the products and/or phases of the products, such as the temperature, pH, clarity, color, activity, smell and/or taste of the products. Suitable evaluation equipment includes pH and temperature meters, such as the pH and temperature meter sold by Hanna Instruments (Model No. HI 8314; Ann Arbor, Mich.), which can be used to measure the temperature and the pH of the product. Temperature meters can also include temperature probes, for example, digital and/or water-proof temperature probes, such as temperature probes sold by Cooper-Atkins (Middlefield, Conn.), for example, the Cooper-Atkins digital waterproof temperature probe (Model #DPP400W). The products can be evaluated and analyzed to verify the amounts of the active ingredients and to verify that the products meet industry standards, such as to verify that the products do not contain levels of microbials and heavy metals that are above acceptable levels. Typically, these tests are performed by sending a sample of the product to a commercial testing facility, as described in section 2(g), below.

2. General Methods for Producing the Compositions

In general, the methods useful for making the concentrates provided herein are performed by generating an oil phase and generating a water phase (for the liquid nanoemulsion concentrates) and combining (e.g., using a transfer device) and mixing the phases to form emulsions. The oil and water phases typically are generated in separate vessels. The vessels can be, for example, tanks. Generation of the water phase and generation of the oil phase can be performed simultaneously or sequentially, in any order. Typically, both phases are heated to a desired temperature prior to combining the phases. For example, the phases can be heated to 60° C. prior to combining the phases. The provided methods can include additional steps. In some examples, the additional steps include evaluating properties of the products, adding additional ingredients (e.g., taste-modifying agents), packaging and/or filtering.

The provided methods can be performed using a bench-top manufacturing process (for small batch sizes) or performed using a scaled-up manufacturing process (for larger batch sizes). Each of the provided products can be made with either the bench-top or scaled up process. In one example, the product is first made with the bench-top process and then the method is scaled up to make larger quantities of the product.

The bench-top process can be performed on a bench, counter, table or any other suitable surface. Typically, the bench-top process is used to make emulsions having relatively smaller volumes than those made with the scaled-up process. For example, volumes less than 1 L or about 1 L, or less than 1 gallon or about 1 gallon, for example, less than or about 500 mL, for example, less than or about 1000 mL, 900 mL, 800 mL, 700 mL, 600 mL, 500 mL, 450 mL, 400 mL, 350 mL, 300 mL, 250 mL, 200 mL, 150 mL, 100 mL, or 50 mL or less, can be made using the bench-top process.

For the bench-top process, the equipment can be sufficiently compact to be used on a bench-top or other similar surface, and can be sufficiently compact to be moved, for example, lifted, by the artisan using the methods. For example, the vessels, such as water phase vessels, oil phase vessels, holding vessels, and packaging vessels, can be bench-top vessels. Exemplary bench-top vessels include, for example, flasks, beakers, vials, measuring containers, bottles and/or other bench-top containers. In some examples, the vessel in the bench-top process is a Pyrex® beaker.

Typically, the mixers for use in the bench-top processes of the provided methods are mixers that can be used in the bench-top vessels. Mixers that can be used in the bench-top vessels include, for example, standard mixers, such as hand-held mixers, stir rods, stir bars, magnetic mixers and overhead mixers, including, for example, mechanical and/or electric overhead mixers, and any other mixer that is suitable for use in the bench-top vessel. Exemplary standard mixers include those sold by IKA®, for example, overhead IKA® mixers, such as Model Nos. RW-14 Basic and RE-16S, which are laboratory stirrers and can be used to mix ingredients, such as to generate the oil and water phases. Suitable bench-top mixers also include homogenizers, for example, reversible homogenizers. An exemplary reversible homogenizer is the Arde Barinco reversible homogenizer, Model no. CJ-4E, which can be used to emulsify the phases.

Typically, the heating and cooling apparatuses are those that can be used with the bench-top vessels, such as hot plates, ice baths and/or water baths, into (or onto) which the vessels can be placed, for example, for rapid cooling. The evaluation device used in the bench-top process, for example, the temperature and/or pH meters, typically are capable of being placed in the bench-top vessels.

For the bench-top process, combining the oil and water phases typically is carried out manually, e.g., by pouring, pipetting and/or another manual transfer device.

The scaled-up manufacturing process of the methods typically is used to make products of relatively larger volumes, such as volumes greater than 1 L or about 1 L, or greater than 1 gallon (gal) or about 1 gallon. For example, volumes greater than or about 0.5 L, for example, greater than or about 0.5 L, 1 L, or 2 L, or greater than or about 1 gal, 2 gal, 3 gal, 4 gal, 5 gal, 6 gal, 7 gal, 8 gal, 9 gal, 10 gal, 11 gal, 12 gal, 13 gal, 14 gal, 15 gal, 16 gal, 17 gal, 18 gal, 19 gal, 20 gal, 21 gal, 22 gal, 23 gal, 24 gal, 25 gal, 26 gal, 27 gal, 28 gal, 29 gal, 30 gal, 40 gal, 50 gal, 60 gal, 70 gal, 80 gal, 90 gal, 100 gal, 150 gal, 200 gal, 250 gal, 300 gal, 350 gal, 400 gal, 450 gal, 500 gal, 550 gal, 600 gal, 650 gal, 700 gal, 800 gal, 900 gal, or 1000 gal or more, can be made using the scaled-up manufacturing process.

In general, equipment used for the scaled-up process is compatible with larger volume batches (batch sizes). For example, the vessels for use in the scaled-up processes can be tanks, for example, water-jacketed tanks, which are equipped with water jackets that can be used as heating apparatuses to heat the oil and water phase ingredients during generation of the oil and water phases. The water jackets typically are controlled via control panels. The transfer device can include devices attached to and connecting the tanks, such as transfer pumps and associated fittings, for example, ball valves and hoses that are attached to the tanks. Mixers for use in the scaled-up process can be standard mixers, for example, mounted mixers, such as LIGHTNIN® mixers, e.g., Model Nos. XJC117 (a fixed-mount, gear drive high-flow mixer) and ND2.

Prior to beginning the methods, the water jacket lines on any water jacketed oil phase and water phase tank can be bled. The water jacket switches can then be turned on to maintain a pressure in the water jackets of between at or about 20 psi and at or about 40 psi (pounds per square inch). If the pressure in the water jacket falls below 20 psi during the method, the line can be bled and checked for bubbles while purging the line.

a. Water Phase Ingredients

The water phase includes one or more polar solvents, such as water, diols, such as propylene glycol and sugar alcohols, such as glycerin, and, in some examples includes other water phase ingredients. Typically, water phase ingredients are hydrophilic and/or amphipathic ingredients of the liquid nanoemulsion concentrate. For example, oils and other lipophilic ingredients typically are not added to the water phase. Certain ingredients, for example, ingredients having hydrophobic and hydrophilic moieties, for example, surfactants and co-surfactants, can be added to either the oil or the water phase, or to the oil and the water phase. Exemplary water phase ingredients include, but are not limited to, polar solvents, e.g., water, typically filtered water, propylene glycol, glycerin and other diols; emulsion stabilizers; pH adjusters, for example, phosphoric acid and/or citric acid; flavors; surfactants; co-surfactants, for example, phosphatidylcholine and sucrose fatty acid esters; and preservatives.

Water phase ingredients can be added to the water phase simultaneously and/or sequentially, in a specific order. In one example, one or more water phase ingredients is added first and heated, prior to addition of further ingredient(s). In one example, when the water phase ingredients include a polar solvent and an emulsion stabilizer, these ingredients are added sequentially, in the following order: 1) polar solvent, and 2) emulsion stabilizer. In one example, when the water phase ingredients include water and an emulsion stabilizer, these ingredients are added sequentially, in the following order: 1) water, and 2) emulsion stabilizer. In another example, when the water phase ingredients include a surfactant, a polar solvent (e.g., water) and an emulsion stabilizer, these ingredients are added to the water phase vessel sequentially, in the following order: 1) surfactant; 2) polar solvent (e.g., water); and 3) emulsion stabilizer. Alternatively, the water phase ingredients can be added in any other order. Typically, when the water phase includes a surfactant, particularly when the surfactant is a surfactant that is solid at room temperature, for example, tocopherol polyethylene glycol succinate surfactant, the surfactant is the first water phase ingredient added to the water phase vessel. Typically, when the water phase ingredients include an emulsion stabilizer, the emulsion stabilizer is the last ingredient added to the water phase vessel.

b. Water Phase Production

To produce the water phase, appropriate amounts of the water phase ingredients are added to the water phase vessel. Water phase vessels can include tanks, for example, water-jacketed tanks such as, but not limited to, the Overly 550 gallon water-jacketed tank, or any other tank described herein. The amounts of the water phase ingredients are measured, e.g., weighed, either prior to adding to the water phase vessel or are measured in the water phase vessel. In one example, the water phase ingredients are measured by weighing the ingredients on a scale (e.g., one or more of the scales described herein; the choice of scale depends on the desired amount of the ingredient), before addition to the water phase vessel. Typically, the appropriate amount of the water phase ingredient is calculated based on the desired concentration (e.g., weight/weight (w/w), molarity (M), volume/weight (v/w) or volume/volume (v/v)), of the ingredient in the final product.

Water phase ingredients can include water, typically purified water. In one example, unpurified water, for example, city water, is purified to remove impurities using one or more purifiers (e.g., purifiers described herein) prior to adding it to the water phase vessel. In another example, unpurified water, for example, city water, is purified by passing the water through the following purifiers, typically sequentially, in the following order: a carbon filter, an ion exchange purifier, a reverse osmosis purifier and an end-point filter, for example, a 100 micron end-point filter.

In general, the water phase ingredients are added, mixed and/or heated in the water phase vessel. The water phase vessel can be a water phase tank, for example, a water-jacketed tank, such as one of the tanks described herein (e.g., an Overly 550 gallon water jacketed tank). In one example, ingredients are heated to temperatures between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. In one example, the water phase ingredients are heated to a temperature of at or about 60° C., for example, by adjusting the temperature on a water-jacketed tank or using another heating apparatus.

The mixing can be carried out with a standard mixer, a homogenizer, or any other suitable mixer, such as, but not limited to, the mixers described herein. Exemplary mixers include standard mixers, such as Lightnin® mixers (e.g., Model No. XJC117, a fixed-mount gear drive high-flow mixer) and homogenizers, such as Arde Barinco reversible homogenizers (e.g., Model No. CJ-4E). The mixer can be attached to the top of the water phase vessel, for example, attached to the tank, such as mounted on the top of the tank.

The water phase ingredients can be added to the water phase simultaneously or sequentially in any order. Typically, the water, e.g., purified water, is added before adding the other water phase ingredients. In one example, one or more of the ingredients are mixed and/or heated in the water phase tank before adding the other water phase ingredients.

In an exemplary method provided herein, the water phase is generated by combining water, e.g., purified water, and a preservative in the water phase vessel. The water phase is then mixed using a mixer such as a homogenizer, for example an Arde Barinco reversible homogenizer (e.g., Model No. CJ-4E), typically using the "reverse" setting. The homogenizer can be attached to the top of the water phase vessel. The water phase mixture is then heated to the desired temperature, for example, to a temperature of at or about 60° C. After the mixture of water phase ingredients reaches the desired temperature, e.g., at or about 60° C., an emulsion stabilizer, such as the SALADIZER® brand emulsion stabilizer (blend of xanthan gum, guar gum and sodium alginate) is added to the water phase. The water phase mixture is then mixed, for example, using a homogenizer, until the ingredients are mostly dispersed. Additional water phase ingredients are then added to the water phase tank at a temperature of at or about 60° C. The mixture is then mixed until the ingredients are dispersed, using a mixer, such as a standard water phase mixer, for example, a Lightnin® mixer (e.g., Model No. XJC117). Typically the heat is maintained at a temperature of at or about 60° C. Typically, the ingredients are mixed until combined and maintained at the desired temperature e.g., at or about 60° C., until combining with the oil phase.

c. Oil Phase Ingredients

The oil phase includes the water-soluble vitamin E derivative surfactant, e.g., TPGS, the non-polar compound(s), for example, non-polar compounds that contain the non-polar active ingredients and, in some examples, other oil phase ingredients. Typically, oil phase ingredients include one or more lipophilic and/or amphipathic ingredients of the liquid nanoemulsion concentrate. Oil phase ingredients typically do not include aqueous ingredients or hydrophilic ingredients. Certain ingredients, for example, ingredients having hydrophobic and hydrophilic moieties, for example, surfactants and co-surfactants, can be added to either the oil or the water phase, or to the oil and the water phase. Exemplary of ingredients used in the oil phase of the provided concentrates are non-polar compounds, for example, non-polar active ingredients, including any of the non-polar active ingredients provided herein; emulsion stabilizers, pH adjusters, for example, phosphoric acid and/or citric acid; surfactants; co-surfactants, for example, phosphatidylcholine and/or sucrose fatty acid esters; preservatives, and oils, for example, non-polar solvents and other oil phase ingredients.

Oil phase ingredients can be added to the oil phase simultaneously and/or sequentially, for example, in any order or in a specific order. In one example, one or more oil phase ingredients is added first and heated, prior to addition of further ingredient(s). In one example, when the oil phase ingredients include a surfactant, a preservative, a solvent, a co-surfactant, and a non-polar compound, these ingredients are added sequentially, in the following order: 1) surfactant; 2) preservative; 3) solvent; 4) co-surfactant; 5) non-polar compound; and 6) emulsion stabilizer. In another example, when the oil phase ingredients include a surfactant, a preservative and a non-polar compound, the ingredients are added sequentially, in the following order: 1) surfactant; 2) preservative; and 3) non-polar compound. In another example, when the oil phase ingredients include a surfactant, a preservative, a non-polar compound and an emulsion stabilizer, the ingredients are added sequentially, in the following order: 1) surfactant; 2) preservative; 3) non-polar compound; and 4) emulsion stabilizer. Alternatively, the oil phase ingredients can be added in a different order, for example, any order. Two or more oil phase ingredients can be added simultaneously.

Typically, when the oil phase includes a surfactant, particularly when the surfactant is a surfactant that is solid at room temperature, for example, tocopherol polyethylene glycol succinate surfactant, the surfactant is the first oil phase ingredient added to the oil phase vessel. Typically, when the oil phase ingredients include an emulsion stabilizer, the emulsion stabilizer is the last ingredient added to the oil phase vessel. Typically, the non-polar compound either is the last ingredient added to the oil phase vessel, or is added immediately prior to addition of the emulsion stabilizer, which is the last ingredient added to the oil phase vessel.

d. Oil Phase Production

To produce the oil phase, appropriate amounts of the oil phase ingredients are added to the oil phase vessel. Oil phase vessels can include tanks, for example, water-jacketed tanks, such as, but not limited to, the Royal 190 Gallon water jacketed tank, or any other tank described herein. The amounts of the oil phase ingredients are measured, e.g., weighed, either prior to adding to the oil phase vessel or are weighed/measured in the oil phase vessel. In one example, the oil phase ingredients are measured by weighing the ingredients on a scale (e.g., one or more of the scales described herein; the choice of scale depends on the desired amount of the ingredient), before addition to the oil phase vessel. Typically, the appropriate amount of the oil phase ingredient is calculated based on the desired concentration (e.g., weight/weight (w/w), molarity (M), volume/weight (v/w) or volume/volume (v/v)), of the ingredient in the final product.

In general, the oil phase ingredients are added, mixed and/or heated in the oil phase vessel. Mixing the oil phase ingredients can be carried out with a standard mixer or other mixer, such as, but not limited to, the mixers described herein, for example, a Lightnin® mixer (e.g., Model No. XJC117, a fixed-mount gear drive high-flow mixer). Heating the oil phase ingredients is carried out using a heating apparatus, such as those described herein, typically a water jacket on a water-jacketed tank. In one example, the ingredients are heated to temperatures between at or about 45° C. and at or about 85° C., for example, to at or about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C. or 85° C. In one example, the oil phase ingredients are heated to a temperature of at or about 60° C., for example, by adjusting the temperature on a water jacketed tank.

The oil phase ingredients can be added to the oil phase vessel simultaneously or sequentially in any order. In one example, one or more of the ingredients are added, mixed and/or heated, prior to the addition of the other ingredients to the vessel.

In an exemplary method provided herein, the oil phase is generated by combining an oil, such as a fatty acid (e.g., coconut oil) and a stimulant (e.g., theobromine) in the oil phase vessel. The oil phase is then heated to the desired temperature, for example, to a temperature of at or about 60° C., by adjusting the temperature on a water-jacketed tank, until dissolved. After the mixture of oil phase ingredients reaches the desired temperature, e.g., at or about 60° C., a surfactant, for example, TPGS, such as the TPGS compositions described herein is added to the oil phase. In some examples, the oil phase ingredients are mixed (e.g., using a mixer as provided herein) during generation of the oil phase. Typically, the oil phase ingredients are mixed until combined and maintained at the desired temperature, e.g., at or about at 60° C., prior to combining with the water phase.

e. Combining Phases

After the oil phase and the water phase are generated, the phases can be combined, for example, by using transfer device, and mixed, e.g., homogenized, to form an emulsion. In one example, the oil phase is transferred from the oil phase vessel to the water phase vessel. In another example, the water phase is transferred from the water phase vessel to the oil phase vessel. In another example, the oil and water phases are transferred to another vessel, such as an emulsifying vessel.

Transfer device can include any device for transferring the contents of one vessel to another vessel, as described above. For example, suitable transfer device include transfer pumps and associated equipment, such as, but not limited to, combinations of sanitary fittings, hoses and/or ball valves; manual transfer device, for example, pouring and/or pipetting device; and any other suitable transfer device known to those of skill in the art. Typically, the phases are kept clean, e.g., sterile, during transfer. Sterility of the phases can be maintained, for example, by transfer device having sanitary fittings and/or by combining the phases in a sterile environment. In one example, the transfer device include a transfer pump, for example, a Teel pump (Model No. 2P377B; Granger, Inc.), sanitary fittings, transfer hoses, for example, food grade hoses, such as those sold by Sani-Tech West, and ball valves, which are attached to the tanks and connect the tanks.

Simultaneous with and/or subsequent to the combination of the phases, a mixer, for example, a homogenizer (e.g., a reversible homogenizer), can be used to emulsify the water and oil phases. In one example, a homogenizer, e.g., a homogenizer mounted on one of the tanks, is turned on, the ball valves are opened, and the transfer pump is turned on to effect transfer of the contents of one tank to another, for example, to transfer the contents of the oil phase tank to the water phase tank. As the phases are combined, they can be mixed by the homogenizer to form an emulsion. The position of the homogenizer in the tank can be adjusted, for example, by adjusting a baffle plate, e.g., moving the baffle plate further into/out of the mixture, in order to achieve and maintain the emulsion. Typically, the phases are homogenized (i.e., emulsified) by operating the mixer, e.g., homogenizer, at a speed sufficient to form an emulsion. In one example, the homogenizer is operated at a speed of between at or about 1000 and at or about 1500 rpm. Mixing typically is continued until the phases are combined, typically in an emulsion.

f. Cooling

The emulsion can be cooled during and/or after mixing to promote stability and emulsification, for example, by preventing or minimizing oxidization. The cooling can be rapid cooling and can be performed using one or more cooling apparatuses, for example, any of the cooling apparatuses described herein or any cooling apparatus known to those of skill in the art. Suitable cooling apparatuses for use with the methods include recirculating coolers and water and ice baths. An exemplary cooling apparatus is a recirculating cooler, such as those sold by Turmoil (Model No. OC-1000 RO; West Swanzey, N.H.). When the cooling apparatus is a recirculating cooler, fluid from the vessel containing the combined oil and water phases is circulated through the cooler, typically while mixing, and then back to the vessel, to rapidly cool and maintain the temperature of the mixture during mixing. Typically, the phases are mixed and cooled until the phases are emulsified and the temperature of the emulsification reaches between at or about 25° C. and at or about 43° C., typically between at or about 30° C. and at or about 35° C. For example, the emulsification can be cooled to a temperature of at or about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C. or 43° C. Typically, when the cooling is rapid cooling, the temperature can be reached in less than or about 2 hours, typically less than or about 1 hour. For example, the emulsification can be cooled to the desired temperature, e.g., between at or about 25° C. and at or about 43° C., in at or about 30 minutes to at or about 60 minutes, such as in at or about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

Cooling can be performed before or after additional steps, such as adding additional ingredients and/or evaluation of the product. In one example, the cooling is carried out after the addition of additional ingredients, for example, taste-modifying agents, and/or pH adjusting agents.

g. Filtration, Additions, Evaluation and Packaging

After combining the oil and water phases to form a mixture, i.e., emulsion, one or more additional steps can be carried out to modify, evaluate, analyze and/or package the product. Typically, taste-modifying agents are added to the emulsion, such as flavoring agents (e.g., flavoring agents that confer fruit flavors, such as peach, or other flavors, such as pina colada) and sweetening agents (e.g., sucralose). Other ingredients can be added, such as masking agents (e.g., NAT masking agent) and pH adjusting agents (e.g., acids, such as, but not limited to citric acid). The pH adjusting agent can be used to adjust the pH of the emulsion, for example, to a pH of between at or about 2 and at or about 5, e.g., to at or about 2 and at or about 3.5. Thus, the provided products typically have a pH of between at or about 2 and at or about 5, e.g., at or about 2 and at or about 3.5, such as a pH of at or about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.

Before and/or after adding additional ingredients, the product can be evaluated, such as by measuring the pH and/or the temperature. Measurements can be taken using an instrument such as those described herein. In one example, additional ingredients (e.g., pH adjusters) are added based on information obtained by evaluating the product. The product can be analyzed and evaluated to verify and/or determine other properties of the product, for example, to verify that the product contains the appropriate amounts of the active ingredients and other ingredients. For example, the products can be evaluated to verify that microbial and heavy metal (e.g., arsenic, cadmium, mercury, lead and others) levels are within the acceptable range according to food and beverage standards. In one example, the acceptable microbial levels are not more than 1,000 cfu/g microbes (e.g., yeast, bacteria, mold and other microbes) and negative for *E. coli* and *Salmonella*. In another example, the acceptable heavy metal levels are not more than 10 ppm heavy metals and not more than 0.2 ppm lead and 2 ppm arsenic. When a standard exists for a particular amount and/or property, the amount/property is verified by tests in accordance with U.S. Pharmacopeia (USP) and/or AOAC (Association of Analytical Communities) standards. Samples can be analyzed in accordance with these standards by sending a sample of the product to a commercial testing facility, such as Eurofins U.S. (Des Moines, Iowa) or Advanced Botanical Consulting & Testing, Inc. (Tustin, Calif.), or any other facility that performs tests in accordance with these standards.

For example, the amount of some active ingredients, such as caffeine anhydrous, chromium picolinate and vitamin B12, typically is verified according to USP standards. The density and pH of the composition and the level of microbes, e.g., yeast, mold, *E. coli* and *Salmonella*, also typically are verified according to USP standards. The amount of fatty acids, e.g., coconut oil, can be verified according to AOAC standards, for example, by gas chromatography (GC), gas liquid chromatography (GLC) or other fatty acid profiling methods. The levels of heavy metals, such as lead and arsenic, are tested using inductively coupled plasma mass spectrometry (ICP-MS), or by sending a sample of the composition for testing to a testing facility, such as Eurofins U.S. (Des Moines, Iowa) or Advanced Botanical Consulting & Testing, Inc. (Tustin, Calif.), or any other facility capable of performing such tests. Additionally, Fourier transform infrared spectroscopy (FTIR) typically is used to obtain a fingerprint of the product, to verify that no other compounds except the desired ingredients are present in the product.

The emulsifications can be purified, for example, filtered, prior to use, using any of purification device described herein or any other suitable purification device. Water can be added in the case of evaporation, to bring the product up to the appropriate volume. HPLC, GC, GLC, FTIR and ICP-MS can be performed according to well-known methods (see, for example, Analytical Chemistry: An Introduction, 6th Ed., Douglas A. Skoog et al. (1994) Chapters 22 (FTIR) and 27 (GC/GLC, HPLC) and U.S. Pat. No. 6,265,717 (ICP-MS)).

After evaluation, purification, and/or addition of all the ingredients, the product can be packaged, for example, into large containers for storage or into smaller containers for administration, such as bottles or ampoules (as described below). The products can be transferred to the packaging containers using transfer device, such as transfer device described herein, including transfer pumps and fittings as described above or by manual transfer. For example, the product can be packaged for storage in containers, such as totes, e.g., 275 gallon totes (such as the 275 gallon bottle with a reconditioned CageTote tank IBC, Item No. REN275; Qualsery Enterprises, Inc. (www.qualservcontainer.com)), by transferring the mixture using a food grade hose (Sani-Tech® STHT-R-HD braid-reinforced heavy duty silicone hose; Sani-Tech West). After transfer, the tote can be closed and sealed, e.g., tied, such as with a cable tie.

h. Cleaning the Equipment

The equipment used in the provided methods can be cleaned prior to, and typically after, use. For example, the methods include cleaning all the equipment in a sink and/or rinsing the vessels, e.g., tanks, and hose lines. The tanks can be cleaned by filling with hot water, washing with soap and water, rinsing with water. The pH of the water can be checked before discharging the water from the vessel. The water can be adjusted to the desired pH, for example to a pH between 6 and 9, by adding a pH adjusting agent, such as soda ash, citric acid and/or $H_3PO_4$. After discharging the water from the vessel, the tanks can be sanitized, such as with isopropyl alcohol (IPA), and let dry.

F. Examples

Example 1

Method of Producing TPGS Compositions d-α-Tocopheryl polyethylene glycol 1000 succinate (TPGS 1000) was synthesized from vitamin E succinate according to the following general procedure.

Polyethylene glycol (PEG) 1000 (168.7 kg) was added to a reaction flask containing 1430 L of toluene, followed by the addition of 71.5 kg of vitamin E (α-tocopheryl acid) succinate and 2.86 kg of p-toluene sulfonic acid. The reaction mixture was heated to 110-112° C. and refluxed for up to 6.5 hours, removing the water formed during the esterification reaction by azeotropic distillation. The reaction was terminated when the desired amounts of TPGS monomer and TPGS dimer were formed, as indicated by high performance liquid chromatography (HPLC) and thin layer chromatography (TLC), resulting in the TPGS compositions set forth in Table 1 below. Each TPGS composition in Table 1 was formed by terminating the reaction at a different time point, up to 6.5 hours, and contained various amounts of TPGS monomer and TPGS dimer. The remainder of the TPGS compositions was made up of unreacted starting materials, such as vitamin E and PEG. The reaction was terminated by cooling the reaction mixture to room temperature, followed by washing with 25 L of a 10% solution of $NaHCO_3$. The solution stirred for 10 minutes, and after stirring was allowed to separate into layers. The organic (toluene) layer was removed, 6 kg of activated carbon (charcoal) was added, and the solution was heated to 55-60° C. and maintained at this temperature for 1 hour. The solution was then cooled to room temperature, filtered through 10 kg of Celite® Hyflo® filter aid (Sigma Aldrich, St. Louis, Mo.) and then washed with 100 L of toluene. The filtered toluene solution was concentrated by vacuum distillation below 60° C. to remove the toluene. Water (140 L) was added to remove traces of toluene and was then removed via vacuum distillation below 60° C. to obtain ~180 kg of a crude α-tocopheryl polyethylene glycol 1000 succinate composition that contained a mixture of TPGS monomer and TPGS dimer, along with unreacted PEG 1000 and α-tocopherol.

TABLE 1

Amounts of TPGS monomer and TPGS dimer formed during reaction

| TPGS composition | Monomer (%) | Dimer (%) | Total (% monomer + % dimer) |
| --- | --- | --- | --- |
| 1 | 43.90 | 53.90 | 97.80 |
| 2 | 42.80 | 48.80 | 91.60 |
| 3 | 40.95 | 53.15 | 94.10 |
| 4 | 43.52 | 49.80 | 93.32 |
| 5 | 55.88 | 29.27 | 85.15 |
| 6 | 52.92 | 33.70 | 86.62 |
| 7 | 42.76 | 51.10 | 93.86 |
| 8 | 40.39 | 54.90 | 95.29 |
| 9 | 57.70 | 40.40 | 98.10 |
| 10 | 39.35 | 35.56 | 74.91 |
| 11 | 60.00 | 38.10 | 98.10 |

A series of extractions were performed on the crude TPGS composition. The crude TPGS composition (~180 kg) was dissolved in 360 L of methanol and then 540 L of cyclohexane was added. The solution was stirred and then allowed to separate into layers. The cyclohexane layer was removed and an additional 540 L of cyclohexane was added to the remaining methanol layer. The solution was stirred and then allowed to separate into layers. The cyclohexane layer was again removed and an additional 540 L of cyclohexane was added to the remaining methanol layer. The solution was again stirred and allowed to separate into layers. The cyclohexane layer was removed, and the remaining methanol layer was further diluted with an additional 270 L of methanol. Activated carbon (18 kg) was added and the solution was heated to 55-60° C. and maintained at this temperature for 1 hour. The solution was then cooled to room temperature, filtered through 30 kg of Celite® Hyflo® filter aid, and washed with 100 L of methanol. The methanol solution was passed through a micron filter, then concentrated via vacuum distillation below 60° C. to obtain ~98-102 kg of a TPGS composition. All traces of solvent were then removed by purging with nitrogen at 55° C. for two hours to obtain ~98-102 kg of a purified TPGS composition that contained TPGS monomer and TPGS dimer.

One typical batch of TPGS prepared to contain a high dimer concentration, and used in the Examples below, had the following components:
TPGS monomer: 48%
TPGS dimer: 51%
Vitamin E: 0.42%
Vitamin E succinate: 0.46%.
Other typical batches contained:
TPGS monomer: 46.09%-43.15% w/w
TPGS dimer: 39.07%-50.28% w/w
Other: up to about 3%-3.2% w/w.

Example 2

Evaluation of the Clarity of the TPGS-Containing Compositions by a Turbidity Analysis The clarity of the TPGS compositions prepared above was evaluated by a turbidity analysis. TPGS compositions 1-11 were formulated as 1 g concentrates and were each dissolved in 8 oz. of water. The resulting aqueous liquid dilution compositions then were evaluated for clarity by measuring turbidity using a nephelometer. Results of the evaluation are set forth in Table 2 below.

Each of the eleven TPGS compositions listed in Table 1 above was diluted in water (purified according to the provided methods) using the following steps.

Eight ounces of water was heated in a Pyrex® beaker by placing the beaker on a Thermolyne hot plate (Model #846925) until the water reached 49.8° C. The TPGS composition concentrate was then added to the heated water and stirred with a stir rod until dispersed. The resulting aqueous TPGS composition was cooled to room temperature (about 25° C.). The cooled aqueous TPGS composition was added to an amber-glass screw-top vial (Alcon) for evaluation.

The vials containing the aqueous TPGS compositions were sent to ACZ Laboratories, Inc. (Steamboat Springs, Colo.) for turbidity analysis using a nephelometer. Results are listed in the form of Nephelometric Turbidity Units (NTU) and are indicated in Table 2 below.

TABLE 2

| TPGS composition | Monomer (%) | Dimer (%) | Total (% monomer + % dimer) | Turbidity (NTU) |
|---|---|---|---|---|
| | Turbidity (NTU) of aqueous TPGS compositions | | | |
| 1 | 43.90 | 53.90 | 97.80 | 8 |
| 2 | 42.80 | 48.80 | 91.60 | 8.2 |
| 3 | 40.95 | 53.15 | 94.10 | 10 |
| 4 | 43.52 | 49.80 | 93.32 | 10 |
| 5 | 55.88 | 29.27 | 85.15 | 14 |
| 6 | 52.92 | 33.70 | 86.62 | 14 |
| 7 | 42.76 | 51.10 | 93.86 | 18.5 |
| 8 | 40.39 | 54.90 | 95.29 | 39.4 |
| 9 | 57.70 | 40.40 | 98.10 | 71 |
| 10 | 39.35 | 35.56 | 74.91 | 80 |
| 11 | 60.00 | 38.10 | 98.10 | 80 |

Example 3

Liquid Nanoemulsion Concentrate Containing Water-Soluble Vitamin E Derivative Mixture Tables 3-49, below, set forth the ingredients used to make liquid nanoemulsion concentrates containing the TPGS compositions described above in Example 1 The concentrates were made according to the provided methods using a bench-top process. The concentrates contained between 3.5% and 25.75%, by weight, one or more non-polar compounds that contain one or more non-polar active ingredients. The tables indicate the amount (in mg) of each ingredient contained per 1 mL serving of the product and the percentage by weight (wt %) and amount (g) of each ingredient per batch. The column labeled "phase" indicates to which phase of the production process each ingredient was added. "Water" indicates that a particular ingredient was added during production of the water phase, "oil" indicates the ingredient was added during production of the oil phase and "emulsion/flavor" indicates the ingredient was added during or after mixing of the water and oil phases, as described in further detail in this Example, below.

Ingredients used in nanoemulsion concentrates include:
TPGS prepared as described in Example 1 above;
an emulsion stabilizer that was either a blend of xanthan gum, guar gum and sodium alginate, sold under the product name SALADIZER®, available from TIC Gums, Inc. (Belcamp, Md.); a modified gum acacia sold under the name Tic Pretested® Ticamulsion® A-2010 Powder (Tic Gums, Inc., Belcamp, Md.); or an ester gum sold under the name Ester Gum 8BG by Pinova/Hercules, Brunswick, Ga. (its preparation is described in U.S. Pat. No. 6,455,512);
a natural (GRAS-certified) preservative, benzyl alcohol;
a co-surfactant that was either a sucrose fatty acid ester (sold under the trade name DK Ester®, produced by Dai-Ichi Kogyo Seiyaku Co., Ltd of Japan) or a phospholipid surfactant sold under the name Lecithin Ultralec® P (ADM Co., Decatur, Ill.);
citric acid, a pH adjuster;
a soluble fiber, inulin, sold as Oliggo-Fiber Instant Inulin (Fibruline® Instant) (supplied by Cosucra-Groupe Warcoing SA, Belgium, sold by Gillco Products, San Marcos, Calif.);
one or more non-polar compounds that included:
a fish oil, including Omega 30 TG Food Grade (Non-GMO) MEG-3™ Fish Oil by Ocean Nutrition Canada Limited (Nova Scotia, Mass.), a fish oil that contains about 30% of the non-polar active ingredients DHA and EPA; Marinol C-38 (supplied by Lipid Nutrition B.V., Channahon, Ill.), which contains about 52% omega-3 fatty acids, including at least 38% DHA/EPA, more specifically includes about 22% EPA and 14% DHA; Marinol D-40 (supplied by Lipid Nutrition B.V., Channahon, Ill.), which contains about 40% DHA and 7% EPA; omega-3 fish oil 70TG that was 61% by weight DHA/EPA; fish oils containing 30% or 65% DHA, sold by GC Rieber oils (Kristiansund, Norway); ONC TG fish oil sold by Ocean Nutrition Canada (Dartmouth, Nova Scotia); Omevital™ 30% MP Gold, a fish oil that contains 30% DHA/EPA (Cognis, Monheim am Rhein, North Rhine-Westphalia, Germany); and a fish oil containing 60% DHA (sold by FINA LLC, Cincinnati, Ohio);
a flaxseed oil supplied by Sanmark LLC, Greensboro, N.C. (Sanmark Limited, Dalian, Liaoning Province, China), which contains not less than (NLT) 50% C18:3 alpha-linolenic acid, and further contains other fatty acids, such as 3-8% C16:0 palmitic acid, 2-8% C18:0 stearic acid, 11-24% C18:1 oleic acid, 11-24% C18:2 linoleic acid and 0-3% other fatty acids;
oil-soluble vitamins, that included alpha-tocopheryl acetate, vitamin A palmitate (200 mcg/g or 400 mcg/day), vitamin A (1.7 mIU/g) and vitamin D3;
a conjugated linoleic acid (CLA) that contains 74.5% CLA (Clarinol® CLA, Stepan Lipid Nutrition, Maywood, N.J.);
an algal oil, including Martek DHA™-S (supplied by Martek Biosciences Corporation, Columbia, Md.), derived from the marine alga *Schizochytrium* sp., containing not less than 35% DHA and 16.1% (22:5ω6) docosapentaenoic acid, 1.3% (20:5ω3) eicosapentaenoic acid, 0.6% (20:4ω6) arachidonic acid, 1.6% (18:2ω6) linoleic acid, 16.9% (18:1ω9) oleic acid and 19.8% other fatty acids; and V-Pure algae oil which contains DHA/EPA;
free fatty acids that include Omega 21% DHA and 24% DHA/EPA;
a soybean oil that contains the fatty acids alpha-linolenic acid (C-18:3; 7-10%); linoleic acid (C-18:2; 51%); oleic acid (C-18:1; 23%); stearic acid (4%); and palmitic acid (10%); and
a coconut oil that contains the polyunsaturated fatty acids linoleic and oleic acids;
and a polar solvent, including water, which was purified city water, purified as described below, glycerin and propylene glycol.

Ingredients marked with a * were added in the indicated amount of overage to ensure the final composition contained the stated amount of this ingredient.

The clarity of the concentrates listed in Tables 3-49 was tested as described in Example 2 above, where 1 g of a concentrate was diluted in 8 oz. of water. Concentrates containing between 3.5% and 5.7% non-polar compound exhibited turbidity values between 2-4 NTUs; concentrates containing between 6-9% non-polar compound exhibited turbidity values between 3-6 NTUs; concentrates containing 10% non-polar compound exhibited turbidity values between 6-8 NTUs; concentrates containing 12.8% non-polar compound exhibited turbidity values between 8-12 NTUs; concentrates containing 14.25% non-polar compound exhibited turbidity values between 10-24 NTUs; and concentrates containing 25.75% non-polar compound exhibited turbidity values between 20-24 NTUs.

TABLE 3

Liquid nanoemulsion concentrate containing 3.5% fish oil (5% overage)

| Ingredient | mg/1 mL serving | Phase | wt % of composition | g/batch |
|---|---|---|---|---|
| Water (polar solvent) | 1408.76 | Water | 70.436 | 211.31 |
| SALADIZER ® (emulsion stabilizer) | 1.200 | Water | 0.06 | 0.18 |
| Fish oil 70TG (61%)* (non-polar compound) | 70 | Oil | 3.5 | 10.50 |
| Benzyl alcohol (preservative/natural flavor) | 10.000 | Oil | 0.5 | 1.50 |
| TPGS | 504.0 | Oil | 25.2 | 75.60 |
| SALADIZER ® (emulsion stabilizer) | 0.44 | Oil | 0.0233 | 0.07 |
| Citric acid (pH adjuster) | 5.60 | Emulsion/Flavor | 0.28 | 0.84 |
| Totals | 2000.00 | | 100.000 | 300 |

TABLE 4

Liquid nanoemulsion concentrate containing 4% fish oil (5% overage)

| Ingredient | mg/1 mL serving | Phase | wt % of composition | g/batch |
|---|---|---|---|---|
| Water (polar solvent) | 1398.76 | Water | 69.937 | 209.81 |
| SALADIZER ® (emulsion stabilizer) | 1.200 | Water | 0.06 | 0.18 |
| Marinol D-40 fish oil* (non-polar compound) | 80 | Oil | 4 | 12.00 |
| Benzyl alcohol (preservative/natural flavor) | 10.00 | Oil | 0.5 | 1.50 |
| TPGS | 504.0 | Oil | 25.2 | 75.60 |
| SALADIZER ® (emulsion stabilizer) | 0.44 | Oil | 0.0233 | 0.07 |
| Citric acid (pH adjuster) | 5.60 | Emulsion/Flavor | 0.28 | 0.84 |
| Totals | 2000.00 | | 100.000 | 300 |

TABLE 5

Liquid nanoemulsion concentrate containing 4.25% fish oil (5% overage)

| Ingredient | mg/1 mL serving | Phase | wt % of composition | g/batch |
|---|---|---|---|---|
| Water (polar solvent) | 1393.76 | Water | 69.687 | 209.06 |
| SALADIZER ® (emulsion stabilizer) | 1.200 | Water | 0.06 | 0.18 |
| Marinol C-38 fish oil* (non-polar compound) | 85 | Oil | 4.25 | 12.75 |
| Benzyl alcohol (preservative/natural flavor) | 10.000 | Oil | 0.5 | 1.50 |
| TPGS | 504.0 | Oil | 25.2 | 75.60 |
| SALADIZER ® (emulsion stabilizer) | 0.44 | Oil | 0.0233 | 0.07 |
| Citric acid (pH adjuster) | 5.60 | Emulsion/Flavor | 0.28 | 0.84 |
| Totals | 2000.00 | | 100.000 | 300 |

TABLE 6

Liquid nanoemulsion concentrate containing 5% fish oil (5% overage)

| Ingredient | mg/1 mL serving | Phase | wt % of composition | g/batch |
|---|---|---|---|---|
| Water (polar solvent) | 1308.76 | Water | 65.438 | 196.314 |
| SALADIZER ® (emulsion stabilizer) | 1.200 | Water | 0.06 | 0.2 |
| Omega 30 TG fish oil* (non-polar compound) | 100 | Oil | 5.00 | 15.0 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 1930.00 | | 96.500 | 289.5 |

TABLE 7

Liquid nanoemulsion concentrate containing 5% flaxseed oil

| Ingredient | mg/1 mL serving | Phase | wt % of composition | g/batch |
|---|---|---|---|---|
| Water (polar solvent) | 1375.00 | Water | 68.749 | 171.88 |
| SFAE (DK ESTER F-160) (co-surfactant) | 52.00 | Water | 2.600 | 6.50 |
| Sanmark Flax oil (50% ALA) (non-polar compound) | 100 | Oil | 5.000 | 12.50 |
| Benzyl alcohol (preservative) | 10.000 | Oil | 0.500 | 1.25 |
| TPGS | 168 | Oil | 8.400 | 21.00 |
| SFAE (DK ESTER F-160) (co-surfactant) | 284 | Oil | 14.199 | 35.50 |
| Citric acid (pH adjuster) | 11.00 | Emulsion/Flavor | 0.552 | 1.38 |
| Totals | 2000.00 | | 100.000 | 250.00 |

TABLE 8

Liquid nanoemulsion concentrate containing 5% fish oil

| Ingredient | mg/1 mL serving | Phase | wt % of composition | g/batch |
|---|---|---|---|---|
| Water (polar solvent) | 1320.30 | Water | 66.02 | 198.05 |

TABLE 8-continued

Liquid nanoemulsion concentrate containing 5% fish oil

| Ingredient | mg/1 mL serving | Phase | wt % of composition | g/batch |
|---|---|---|---|---|
| SALADIZER ® (emulsion stabilizer) | 0.100 | Water | 0.0005 | 0.01500 |
| GC Rieber fish oil (65% DHA) (non-polar compound) | 100 | Oil | 5.00 | 15.00 |
| Benzyl alcohol (preservative/natural flavor) | 10.000 | Oil | 0.50 | 1.50 |
| TPGS | 564.0 | Oil | 28.20 | 84.60 |
| Citric acid (pH adjuster) | 5.60 | Emulsion/Flavor | 0.28 | 0.84 |
| Totals | 2000.00 | | 100.000 | 300.00 |

TABLE 9

Liquid nanoemulsion concentrate containing 5% fish oil

| Ingredient | mg/1 mL serving | Phase | wt % of composition | g/batch |
|---|---|---|---|---|
| Water (polar solvent) | 1375.75 | Water | 68.79 | 3439.33 |
| SALADIZER ® (emulsion stabilizer) | 3.400 | Water | 0.170 | 8.50 |
| Omega 30 TG fish oil (non-polar compound) | 100 | Oil | 5.00 | 250.00 |
| Benzyl alcohol (preservative/natural flavor) | 10.000 | Oil | 0.50 | 25.00 |
| TPGS | 504.0 | Oil | 25.20 | 1260.00 |
| SALADIZER ® (emulsion stabilizer) | 1.27 | Oil | 0.064 | 3.18 |
| Citric acid (pH adjuster) | 5.60 | Emulsion/Flavor | 0.280 | 14.00 |
| Totals | 2000.00 | | 100.000 | 5000.00 |

TABLE 10

Liquid nanoemulsion concentrate containing 5% fish oil

| Ingredient | mg/1 mL serving | Phase | wt % of composition | g/batch |
|---|---|---|---|---|
| Glycerin (polar solvent) | 1386.00 | Water | 69.30 | 346.50 |
| Omega 30 TG fish oil (non-polar compound) | 100 | Oil | 5.00 | 25.00 |
| Benzyl alcohol (preservative) | 10.000 | Oil | 0.50 | 2.50 |
| TPGS | 504.0 | Oil | 25.20 | 126.00 |
| Totals | 2000.00 | | 100.000 | 500.00 |

TABLE 11

Liquid nanoemulsion concentrate containing 5% fish oil

| Ingredient | mg/1 mL serving | Phase | wt % of composition | g/batch |
|---|---|---|---|---|
| Water (polar solvent) | 1349.73 | Water | 67.49 | 371.18 |
| SALADIZER ® (emulsion stabilizer) | 3.400 | Water | 0.171 | 0.94 |
| Omega 30 TG fish oil (non-polar compound) | 100 | Oil | 5.00 | 27.50 |

TABLE 11-continued

Liquid nanoemulsion concentrate containing 5% fish oil

| Ingredient | mg/1 mL serving | Phase | wt % of composition | g/batch |
|---|---|---|---|---|
| Benzyl alcohol (preservative) | 10.000 | | 0.50 | 2.75 |
| Lecithin Ultralec-P | 26.000 | Oil | 1.30 | 7.15 |
| TPGS | 504.0 | Oil | 25.20 | 138.60 |
| SALADIZER ® (emulsion stabilizer) | 1.27 | Oil | 0.064 | 0.35 |
| Citric acid (pH adjuster) | 5.60 | Emulsion/Flavor | 0.280 | 1.54 |
| Totals | 2000.00 | | 100.000 | 550.00 |

TABLE 12

Liquid nanoemulsion concentrate containing 5% fish oil

| Ingredient | mg/1 mL serving | Phase | wt % of composition | g/batch |
|---|---|---|---|---|
| Propylene glycol (polar solvent) | 1386.00 | Water | 69.30 | 346.50 |
| Omega 30 TG fish oil (non-polar compound) | 100 | Oil | 5.000 | 25.00 |
| Benzyl alcohol (preservative) | 10.000 | Oil | 0.50 | 2.50 |
| TPGS | 504.0 | Oil | 25.20 | 126.00 |
| Totals | 2000.00 | | 100.000 | 500.00 |

TABLE 13

Liquid nanoemulsion concentrate containing 5.5% alpha-tocopheryl acetate

| Ingredient | mg/1 mL serving | Phase | wt % of composition | g/batch |
|---|---|---|---|---|
| Water (polar solvent) | 1371.97 | Water | 68.60 | 342.99 |
| Alpha-tocopheryl acetate (non-polar compound) | 110 | Oil | 5.50 | 27.50 |
| Benzyl alcohol (preservative) | 10.000 | Oil | 0.50 | 2.50 |
| TPGS | 504.0 | Oil | 25.20 | 126.00 |
| Citric acid (pH adjuster) | 4.03 | Emulsion/Flavor | 0.20 | 1.01 |
| Totals | 2000.00 | | 100.000 | 500.00 |

TABLE 14

Liquid nanoemulsion concentrate containing 5.65% CLA and 0.02% vitamin A palmitate

| Ingredient | mg/1 mL serving | Phase | wt % of composition | g/batch |
|---|---|---|---|---|
| Water (polar solvent) | 1326.33 | Water | 66.32 | 198.95 |
| SALADIZER ® (emulsion stabilizer) | 3.400 | Water | 0.170 | 0.51 |
| Clarinol ® CLA (74.5% CLA) (non-polar compound) | 113 | Oil | 5.65 | 16.95 |
| Vitamin A palmitate (200 mcg/g) | 0.400 | Oil | 0.02 | 0.06 |

TABLE 14-continued

Liquid nanoemulsion concentrate containing 5.65% CLA and 0.02% vitamin A palmitate

| Ingredient | mg/1 mL serving | Phase | wt % of composition | g/batch |
|---|---|---|---|---|
| Benzyl alcohol (preservative/natural flavor) | 10.000 | Oil | 0.50 | 1.50 |
| TPGS | 540.0 | Oil | 27.00 | 81.00 |
| SALADIZER ® (emulsion stabilizer) | 1.27 | Oil | 0.063 | 0.19 |
| Citric acid (pH adjuster) | 5.60 | Emulsion/Flavor | 0.280 | 0.84 |
| Totals | 2000.00 | | 100.000 | 300.00 |

TABLE 15

Liquid nanoemulsion concentrate containing 5.65% CLA and 0.02% vitamin A palmitate

| Ingredient | mg/1 mL serving | Phase | wt % of composition | g/batch |
|---|---|---|---|---|
| Water (polar solvent) | 1362.33 | Water | 68.12 | 340.58 |
| SALADIZER ® (emulsion stabilizer) | 3.400 | Water | 0.170 | 0.85 |
| Clarinol ® CLA (74.5% CLA) (non-polar compound) | 113 | Oil | 5.65 | 28.25 |
| Vitamin A palmitate (200 mcg/g) | 0.400 | Oil | 0.02 | 0.10 |
| Benzyl alcohol (preservative/natural flavor) | 10.000 | Oil | 0.50 | 2.50 |
| TPGS | 504.0 | Oil | 25.20 | 126.00 |
| SALADIZER ® (emulsion stabilizer) | 1.27 | Oil | 0.064 | 0.32 |
| Citric acid (pH adjuster) | 5.60 | Emulsion/Flavor | 0.280 | 1.40 |
| Totals | 2000.00 | | 100.000 | 500.00 |

TABLE 16

Liquid nanoemulsion concentrate containing 6.25% algal oil

| Ingredient | mg/1 mL serving | Phase | wt % of composition | g/batch |
|---|---|---|---|---|
| Water (polar solvent) | 1349.73 | Water | 67.69 | 270.75 |
| SALADIZER ® (emulsion stabilizer) | 1.200 | Water | 0.060 | 0.24 |
| Martek -S algal oil (non-polar compound) | 125 | Oil | 6.25 | 25.00 |
| Benzyl alcohol (preservative/natural flavor) | 10.000 | Oil | 0.50 | 2.00 |
| TPGS | 504.0 | Oil | 25.20 | 100.8 |
| SALADIZER ® (emulsion stabilizer) | 0.44 | Oil | 0.02 | 0.09 |
| Citric acid (pH adjuster) | 5.60 | Emulsion/Flavor | 0.280 | 1.12 |
| Totals | 2000.00 | | 100.000 | 400.00 |

TABLE 17

Liquid nanoemulsion concentrate containing 6.35% vitamin A (5% overage)

| Ingredient | mg/1 mL serving | Phase | wt % of composition | g/batch |
|---|---|---|---|---|
| Water (polar solvent) | 1351.76 | Water | 67.59 | 337.94 |
| SALADIZER ® (emulsion stabilizer) | 1.200 | Water | 0.060 | 0.30 |
| Vitamin A (1,700,000 IU/g)* (non-polar compound) | 127 | Oil | 6.35 | 31.75 |
| Benzyl alcohol (preservative/natural flavor) | 10.000 | Oil | 0.50 | 2.50 |
| TPGS | 504.0 | Oil | 25.20 | 126.00 |
| SALADIZER ® (emulsion stabilizer) | 0.44 | Oil | 0.02 | 0.11 |
| Citric acid (pH adjuster) | 5.60 | Emulsion/Flavor | 0.280 | 1.40 |
| Totals | 2000.00 | | 100.000 | 500.00 |

TABLE 18

Liquid nanoemulsion concentrate containing 7.8% fish oil (5% overage) and 2.5% soybean oil

| Ingredient | mg/1 mL serving | Phase | wt % of composition | g/batch |
|---|---|---|---|---|
| Water (polar solvent) | 1272.76 | Water | 63.64 | 190.91 |
| SALADIZER ® (emulsion stabilizer) | 1.200 | Water | 0.060 | 0.18 |
| Marinol D-40 fish oil* (non-polar compound) | 156 | Oil | 7.80 | 23.40 |
| Soybean oil (non-polar compound) | 50.000 | Oil | 2.50 | 7.50 |
| Benzyl alcohol (preservative/natural flavor) | 10.000 | Oil | 0.50 | 1.50 |
| TPGS | 504.0 | Oil | 25.20 | 75.60 |
| SALADIZER ® (emulsion stabilizer) | 0.44 | Oil | 0.023 | 0.07 |
| Citric acid (pH adjuster) | 5.60 | Emulsion/Flavor | 0.280 | 0.84 |
| Totals | 2000.00 | | 100.000 | 300.00 |

TABLE 19

Liquid nanoemulsion concentrate containing free fatty acids (2.5% overage)

| Ingredient | mg/1 mL serving | Phase | wt % of composition | g/batch |
|---|---|---|---|---|
| Water (polar solvent) | 1313.76 | Water | 65.69 | 197.06 |
| SALADIZER ® (emulsion stabilizer) | 1.200 | Water | 0.060 | 0.18 |
| Omega 21% DHA (24% DHA/EPA) as FFA* (non-polar compound) | 165 | Oil | 8.25 | 24.75 |
| Benzyl alcohol (preservative/natural flavor) | 10.00 | Oil | 0.50 | 1.50 |
| TPGS | 504.0 | Oil | 25.20 | 75.60 |
| SALADIZER ® (emulsion stabilizer) | 0.44 | Oil | 0.02 | 0.07 |

TABLE 19-continued

Liquid nanoemulsion concentrate containing free fatty acids (2.5% overage)

| Ingredient | mg/1 mL serving | Phase | wt % of composition | g/batch |
|---|---|---|---|---|
| Citric acid (pH adjuster) | 5.60 | Emulsion/Flavor | 0.280 | 0.84 |
| Totals | 2000.00 | | 100.000 | 300.00 |

TABLE 20

Liquid nanoemulsion concentrate containing 8.25% coconut oil

| Ingredient | mg/1 mL serving | Phase | wt % of composition | g/batch |
|---|---|---|---|---|
| Water (polar solvent) | 1255.30 | Water | 62.77 | 188.30 |
| SALADIZER ® (emulsion stabilizer) | 0.100 | Water | 0.005 | 0.015 |
| Coconut oil (non-polar compound) | 165 | Oil | 8.25 | 24.75 |
| Benzyl alcohol (preservative/natural flavor) | 10.000 | Oil | 0.50 | 1.50 |
| TPGS | 564.0 | Oil | 28.20 | 84.60 |
| Citric acid (pH adjuster) | 5.60 | Emulsion/Flavor | 0.28 | 0.84 |
| Totals | 2000.00 | | 100.000 | 300.00 |

TABLE 21

Liquid nanoemulsion concentrate containing 8.5% fish oil (5% overage)

| Ingredient | mg/1 mL serving | Phase | wt % of composition | g/batch |
|---|---|---|---|---|
| Water (polar solvent) | 1308.76 | Water | 65.44 | 196.31 |
| SALADIZER ® (emulsion stabilizer) | 1.200 | Water | 0.060 | 0.18 |
| Omega 30 TG fish oil* (non-polar compound) | 170 | Oil | 8.50 | 25.50 |
| Benzyl alcohol (preservative/natural flavor) | 10.000 | Oil | 0.50 | 1.50 |
| TPGS | 504.0 | Oil | 25.20 | 75.60 |
| SALADIZER ® (emulsion stabilizer) | 0.44 | Oil | 0.02 | 0.07 |
| Citric acid (pH adjuster) | 5.60 | Emulsion/Flavor | 0.280 | 0.84 |
| Totals | 2000.00 | | 100.000 | 300.00 |

TABLE 22

Liquid nanoemulsion concentrate containing 9% algal oil and

| Ingredient | mg/1 mL serving | Phase | wt % of composition | g/batch |
|---|---|---|---|---|
| Water (polar solvent) | 1298.74 | Water | 64.94 | 519.50 |
| SALADIZER ® (emulsion stabilizer) | 1.200 | Water | 0.060 | 0.48 |
| Martek -S algal oil (non-polar compound) | 180 | Oil | 9.00 | 72.0 |
| Benzyl alcohol (preservative/natural flavor) | 10.000 | Oil | 0.50 | 4.00 |
| TPGS | 504.0 | Oil | 25.20 | 201.60 |
| SALADIZER ® (emulsion stabilizer) | 0.44 | Oil | 0.022 | 0.18 |
| Citric acid (pH adjuster) | 5.60 | Emulsion/Flavor | 0.280 | 2.24 |
| Totals | 2000.00 | | 100.000 | 800.00 |

TABLE 23

Liquid nanoemulsion concentrate containing 9% algal oil

| Ingredient | mg/1 mL serving | Phase | wt % of composition | g/batch |
|---|---|---|---|---|
| Water (polar solvent) | 1298.76 | Water | 64.94 | 194.81 |
| SALADIZFR ® (emulsion stabilizer) | 1.200 | Water | 0.060 | 0.18 |
| Martek algal oil (40% DHA/EPA) (non-polar compound) | 180 | Oil | 9.00 | 27.00 |
| Benzyl alcohol (preservative/natural flavor) | 10.000 | Oil | 0.50 | 1.50 |
| TPGS | 504.0 | Oil | 25.20 | 75.60 |
| SALADIZER ® (emulsion stabilizer) | 0.44 | Oil | 0.02 | 0.07 |
| Citric acid (pH adjuster) | 5.60 | Emulsion/Flavor | 0.280 | 0.84 |
| Totals | 2000.00 | | 100.000 | 300.00 |

TABLE 24

Liquid nanoemulsion concentrate containing 9% algal oil (5% overage)

| Ingredient | mg/1 mL serving | Phase | wt % of composition | g/batch |
|---|---|---|---|---|
| Water (polar solvent) | 1298.76 | Water | 64.938 | 194.81415 |
| SALADIZER ® (emulsion stabilizer) | 1.200 | Water | 0.06 | 0.2 |
| Martek algal oil (35% DHA/EPA)* (non-polar compound) | 180 | Oil | 9.00 | 27.0 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300.00 |

TABLE 25

Liquid nanoemulsion concentrate containing 10.5% flaxseed oil

| Ingredient | mg/1 mL serving | Phase | wt % of composition | g/batch |
|---|---|---|---|---|
| Water (polar solvent) | 1265.00 | Water | 63.250 | 158.125 |
| SFAE (DK ESTER F-160) (co-surfactant) | 52.000 | Water | 2.60 | 6.5 |
| Sanmark Flax Oil (50% ALA) (non-polar compound) | 210 | Oil | 10.50 | 26.3 |
| Benzyl alcohol (preservative/natural flavor) | 10.000 | Oil | 0.50 | 1.3 |
| TPGS | 168 | Oil | 8.4000 | 21.000 |
| SFAE (DK ESTER F-160) (co-surfactant) | 284 | Oil | 14.2000 | 35.500 |
| Citric acid (pH adjuster) | 11.00 | Emulsion/Flavor | 0.5500 | 1.3750 |
| Totals | 2000.00 | | 100.000 | 250 |

TABLE 26

Liquid nanoemulsion concentrate containing 10% fish oil

| Ingredient | mg/1 mL serving | Phase | wt % of composition | g/batch |
|---|---|---|---|---|
| Water (polar solvent) | 1278.76 | Water | 63.938 | 511.504 |
| SALADIZER ® (emulsion stabilizer) | 1.200 | Water | 0.06 | 0.5 |
| Omega 30 TG fish oil (non-polar compound) | 200 | Oil | 10.00 | 80.0 |
| Benzyl alcohol (preservative/natural flavor) | 10.000 | Oil | 0.50 | 4.0 |
| TPGS | 504.0 | Oil | 25.20 | 201.60 |
| SALADIZER ® (emulsion stabilizer) | 0.44 | Oil | 0.0220 | 0.176 |
| Citric acid (pH adjuster) | 5.60 | Emulsion/Flavor | 0.2800 | 2.2400 |
| Totals | 2000.00 | | 100.000 | 800 |

TABLE 27

Liquid nanoemulsion concentrate containing 10.25% fish oil

| Ingredient | mg/1 mL serving | Phase | wt % of composition | g/batch |
|---|---|---|---|---|
| Water (polar solvent) | 1215.30 | Water | 60.765 | 425.355 |
| SALADIZER ® (emulsion stabilizer) | 0.100 | Water | 0.01 | 0.0350 |
| GC Rieber fish oil (30% DHA blend) (non-polar compound) | 205 | Oil | 10.25 | 71.8 |
| Benzyl alcohol (preservative/natural flavor) | 10.000 | Oil | 0.50 | 3.5 |
| TPGS | 564.0 | Oil | 28.20 | 197.40 |
| Citric acid (pH adjuster) | 5.60 | Emulsion/Flavor | 0.2800 | 1.9600 |
| Totals | 2000.00 | | 100.000 | 700 |

TABLE 28

Liquid nanoemulsion concentrate containing 10.25% fish oil (5% overage)

| Ingredient | mg/1 mL serving | Phase | wt % of composition | g/batch |
|---|---|---|---|---|
| Water (polar solvent) | 1215.30 | Water | 60.765 | 182.295 |
| SALADIZER ® (emulsion stabilizer) | 0.100 | Water | 0.01 | 0.0150 |
| GC Rieber fish oil (65% DHA)* (non-polar compound) | 205 | Oil | 10.25 | 30.8 |
| Benzyl alcohol (preservative/natural flavor) | 10.000 | Oil | 0.50 | 1.5 |
| TPGS | 564.0 | Oil | 28.20 | 84.60 |
| Citric acid (pH adjuster) | 5.60 | Emulsion/Flavor | 0.2800 | 0.8400 |
| Totals | 2000.00 | | 100.000 | 300 |

TABLE 29

Liquid nanoemulsion concentrate containing 10.25% flaxseed oil and 0.25%

| Ingredient | mg/1 mL serving | Phase | wt % of composition | g/batch |
|---|---|---|---|---|
| Water (polar solvent) | 1268.76 | Water | 63.438 | 317.19 |
| SALADIZER ® (emulsion stabilizer) | 1.200 | Water | 0.06 | 0.3 |
| Omega 30TG fish oil (non-polar compound) | 5 | Oil | 0.25 | 1.3 |
| Sanmark Flax Oil (50% ALA) (non-polar compound) | 205 | Oil | 10.25 | 51.3 |
| Benzyl alcohol (preservative/natural flavor) | 10.000 | Oil | 0.50 | 2.5 |
| TPGS | 504.0 | Oil | 25.20 | 126.00 |
| SALADIZER ® (emulsion stabilizer) | 0.44 | Oil | 0.0220 | 0.110 |
| Citric acid (pH adjuster) | 5.60 | Emulsion/Flavor | 0.2800 | 1.4000 |
| Totals | 2000.00 | | 100.000 | 500 |

TABLE 30

Liquid nanoemulsion concentrate containing 10.5% algal oil (5% overage) and 0.0011% vitamin D3

| Ingredient | mg/1 mL serving | Phase | wt % of composition | g/batch |
|---|---|---|---|---|
| Water (polar solvent) | 1268.74 | Water | 63.437 | 507.496 |
| SALADIZER ® (emulsion stabilizer) | 1.200 | Water | 0.06 | 0.5 |
| Martek -S algal oil (5% overage) (non-polar compound) | 210 | Oil | 10.50 | 84.0 |
| Vitamin D3 | 0.0210 | Oil | 0.0011 | 0.0084 |
| Benzyl alcohol (preservative/natural flavor) | 10.000 | Oil | 0.50 | 4.0 |
| TPGS | 504.0 | Oil | 25.20 | 201.60 |
| SALADIZER ® (emulsion stabilizer) | 0.44 | Oil | 0.0220 | 0.176 |

TABLE 30-continued

Liquid nanoemulsion concentrate containing 10.5% algal oil
(5% overage) and 0.0011% vitamin D3

| Ingredient | mg/1 mL serving | Phase | wt % of composition | g/batch |
|---|---|---|---|---|
| Citric acid (pH adjuster) | 5.60 | Emulsion/Flavor | 0.2800 | 2.2400 |
| Totals | 2000.00 | | 100.000 | 800 |

TABLE 31

Liquid nanoemulsion concentrate containing 10.5% fish oil (5% overage)

| Ingredient | mg/1 mL serving | Phase | wt % of composition | g/batch |
|---|---|---|---|---|
| Water (polar solvent) | 1268.76 | Water | 63.438 | 190.314 |
| SALADIZER ® (emulsion stabilizer) | 1.200 | Water | 0.06 | 0.2 |
| Omega 30 TG fish oil* (non-polar compound) | 210 | Oil | 10.50 | 31.5 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300 |

TABLE 32

Liquid nanoemulsion concentrate containing 10.5% algal oil (5% overage)

| Ingredient | mg/1 mL serving | Phase | wt % of composition | g/batch |
|---|---|---|---|---|
| Water (polar solvent) | 1268.76 | Water | 63.438 | 190.31415 |
| SALADIZER ® (emulsion stabilizer) | 1.200 | Water | 0.06 | 0.2 |
| V-pure algal oil* (non-polar compound) | 210 | Oil | 10.50 | 31.5 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300 |

TABLE 33

Liquid nanoemulsion concentrate containing 10.5% fish oil

| Ingredient | mg/1 mL serving | Phase | wt % of composition | g/batch |
|---|---|---|---|---|
| Water (polar solvent) | 1210.30 | Water | 60.515 | 181.545 |
| SALADIZER ® (emulsion stabilizer) | 0.100 | Water | 0.01 | 0.0150 |
| GC Rieber fish oil (65% DHA) (non-polar compound) | 210 | Oil | 10.50 | 31.5 |

TABLE 33-continued

Liquid nanoemulsion concentrate containing 10.5% fish oil

| Ingredient | mg/1 mL serving | Phase | wt % of composition | g/batch |
|---|---|---|---|---|
| Benzyl alcohol (preservative/natural flavor) | 10.000 | Oil | 0.50 | 1.5 |
| TPGS | 564.0 | Oil | 28.20 | 84.60 |
| Citric acid (pH adjuster) | 5.60 | Emulsion/Flavor | 0.2800 | 0.84 |
| Totals | 2000.00 | | 100.000 | 300 |

TABLE 34

Liquid nanoemulsion concentrate containing 10.5% vitamin D3

| Ingredient | mg/1 mL serving | Phase | wt % of composition | g/batch |
|---|---|---|---|---|
| Water (polar solvent) | 1172.76 | Water | 58.638 | 175.914 |
| SALADIZER ® (emulsion stabilizer) | 1.200 | Water | 0.06 | 0.2 |
| Vitamin D3 (non-polar compound) | 210 | Oil | 10.50 | 31.5 |
| Benzyl alcohol (preservative/natural flavor) | 10.000 | Oil | 0.50 | 1.5 |
| TPGS | 600.0 | Oil | 30.00 | 90.00 |
| SALADIZER ® (emulsion stabilizer) | 0.44 | Oil | 0.0220 | 0.066 |
| Citric acid (pH adjuster) | 5.60 | Emulsion/Flavor | 0.0220 | 0.066 |
| Totals | 2000.00 | | 100.000 | 300 |

TABLE 35

Liquid nanoemulsion concentrate containing 10.5% vitamin D3 (5% overage)

| Ingredient | mg/1 mL serving | Phase | wt % of composition | g/batch |
|---|---|---|---|---|
| Water (polar solvent) | 1072.76 | Water | 53.638 | 160.914 |
| SALADIZER ® (emulsion stabilizer) | 1.200 | Water | 0.06 | 0.2 |
| Vitamin D3* (non-polar compound) | 210 | Oil | 10.50 | 31.5 |
| Benzyl alcohol (preservative/natural flavor) | 10.000 | Oil | 0.50 | 1.5 |
| TPGS | 700.0 | Oil | 35.00 | 105.00 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300 |

TABLE 36

Liquid nanoemulsion concentrate containing 10.5% flaxseed oil

| Ingredient | mg/1 mL serving | Phase | wt % of composition | g/batch |
|---|---|---|---|---|
| Water (polar solvent) | 1265.00 | Water | 63.250 | 158.125 |

TABLE 36-continued

Liquid nanoemulsion concentrate containing 10.5% flaxseed oil

| Ingredient | mg/1 mL serving | Phase | wt % of composition | g/batch |
|---|---|---|---|---|
| SFAE (DK ESTER F-160) (co-surfactant) | 52.000 | Water | 2.60 | 6.5 |
| Sanmark Flax Oil (50% ALA) (non-polar compound) | 210 | Oil | 10.50 | 26.3 |
| Benzyl alcohol (preservative/natural flavor) | 10.000 | Oil | 0.50 | 1.3 |
| TPGS | 168 | Oil | 8.4000 | 21.000 |
| SFAE (DK ESTER F-160) (co-surfactant) | 284 | Oil | 14.2000 | 35.500 |
| Citric acid (pH adjuster) | 11.00 | Emulsion/Flavor | 0.5500 | 1.3750 |
| Totals | 2000.00 | | 100.000 | 300 |

TABLE 37

Liquid nanoemulsion concentrate containing 10.75% fish oil (5% overage)

| Ingredient | mg/1 mL serving | Phase | wt % of composition | g/batch |
|---|---|---|---|---|
| Water (polar solvent) | 1263.76 | Water | 63.188 | 884.632 |
| SALADIZER ® (emulsion stabilizer) | 1.200 | Water | 0.06 | 0.8 |
| Cognis Omevital fish oil* (non-polar compound) | 215 | Oil | 10.75 | 150.5 |
| Benzyl alcohol (preservative/natural flavor) | 10.000 | Oil | 0.50 | 7.0 |
| TPGS | 504.0 | Oil | 25.20 | 352.80 |
| SALADIZER ® (emulsion stabilizer) | 0.44 | Oil | 0.0220 | 0.308 |
| Citric acid (pH adjuster) | 5.60 | Emulsion/Flavor | 0.2800 | 3.9200 |
| Totals | 2000.00 | | 100.000 | 1400 |

TABLE 38

Liquid nanoemulsion concentrate containing 11% fish oil (5% overage)

| Ingredient | mg/1 mL serving | Phase | wt % of composition | g/batch |
|---|---|---|---|---|
| Water (polar solvent) | 1382.76 | Water | 69.138 | 345.69 |
| SALADIZER ® (emulsion stabilizer) | 1.200 | Water | 0.06 | 0.3 |
| Omega 30 TG fish oil* (non-polar compound) | 220 | Oil | 11.00 | 55.0 |
| Benzyl alcohol (preservative/natural flavor) | 10.000 | Oil | 0.50 | 2.5 |
| TPGS | 380.0 | Oil | 19.00 | 95.00 |
| SALADIZER ® (emulsion stabilizer) | 0.44 | Oil | 0.0220 | 0.110 |
| Citric acid (pH adjuster) | 5.60 | Emulsion/Flavor | 0.2800 | 1.4000 |
| Totals | 2000.00 | | 100.000 | 500 |

TABLE 39

Liquid nanoemulsion concentrate containing 12% fish oil (5% overage)

| Ingredient | mg/1 mL serving | Phase | wt % of composition | g/batch |
|---|---|---|---|---|
| Water (polar solvent) | 1238.76 | Water | 61.938 | 495.504 |
| SALADIZER ® (emulsion stabilizer) | 1.200 | Water | 0.06 | 0.5 |
| Omega 30 TG fish oil* (non-polar compound) | 240 | Oil | 12.00 | 96.0 |
| Benzyl alcohol (preservative/natural flavor) | 10.000 | Oil | 0.50 | 4.0 |
| TPGS | 504.0 | Oil | 25.20 | 201.60 |
| SALADIZER ® (emulsion stabilizer) | 0.44 | Oil | 0.0220 | 0.176 |
| Citric acid (pH adjuster) | 5.60 | Emulsion/Flavor | 0.2800 | 2.2400 |
| Totals | 2000.00 | | 100.000 | 800 |

TABLE 40

Liquid nanoemulsion concentrate containing 12.25% free fatty acids (2.5% overage)

| Ingredient | mg/1 mL serving | Phase | wt % of composition | g/batch |
|---|---|---|---|---|
| Water (polar solvent) | 1233.76 | Water | 61.688 | 185.064 |
| SALADIZER ® (emulsion stabilizer) | 1.200 | Water | 0.06 | 0.2 |
| Omega 21% DHA as FFA* (non-polar compound) | 245 | Oil | 12.25 | 36.8 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300 |

TABLE 41

Liquid nanoemulsion concentrate containing 12.8% fish oil (5% overage)

| Ingredient | mg/1 mL serving | Phase | wt % of composition | g/batch |
|---|---|---|---|---|
| Water (polar solvent) | 1164.30 | Water | 58.215 | 174.645 |
| SALADIZER ® (emulsion stabilizer) | 0.100 | Water | 0.01 | 0.0150 |
| ONC fish oil* (non-polar compound) | 256 | Oil | 12.80 | 38.4 |
| Benzyl alcohol (preservative/natural flavor) | 10.000 | Oil | 0.50 | 1.5 |
| TPGS | 564.0 | Oil | 28.20 | 84.60 |
| Citric acid (pH adjuster) | 5.60 | Emulsion/Flavor | 0.2800 | 0.8400 |
| Totals | 2000.00 | | 100.000 | 300 |

TABLE 42

Liquid nanoemulsion concentrate containing 12.8% fish oil (5% overage)

| Ingredient | mg/1 mL serving | Phase | wt % of composition | g/batch |
|---|---|---|---|---|
| Water | 1164.3 | Water | 58.215 | 174.645 |
| SALADIZER ® (emulsion stabilizer) | 0.100 | Water | 0.01 | 0.0150 |
| Omega 30TG fish oil* (non-polar compound) | 256 | Oil | 12.80 | 38.4 |
| Benzyl alcohol (preservative) | 10.000 | Oil | 0.50 | 1.5 |
| TPGS | 564.0 | Oil | 28.20 | 84.60 |
| Citric acid (pH adjuster) | 5.60 | Emulsion/Flavor | 0.2800 | 0.8400 |
| Totals | 2000.00 | | 100.000 | 300 |

TABLE 43

Liquid nanoemulsion concentrate containing 13% fish oil and vitamin D3 (5% overage)

| Ingredient | mg/1 mL serving | Phase | wt % of composition | g/batch |
|---|---|---|---|---|
| Water (polar solvent) | 1217.92 | Water | 60.896 | 182.688 |
| SALADIZER ® (emulsion stabilizer) | 1.200 | Water | 0.06 | 0.2 |
| Omega 30 TG fish oil (non-polar compound) | 260 | Oil | 13.00 | 39.0 |
| Vitamin D3 (1,000,000 IU/g; 800 mcg)* (non-polar compound) | 0.8400 | Oil | 0.0420 | 0.12600 |
| Benzyl alcohol (preservative/natural flavor) | 10.000 | Oil | 0.50 | 1.5 |
| TPGS | 504.0 | Oil | 25.20 | 75.60 |
| SALADIZER ® (emulsion stabilizer) | 0.44 | Oil | 0.0220 | 0.066 |
| Citric acid (pH adjuster) | 5.60 | Emulsion/Flavor | 0.2800 | 0.8400 |
| Totals | 2000.00 | | 100.000 | 300 |

TABLE 44

Liquid nanoemulsion concentrate containing 14% fish oil (5% overage)

| Ingredient | mg/1 mL serving | Phase | wt % of composition | g/batch |
|---|---|---|---|---|
| Water (polar solvent) | 1140.30 | Water | 57.015 | 171.045 |
| SALADIZER ® (emulsion stabilizer) | 0.100 | Water | 0.01 | 0.0150 |
| GC Rieber fish oil* (65% DHA blend)* (non-polar compound) | 280 | Oil | 14.00 | 42.0 |
| Benzyl alcohol (preservative/natural flavor) | 10.000 | Oil | 0.50 | 1.5 |
| TPGS | 564.0 | Oil | 28.20 | 84.60 |
| Citric acid (pH adjuster) | 5.60 | Emulsion/Flavor | 0.2800 | 0.8400 |
| Totals | 2000.00 | | 100.000 | 300 |

TABLE 45

Liquid nanoemulsion concentrate containing 14.25% fish oil (5% overage)

| Ingredient | mg/1 mL serving | Phase | wt % of composition | g/batch |
|---|---|---|---|---|
| Water (polar solvent) | 1135.30 | Water | 56.765 | 681.18 |
| SALADIZER ® (emulsion stabilizer) | 0.100 | Water | 0.01 | 0.0600 |
| GC Rieber fish oil (30% DHA blend)* (non-polar compound) | 285 | Oil | 14.25 | 171.0 |
| Benzyl alcohol (preservative/natural flavor) | 10.000 | Oil | 0.50 | 6.0 |
| TPGS | 564.0 | Oil | 28.20 | 338.40 |
| Citric acid (pH adjuster) | 5.60 | Emulsion/Flavor | 0.2800 | 3.3600 |
| Totals | 2000.00 | | 100.000 | 1200 |

TABLE 46

Liquid nanoemulsion concentrate containing 15% CLA (5% overage) and vitamin A palmitate (5% overage)

| Ingredient | mg/1 mL serving | Phase | wt % of composition | g/batch |
|---|---|---|---|---|
| Water (polar solvent) | 1042.71 | Water | 52.136 | 260.6775 |
| Ticamulsion ® A-2010 (emulsion stabilizer) | 20.000 | Water | 1.00 | 5.0 |
| Clarinol CLA (74.5% CLA)* (non-polar compound) | 420 | Oil | 21.00 | 105.0 |
| Vitamin A palmitate (400 mcg/day)* (non-polar compound) | 0.84 | Oil | 0.04 | 0.2100 |
| Ester Gum 8BG (emulsion stabilizer) | 1.25 | Oil | 0.06 | 0.3 |
| Benzyl alcohol (preservative) | 10.000 | Oil | 0.50 | 2.5 |
| Inulin | 40.5 | Water | 2.03 | 10.13 |
| SFAE (1st fraction co-surfactant) | 93.2 | Water | 4.66 | 23.30 |
| SFAE (2nd fraction co-surfactant) | 62.9 | Water | 3.15 | 15.73 |
| SFAE (co-surfactant) | 25.0 | Oil | 1.25 | 6.25 |
| TPGS | 210.0 | Oil | 10.50 | 52.50 |
| Ticamulsion ® A-2010 (emulsion stabilizer) | 10 | Oil | 0.5000 | 2.500 |
| Citric Acid (pH adjuster) | 63.60 | Emulsion/Flavor | 3.1800 | 15.9000 |
| Totals | 2000.00 | | 100.000 | 500 |

TABLE 47

Liquid nanoemulsion concentrate containing 21% fish oil (5% overage) and vitamin A palmitate (5% overage)

| Ingredient | mg/1 mL serving | Phase | wt % of composition | g/batch |
|---|---|---|---|---|
| Water (polar solvent) | 1042.71 | Water | 52.136 | 260.6775 |

TABLE 47-continued

Liquid nanoemulsion concentrate containing 21% fish oil (5% overage) and vitamin A palmitate (5% overage)

| Ingredient | mg/1 mL serving | Phase | wt % of composition | g/batch |
|---|---|---|---|---|
| Ticamulsion ® A-2010 (emulsion stabilizer) | 20.000 | Water | 1.00 | 5.0 |
| FINA fish oil (60% DHA)* (non-polar compound) | 420 | Oil | 21.00 | 105.0 |
| Vitamin A palmitate (400 mcg/day)* | 0.84 | Oil | 0.04 | 0.2100 |
| Ester Gum 8BG (emulsion stabilizer) | 1.25 | Oil | 0.06 | 0.3 |
| Benzyl alcohol (Preservative/natural Flavor) | 10.000 | Oil | 0.50 | 2.5 |
| Inulin | 40.5 | Water | 2.03 | 10.13 |
| SFAE ($1^{st}$ fraction co-surfactant) | 93.2 | Water | 4.66 | 23.30 |
| SFAE ($2^{nd}$ fraction co-surfactant) | 62.9 | Water | 3.15 | 15.73 |
| SFAE (co-surfactant) | 25.0 | Oil | 1.25 | 6.25 |
| TPGS | 210.0 | Oil | 10.50 | 52.50 |
| Ticamulsion ® A-2010 (emulsion stabilizer) | 10 | Oil | 0.5000 | 2.500 |
| Citric acid (pH adjuster) | 63.60 | Emulsion/ Flavor | 3.1800 | 15.9000 |
| Totals | 2000.00 | | 100.000 | 500 |

TABLE 48

Liquid nanoemulsion concentrate containing 21% fish oil (5% overage) and vitamin A palmitate (5% overage)

| Ingredient | mg/1 mL serving | Phase | wt % of composition | g/batch |
|---|---|---|---|---|
| Water (polar solvent) | 1042.71 | Water | 52.136 | 260.6775 |
| Ticamulsion ® A-2010 (emulsion stabilizer) | 20.000 | Water | 1.00 | 5.0 |
| Martek fish oil (35% DHA)* (non-polar compound) | 420 | Oil | 21.00 | 105.0 |
| Vitamin A palmitate (400 mcg/day)* (non-polar compound) | 0.84 | Oil | 0.04 | 0.2100 |
| Ester Gum 8BG (emulsion stabilizer) | 1.25 | Oil | 0.06 | 0.3 |
| Benzyl alcohol (Preservative/natural flavor) | 10.000 | Oil | 0.50 | 2.5 |
| Inulin | 40.5 | Water | 2.03 | 10.13 |
| SFAE ($1^{st}$ fraction co-surfactant) | 93.2 | Water | 4.66 | 23.30 |
| SFAE ($2^{nd}$ fraction co-surfactant) | 62.9 | Water | 3.15 | 15.73 |
| SFAE (co-surfactant) | 25.0 | Oil | 1.25 | 6.25 |
| TPGS | 210.0 | Oil | 10.50 | 52.50 |
| Ticamulsion ® A-2010 (emulsion stabilizer) | 10 | Oil | 0.5000 | 2.500 |
| Citric acid (pH adjuster) | 63.60 | Emulsion/ Flavor | 3.1800 | 15.9000 |
| Totals | 2000.00 | | 100.000 | 500 |

TABLE 49

Liquid nanoemulsion concentrate containing 25.75% fish oil (5% overage) and vitamin A palmitate (5% overage)

| Ingredient | mg/1 mL serving | Phase | wt % of composition | g/batch |
|---|---|---|---|---|
| Water (polar solvent) | 947.71 | Water | 47.386 | 142.1565 |
| Ticamulsion ® A-2010 (emulsion stabilizer) | 20.000 | Water | 1.00 | 3.0 |
| Stepan fish oil (40% DHA/EPA)* (non-polar compound) | 515 | Oil | 25.75 | 77.3 |
| Vitamin A palmitate (400 mcg/day)* (non-polar compound) | 0.84 | Oil | 0.04 | 0.1260 |
| Ester Gum 8BG (emulsion stabilizer) | 1.25 | Oil | 0.06 | 0.2 |
| Benzyl alcohol (Preservative/natural flavor) | 10.000 | Oil | 0.50 | 1.5 |
| Inulin | 40.5 | Water | 2.03 | 6.08 |
| SFAE ($1^{st}$ fraction co-surfactant) | 93.2 | Water | 4.66 | 13.98 |
| SFAE ($2^{nd}$ fraction co-surfactant) | 62.9 | Water | 3.15 | 9.44 |
| SFAE (co-surfactant) | 25.0 | Oil | 1.25 | 3.75 |
| TPGS | 210.0 | Oil | 10.50 | 31.50 |
| Ticamulsion ® A-2010 (emulsion stabilizer) | 10 | Oil | 0.5000 | 1.500 |
| Citric acid (pH adjuster) | 63.60 | Emulsion/ Flavor | 3.1800 | 9.5400 |
| Totals | 2000.00 | | 100.000 | 300 |

The above concentrates were made using the process described below. Before adding to the appropriate phase, as described below, the correct amount of each ingredient (as indicated in Table 3) was weighed out using either a Sartorius Basic Analytical Scale (Model BA110S), an OHAUS Scale (Model CS2000) or a Toledo Scale (Model GD13x/USA). Liquid ingredients were weighed in containers, while dry ingredients were weighed in bags.

Production of the Water Phase:

The water phase was prepared in a 1500 mL Pyrex beaker. The appropriate amount of city water was purified by passing the water through the following purifiers, sequentially, in the following order: a carbon filter, an ion exchange purifier, a reverse osmosis purifier and a 100 micron end-point filter. The water (amount indicated in Tables 3-49, above) finally was passed through a UV sterilizer before it was measured and added to the beaker. The switch controlling the pump and UV sterilizer was then turned off.

The beaker containing the water (or other polar solvent) was placed onto a Thermolyne hot plate (Model No. SP46615). An Arde Barinco reversible homogenizer (Model No. CJ-4E; Arde Barinco, Inc., Norwood, N.J.) was immersed in the water and turned on, using the "forward" setting, at a speed of 30 rpm. The water phase was then heated to 60° C. using the Thermolyne Hotplate while slowly mixing at 30 rpm. The Arde Barinco mixer was then raised and switched to the "reverse" setting to create a vortex.

The indicated amount of the emulsion stabilizer and other "water phase" ingredients were added to the water phase beaker at 60° C. Mixing was continued at 60° C. until the emulsion stabilizer was mostly dispersed in the water phase and until the water phase was ready to be combined with the oil phase. Temperatures were measured with a pH and temperature meter (Hanna Instruments, Model No. HI 8314).

Production of the Oil Phase:

The oil phase was prepared in a 1500 mL Pyrex beaker. The indicated amounts of the TPGS composition prepared according to the method described above in Example 1 and benzyl alcohol were added to the oil phase beaker and heated to 60° C. using a Thermolyne hot plate while mixing with an IKA Mixer (Model No. RE16 S1). After the TPGS and benzyl alcohol were dissolved, the indicated amount of non-polar compound(s) and other "oil phase" ingredients were added and mixed with the IKA Mixer at 60° C. until ready to combine with the water phase. Temperatures were measured with a pH and temperature meter (Hanna Instruments, Model No. HI 8314).

Combining the Water and Oil Phases

Once the water phase and oil phase had been prepared and were at 60° C., the Arde Barinco homogenizer was turned on the "forward" setting at 30 rpm in the water phase beaker and the oil phase was transferred to the water phase beaker by slowly and consistently pouring from the top. Mixing with the homogenizer at 30 rpm continued until the phases had combined.

The ingredients were mixed and cooled in a water bath until the mixture reached 50° C. The indicated amount of pH adjuster was then added and the mixture was continuously mixed at 30 rpm using the Arde Barinco mixer on "forward" and further cooled to 30° C. The mixture was then filtered through a 100-200 micron filter. Additional water was added to account for any evaporation that had occurred during the process. Temperatures and pH were measured with a temperature and pH meter (Hanna Instruments, Model No. HI 8314). The pH of each mixture was measured to confirm that it was between 2.60 and 3.20.

Analysis and Packaging

The resulting concentrates were analyzed to verify that the specified amounts of active and other ingredients were present and that the levels of microbiologicals and heavy metals were in accordance with standards, as described herein. USP standard testing by Eurofins U.S. (Des Moines, Iowa) verified that the products contained not more than 1,000 cfu/g microbes and was negative for *E. coli* and *Salmonella*; ICP/MS testing by Eurofins U.S. verified that the products contained not more than 10 ppm heavy metals, not more than 0.2 ppm lead and not more than 2 ppm arsenic. Fourier transform infrared spectroscopy (FTIR) was used to obtain a fingerprint of the product which was then compared to high performance liquid chromatography (HPLC) standards, to verify that no other compounds except the desired ingredients were present in the product.

Example 4

Pre-Emulsion Concentrates

Three pre-emulsion concentrates were prepared according to the method described below and the ingredients are detailed in Tables 50-52. The pre-emulsion concentrates contained between 40.02% and 69.02%, by weight, of the concentrate, one or more non-polar compounds that contain non-polar active ingredients and the TPGS prepared according to Example 1 above.

The pre-emulsion concentrates contained the TPGS prepared according to Example 1 above; benzyl alcohol (a natural preservative); and one or more non-polar compounds that include a fish oil containing either 30% or 65% DHA (sold by GC Rieber oils; Kristiansund, Norway), vitamin A palmitate (400 mcg/day) and a conjugated linoleic acid (CLA) that contains 74.5% CLA (Clarinol® CLA, Stepan Lipid Nutrition, Maywood, N.J.). Some pre-emulsion concentrates additionally included a co-surfactant that was a sucrose fatty acid ester (sold under the trade name DK Ester®, produced by Dai-Ichi Kogyo Seiyaku Co., Ltd of Japan).

Each of the pre-emulsion concentrates set forth in Tables 50-52 were made using a bench-top process according to the provided methods. Each of the pre-emulsion compositions can alternatively be made by scaling up the bench-top process, to make the pre-emulsion compositions using a scaled-up manufacturing process of the provided methods, for example, to make larger batch sizes of the pre-emulsion compositions. Accordingly, each of the pre-emulsion concentrates in Tables 50-52 also can be made with the provided methods, using the scaled-up process.

The bench-top process for making the pre-emulsion compositions was carried out using the following general steps. Further details for each pre-emulsion composition are provided in each individual Table.

For each of the pre-emulsion compositions set forth in Tables 50-52 below, the indicated amount of each ingredient was weighed using a Toledo Scale (Model GD13x/USA), Sartorius Basic Analytical Scale (Model BA110S) or an OHAUS Scale (Model CS2000). Selection of scale was dependent on the weight of each ingredient being weighed.

The initial ingredients (all ingredients except the non-polar compounds) were added, in the indicated amounts (g/batch), to a vessel (a Pyrex® beaker), and mixed using a standard mixer (IKA® model No. RE-16 1S, which is an overhead mixer (laboratory stirrer) compatible with the bench-top process). While mixing, the ingredients were heated using a heating apparatus, which is a hot plate (a Thermolyne hot Plate Model #SP46615), to reach a temperature of 60° C.

Once these initial ingredients dissolved, e.g., formed a homogeneous mixture, and reached the desired temperature, e.g., 60° C., the non-polar compounds were added. The ingredients then were homogenized by placing a reversible homogenizer (Arde Barinco, Inc.; Model CJ-4E) in the vessel (beaker) and turned on at 850-1200 RPM. Mixing with the homogenizer was continued while maintaining the temperature using the hot plate. The baffle plate on the homogenizer was adjusted to achieve and maintain an emulsion, for example, by moving the baffle plate further into and/or out of the ingredient mixture. The mixture was homogenized until it became homogeneous at 60° C.

Unless otherwise indicated, when the ingredients included a surfactant, a preservative and one or more non-polar active ingredients, these ingredients were added sequentially, in the following order: 1) surfactant; 2) preservative; and 3) non-polar compound. When the ingredients include a surfactant, a preservative, a solvent and one or more non-polar active ingredient(s), these ingredients were added sequentially, in the following order: 1) surfactant; 2) preservative; 3) solvent(s); and 4) non-polar compound. The ingredients were heated with the hot plate until the temperature reached 60° C. A temperature meter (temperature probe (Model # DPP400W, Cooper-Atkins)) was used to evaluate (measure) the temperature of the mixing ingredients.

The composition was then filtered, using a 100 micron end-product filter and packaged (transferred) by filling into one or more storage containers, for example, plastic bottles or 5 gallon pails, where it was cooled to room temperature (about 25° C.). Alternatively, the mixture can be packaged into a bag-in-a-box-type storage container. The mixture became a solid at room-temperature, having a waxy consistency. Thus, each of the pre-emulsion concentrates in Tables 50-52 was a semi-solid or solid at room temperature, having a waxy consistency, and became liquid upon heating, for example, to 60° C.

Ingredients marked with a * in Tables 50-52 were added in the indicated amount of overage to ensure the final composition contained the stated amount of this ingredient.

The clarity of the concentrates listed in Tables 50-52 was tested as described in Example 2 above, where 1 g of a concentrate was diluted in 8 oz. of water. Concentrates containing between 40% and 50% non-polar compound exhibited turbidity values between 32-45 NTUs; and concentrates containing 68% non-polar compound exhibited turbidity values around 60 NTUs.

TABLE 50

Pre-emulsion concentrate containing 40.02% fish oil

| Ingredient | Phase | wt % of composition | g/batch |
| --- | --- | --- | --- |
| TPGS | Oil | 59.48 | 59.48 |
| Benzyl alcohol (preservative/natural flavor) | Oil | 0.50 | 0.50 |
| GC Rieber fish oil (65% DHA blend) (non-polar compound) | Oil | 40.02 | 40.02 |
| Totals | | 100.00 | 100.00 |

TABLE 51

Pre-emulsion concentrate containing 40.02% fish oil

| Ingredient | Phase | wt % of composition | g/batch |
| --- | --- | --- | --- |
| TPGS | Oil | 59.48 | 59.48 |
| Benzyl alcohol (preservative/natural flavor) | Oil | 0.50 | 0.50 |
| GC Rieber fish oil (30% DHA blend) (non-polar compound) | Oil | 40.02 | 40.02 |
| Totals | | 100.00 | 100.00 |

TABLE 52

Pre-emulsion concentrate containing 68% CLA (5% overage) and vitamin A palmitate (5% overage)

| Ingredient | mg/1 mL serving | Phase | wt % of composition | g/batch |
| --- | --- | --- | --- | --- |
| Clarinol CLA* (non-polar compound) | 1380 | Oil | 68.98 | 206.9 |
| Vitamin A palmitate (400 mcg/day)* (non-polar compound) | 0.84 | Oil | 0.04 | 0.1260 |
| Benzyl alcohol (preservative) | 10.000 | Oil | 0.50 | 1.5 |
| SFAE (co-surfactant) | 79.5 | Oil | 3.98 | 11.93 |
| TPGS | 530.0 | Oil | 26.50 | 79.50 |
| Totals | 2000.00 | | 100.000 | 300 |

Example 5

Pre-Emulsion Concentrates

Tables 53-60, below, set forth ingredients that are included in a plurality of different pre-emulsion concentrates, described below. The pre-emulsion concentrates are made according to the provided methods. Each of the pre-emulsion concentrates contains one or more non-polar compound that contains one or more non-polar active ingredients. The tocopheryl polyethylene glycol succinate (TPGS) surfactant prepared as described in Example 1 above is used in each pre-emulsion concentrate.

In some of the pre-emulsion concentrates (where indicated), a solvent is used as an ingredient in the pre-emulsion concentrate. In these pre-emulsion concentrates, the solvent is vitamin E oil, such as the vitamin E oil sold by ADM Natural Health and Nutrition (Decatur, Ill.) under the name Novatol™ 5-67 Vitamin E (D-alpha-tocopherol; ADM product code 410217). This oil contains at least 67.2% tocopherol and approximately 32.8% soybean oil. Pre-emulsion concentrates similar to the pre-emulsion concentrates set forth in these examples alternatively can be made using an alternative or additional solvent(s), for example, a flaxseed oil solvent, such as the flaxseed oil from Sanmark LLC (Greensboro, N.C.; Sanmark Limited, Dalian, Liaoning Province, China), which contains not less than (NLT) 50% C18:3 alpha-linolenic acid.

A. Method of Producing Pre-Emulsion Concentrates

Each of the pre-emulsion concentrates set forth in Examples 5B-5H is made using a bench-top process according to the provided methods. Each of the pre-emulsion compositions can alternatively be made by scaling up the bench-top process, to make the pre-emulsion compositions using a scaled-up manufacturing process of the provided methods, for example, to make larger batch sizes of the pre-emulsion compositions in the following Examples. Accordingly, each of the pre-emulsion concentrates in Examples 5B-5H also can be made with the provided methods, using the scaled-up process.

The bench-top process for making the pre-emulsion compositions in Examples 5B-5H is carried out using the following general steps. Further details for each pre-emulsion composition are provided in each individual example.

For each of the pre-emulsion compositions set forth in Examples 5B-5H below, the indicated amount of each ingredient is weighed using a Toledo Scale (Model GD13x/USA), Sartorius Basic Analytical Scale (Model BA110S) or an OHAUS Scale (Model CS2000). Selection of scale is dependent on the weight of each ingredient being weighed.

The initial ingredients (all ingredients except the non-polar active ingredient(s)) are then added, in the indicated amounts (g/batch), to a vessel (a Pyrex® beaker), and mixed using a standard mixer (IKA® model No. RE-16 1S, which is an overhead mixer (laboratory stirrer) compatible with the bench-top process). While mixing, the ingredients are heated using a heating apparatus, which is a hot plate (a Thermolyne hot Plate Model #SP46615), to reach a temperature of 60° C.

Once these initial ingredients dissolve, e.g., form a homogeneous mixture, and reach the desired temperature, e.g., 60° C., the non-polar active ingredient(s) are added. The ingredients then are homogenized by placing a reversible homogenizer (Arde Barinco, Inc.; Model CJ-4E) in the vessel (beaker) and turning it on at 850-1200 RPM. Mixing with the homogenizer is continued while maintaining the temperature using the hot plate. The baffle plate on the homogenizer is adjusted to achieve and maintain an emulsion, for example, by moving the baffle plate further into and/or out of the ingredient mixture. The mixture is homogenized until it becomes homogeneous at 60° C.

Unless otherwise indicated, when the ingredients include a surfactant, a preservative and one or more non-polar active ingredients, these ingredients are added sequentially, in the following order: 1) surfactant; 2) preservative; and 3) non-polar active ingredient(s). When the ingredients include a surfactant, a preservative, a solvent and one or more non-polar active ingredient(s), these ingredients are added sequentially, in the following order: 1) surfactant; 2) preservative; 3) solvent(s); and 4) non-polar active ingredient(s). The ingredients are heated with the hot plate until the temperature reaches 60° C. A temperature meter (temperature probe (Model # DPP400W, Cooper-Atkins)) is used to evaluate (measure) the temperature of the mixing ingredients.

The composition is then filtered, using a 100 micron end-product filter and packaged (transferred) by filling into one or more storage containers, for example, plastic bottles or 5 gallon pails, where it is cooled to room temperature (about 25° C.). Alternatively, the mixture can be packaged into a bag-in-a-box-type storage container. The mixture becomes a solid at room-temperature, having a waxy consistency. Thus, each of the pre-emulsion concentrates in Examples 5B-5H is a semi-solid or solid at room temperature, having a waxy consistency, and becomes liquid upon heating, for example, to 60° C.

B. Pre-Emulsion Concentrates Having DHA and EPA-Containing Non-Polar Compounds

Tables 52 and 54 below set forth the details of pre-emulsion concentrates that contain between 10% and 30%, by weight, of the concentrate, a fish oil or an algae oil non-polar compound and between 69.5% and 89.5% TPGS. The fish oil and algae oil non-polar compounds contain the non-polar active ingredients omega-3 polyunsaturated fatty acids DHA and/or EPA. These pre-emulsion concentrates are made using the general procedure outlined in Example 5A above. Each pre-emulsion concentrate in Tables 53 and 54 uses the tocopherol polyethylene glycol succinate (TPGS) described above in Example 1 and benzyl alcohol, a natural (GRAS-certified) preservative.

1. Pre-Emulsion Concentrates that Contain Fish Oil Non-Polar Compounds

Table 53 sets forth the ingredients that are included in a plurality of pre-emulsion concentrates that contain a fish oil non-polar compound, which contains different amounts of the non-polar active ingredients omega-3 polyunsaturated fatty acids DHA and EPA. These pre-emulsion concentrates are made using the general procedure outlined in Example 5A above. Each of the pre-emulsion concentrates set forth in Table 53 uses one of two different fish oil non-polar active ingredients. The first fish oil a fish oil that contains about 13% DHA and about 13% EPA, such as the fish oil sold as Denomega™ 100. The second fish oil is a fish oil that contains about 70% (74%) DHA and about 10% (9.3%) EPA, such as the fish oil sold as Omega-3 Fish Oil EE (O3C Nutraceuticals, supplied by Jedwards International Inc., Quincy, Mass.). These pre-emulsion concentrates can be made in any batch size, including 100 g and 150 g batch sizes, and are 0.5 mL serving size.

TABLE 53

Pre-emulsion concentrates containing fish oil

| Ingredient | wt % (of concentrate | wt % (of concentrate | wt % (of concentrate | wt % (of concentrate |
|---|---|---|---|---|
| Fish oil (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

2. Pre-Emulsion Concentrates that Contain Algae Oil Non-Polar Compounds

Table 54 sets forth the ingredients that are included in a plurality of pre-emulsion concentrates that contain an algae oil non-polar compound, which contains 35% of the non-polar active ingredient omega-3 polyunsaturated fatty acid DHA. These pre-emulsion concentrates are made using the general procedure outlined in Example 5A above. These pre-emulsion concentrates can be made in any batch size, including 100 g, 150 g and 280 g batch sizes, and are 0.5 mL serving size.

TABLE 54

Pre-emulsion concentrates containing algae oil

| Ingredient | wt % (of concentrate | wt % (of concentrate | wt % (of concentrate | wt % (of concentrate |
|---|---|---|---|---|
| Algae oil (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

C. Pre-Emulsion Concentrates Having ALA-Containing Non-Polar Compounds

Table 55 below sets forth the details of pre-emulsion concentrates that contain between 10% and 30%, by weight, of the concentrate, a flaxseed oil non-polar compound and between 69.5% and 89.5% TPGS. The flaxseed oil contains not less than (NLT) 50% C18:3 alpha-linolenic acid (such as the flaxseed oil sold by Sanmark LLC, Greensboro, N.C.; Sanmark Limited, Dalian, Liaoning Province, China). These pre-emulsion concentrates are made using the general procedure outlined in Example 5A above. Each pre-emulsion concentrate in Table 55 uses the tocopherol polyethylene glycol succinate (TPGS) described above in Example 1 and benzyl alcohol, a natural (GRAS-certified) preservative. These pre-emulsion concentrates can be made in any batch size, including 150 g batch sizes, and are 0.5 mL serving size.

TABLE 55

Pre-emulsion concentrates containing flaxseed oil

| Ingredient | wt % (of concentrate | wt % (of concentrate | wt % (of concentrate | wt % (of concentrate |
|---|---|---|---|---|
| Flaxseed oil (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

D. Pre-Emulsion Concentrates Having GLA-Containing Non-Polar Compounds

Table 56 below sets forth the details of pre-emulsion concentrates that contain between 10% and 30%, by weight, of the concentrate, a borage oil non-polar compound and between 69.5% and 89.5% TPGS. The borage oil contains not less than (NLT) 22% of the non-polar active ingredient omega-6 fatty acid C 18:3 gamma-linolenic acid (GLA) (such as the borage oil sold by Sanmark LLC, Greensboro, N.C.; Sanmark Limited, Dalian, Liaoning Province, China). The borage oil compound is derived by pressing and isolating oil from the seeds of *Borago officinalis* L. These pre-emulsion concentrates are made using the general procedure outlined in Example 5A above. Each pre-emulsion concentrate in Table 56 uses the tocopherol polyethylene glycol succinate (TPGS) described above in Example 1 and benzyl alcohol, a natural (GRAS-certified) preservative. These pre-emulsion concentrates can be made in any batch size, including 150 g batch sizes, and are 0.5 mL serving size.

TABLE 56

Pre-emulsion concentrates containing borage oil

| Ingredient | wt % (of concentrate | wt % (of concentrate | wt % (of concentrate | wt % (of concentrate |
|---|---|---|---|---|
| Borage oil (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

E. Pre-Emulsion Concentrates Having Fatty Acid-Containing Non-Polar Compounds

Table 57 below sets forth the details of pre-emulsion concentrates that contain between 10% and 30%, by weight, of the concentrate, a saw palmetto lipophilic extract non-polar compound and between 69.5% and 89.5% TPGS. The saw palmetto, lipophilic extract contains between about 85% and 90% total fatty acids, including 0.8% caproic acid, 2% caprylic acid, 2.4% capric acid, 27.1% lauric acid, 10.3% myristic acid, 8.1% palmitic acid, 0.2% palmitoleic acid, 2% stearic acid, 26.7% oleic acid, 4.9% linoleic acid, 0.7% linolenic acid and 0.42% phytosterols (including 0.42% beta sitosterol, 0.09% campesterol and 0.03% stigmasterol) (such as the extract sold by Natural Medicinals, Inc., Felda, Fla.). These pre-emulsion concentrates are made using the general procedure outlined in Example 5A above. Each pre-emulsion concentrate in Table 57 uses the tocopherol polyethylene glycol succinate (TPGS) described above in Example 1 and benzyl alcohol, a natural (GRAS-certified) preservative. These pre-emulsion concentrates can be made in any batch size, including 150 g batch sizes, and are 0.5 mL serving size.

TABLE 57

Pre-emulsion concentrates containing saw palmetto extract

| Ingredient | wt % (of concentrate | wt % (of concentrate | wt % (of concentrate | wt % (of concentrate |
|---|---|---|---|---|
| Saw palmetto extract (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

F. Pre-Emulsion Concentrates Having CLA-Containing Non-Polar Compounds

Table 58 below sets forth the details of pre-emulsion concentrates that contain between 10% and 30%, by weight, of the concentrate, the non-polar active ingredient conjugated linoleic acid (CLA) and between 69.5% and 89.5% TPGS. The CLA compound contains 70% CLA (such as the CLA compound sold by Sanmark, LTD; Dalian, Liaoning Province, China; product code 01057-A80). These pre-emulsion concentrates are made using the general procedure outlined in Example 5A above. Each pre-emulsion concentrate in Table 58 uses the tocopherol polyethylene glycol succinate (TPGS) described above in Example 1 and benzyl alcohol, a natural (GRAS-certified) preservative. These pre-emulsion concentrates can be made in any batch size, including 150 g batch sizes, and are 0.5 mL serving size.

TABLE 58

Pre-emulsion concentrates containing CLA-containing compound

| Ingredient | wt % (of concentrate | wt % (of concentrate | wt % (of concentrate | wt % (of concentrate |
|---|---|---|---|---|
| CLA (70%) (non-polar compound) | 10 | 10 | 20 | 30 |
| TPGS | 89.5 | 79.5 | 79.5 | 69.5 |
| Benzyl alcohol (preservative) | 0.5 | 0.5 | 0.5 | 0.5 |
| Vitamin E oil (non-polar solvent) | 0 | 10 | 0 | 0 |
| Total | 100 | 100 | 100 | 100 |

G. Pre-Emulsion Concentrates Having Coenzyme Q-Containing Non-Polar Compounds

Table 59 below sets forth the details of pre-emulsion concentrates that contain between 10% and 31.5%, by weight, of the concentrate, the non-polar active ingredient coenzyme Q10 and between 68% and 87% TPGS. The coenzyme Q10 (coQ10) compound contains greater than 98% ubidicarenone (ubiquinone), such as the coQ10 compound sold under the name Kaneka Q10™ (USP Ubidicarenone; Kaneka Nutrients, L.P., Pasadena, Tex.). These pre-emulsion concentrates are made using the general procedure outlined in Example 5A above. Each pre-emulsion concentrate in Table 59 uses the tocopherol polyethylene glycol succinate (TPGS) described above in Example 1 and benzyl alcohol, a natural (GRAS-certified) preservative. These pre-emulsion concentrates can be made in any batch size, including 150 g, 250 g, 500 g, 1584 g, 2112 g and 3000 g batch sizes, and are 0.5 mL, 0.6 mL or 0.8 mL serving size. The amount of each ingredient in Table 59 is listed as wt % of the total weight of the pre-emulsion concentrate.

TABLE 59

Pre-emulsion concentrates containing coenzyme Q10

| Ingredient | wt % | wt % | wt % | wt % | wt % | wt % |
|---|---|---|---|---|---|---|
| CoQ10 (ubidicarenone) (non-polar compound) | 10 | 12.5 | 16.7 | 22 | 30 | 31.5 |
| TPGS | 79.5 | 87.0 | 82.8 | 77.5 | 69.5 | 68.0 |
| Benzyl alcohol (preservative) | 0.5 | 0.5 | 0.5 | 0.5 | 0.5 | 0.5 |
| Vitamin E oil (non-polar solvent) | 10 | 0 | 0 | 0 | 0 | 0 |
| Total | 100 | 100 | 100 | 100 | 100 | 100 |

H. Pre-Emulsion Concentrates Having Phytosterol-Containing Non-Polar Compounds

Table 60 below sets forth the details of pre-emulsion concentrates that contain between 5% and 50%, by weight, of the concentrate, phytosterol non-polar active ingredients and between 49.5% and 79.5% TPGS. The phytosterol-containing compound contains kosher, pareve and halal plant sterols that contain a minimum of 95% plant sterols, such as the compound sold under the name CardioAid™ (distributed by B&D Nutrition; manufactured by ADM Natural Health and Nutrition; Decatur, Ill.).

Certain pre-emulsion concentrates set forth in Table 60 contain one or more additional non-polar compounds, such as a conjugated linoleic acid (CLA) compound that contains 80% CLA (such as sold by Sanmark, LTD; Dalian, Liaoning Province, China; product code 01057-A80); a safflower oil that is a high linoleic safflower oil that contains between 5% and 10% C:16 palmitic acid, between 1% and 3% C:18 stearic acid, between 12% and 18% 18:1 oleic acid, between 70% and 80% C18:2 linoleic acid and less than 1% C18:3 linolenic acid (such as sold by Jedwards, International, Inc., Quincy, Mass.; and/or a saw palmetto extract that is a saw palmetto, lipophilic extract, which contains between about 85% and 90% total fatty acids, including 0.8% caproic acid, 2% caprylic acid, 2.4% capric acid, 27.1% lauric acid, 10.3% myristic acid, 8.1% palmitic acid, 0.2% palmitoleic acid, 2% stearic acid, 26.7% oleic acid, 4.9% linoleic acid, 0.7% linolenic acid and 0.42% phytosterols (including 0.42% beta sitosterol, 0.09% campesterol, 0.03% stigmasterol) (such as sold by Natural Medicinals, Inc., Felda, Fla.). Other pre-emulsion concentrates, similar to the pre-emulsion concentrates set forth in Table 60, can be made by including one or more other additional non-polar compounds, for example, CoQ10, fish oil, algae oil, borage oil, and/or another non-polar compound, for example, any of the non-polar compounds described herein.

Each pre-emulsion concentrate in Table 60 uses the tocopherol polyethylene glycol succinate (TPGS) described above in Example 1 and benzyl alcohol, a natural (GRAS-certified) preservative. These pre-emulsion concentrates can be made in any batch size, including 100 g and 150 g batch sizes, and are 0.5 mL or 1 mL serving size. The amount of each ingredient in Table 60 is listed as wt % of the total weight of the pre-emulsion concentrate.

These pre-emulsion concentrates are made using the general procedure outlined in Example 5A above, with the following modifications. The initial ingredients, where indicated, are added sequentially in the following order, to a vessel (a Pyrex® beaker): 1) any solvent(s) and additional non-polar compound(s), in any order; 2) preservative; and 3) phytosterol-containing non-polar active ingredient. These ingredients are then mixed, using a standard mixer, and heated until the temperature reaches about 82.2° C. and the ingredients dissolve (about 1 hour).

After the initial ingredients dissolve, the mixture is filtered, without cooling, through a 100 micron filter. The surfactant (TPGS, prepared according to the method set forth in Example 1 above) is then added to the mixture and the mixture is homogenized using a reversible homogenizer at 850-1200 RPM. Mixing with the homogenizer is continued while maintaining a temperature of between about 60° C. and about 82.2° C., using the hot plate. The baffle plate on the homogenizer is adjusted to achieve and maintain an emulsion, for example, by moving the baffle plate further into and/or out of the ingredient mixture. Homogenization is continued until the surfactant dissolves. A temperature probe (Model #DPP400W, Cooper-Atkins) is used for evaluation, as a temperature meter to measure the temperature of the ingredients. After all ingredients have dissolved, the mixture is filtered (before cooling) through a 100 micron filter. The filtered mixture is added to a vessel (a Pyrex® beaker), then packaged. The mixture becomes a solid at room-temperature, having a waxy consistency. Thus, each of the pre-emulsion concentrates in Table 60 is a semi-solid or solid at room temperature, having a waxy consistency, and becomes liquid upon heating, for example, to 60° C.

TABLE 60

Pre-emulsion concentrates containing phytosterols

| Ingredient | wt % | wt % | wt % | wt % | wt % | wt % | wt % |
|---|---|---|---|---|---|---|---|
| Phytosterols (NLT 95%) (non-polar compound) | 5 | 5 | 10 | 10 | 10.5 | 10.5 | 10.5 |
| Saw palmetto extract (non-polar compound) | 0 | 0 | 0 | 0 | 5 | 1 | 1 |
| CLA (NLT 80%) (non-polar compound) | 0 | 45 | 0 | 40 | 0 | 34 | 0 |
| Safflower oil (non-polar compound) | 0 | 0 | 0 | 0 | 0 | 0 | 34 |
| TPGS | 49.5 | 49.5 | 79.5 | 49.5 | 54 | 54 | 54 |
| Benzyl alcohol (preservative) | 0.5 | 0.5 | 0.5 | 0.5 | 0.5 | 0.5 | 0.5 |
| Vitamin E oil (non-polar solvent) | 0 | 0 | 10 | 0 | 0 | 0 | 0 |
| Flaxseed oil (non-polar solvent) | 45 | 0 | 0 | 0 | 30 | 0 | 0 |
| Total | 100 | 100 | 100 | 100 | 100 | 100 | 100 |

Example 6

Liquid Nanoemulsion Concentrates Having Water as the Polar Solvent

Tables 61-72, below, set forth ingredients that are included in a plurality of different liquid nanoemulsion concentrates, described below. The liquid nanoemulsion concentrates are made according to the provided methods. Each of the liquid nanoemulsion concentrates contains one or more non-polar compound that contains one or more non-polar active ingredients, water as the polar solvent and the tocopheryl polyethylene glycol succinate (TPGS) surfactant prepared as described in Example 1 above.

These concentrates are prepared using the general procedure outlined in Example 6A below. Each of Tables 61-72 sets forth the percentage, by weight (of the total concentrate), for each ingredient and in the "phase" column, whether each ingredient is added to the water phase ("water"), the oil phase ("oil") or is added later, to the emulsion that is formed by emulsifying the oil and water phases ("emulsion"). Each liquid nanoemulsion concentrate in Tables 61-72 uses the tocopherol polyethylene glycol succinate (TPGS) described above in Example 1.

A. Liquid Nanoemulsion Concentrates with PUFA-Containing Non-Polar Compounds

Tables 61-66 set forth the details of liquid nanoemulsion concentrates that contain polyunsaturated fatty acid (PUFA)-containing non-polar compounds. The PUFA non-polar active ingredients include omega-3 fatty acids, omega-6 fatty acids, conjugated fatty acids and other fatty acids. Each liquid nanoemulsion concentrate set forth in Tables 61-66 contains either fish oil, algae oil, vitamin oil or flaxseed oil non-polar compounds that contain the non-polar active ingredients omega-3 polyunsaturated fatty acids DHA, EPA and/or ALA.

a. Liquid Nanoemulsion Concentrates that Contain Fish Oil Non-Polar Compounds

Table 61 sets forth the ingredients that are included in a plurality of liquid nanoemulsion concentrates that contain a fish oil non-polar compound, which contains different amounts of the non-polar active ingredients omega-3 polyunsaturated fatty acids DHA and EPA. These liquid nanoemulsion concentrates are made using the general procedure outlined in Example 6A above. Each of the liquid nanoemulsion concentrates set forth in Table 61 uses one of three different fish oil non-polar active ingredients: a fish oil that contains about 13% DHA and about 13% EPA, such as the fish oil sold as Denomega™ 100; a fish oil that contains about 70% DHA and about 10% EPA, such as the fish oil sold as Omega-3 Fish Oil EE (O3C Nutraceuticals, supplied by Jedwards International Inc., Quincy, Mass.); or a fish oil that contains about 30% of the non-polar active ingredients DHA and EPA (sold under the name Omega 30 TG Food Grade (Non-GMO) MEG-3™ Fish Oil by Ocean Nutrition Canada Limited, Nova Scotia, Mass.). The liquid nanoemulsion concentrates set forth in Table 61 can be made in any batch size, including 250 g and 500 g batch sizes, and are 2 mL serving size.

TABLE 61

| Liquid nanoemulsion concentrates with fish oil | | | | | | | |
|---|---|---|---|---|---|---|---|
| Ingredient | Phase | wt % | wt % | wt % | wt % | wt % | wt % |
| Fish oil (non-polar compound) | Oil | 5 | 5 | 8.5 | 9 | 10 | 12 |
| Water | Water | 74.25 | 68.79 | 65.44 | 64.94 | 68.79 | 61.94 |
| Emulsion stabilizer | Water | 0.34 | 0.17 | 0.06 | 0.06 | 0.17 | 0.06 |
| TPGS | Oil | 18 | 25.2 | 25.5 | 25.20 | 20.2 | 25.20 |
| Emulsion stabilizer | Oil | 0.064 | 0.064 | 0.022 | 0.022 | 0.064 | 0.0220 |
| Benzyl alcohol (preservative) | Oil | 0.5 | 0.5 | 0.5 | 0.5 | 0.5 | 0.5 |
| D-limonene (flavor) | Emulsion | 0.525 | 0 | 0 | 0 | 0 | 0 |
| Lemon oil (flavor) | Emulsion | 0.37 | 0 | 0 | 0 | 0 | 0 |
| Phosphatidylcholine (co-surfactant) | Oil | 0.67 | 0 | 0 | 0 | 0 | 0 |
| Citric acid (pH adjuster) | Emulsion | 0.28 | 0.28 | 0.28 | 0.28 | 0.28 | 0.28 |
| Totals | | 100 | 100 | 100 | 100 | 100 | 100 |

1. Omega-3-Containing Non-Polar Compounds

Tables 61-63 below set forth the details of liquid nanoemulsion concentrates that contain between 5% and 12%, by weight, of the concentrate, fish oil, algae oil, vitamin oil or flaxseed oil non-polar compounds and between 17.75% and 25.2% TPGS. The fish oil, algae oil and flaxseed oil non-polar compounds contain the non-polar active ingredients omega-3 polyunsaturated fatty acids DHA, EPA and/or ALA. These liquid nanoemulsion concentrates are made using the general procedure outlined in Example 6A above. Each liquid nanoemulsion concentrate in Tables 61-63 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, MD); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank.

b. Liquid Nanoemulsion Concentrates that Contain Algae Oil Non-Polar Compounds

Table 62 sets forth the ingredients that are included in a plurality of liquid nanoemulsion concentrates that contain an algae oil non-polar compound, which contains different amounts of the non-polar active ingredients omega-3 polyunsaturated fatty acids DHA and/or EPA. These liquid nanoemulsion concentrates are made using the general procedure outlined in Example 6A above. Each of the liquid nanoemulsion concentrates set forth in Table 62 uses one of two different algae oil non-polar compounds: an algae oil that contains 35% of the non-polar active ingredient DHA or an algal oil that contains about 40% DHA, such as an oil derived from microalgae, sold as V Pure® DHA 40% Standard TAG Oil. The non-polar compounds are added at amounts such that the non-polar active ingredient makes up either 3.5%, 5% or 10%, by weight (w/w), of the final concentrate. The liquid nanoemulsion concentrates set forth in Table 62 can be made in any batch size, including 150 g, 200 g, 300 g and 500 g batch sizes, and are 2 mL serving size.

TABLE 62

Liquid nanoemulsion concentrates with algae oil

| Ingredient | Phase | wt % | wt % | wt % | wt % |
|---|---|---|---|---|---|
| Algae oil (non-polar compound) | Oil | 5 | 5 | 10 | 10.5 |
| Water | Water | 75.8165 | 68.7865 | 63.938 | 63.438 |
| Emulsion stabilizer | Water | 0.34 | 0.17 | 0.06 | 0.06 |
| TPGS | Oil | 18 | 25.2 | 25.2 | 25.2 |
| Emulsion stabilizer | Oil | 0.0635 | 0.0635 | 0.022 | 0.0220 |
| Benzyl alcohol (preservative) | Oil | 0.5 | 0.5 | 0.5 | 0.5 |
| Citric acid (pH adjuster) | Emulsion | 0.28 | 0.28 | 0.28 | 0.28 |
| Totals | | 100 | 100 | 100 | 100 | c. Flaxseed Oil Non-Polar Compounds

Table 63 sets forth the ingredients that are included in a plurality of liquid nanoemulsion concentrates that contain a flaxseed oil non-polar compound, which contains not less than (NLT) 50% of the non-polar active ingredient C 18:3 alpha-linolenic acid (such as the flaxseed oil sold by Sanmark LLC, Greensboro, N.C.; Sanmark Limited, Dalian, Liaoning Province, China). These liquid nanoemulsion concentrates are made using the general procedure outlined in Example 6A above. The flaxseed oil is added at amounts such that the non-polar active ingredient makes up either 5%, 10% or 10.5%, by weight (w/w), of the final concentrate. The liquid nanoemulsion concentrates set forth in Table 63 can be made in any batch size, including 250 g and 500 g batch sizes, and are 2 mL serving size.

TABLE 63

Liquid nanoemulsion concentrates with flaxseed oil

| Ingredient | Phase | wt % | wt % | wt % | wt % |
|---|---|---|---|---|---|
| Flaxseed oil (50% ALA) (non-polar compound) | Oil | 5 | 5 | 10 | 10.5 |
| Water | Water | 71.74 | 68.7865 | 68.7865 | 63.438 |
| Emulsion stabilizer | Water | 0.06 | 0.17 | 0.17 | 0.06 |
| TPGS | Oil | 17.75 | 25.2 | 20.2 | 25.2 |
| Emulsion stabilizer | Oil | 0.34 | 0.0635 | 0.0635 | 0.0220 |
| Benzyl alcohol (preservative) | Oil | 0.50 | 0.50 | 0.50 | 0.50 |
| Citric acid (pH adjuster) | Emulsion | 0.19 | 0.28 | 0.28 | 0.28 |
| Vitamin E oil (non-polar solvent) | Oil | 3.75 | 0 | 0 | 0 |
| Phosphatidyl-choline (co-surfactant) | Oil | 0.6690 | 0 | 0 | 0 |
| Totals | | 100 | 100 | 100 | 100 |

2. Omega-6-Containing Non-Polar Compounds

Table 64 below sets forth the details of liquid nanoemulsion concentrates that contain between 5% and 10%, by weight, of the concentrate, borage oil non-polar compounds and between 17.75% and 25.2% TPGS. The borage oil non-polar compounds, derived by pressing and isolating oil from the seeds of *Borago officinalis*, contain not less than (NLT) 22% of the non-polar active ingredient C 18:3 gamma-linolenic acid (GLA), an omega-6 fatty acid. An exemplary barrage oil is sold by Sanmark LLC, Greensboro, N.C. (Sanmark Limited, Dalian, Liaoning Province, China). These liquid nanoemulsion concentrates are made using the general procedure outlined in Example 6A above. Each liquid nanoemulsion concentrate in Tables 64 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrates set forth in Table 64 can be made in any batch size, including 250 g and 500 g batch sizes, and are 2 mL serving size.

TABLE 64

Liquid nanoemulsion concentrates with borage oil

| Ingredient | Phase | wt % | wt % | wt % |
|---|---|---|---|---|
| Borage oil (22% GLA) (non-polar compound) | Oil | 5 | 5 | 10 |
| Water | Water | 71.74 | 68.7865 | 68.7865 |
| Emulsion stabilizer | Water | 0.06 | 0.17 | 0.17 |
| TPGS | Oil | 17.75 | 25.2 | 20.2 |
| Emulsion stabilizer | Oil | 0.34 | 0.0635 | 0.0635 |
| Benzyl alcohol (preservative) | Oil | 0.50 | 0.50 | 0.50 |
| Citric acid (pH adjuster) | Emulsion | 0.19 | 0.28 | 0.28 |
| Vitamin E oil (non-polar solvent) | Oil | 3.75 | 0 | 0 |
| Phosphatidylcholine (co-surfactant) | Oil | 0.6690 | 0 | 0 |
| Totals | | 100 | 100 | 100 |

3. CLA-Containing Non-Polar Compounds

Table 65 below set forth the details of liquid nanoemulsion concentrates that contain between 5% and 10%, by weight, of the concentrate, a conjugated linoleic acid (CLA)-containing compound that contains 80% of the non-polar active ingredient CLA, such as the CLA compound sold by Sanmark, LTD (Dalian, Liaoning Province, China; product code 01057-A80). These liquid nanoemulsion concentrates are made using the general procedure outlined in Example 6A above. Each liquid nanoemulsion concentrate in Table 65 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrates set forth in Table 65 can be made in any batch size, including 250 g and 500 g batch sizes, and are 2 mL serving size.

TABLE 65

Liquid nanoemulsion concentrates with CLA-containing compounds

| Ingredient | Phase | wt % | wt % | wt % |
|---|---|---|---|---|
| CLA compound (80% CLA) (non-polar compound) | Oil | 5 | 5 | 10 |
| Water | Water | 71.74 | 68.7865 | 68.7865 |
| Emulsion stabilizer | Water | 0.06 | 0.17 | 0.17 |
| TPGS | Oil | 17.75 | 25.2 | 20.2 |
| Emulsion stabilizer | Oil | 0.34 | 0.0635 | 0.0635 |
| Benzyl alcohol (preservative) | Oil | 0.50 | 0.50 | 0.50 |
| Citric acid (pH adjuster) | Emulsion | 0.19 | 0.28 | 0.28 |
| Vitamin E oil (non-polar solvent) | Oil | 3.75 | 0 | 0 |
| Phosphatidylcholine (co-surfactant) | Oil | 0.6690 | 0 | 0 |
| Totals | | 100 | 100 | 100 |

4. Fatty Acid-Containing Non-Polar Compounds

Table 66 below sets forth the details of liquid nanoemulsion concentrates that contain between 5% and 10%, by weight, of the concentrate, a saw palmetto extract non-polar compound that contains about 90% of the non-polar active ingredient fatty acids, including 0.8% caproic acid, 2% caprylic acid, 2.4% capric acid, 27.1% lauric acid, 10.3% myristic acid, 8.1% palmitic acid, 0.2% palmitoleic acid, 2% stearic acid, 26.7% oleic acid, 4.9% linoleic acid, 0.7% linolenic acid and 0.42% phytosterols (including 0.42% beta sitosterol, 0.09% campesterol and 0.03% stigmasterol). An exemplary saw palmetto extract is the Saw Palmetto, Lipophilic Extract, commercially available from Natural Medicinals, Inc. (Felda, Fla.).

The liquid nanoemulsion concentrates set forth in Table 66 are made using the general procedure outlined in Example 6A above. Each liquid nanoemulsion concentrate in Table 66 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrates set forth in Table 66 can be made in any batch size, including 250 g and 500 g batch sizes, and are 2 mL serving size.

TABLE 66

Liquid nanoemulsion concentrates with saw palmetto extract

| Ingredient | Phase | wt % | wt % | wt % |
|---|---|---|---|---|
| Saw palmetto extract (90% fatty acids) (non-polar compound) | Oil | 5 | 5 | 10 |
| Water | Water | 71.74 | 68.7865 | 68.7865 |
| Emulsion stabilizer | Water | 0.06 | 0.17 | 0.17 |
| TPGS | Oil | 17.75 | 25.2 | 20.2 |
| Emulsion stabilizer | Oil | 0.34 | 0.0635 | 0.0635 |
| Benzyl alcohol (preservative) | Oil | 0.50 | 0.50 | 0.50 |
| Citric acid (pH adjuster) | Emulsion | 0.19 | 0.28 | 0.28 |
| Vitamin E oil (non-polar solvent) | Oil | 3.75 | 0 | 0 |
| Phosphatidylcholine (co-surfactant) | Oil | 0.6690 | 0 | 0 |
| Totals | | 100 | 100 | 100 |

C. Coenzyme Q-Containing Non-Polar Compounds

Table 67 below sets forth the details of liquid nanoemulsion concentrates that contain between 5% and 5.25%, by weight, of the concentrate, a coenzyme Q 10 (CoQ10)-containing compound that contains greater than 98% ubidecarenone (ubiquinone), such as the CoQ10 compound sold under the name Kaneka Q10™ (USP Ubidecarenone) by Kaneka Nutrients, L.P., Pasadena, Tex. These liquid nanoemulsion concentrates are made using the general procedure outlined in Example 6A above. Each liquid nanoemulsion concentrate in Table 67 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrates set forth in Table 67 can be made in any batch size, including a 500 g and 650 g batch size, and are 2 mL serving size.

TABLE 67

Liquid nanoemulsion concentrates with CoQ10

| Ingredient | Phase | wt % | wt % |
|---|---|---|---|
| CoQ10 (non-polar compound) | Oil | 5 | 5.25 |
| Water | Water | 71.74 | 64.24 |
| Emulsion stabilizer | Water | 0.06 | 0.34 |
| TPGS | Oil | 17.75 | 25.00 |
| Emulsion stabilizer | Oil | 0.34 | 0.06 |
| Benzyl alcohol (preservative) | Oil | 0.50 | 0.50 |
| Citric acid (pH adjuster) | Emulsion | 0.19 | 0.19 |
| Vitamin E oil (non-polar solvent) | Oil | 3.75 | 3.75 |
| Phosphatidylcholine (co-surfactant) | Oil | 0.6690 | 0.6690 |
| Totals | | 100 | 100 |

D. Phytosterol-Containing Non-Polar Compounds

Table 68 below sets forth the details of a liquid nanoemulsion concentrate that contains 5.25%, by weight, of the concentrate, a phytosterols-containing compound that contains kosher, pareve and halal plant sterols that are produced under current food GMPs and contain a minimum of 95% plant sterols, such as the compound sold under the name Cardio-Aid™, distributed by B&D Nutrition and manufactured by ADM Natural Health and Nutrition (Decatur, Ill.). This liquid nanoemulsion concentrate is made using the general procedure outlined in Example 6A above. The liquid nanoemulsion concentrate in Table 68 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrate set forth in Table 68 can be made in any batch size, including a 250 g batch size, and are 2 mL serving size.

TABLE 68

Liquid nanoemulsion concentrates with phytosterols-containing compound

| Ingredient | Phase | wt % |
|---|---|---|
| Phytosterols (non-polar compound) | Oil | 5.25 |
| Water | Water | 68.29 |
| Emulsion stabilizer | Water | 0.17 |
| TPGS | Oil | 20.00 |
| Benzyl alcohol (preservative) | Oil | 0.50 |
| Phosphoric acid (pH adjuster) | Emulsion | 0.40 |
| Flaxseed oil (non-polar solvent) | Oil | 5.25 |
| Phosphatidylcholine (co-surfactant) | Oil | 0.15 |
| Totals | | 100 |

E. Vitamin D3-Containing Non-Polar Compounds

Table 69 below sets forth the details of a liquid nanoemulsion concentrate that contains 10.50%, by weight, of the concentrate the non-polar active ingredient vitamin D3 (100,000 IU), such as the vitamin D3 sold by DSM Nutritional Products (Parsippany, N.J.). This liquid nanoemulsion concentrate is made using the general procedure outlined in Example 6A above. The liquid nanoemulsion concentrate in Table 69 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrate set forth in Table 69 can be made in any batch size, including a 7500 g batch size, and are 2 mL serving size.

TABLE 69

Liquid nanoemulsion concentrate with vitamin D3

| Ingredient | Phase | wt % |
|---|---|---|
| Vitamin D3 (non-polar compound) | Oil | 10.50 |
| Water | Water | 63.438 |
| Emulsion stabilizer | Water | 0.06 |
| TPGS | Oil | 25.20 |
| Emulsion stabilizer | Oil | 0.022 |
| Benzyl alcohol (preservative) | Oil | 0.50 |
| Citric acid (pH adjuster) | Emulsion | 0.28 |
| Totals | | 100 |

F. Resveratrol-Containing Non-Polar Compounds

Table 70 below sets forth the details of a liquid nanoemulsion concentrate that contains 4.4%, by weight, of the concentrate the non-polar active ingredient resveratrol. The resveratrol is a resveratrol that contains trans-resveratrol, such as the resveratrol sold under the name ReserveNature™ (Jiaherb, Shaanxi, China), that contains trans-resveratrol from the botanical source *Polygonum cuspidatum*. This liquid nanoemulsion concentrate is made using the general procedure outlined in Example 6A above. The resveratrol non-polar active ingredient is added at an amount of 4.4%, by weight, of the final concentrate, whereby the concentrate contains 4% resveratrol. The liquid nanoemulsion concentrate in Table 70 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank. The liquid nanoemulsion concentrate set forth in Table 70 can be made in any batch size, including a 500 g batch size, and are 2 mL serving size.

TABLE 70

Liquid nanoemulsion concentrate with vitamin D3

| Ingredient | Phase | wt % |
|---|---|---|
| Trans-resveratrol (98%) (non-polar compound) | Oil | 4.40 |
| Water | Water | 60.00 |
| Emulsion stabilizer | Water | 0.34 |
| TPGS | Oil | 25.00 |
| Emulsion stabilizer | Oil | 0.06 |
| Benzyl alcohol (preservative) | Oil | 0.50 |
| Citric acid (pH adjuster) | Emulsion | 0.19 |
| Rice bran oil | Oil | 9.507 |
| Totals | | 100 |

G. Liquid Nanoemulsion Concentrates with Various Non-Polar Active Ingredients

Tables 71 and 72 below set forth the details of liquid nanoemulsion concentrates that contain two or more non-polar compounds that each contain one or more non-polar active ingredients, such as polyunsaturated fatty acids (PUFAs) (e.g., omega-3 fatty acids and omega-6 fatty acids), coenzyme Q10 and vitamins. These concentrates are made using the general procedure outlined in Example 6A above. Each liquid nanoemulsion concentrate in Tables 71 and 72 uses the tocopherol polyethylene glycol succinate (TPGS) described above in Example 1; benzyl alcohol, a natural (GRAS-certified) preservative; an emulsion stabilizer that is a blend of xanthan gum, guar gum and sodium alginate (such as the SALADIZER® brand emulsion stabilizer from TIC Gums, Inc.; Belcamp, Md.); citric acid; and water that is purified city water, purified according to the provided methods by passage through the following purifiers, sequentially: a carbon filter, an ion exchange purifier, a reverse osmosis purifier and an end-point filter, for example, a 100 micron end-point filter, before addition to the water phase tank.

The liquid nanoemulsion concentrates contain two or more of the following non-polar compounds that contain the non-polar active ingredients: a borage oil compound, derived by pressing and isolating oil from the seeds of *Borago officinalis* L., that contains not less than (NLT) 22% of the non-polar active ingredient C18:3 gamma-linolenic acid (GLA), such as the borage oil sold by Sanmark LLC, Greensboro, N.C. (Sanmark Limited, Dalian, Liaoning Province, China); a flaxseed oil compound that contains not less than (NLT) 55% of the non-polar active ingredient C18:3 alpha-linolenic acid, such as the flaxseed oil sold as Fresh Flax Oil (Barleans Organic Oils, LLC, Ferndale, Wash.); a fish oil that contains about 30% of the non-polar active ingredients DHA and EPA (such as sold under the name Omega 30 TG Food Grade (Non-GMO) MEG-3™ Fish Oil by Ocean Nutrition Canada Limited, Nova Scotia, Mass.); a coenzyme Q-containing non-polar compound that contains greater than 98% ubidecarenone (ubiquinone), such as sold under the name Kaneka Q10™ (USP Ubidecarenone) by Kaneka Nutrients, L.P. (Pasadena, Tex.); vitamin D3 and vitamin A palmitate, such as those sold by DSM Nutritional Products (Parsippany, N.J.); and vitamin E oil that contains at least 67.2% tocopherol and approximately 32.8% soybean oil, such as the vitamin E oil sold by ADM Natural Health and Nutrition (Decatur, Ill.), under the name Novatol™ 5-67 Vitamin E (D-alpha-tocopherol; ADM product code 410217).

1. Liquid Nanoemulsion Concentrates Formulated for Women

Table 71 sets forth the ingredients that are included in a 250 g batch (2 mL serving size) of a liquid nanoemulsion concentrate that contains non-polar compounds that contain the non-polar active ingredients omega-3 fatty acids (e.g., EPA, DHA, GLA and ALA), omega-6 fatty acids, coenzyme Q10 and vitamins D3 and E. The borage oil is added in an amount of 4.55%, by weight (w/w), of the final concentrate, whereby the concentrate contains 1.0% GLA; the flaxseed oil is added in an amount of 2.4%, by weight (w/w), of the final concentrate, whereby the concentrate contains 1.2% ALA; the fish oil is added in an amount of 0.2%, by weight, of the final concentrate, whereby the concentrate contains 0.06% EPA+DHA; the CoQ10 is added in an amount such that it makes up 0.5%, by weight (w/w), of the final concentrate; and the vitamins D3 and E are added in amounts that correspond to the dietary reference intakes (DRI) for women.

TABLE 71

Liquid nanoemulsion concentrate formulated for women

| Ingredient | Phase | wt % |
|---|---|---|
| Borage oil (22% GLA) (non-polar compound) | Oil | 4.55 |
| Flaxseed oil (50% ALA) (non-polar compound) | Oil | 2.40 |
| Fish oil (30% DHA + EPA) (non-polar compound) | Oil | 0.20 |
| CoQ10 (98% ubidecarenone) (non-polar compound) | Oil | 0.50 |
| Vitamin E oil (non-polar compound) | Oil | 0.75 |
| Vitamin D3 (non-polar compound) | Oil | $5.0 \times 10^{-6}$ |
| Water | Water | 65.538 |
| Emulsion stabilizer | Water | 0.06 |
| TPGS | Oil | 25.20 |
| Emulsion stabilizer | Oil | 0.0220 |
| Benzyl alcohol (preservative) | Oil | 0.50 |
| Citric acid (pH adjuster) | Emulsion | 0.2800 |
| Totals | | 100 |

2. Liquid Nanoemulsion Concentrates Formulated for Children

Table 72 sets forth the ingredients that are included in a 250 g batch (2 mL serving size) of a liquid nanoemulsion concentrate that contains non-polar compounds that contain the non-polar active ingredients omega-3 fatty acids (e.g., EPA, DHA, GLA and ALA) and vitamins A, D3 and E. The flaxseed oil is added in an amount of 4.2%, by weight (w/w), of the final concentrate, whereby the concentrate contains 2.1% ALA; the fish oil is added in an amount of 0.2%, by weight, of the final concentrate, whereby the concentrate contains 0.06% EPA+DHA; and the vitamins A, D3 and E are added in amounts that correspond to the dietary reference intakes (DRI) for children.

TABLE 72

Liquid nanoemulsion concentrate formulated for children

| Ingredient | Phase | wt % |
|---|---|---|
| Flaxseed oil (50% ALA) (non-polar compound) | Oil | 4.20 |
| Fish oil (30% DHA + EPA) (non-polar compound) | Oil | 0.20 |
| Vitamin E oil (non-polar compound) | Oil | 1.50 |
| Vitamin D3 (non-polar compound) | Oil | 0.04 |
| Vitamin A palmitate (non-polar compound) | Oil | 0.14 |
| Water | Water | 67.858 |
| Emulsion stabilizer | Water | 0.06 |
| TPGS | Oil | 25.20 |
| Emulsion stabilizer | Oil | 0.220 |
| Benzyl alcohol (preservative) | Oil | 0.50 |
| Citric acid (pH adjuster) | Emulsion | 0.280 |
| Totals | | 100 |

H. Liquid Nanoemulsion Concentrate with TPGS and SFAE Surfactants

Table 73 below sets forth the details of a liquid nanoemulsion concentrate that contains non-polar compounds that contain non-polar active ingredients, such as polyunsaturated fatty acids (PUFAs) (e.g., omega-3 fatty acids and omega-6 fatty acids) and vitamins and a mixture of sucrose fatty acid ester (SFAE) and TPGS surfactants. The PUFA-containing non-polar compound is a conjugated linoleic acid (CLA) oil that contains about 80% CLA (such as sold under the name Clarinol G-80, by Lipid Nutrition B.V., Channahon, Ill.) and the vitamin-containing non-polar compound is vitamin A palmitate, which contains 1.7 mIU/g vitamin A, such as produced by DSM Nutritional Products, Inc. (Belvidere, N.J.) and distributed through Stauber Performance Ingredients, Inc. (Fullerton, Calif.). The TPGS is the TPGS that is prepared according to the method described in Example 1, above, and an exemplary SFAE surfactant is sold as Ryoto Sugar Ester S-1760 (Mitsubishi-Kagaku Foods Corporation, Tokyo, Japan). The liquid nanoemulsion concentrates further contain additional ingredients, including a soluble fiber, such as a chicory inulin (such as sold by Oliggo-Fiber Instant Inulin (Fibruline® Instant), produced by Cosucra Groupe (Warcoing, Belgium) and distributed through Gillco Products Inc. (San Marcos, Calif.)); emulsion stabilizers that include a modified gum acacia and an ester gum (such as Tic Pre-tested® Ticamulsion A-2010 Powder (TIC Gums, Inc., Belcamp, Md.) and Ester Gum 8BG (Pinova/Hercules, Brunswick, Ga.), respectively); benzyl alcohol, a preservative that is a natural (GRAS-certified) preservative; an antifoaming agent, such as Tramfloc 1147 (Tramfloc Inc, Formey, Tex.);

and water that is city water, which is purified prior to addition to the water phase vessel, by passage through the following purifiers, sequentially in the following order: a carbon filter, an ion exchange purifier, a reverse osmosis purifier, a UV sterilizer and an end-point filter (a 100 micron end-point filter).

These concentrates are made using the general procedure described below.

The liquid nanoemulsion concentrate is made using a bench-top process of the provided methods. To make larger batch sizes, the bench-top process can be scaled up to make the concentrate using a scaled-up manufacturing process of the provided methods as described herein.

The bench-top process for making the concentrate is performed using the following steps:

To make the concentrate, the indicated amount of each ingredient is weighed using a Sartorius Basic Analytical Scale (Model BA110S) or a CTS 6000 Scale (Model CTS-6000). Selection of scale(s) depends on the weight of the particular ingredient(s).

To generate the water phase, the water phase ingredients (indicated by "water" in the table in the "phase" column) are added in the indicated amount (g/batch) to a water phase vessel (such as a Pyrex® beaker), and mixed using a reversible homogenizer (such as Arde Barinco, Inc., Model CJ-4E). During mixing, the water phase ingredients are heated until the ingredients reach the desired temperature of 60° C., using a hot plate as the heating apparatus (such as a Thermolyne hot plate, Model #SP46615, Barnstead International, Dubuque, Iowa). In the initial step, water is added to the water phase vessel and heated to 60° C. while slowly mixing at 30 RPM on forward. Subsequently, the homogenizer is raised, switched to reverse mode and lowered back into the water to generate a vortex at a speed of 20-30 RPM prior to adding additional water phase ingredients. The water phase ingredients are added to the water phase vessel, sequentially, in the following order: 1) Ticamulsion® stabilizer; 2) antifoam; 3) $1^{st}$ fraction surfactant; 4) $2^{nd}$ fraction surfactant; and 5) soluble fiber, and are mixed while heating to a temperature of 60° C., which was maintained until combining with the oil phase. After addition of all of the water phase ingredients, the homogenizer is raised, switched to forward mode, and lowered back into the water phase vessel to allow mixing at a speed of 30 RPM. The temperature of the water phase and speed of mixing is maintained before combining and emulsifying the water and oil phases. A temperature meter (such as a temperature probe, Model #DPP400W, Cooper-Atkins) is used to evaluate (measure) the temperature of the water phase. The water phase ingredients include a polar solvent (water) and additional water phase ingredients, where indicated.

The oil phase ingredients (indicated by "oil" in the table in the "phase" column) are added to an oil phase vessel (a Pyrex® beaker) sequentially, in the following order: 1) TPGS surfactant; 2) preservative; 3) ester gum emulsion stabilizer; 4) vitamin non-polar active ingredient; and heating to a temperature of 60° C., followed by the addition of 5) non-polar active ingredient; 6) SFAE surfactant; and 7) Ticamulsion® stabilizer. The composition is mixed using a standard mixer, such as the IKA® model No. RE-16 1S, which is an overhead mixer (laboratory stirrer) compatible with the bench-top process.

As the oil phase ingredients are mixed, they are heated using a hot plate as a heating apparatus (such as a Thermolyne hot plate, Model #SP46615, Barnstead International, Dubuque, Iowa), to a desired temperature of 60° C. and generally mixed at this temperature until ingredients dissolve, and maintained at the temperature before mixing with the water phase. A temperature meter (such as a temperature probe, Model #DPP400W, Cooper-Atkins) is used to evaluate (measure) the temperature of the oil phase.

After both phases reach the appropriate temperatures (60° C.) and the oil phase components dissolve, the phases are combined and emulsified. Emulsification is effected with a reversible homogenizer (such as Arde Barinco, Inc., Model CJ-4E). The reversible homogenizer, which is used to mix the water phase ingredients, is maintained at 30 RPM for mixing during the emulsification step. While mixing with the homogenizer at this speed, the oil phase is transferred to the water phase vessel by pouring it from the oil phase vessel into the water phase vessel. Mixing with the homogenizer is continued at 30 RPM.

A pH adjuster (e.g., citric acid) is added after combining and emulsifying the oil and water phases (indicated by "emulsion" in the phase column) while mixing with the reversible homogenizer (such as Arde Barinco, Inc., Model CJ-4E). The pH of the emulsion is measured using a pH and temperature meter (such as Hanna Instruments, model HI 8314). The pH is adjusted with the appropriate amount of a pH adjuster (amount indicated in the table), for example, citric acid, until the emulsion reaches a pH of between 2.0 and 3.0.

As a final step, the concentrate is filtered using a 200-1000 micron end-product filter, before hot-filling into a package container.

Table 73, below, sets forth the ingredients to make a 320 g batch (2 mL serving size) of the liquid nanoemulsion concentrate. Also indicated in the table, in the "phase" column, is whether each ingredient was added to the water phase ("water"), the oil phase ("oil") or was added later, to the emulsion formed after combining the oil and water phases in the emulsification step ("emulsion"). The CLA oil non-polar compound is added in an amount of 21%, by weight, of the final concentrate, whereby the concentrate contains 15% of the non-polar active ingredient CLA; the vitamin A palmitate is added in an amount such that the nanoemulsion concentrate contains 400 micrograms (mcg) vitamin A per gram of concentrate; and the antifoaming agent is added to the aqueous phase (approximately 1 drop per liter) as described above.

TABLE 73

Liquid nanoemulsion concentrate with a mixture of surfactants

| Ingredient | Phase | wt % |
|---|---|---|
| CLA oil (80% CLA) (non-polar compound) | Oil | 21.00 |
| Vitamin A palmitate (non-polar compound) | Oil | 0.04 |
| Chicory inulin (soluble fiber) | Water | 2.03 |
| Gum acacia (emulsion stabilizer) | Water | 1.00 |
| SFAE ($1^{st}$ fraction surfactant) | Water | 4.66 |
| SFAE ($2^{nd}$ fraction surfactant) | Water | 3.15 |
| Water | Water | 52.136 |
| SFAE (surfactant) | Oil | 1.25 |
| TPGS | Oil | 10.50 |
| Ester gum (emulsion stabilizer) | Oil | 0.06 |
| Gum acacia (emulsion stabilizer) | Oil | 0.50 |
| Benzyl alcohol (preservative) | Oil | 0.50 |
| Citric acid (pH adjuster) | Emulsion | 3.18 |
| Totals | | 100 |

Example 7

Liquid Nanoemulsion Concentrates with Other Polar Solvents

Tables 74 and 75, below, set forth ingredients that are included in a plurality of different liquid nanoemulsion concentrates, described below. The liquid nanoemulsion concentrates are made according to the provided methods. Each of the liquid nanoemulsion concentrates contains one or more non-polar compound that contains one or more non-polar active ingredients, either glycerin or propylene glycol as the polar solvent and the tocopheryl polyethylene glycol succinate (TPGS) surfactant prepared as described in Example 1 above.

These concentrates are prepared using the general procedure outlined in Example 6A above. Each of Tables 74 and 75 sets forth the percentage, by weight (of the total concentrate), for each ingredient and in the "phase" column, whether each ingredient is added to the polar solvent phase ("water"), the oil phase ("oil") or is added later, to the emulsion that is formed by emulsifying the oil and polar solvent phases ("emulsion"). Each liquid nanoemulsion concentrate in Tables 74 and 75 uses the tocopherol polyethylene glycol succinate (TPGS) described above in Example 1.

A. Liquid Nanoemulsion Concentrates with PUFA-Containing Non-Polar Compounds

Table 74 sets forth the details of liquid nanoemulsion concentrates that contain polyunsaturated fatty acid (PUFA)-containing non-polar compounds. The PUFA non-polar active ingredients include omega-3 fatty acids, omega-6 fatty acids, conjugated fatty acids and other fatty acids. Each liquid nanoemulsion concentrate set forth in Table 74 contains either flaxseed oil (such as a flaxseed oil compound that contains not less than (NLT) 55% of the non-polar active ingredient C18:3 alpha-linolenic acid, such as the flaxseed oil sold as Fresh Flax Oil (Barleans Organic Oils, LLC, Ferndale, Wash.)), borage oil (such as a borage oil compound derived by pressing and isolating oil from the seeds of *Borago officinalis* L., that contains not less than (NLT) 22% of the non-polar active ingredient C 18:3 gamma-linolenic acid (GLA), such as the borage oil sold by Sanmark LLC, Greensboro, N.C. (Sanmark Limited, Dalian, Liaoning Province, China)), CLA oil (such as a conjugated linoleic acid (CLA)-containing compound that contains 80% of the non-polar active ingredient CLA, such as the CLA compound sold under the trade name Tonalin® (Cognis Corporation, Cincinnati, Ohio), which contains (w/w) 1.7% C 16:0 palmitic acid, 2.6% C:18 stearic acid, 13.00% C18:1 C9 oleic acid, 0.20% C18:2 C9 C12 linoleic acid and 81.00% conjugated linoleic acid (CLA), which includes 39.70% conjugated C9, T11 isomer and 39.50% conjugated T10, C12 isomer; or fish oil (such as a fish oil that contains about 30% of the non-polar active ingredients DHA and EPA (sold under the name Omega 30 TG Food Grade (Non-GMO) MEG-3™ Fish Oil by Ocean Nutrition Canada Limited, Nova Scotia, Mass.)) non-polar compounds that contain the non-polar active ingredients omega-3 and omega-6 polyunsaturated fatty acids DHA, EPA, GLA and/or ALA. The polar solvent is either glycerin or propylene glycol.

TABLE 74

Liquid nanoemulsion concentrate with PUFAs and glycerin or propylene glycol polar solvent

| Ingredient | Phase | wt % | wt % | wt % | wt % |
|---|---|---|---|---|---|
| Flaxseed oil (55% ALA) (non-polar compound) | Oil | 5 | 0 | 0 | 0 |
| Borage oil (22% GLA) (non-polar compound) | Oil | 0 | 5 | 0 | 0 |
| CLA oil (non-polar compound) | Oil | 0 | 0 | 5 | 0 |

TABLE 74-continued

Liquid nanoemulsion concentrate with PUFAs and glycerin or propylene glycol polar solvent

| Ingredient | Phase | wt % | wt % | wt % | wt % |
|---|---|---|---|---|---|
| Fish oil (non-polar compound) | Oil | 0 | 0 | 0 | 5 |
| Glycerin or propylene glycol (polar solvent) | Water | 69.3 | 69.3 | 69.3 | 69.3 |
| TPGS | Oil | 25.2 | 25.2 | 25.2 | 25.2 |
| Benzyl alcohol (preservative) | Oil | 0.5 | 0.5 | 0.5 | 0.5 |
| Totals | | 100 | 100 | 100 | 100 |

B. Liquid Nanoemulsion Concentrates with Coenzyme Q10-Containing Non-Polar Compounds Table 75 sets forth the details of liquid nanoemulsion concentrates that each contain a non-polar compound that contains coenzyme Q, that are prepared using the general procedure outlined in Example 6A above. The non-polar compound in each of these concentrates is a coenzyme Q10 (CoQ10)-containing compound that contains greater than 98% ubidecarenone (ubiquinone), such as sold under the trade name Kaneka Q10™ (USP Ubidecarenone) by Kaneka Nutrients, L.P. (Pasadena, Tex.). The CoQ10 compound is added at an amount of 5.25%, by weight (w/w), of the final concentrate. In addition to the non-polar compound, TPGS surfactant and benzyl alcohol preservative, the concentrates in Table 75 further contain a non-polar solvent, vitamin E oil, which contains at least 67.2% tocopherol and approximately 32.8% soybean oil (such as sold by ADM Natural Health and Nutrition (Decatur, Ill.) under the name Novatol™ 5-67 Vitamin E (D-alpha-tocopherol; ADM product code 410217), and a phosphatidylcholine co-surfactant that is derived from soy extract and contains greater than 95% phosphatidylcholine (such as sold under the trade name S-100, by Lipoid, LLC (Newark, N.J.)). The polar solvent is either glycerin or propylene glycol.

TABLE 75

Liquid nanoemulsion concentrates with CoQ10 and glycerin or propylene glycol polar solvent

| Ingredient | Phase | wt % |
|---|---|---|
| CoQ10 (non-polar compound) | Oil | 5.25 |
| Glycerin or propylene glycol (polar solvent) | Water | 72.08 |
| TPGS | Oil | 17.75 |
| Vitamin E oil (non-polar solvent) | Oil | 3.75 |
| Phosphatidylcholine (co-surfactant) | Oil | 0.669 |
| Benzyl alcohol (preservative) | Oil | 0.5 |
| Totals | | 100 |

Example 8

Liquid Dilution Compositions

In this example, flavored waters (liquid dilution compositions/beverage compositions) are prepared that use the liquid nanoemulsion concentrates described in Examples 3-7 above that contain various non-polar compounds that contain non-polar active ingredients. Each of the waters contains bicarbonate, citric acid and/or vitamin C (ascorbic acid) as a stabilizing system for the non-polar active ingredients. The liquid dilution compositions are prepared according to the following general bench-top method.

Water, juice (when included), non-polar active ingredients and vitamin C (when included) are added to a Pyrex beaker and are mixed until dissolved using a standard mixer, such as an IKA® model No. RE-16 1S, which is an overhead mixer (laboratory stirrer) compatible with the bench-top process. Antifoaming agent (such as Tramfloc 1147, sold by Tramfloc Inc, Formey, Tex.) and potassium or sodium bicarbonate are added and the solution mixes and heats to 80° C. using a hot plate (such as the Thermolyne hot plate Model #SP46615, Barnstead International, Dubuque, Iowa). Sweeteners and flavors are added while mixing and maintaining a temperature of 80° C. Finally, citric acid, phosphoric acid and antifoaming agent are added together while mixing, and the solution is hot filled into a container and sealed. The container is cooled to 30° C. and stored at room temperature. The final pH of each flavored water is approximately 3.80.

The flavored waters set forth in Tables 76-79 can be prepared as any flavor or combination of flavors and include the following ingredients: juice concentrates, such as cherry and blueberry (such as sold by Shoreline Fruit (Traverse City, Mich.) and Schare and Associates (Long Beach, N.Y.); juice extract, such as cranberry juice extract; flavors, such as pomegranate grape, mixed berry, peach mango, citrus, peach, vanilla, cherry, mixed berry, natural blackberry and banana (such as sold by Creative Flavor Concepts (Irvine, Calif.), Mission Flavors and Fragrances, Inc. (Foothill Ranch, Calif.) and Cargill); sucralose that is FCC VI Grade (such as manufactured by Changzhou Tianhua Imports & Exports Co., Ltd and sold by Ausvita); food grade 80% phosphoric acid (such as sold by Univar); an antifoaming agent (such as Tramfloc 1147, sold by Tramfloc Inc, Formey, Tex.); and water, which is city water, which is purified prior to addition to the water phase vessel, by passage through the following purifiers, sequentially in the following order: a charcoal filter, a particle filter, a water softener, a reverse osmosis purifier, a UV sterilizer and an end-point filter (a 50 micron end-point filter).

A. Flavored Waters Containing Potassium Bicarbonate and Citric Acid

The flavored waters set forth in Table 76 below contain between 1 g and 4 g (0.424 wt % to 1.695 wt %) of potassium bicarbonate and between 244.6 mg and 5.2446 g (0.104 wt % to 2.222 wt %) of citric acid per serving. Each flavored water contains one or more of the liquid nanoemulsion concentrates prepared according to Examples 3-7, above. Exemplary concentrates include the vitamin D3 concentrates, the fish oil concentrates, the flaxseed oil concentrates, the resveratrol concentrates, the coenzyme Q10 concentrates and any other concentrate prepared according to Examples 3-7, above. The concentrates can be added in any combination. Table 76 sets forth the ingredients of flavored waters that include a total of 0.498 wt %, 0.894 wt %, 1.055 wt % and 3.818 wt % liquid nanoemulsion concentrate.

TABLE 76

| Flavored waters with potassium bicarbonate and citric acid | | | | |
|---|---|---|---|---|
| Ingredient | wt % | wt % | wt % | wt % |
| Water | 92.03-98.09 | 92.03-98.09 | 92.03-98.09 | 92.03-98.09 |
| Juice Concentrate | 0-0.759 | 0-0.759 | 0-0.759 | 0-0.759 |
| Liquid nanoemulsion concentrate | 0.498 | 0.894 | 1.055 | 3.818 |
| Vitamin B12 (non-polar compound) | 0-0.00000102 | 0-0.00000102 | 0-0.00000102 | 0-0.00000102 |
| Flavor | 0.100-0.29 | 0.100-0.29 | 0.100-0.29 | 0.100-0.29 |
| Potassium bicarbonate (stabilizer) | 0.424-1.695 | 0.424-1.695 | 0.424-1.695 | 0.424-1.695 |
| Phosphoric acid (pH adjuster) | 0.440-1.093 | 0.440-1.093 | 0.440-1.093 | 0.440-1.093 |
| Citric acid (stabilizer) | 0.104-2.222 | 0.104-2.222 | 0.104-2.222 | 0.104-2.222 |
| Sucralose (sweetener) | 0.008-0.081 | 0.008-0.081 | 0.008-0.081 | 0.008-0.081 |
| Total | 100 | 100 | 100 | 100 |

B. Flavored Waters Containing Potassium Bicarbonate, Citric Acid and Vitamin C

The flavored waters set forth in Table 77 below contain between 3 g and 4 g (1.271 wt % to 1.695 wt %) of potassium bicarbonate, between 2.2446 g and 2.4446 g (0.951 wt % to 1.036 wt %) of citric acid and between 0.12 g and 0.125 g (0.051 wt % to 0.053 wt %) of vitamin C per serving. Each flavored water contains one or more of the liquid nanoemulsion concentrates prepared according to Examples 3-7, above. Exemplary concentrates include the vitamin D3 concentrates, the fish oil concentrates, the flaxseed oil concentrates, the resveratrol concentrates, the coenzyme Q10 concentrates and any other concentrate prepared according to Examples 3-7, above. The concentrates can be added in any combination. Table 77 sets forth the ingredients of flavored waters that include a total of 0.498 wt %, 0.894 wt %, 1.055 wt % and 3.436 wt % liquid nanoemulsion concentrate.

TABLE 77

Flavored waters with potassium bicarbonate, citric acid and vitamin C

| Ingredient | wt % | wt % | wt % | wt % |
|---|---|---|---|---|
| Water | 93.105-96.34 | 93.105-96.34 | 93.105-96.34 | 93.105-96.34 |
| Juice Concentrate | 0-0.305 | 0-0.305 | 0-0.305 | 0-0.305 |
| Liquid nanoemulsion concentrate | 0.498 | 0.894 | 1.055 | 3.818 |
| Vitamin B12 (non-polar compound) | 0-0.00000102 | 0-0.00000102 | 0-0.00000102 | 0-0.00000102 |
| Flavor | 0.086-0.44 | 0.086-0.44 | 0.086-0.44 | 0.086-0.44 |
| Potassium bicarbonate (stabilizer) | 1.271-1.695 | 1.271-1.695 | 1.271-1.695 | 1.271-1.695 |
| Phosphoric acid (pH adjuster) | 0.440-0.886 | 0.440-0.886 | 0.440-0.886 | 0.440-0.886 |
| Citric acid (stabilizer) | 0.951-1.036 | 0.951-1.036 | 0.951-1.036 | 0.951-1.036 |
| Vitamin C (ascorbic acid) stabilizer/non-polar compound) | 0.051-0.053 | 0.051-0.053 | 0.051-0.053 | 0.051-0.053 |
| Sucralose (sweetener) | 0.010-0.015 | 0.010-0.015 | 0.010-0.015 | 0.010-0.015 |
| Total | 100 | 100 | 100 | 100 |

C. Flavored Waters that Contain a Sweetener

In this example, flavored waters that contain omega-3 polyunsaturated fatty acids, from fish oil, vitamin D3, vitamin B1, vitamin B3, vitamin B5, vitamin B6, vitamin B12, yerba mate, ginseng and/or gingko biloba are prepared according to the method described in Example 5A, above. Each of the waters contains bicarbonate and citric acid as a stabilizing system for the non-polar active ingredients and a sweetener. The sweetener is either sucralose, xylitol (such as sold by Nutra Food Ingredients) and/or stevia leaf powder extract (such as sold by MiniStar International Inc. (Product code STE091)). Each flavored water contains one or more of the liquid nanoemulsion concentrates prepared according to Examples 3-7, above. Exemplary concentrates include the vitamin D3 concentrates, the fish oil concentrates, the flaxseed oil concentrates, the resveratrol concentrates, the coenzyme Q10 concentrates and any other concentrate prepared according to Examples 3-7, above. The concentrates can be added in any combination. Additional ingredients in the flavored waters include any combination of additional non-polar compounds that contain non-polar active ingredients, potassium bicarbonate, citric acid, flavors and water. Tables 78 and 79, below, sets forth the ingredients of exemplary flavored waters that include either sucralose, xylitol and/or stevia as the sweetener.

TABLE 78

Flavored water containing sucralose

| Ingredient | g per batch | mg per serving | Percent (by weight) |
|---|---|---|---|
| Water | 490.17232 | 464683.3574 | 98.034 |
| Vitamin D3 concentrate (100,000 IU/g) (non-polar active ingredient) | 0.01097 | 10.4 | 0.002 |
| Fish Oil Concentrate (Omega-3, 2% EPA DHA) (non-polar active ingredient) | 2.10970 | 2000.0 | 0.422 |
| Yerba Mate 8% (non-polar active ingredient) | 0.02110 | 20.0 | 0.004 |
| Ginkgo Biloba 24/6 (non-polar active ingredient) | 0.0158228 | 15.0 | 0.003 |
| Ginseng Panax (7% HPLC, Red Korean Ginseng) (JIA Herb) (non-polar active ingredient) | 0.03165 | 30.0 | 0.006 |
| Vitamin B1 (Thiamine) + 5% (non-polar active ingredient) | 0.00068 | 0.64 | 0.00014 |
| Vitamin B3 (Niacin/Niacinamide) + 5% (non-polar active ingredient) | 0.00886 | 8.4 | 0.002 |
| Vitamin B5 (Pantothenic Acid ) + 5% (non-polar active ingredient) | 0.00559 | 5.3 | 0.001 |
| Vitamin B6 + 5 % (non-polar active ingredient) | 0.00148 | 1.4 | 0.0003 |
| Vitamin B12 + >5% (non-polar active ingredient) | 0.00000274 | 0.0026 | 0.0000005 |
| Flavor | 0.70992 | 673.0 | 0.142 |
| Sucralose (sweetener) | 0.08175 | 77.5 | 0.016 |
| Citric Acid (stabilizer) | 3.34916 | 3175.0 | 0.6698 |
| Potassium Bicarbonate (stabilizer) | 3.48101 | 3300.0 | 0.696 |
| Total | 500 | 474000 | 100 |

TABLE 79

Flavored water containing stevia and xylitol

| Ingredient | g per batch | mg per serving | Percent (by weight) |
|---|---|---|---|
| Water | 291.10914 | 459952.4574 | 97.036 |
| Vitamin D3 concentrate (100,000 IU/g) (non-polar active ingredient) | 0.00658 | 10.4 | 0.002 |
| Fish Oil Concentrate (Omega-3, 2% EPA DHA) (non-polar active ingredient) | 1.26582 | 2000.0 | 0.422 |
| Yerba Mate 8% (non-polar active ingredient) | 0.01266 | 20.0 | 0.004 |
| Ginkgo Biloba 24/6 (non-polar active ingredient) | 0.0094937 | 15.0 | 0.003 |
| Vitamin B1 (Thiamine) + 5% (non-polar active ingredient) | 0.00041 | 0.64 | 0.00014 |
| Vitamin B3 (Niacin/Niacinamide) + 5% (non-polar active ingredient) | 0.00532 | 8.4 | 0.002 |
| Vitamin B5 (Pantothenic Acid) + 5% (non-polar active ingredient) | 0.00335 | 5.3 | 0.001 |
| Vitamin B6 + 5% (non-polar active ingredient) | 0.00089 | 1.4 | 0.0003 |
| Vitamin B12 + >5% (non-polar active ingredient) | 0.0000016 | 0.0026 | 0.0000005 |
| Flavor | 0.23203 | 366.6 | 0.077 |
| Stevia Leaf Powder Extract (sweetener) | 0.05114 | 137.0 | 0.017 |
| Xylitol (sweetener) | 3.20506 | 80.8 | 1.068 |
| Citric Acid (stabilizer) | 2.00949 | 3175.0 | 0.6698 |
| Potassium Bicarbonate (stabilizer) | 2.08861 | 3300.0 | 0.696 |
| Total | 300 | 474000 | 100 |

Example 9

Preparation and Comparison of Liquid Nanoemulsion Concentrates Containing Non-Polar Compounds and High-Dimer TPGS Liquid nanoemulsion concentrates that contained either 10%, 15% or 20% by weight fish oil, a non-polar compound containing non-polar active ingredients, and the TPGS composition described above in Example 1 were prepared. For comparison, liquid nanoemulsion concentrates that contained either 10%, 15% or 20% by weight fish oil and a commercially available TPGS composition (~86% TPGS monomer and ~11% TPGS dimer; Eastman Chemical Company, Kingsport, Tenn.) also were prepared. The liquid nanoemulsion concentrates were prepared according to the method described in Example 3, above.

The tables below indicate the amount (in mg) of each ingredient contained per 1 mL serving of the liquid nanoemulsion concentrate and the percentage by weight (wt %) of each ingredient. The column labeled "phase" indicates to which phase of the production process (described in Example 3, above) each ingredient was added. "Water" indicates that a particular ingredient was added during production of the water phase, "oil" indicates the ingredient was added during production of the oil phase and "emulsion/flavor" indicates the ingredient was added during or after mixing of the water and oil phases.

The liquid nanoemulsion concentrates contained the following ingredients: TPGS, either prepared as described in Example 1 above or a commercially available TPGS composition that was made up of ~86% TPGS monomer and ~11% TPGS dimer (Eastman Chemical Company, Kingsport, Tenn.); an emulsion stabilizer that was a blend of xanthan gum, guar gum and sodium alginate, sold under the product name SALADIZER®, available from TIC Gums, Inc. (Belcamp, Md.); a natural (GRAS-certified) preservative, benzyl alcohol; citric acid, a pH adjuster; a non-polar compound, a fish oil that contains 2% EPA and DHA, sold as ONC TG fish oil by Ocean Nutrition Canada (Dartmouth, Nova Scotia); and a polar solvent, water, which was purified city water, purified as described above.

Tables 80-82, below, set forth the ingredients and amounts used to make the liquid nanoemulsion concentrates that contained either 10%, 15% or 20%, by weight, of the non-polar compound fish oil.

TABLE 80

Liquid nanoemulsion concentrate containing 10% fish oil

| Ingredient | mg/1 mL serving | Phase | wt % of composition |
|---|---|---|---|
| Water (polar solvent) | 1220.30 | Water | 61.015 |
| SALADIZER® (emulsion stabilizer) | 0.100 | Water | 0.01 |
| ONC Fish oil (non-polar compound) | 200 | Oil | 10.00 |
| Benzyl alcohol (preservative/natural flavor) | 10.000 | Oil | 0.50 |
| TPGS | 564.0 | Oil | 28.20 |
| Citric acid (pH adjuster) | 5.60 | Emulsion/Flavor | 0.2800 |
| Totals | 2000.00 | | 100.000 |

TABLE 81

Liquid nanoemulsion concentrate containing 15% fish oil

| Ingredient | mg/1 mL serving | Phase | wt % of composition |
|---|---|---|---|
| Water (polar solvent) | 1120.30 | Water | 56.015 |
| SALADIZER® (emulsion stabilizer) | 0.100 | Water | 0.01 |

TABLE 81-continued

Liquid nanoemulsion concentrate containing 15% fish oil

| Ingredient | mg/1 mL serving | Phase | wt % of composition |
|---|---|---|---|
| ONC Fish oil (non-polar compound) | 300 | Oil | 15.00 |
| Benzyl alcohol (preservative/natural flavor) | 10.000 | Oil | 0.50 |
| TPGS | 564.0 | Oil | 28.20 |
| Citric acid (pH adjuster) | 5.60 | Emulsion/Flavor | 0.2800 |
| Totals | 2000.00 | | 100.000 |

TABLE 82

Liquid nanoemulsion concentrate containing 20% fish oil

| Ingredient | mg/1 mL serving | Phase | wt % of composition |
|---|---|---|---|
| Water (polar solvent) | 1184.30 | Water | 59.215 |
| SALADIZER ® (emulsion stabilizer) | 0.100 | Water | 0.01 |
| ONC Fish oil (non-polar compound) | 400 | Oil | 20.00 |
| Benzyl alcohol (preservative/natural flavor) | 10.000 | Oil | 0.50 |
| TPGS | 400.0 | Oil | 20.00 |
| Citric acid (pH adjuster) | 5.60 | Emulsion/Flavor | 0.2800 |
| Totals | 2000.00 | | 100.000 |

The clarity of each of compositions containing the concentrates that contained the high dimer (about 51%) TPGS composition, prepared according to Example 1 above, was determined and compared to the clarity of the concentrates that contained the commercially available standard TPGS composition (low dimer) from Eastman Chemical Company. The clarity of each concentrate was evaluated by a turbidity analysis using a nephelometer. The concentrates were prepared for the analysis using the following steps.

Eight ounces of water was heated in a Pyrex® beaker by placing the beaker on a Thermolyne hot plate (Model #846925) until the water reached 49.8° C. The concentrate was then added to the heated water and stirred with a stir rod until dispersed. The resulting aqueous composition was cooled to room temperature (about 25° C.). The cooled aqueous composition was added to an amber-glass screw-top vial (Alcon) for evaluation. The vials that contained the aqueous compositions were sent to ACZ Laboratories, Inc. (Steamboat Springs, Colo.) for turbidity analysis using a nephelometer. Results of the analysis are listed in the form of Nephelometric Turbidity Units (NTU) and are indicated in Tables 83-85 below.

TABLE 83

Turbidity (NTU) of aqueous compositions containing 10% fish oil

| Composition | Turbidity (NTU) |
|---|---|
| TPGS (Example 1) + 10% fish oil | 12.1 |
| TPGS (Eastman) + 10% fish oil | 76.8 |

TABLE 84

Turbidity (NTU) of aqueous compositions containing 15% fish oil

| Composition | Turbidity (NTU) |
|---|---|
| TPGS (Example 1) + 15% fish oil | 38.5 |
| TPGS (Eastman) + 15% fish oil | 233 |

TABLE 85

Turbidity (NTU) of aqueous compositions containing 20% fish oil

| Composition | Turbidity (NTU) |
|---|---|
| TPGS (Example 1) + 15% fish oil | 718 |
| TPGS (Eastman) + 15% fish oil | 1000 |

As the data demonstrate, the aqueous compositions that contained the liquid nanoemulsion concentrates that were prepared with the high dimer TPGS, prepared as described in Example 1 (i.e., TPGS compositions that contained the higher amounts of TPGS dimer and lower amounts of TPGS monomer), exhibited significantly lower turbidity than those compositions that contained the liquid nanoemulsion concentrates prepared using commercially available TPGS (i.e., TPGS compositions that contained higher amounts of TPGS monomer and lower amounts of TPGS dimer).

Example 10

Preparation of Flavored Shots for Direct Ingestion Containing Active Ingredients and the TPGS Composition A series of 4 mL flavored shots for direct consumption were prepared. These contained the high dimer TPGS preparation (51% dimer, 48% monomer), as described in Example 1, one or more active ingredients, and other optional ingredients. The compositions are intended for ingestion in a single shot, and can be provided in an ampoule.

Exemplary formulations were prepared as follows. The water phase was prepared by adding water, potassium sorbate, sodium benzoate, SALADIZER®, glycerin and inulin, then heating to 160° F. The oil phase was prepared by adding oat oil, benzyl alcohol, TEA (triethanolamine), and parabens (optional), dissolving phosphatidylcholine or lecithin at 160° F., then adding TPGS, followed by polyethylene glycol 400 distearate (PEG 400 DS). The oil phase was then added to the water phase using homogenization Arde Barinco shear. Flavors, sucralose or other sweeteners, and color, if any were added. The formulations were hot filled into a container, such as an ampoule, and cooled down.

Tables 85-91, below set forth exemplary ingredients and amounts (in mg) of each ingredient in each 4 mL serving of and the percentage by weight (wt %) and amount (g) of each ingredient per batch. The column labeled "phase" indicates to which phase of the production process (described in Example 3, above) each ingredient was added. "Water" indicates that a particular ingredient was added during production of the water phase, "oil" indicates the ingredient was added during production of the oil phase and "emulsion/flavor" indicates the ingredient was added during or after mixing of the water and oil phases.

The flavored shots were prepared using the following ingredients:

TPGS, prepared as described in Example 1 above;

an emulsion stabilizer that is a blend of xanthan gum, guar gum and sodium alginate, sold under the product name SALADIZER®, available from TIC Gums, Inc. (Belcamp, Md.);

one or more preservatives that included a natural (GRAS-certified) preservative, benzyl alcohol, potassium sorbate, sodium benzoate, methyl paraben and propyl paraben;

a pH adjuster, citric acid;

one or more polar solvents that included glycerin and water;

one or more non-polar solvents that included vitamin E oil (Novatol 5-67; Item #410217; ADM Co., Decatur, Ill.) and oat oil;

one or more co-surfactants that included triethanolamine (TEA) and a phospholipid co-surfactant, lecithin, sold under the name Lecithin Ultralec® P (ADM Co., Decatur, Ill.);

a soluble fiber, inulin, sold as Oliggo-Fiber Instant Inulin (Fibruline® Instant) (supplied by Cosucra-Groupe Warcoing SA, Belgium, sold by Gillco Products, San Marcos, Calif.);

a polymer, polyethylene glycol 400 distearate (PEG 400 DS), sold by Stepan Lipid Nutrition, Maywood, N.J.;

one or more flavoring agents that included peach (PH-147) and vanilla (VA-158), sold by Mission Flavors and Fragrances, Inc. (Foothill Ranch, Calif.);

a sweetener, sucralose;

one or more additional active ingredients that included caffeine, synephrine HCl (>95%), 4-amino-3-phenylbutyric acid for energizing compositions, and theanine, *Erythrina* extract and melatonin for calming compositions; and one or more non-polar compounds that included one or more of:

a fish oil that contains 2% EPA and DHA, sold as ONC TG fish oil by Ocean Nutrition Canada (Dartmouth, Nova Scotia);

a coenzyme Q10 (CoQ10) compound that contains greater than 98% ubidicarenone (ubiquinone), sold under the name Kaneka Q10™ (USP Ubidicarenone; Kaneka Nutrients, L.P., Pasadena, Tex.); and green tea extract that contained 60% EGCG (epigallocatechin gallate) (sold by Guilin Layn Natural Ingredients Corp., Guilin, China).

TABLE 85

Flavored shot containing 5% CoQ10

| Ingredient | mg /4 mL serving | Phase | wt % of composition | g/batch |
|---|---|---|---|---|
| Water (polar solvent) | 2657.112 | Water | 66.4278 | 332.139 |
| Glycerin (polar solvent) | 300 | Water | 7.5 | 37.5 |
| Potassium sorbate (preservative) | 2 | Water | 0.05 | 0.25 |
| Sodium benzoate (preservative) | 2 | Water | 0.05 | 0.25 |
| SALADIZER ® (emulsion stabilizer) | 10 | Water | 0.25 | 1.25 |
| Inulin (soluble fiber) | 150 | Water | 3.75 | 18.75 |
| CoQ10 (non-polar compound) | 200 | Oil | 5 | 25 |
| TPGS | 70 | Oil | 1.75 | 8.75 |
| Vitamin E oil (non-polar solvent) | 200 | Oil | 5 | 25 |
| Benzyl alcohol (preservative/sterilizer) | 20 | Oil | 0.5 | 2.5 |
| PEG 400 DS (polymer) | 90 | Oil | 2.25 | 11.25 |
| Lecithin (co-surfactant) | 100 | Oil | 2.5 | 12.5 |
| Citric acid (pH adjuster) | 50 | Emulsion/Flavor | 1.25 | 6.25 |
| Sucralose (sweetener) | 106.668 | Emulsion/Flavor | 2.6667 | 13.3335 |
| Peach (flavoring agent) | 22.22 | Emulsion/Flavor | 0.5555 | 2.7775 |
| Vanilla (flavoring agent) | 18 | Emulsion/Flavor | 0.45 | 2.25 |
| Totals | 4000.00 | | 100.000 | 550 |

TABLE 86

Flavored shot containing 15% fish oil

| Ingredient | mg/4 mL serving | Phase | wt % of composition | g/batch |
|---|---|---|---|---|
| Water (polar solvent) | 2549.612 | Water | 63.7403 | 318.70 |
| Glycerin (polar solvent) | 200 | Water | 5 | 25 |
| Potassium sorbate (preservative) | 2 | Water | 0.05 | 0.25 |
| Sodium benzoate (preservative) | 2 | Water | 0.05 | 0.25 |
| SALADIZER ® (emulsion stabilizer) | 10 | Water | 0.25 | 1.25 |
| Inulin (soluble fiber) | 150 | Water | 3.75 | 18.75 |
| Fish oil (EPA/DHA) (non-polar compound) | 600 | Oil | 15 | 75 |
| TPGS | 70 | Oil | 1.75 | 8.75 |
| Benzyl alcohol (preservative/sterilizer) | 20 | Oil | 0.5 | 2.5 |
| PEG 400 DS (polymer) | 90 | Oil | 2.25 | 11.25 |
| Lecithin (co-surfactant) | 100 | Oil | 2.5 | 12.5 |
| Citric acid (pH adjuster) | 57.5 | Emulsion/Flavor | 1.4375 | 7.1875 |
| Sucralose (sweetener) | 106.668 | Emulsion/Flavor | 2.6667 | 13.3335 |
| Peach (flavoring agent) | 22.22 | Emulsion/Flavor | 0.5555 | 2.7775 |
| Vanilla (flavoring agent) | 18 | Emulsion/Flavor | 0.45 | 2.25 |
| Totals | 4000.00 | | 100.000 | 550 |

TABLE 87

Flavored shot containing 4.5% caffeine

| Ingredient | mg/4 mL serving | Phase | wt % of composition | g/batch |
|---|---|---|---|---|
| Water (polar solvent) | 2871.612 | Water | 71.7903 | 358.9515 |
| Glycerin (polar solvent) | 100 | Water | 2.5 | 12.5 |
| Potassium sorbate (preservative) | 2 | Water | 0.05 | 0.25 |
| Sodium benzoate (preservative) | 2 | Water | 0.05 | 0.25 |

TABLE 87-continued

Flavored shot containing 4.5% caffeine

| Ingredient | mg/4 mL serving | Phase | wt % of composition | g/batch |
|---|---|---|---|---|
| SALADIZER ® (emulsion stabilizer) | 10 | Water | 0.25 | 1.25 |
| Inulin (soluble fiber) | 150 | Water | 3.75 | 18.75 |
| Caffeine (active ingredient) | 180 | Water | 4.5 | 22.5 |
| TPGS | 70 | Oil | 1.75 | 8.75 |
| Oat oil (non-polar solvent) | 200 | Oil | 5 | 25 |
| Benzyl alcohol (preservative/sterilizer) | 20 | Oil | 0.5 | 2.5 |
| PEG 400 DS (polymer) | 90 | Oil | 2.25 | 11.25 |
| Lecithin (co-surfactant) | 100 | Oil | 2.5 | 12.5 |
| Citric acid (pH adjuster) | 57.5 | Emulsion/Flavor | 1.4375 | 7.1875 |
| Sucralose (sweetener) | 106.668 | Emulsion/Flavor | 2.6667 | 13.3335 |
| Peach (flavoring agent) | 22.22 | Emulsion/Flavor | 0.5555 | 2.7775 |
| Vanilla (flavoring agent) | 18 | Emulsion/Flavor | 0.45 | 2.25 |
| Totals | 4000.00 | | 100.000 | 550 |

TABLE 88

Flavored shot containing 4.5% synephrine

| Ingredient | mg/4 mL serving | Phase | wt % of composition | g/batch |
|---|---|---|---|---|
| Water (polar solvent) | 2871.612 | Water | 71.7903 | 358.9515 |
| Glycerin (polar solvent) | 100 | Water | 2.5 | 12.5 |
| Potassium sorbate (preservative) | 2 | Water | 0.05 | 0.25 |
| Sodium benzoate (preservative) | 2 | Water | 0.05 | 0.25 |
| SALADIZER ® (emulsion stabilizer) | 10 | Water | 0.25 | 1.25 |
| Inulin (soluble fiber) | 150 | Water | 3.75 | 18.75 |
| Synephrine HCl (>95%) (active ingredient) | 180 | Water | 4.5 | 22.5 |
| TPGS | 70 | Oil | 1.75 | 8.75 |
| Oat oil (non-polar solvent) | 200 | Oil | 5 | 25 |
| Benzyl alcohol (preservative/sterilizer) | 20 | Oil | 0.5 | 2.5 |
| PEG 400 DS (polymer) | 90 | Oil | 2.25 | 11.25 |
| Lecithin (co-surfactant) | 100 | Oil | 2.5 | 12.5 |
| Citric acid (pH adjuster) | 57.5 | Emulsion/Flavor | 1.4375 | 7.1875 |
| Sucralose (sweetener) | 106.668 | Emulsion/Flavor | 2.6667 | 13.3335 |
| Peach (flavoring agent) | 22.22 | Emulsion/Flavor | 0.5555 | 2.7775 |
| Vanilla (flavoring agent) | 18 | Emulsion/Flavor | 0.45 | 2.25 |
| Totals | 4000.00 | | 100.000 | 550 |

TABLE 89

Flavored shot containing 15% 4-amino-3-phenylbutyric acid

| Ingredient | mg/4 mL serving | Phase | wt % of composition | g/batch |
|---|---|---|---|---|
| Water (polar solvent) | 2451.612 | Water | 61.293 | 612.903 |
| Glycerin (polar solvent) | 100 | Water | 2.5 | 25 |
| Potassium sorbate (preservative) | 2 | Water | 0.05 | 0.5 |
| Sodium benzoate (preservative) | 2 | Water | 0.05 | 0.5 |
| SALADIZER ® (emulsion stabilizer) | 10 | Water | 0.25 | 2.5 |
| Inulin (soluble fiber) | 150 | Water | 3.75 | 37.5 |
| 4-amino-3-phenylbutyric acid HCl (active ingredient) | 600 | Water | 15 | 150 |
| TPGS | 70 | Oil | 1.75 | 17.5 |
| Oat oil (non-polar solvent) | 200 | Oil | 5 | 50 |
| Benzyl alcohol (preservative/sterilizer) | 20 | Oil | 0.5 | 5 |
| PEG 400 DS (polymer) | 90 | Oil | 2.25 | 22.5 |
| Lecithin (co-surfactant) | 100 | Oil | 2.5 | 25 |
| Triethanolamine (co-surfactant) | 57.5 | Oil | 1.4375 | 14.375 |
| Sucralose (sweetener) | 106.668 | Emulsion/Flavor | 2.6667 | 26.667 |
| Peach (flavoring agent) | 22.22 | Emulsion/Flavor | 0.5555 | 5.555 |
| Vanilla (flavoring agent) | 18 | Emulsion/Flavor | 0.45 | 4.5 |
| Totals | 4000.00 | | 100.000 | 1100 |

TABLE 90

Flavored shot containing 15% 4-amino-3-phenylbutyric acid

| Ingredient | mg/4 mL serving | Phase | wt % of composition | g/batch |
|---|---|---|---|---|
| Water (polar solvent) | 2450.612 | Water | 61.250 | 612.653 |
| Glycerin (polar solvent) | 100 | Water | 2.5 | 25 |
| Potassium sorbate (preservative) | 2 | Water | 0.05 | 0.5 |
| Sodium benzoate (preservative) | 2 | Water | 0.05 | 0.5 |
| SALADIZER ® (emulsion stabilizer) | 10 | Water | 0.25 | 2.5 |
| Inulin (soluble fiber) | 150 | Water | 3.75 | 37.5 |
| 4-amino-3-phenylbutyric acid HCl (active ingredient) | 600 | Water | 15 | 150 |
| TPGS | 70 | Oil | 1.75 | 17.5 |
| Oat oil (non-polar solvent) | 200 | Oil | 5 | 50 |
| Benzyl alcohol (preservative/sterilizer) | 20 | Oil | 0.5 | 5 |
| PEG 400 DS (polymer) | 90 | Oil | 2.25 | 22.5 |
| Lecithin (co-surfactant) | 100 | Oil | 2.5 | 25 |
| Triethanolamine (co-surfactant) | 57.5 | Oil | 1.4375 | 14.375 |
| Methyl paraben (preservative) | 1 | Oil | 0.025 | 0.25 |
| Propyl paraben (preservative) | 1 | Oil | 0.025 | 0.25 |

TABLE 90-continued

Flavored shot containing 15% 4-amino-3-phenylbutyric acid

| Ingredient | mg/4 mL serving | Phase | wt % of composition | g/batch |
|---|---|---|---|---|
| Sucralose (sweetener) | 106.668 | Emulsion/Flavor | 2.666 | 26.667 |
| Peach (flavoring agent) | 22.22 | Emulsion/Flavor | 0.5555 | 5.555 |
| Vanilla (flavoring agent) | 18 | Emulsion/Flavor | 0.45 | 4.5 |
| Totals | 4001.00 | | 100.000 | 1100.275 |

TABLE 91

Flavored shot containing 7.5% green tea

| Ingredient | mg/4 mL serving | Phase | wt % of composition | g/batch |
|---|---|---|---|---|
| Water (polar solvent) | 2749.612 | Water | 68.7403 | 343.7015 |
| Glycerin (polar solvent) | 100 | Water | 2.5 | 12.5 |
| Potassium sorbate (preservative) | 2 | Water | 0.05 | 0.25 |
| Sodium benzoate (preservative) | 2 | Water | 0.05 | 0.25 |
| SALADIZER ® (emulsion stabilizer) | 10 | Water | 0.25 | 1.25 |
| Inulin (soluble fiber) | 150 | Water | 3.75 | 18.75 |
| Green tea 60% EGCG (active ingredient) | 300 | Water | 7.5 | 37.5 |
| TPGS | 70 | Oil | 1.75 | 8.75 |
| Oat oil (non-polar solvent) | 200 | Oil | 5 | 25 |
| Benzyl alcohol (preservative/sterilizer) | 20 | Oil | 0.5 | 2.5 |
| PEG 400 DS (polymer) | 90 | Oil | 2.25 | 11.25 |
| Lecithin (co-surfactant) | 100 | Oil | 2.5 | 12.5 |
| Methyl paraben (preservative) | 1 | Oil | 0.025 | 0.125 |
| Propyl paraben (preservative) | 1 | Oil | 0.025 | 0.125 |
| Citric acid (pH adjuster) | 57.5 | Emulsion/Flavor | 1.4375 | 7.1875 |
| Sucralose (sweetener) | 106.668 | Emulsion/Flavor | 2.6667 | 13.3335 |
| Peach (flavoring agent) | 22.22 | Emulsion/Flavor | 0.5555 | 2.7775 |
| Vanilla (flavoring agent) | 18 | Emulsion/Flavor | 0.45 | 2.25 |
| Totals | 4000.00 | | 100.000 | 550 |

TABLE 92

Calming composition

| | (g) per batch | wt % |
|---|---|---|
| Water Ingredients | | |
| Water | 833.9 | 83.39 |
| Potassium Sorbate | 0.40 | 0.04 |
| Sodium Benzoate | 0.40 | 0.04 |
| Ticamulsion emulsion stabilizer | 5.0 | 0.5 |
| Saladizer emulsion stabilizer | 1.65 | 0.165 |
| Erythrina Extract | 77.50 | 7.75 |
| Melatonin | 0.63 | 0.06 |
| L-Theanine | 12.50 | 1.25 |
| G-Phosphatidylcholine | 20.00 | 2.0 |
| Oil Ingredients | | |
| Vitamin E TPGS | 30.10 | 3.0 |
| Flavor Ingredients | | |
| Sucralose | 4.5000 | 0.45 |
| Vanilla (VA-158) | 3.6950 | 0.037 |
| Banana (BA-146) | 0.4938 | 0.049 |
| Citric Acid | 9.26 | 0.926 |
| Total Ingredients grams | 1000.00 | 100 |

Since modifications will be apparent to those of skill in the art, it is intended that this invention be limited only by the scope of the appended claims.

The invention claimed is:

1. A composition, comprising:
   a) a water-soluble vitamin E derivative mixture present in an amount from 1% to 99%, inclusive, by weight, of the composition, wherein:
      the water-soluble vitamin E derivative mixture comprises at least 13 wt % water-soluble vitamin E derivative dimer and up to 87%, by weight, water-soluble vitamin E derivative monomer; and
      the water-soluble vitamin E derivative is a polyalkylene glycol derivative of vitamin E; and
   b) a non-polar compound or a mixture of non-polar compounds other than the water-soluble vitamin E derivative mixture.

2. The composition of claim 1, wherein the water-soluble vitamin E derivative mixture is present in an amount less than 15%, by weight, of the composition and the non-polar compound is present in an amount for direct consumption.

3. The composition of claim 1, wherein the water-soluble vitamin E derivative mixture contains at least 40%, by weight, vitamin E derivative dimer and less than 55%, by weight, vitamin E derivative monomer.

4. The composition of claim 1, wherein the water-soluble vitamin E derivative mixture:
   contains at least 30% and up to 55%, inclusive, vitamin E derivative dimer; and
   contains less than 70% vitamin E derivative monomer.

5. The composition of claim 1, wherein the amount of dimer in the water-soluble vitamin E derivative mixture is greater than 29%, by weight, and the total amount of the dimer and monomer in the water-soluble vitamin E derivative mixture is at least 95%, 96%, 97%, 98%, or 99%, by weight, of the mixture.

6. The composition of claim 1, wherein the monomer in the water-soluble vitamin E derivative mixture comprises between about 30% and 69%, by weight, of the water-soluble vitamin E derivative mixture.

7. The composition of claim 1, wherein the polyalkylene glycol derivative of vitamin E is a polyethylene glycol (PEG) derivative of vitamin E.

8. The composition of claim 7, wherein the PEG derivative of vitamin E is selected from among tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate.

9. The composition of claim 1, wherein the water-soluble vitamin E derivative is a PEG derivative of vitamin E that is tocopheryl polyethylene glycol succinate (TPGS), a TPGS analog or a TPGS homolog.

10. The composition of claim 8, wherein the PEG derivative of vitamin E is a D-α-tocopheryl polyethylene glycol succinate.

11. The composition of claim 8, wherein the PEG derivative of vitamin E is D-α-tocopheryl polyethylene glycol succinate 1000 (TPGS 1000).

12. The composition of claim 9, wherein the monomer in the water-soluble vitamin E derivative mixture comprises between or between about 30% and 69%, by weight, of the water-soluble vitamin E derivative mixture.

13. The composition of claim 1, wherein the dimer comprises between about 29% and 75%, by weight, of the water-soluble vitamin E derivative mixture.

14. The composition of claim 1, wherein:
the monomer comprises between about 35% and 65%, inclusive, by weight, of the water-soluble vitamin E derivative mixture and the dimer comprises between about 25% and 65%, by weight, of the water-soluble vitamin E derivative mixture; and
the monomer and dimer together comprise at least 70%, by weight, of the water-soluble vitamin E derivative mixture in the composition.

15. The composition of claim 1, wherein the non-polar compound contains a non-polar active ingredient selected from among polyunsaturated fatty acids (PUFA), coenzyme Q, phytosterols, resveratrol, carotenoids, micronutrients, alpha lipoic acid and oil-soluble vitamins.

16. The composition claim 15, wherein the non-polar compound that contains a PUFA is selected from among fish oil, algae (algal) oil, flaxseed oil, borage oil, saw palmetto extract, safflower oil, coconut oil, soybean oil and conjugated linoleic acid (CLA)-containing compounds and mixtures thereof.

17. The composition of claim 16, wherein the PUFA is selected from among omega-3 fatty acids, omega-6 fatty acids and omega-9 fatty acids.

18. The composition of claim 16, wherein the PUFA is selected from among one or more of a docosahexaenoic acid (DHA), an eicosapentaenoic acid (EPA), an alpha-linolenic acid (ALA), a gamma-linolenic acid (GLA), a conjugated linoleic acid (CLA) and an oleic acid.

19. The composition of claim 1, wherein the non-polar compound is selected from among one or more of:
a coenzyme Q10;
an oil-soluble vitamin that is selected from among vitamin B12, vitamin D3, vitamin A palmitate, vitamin E, vitamin B1, vitamin B3, vitamin B5, vitamin B6, vitamin C and mixtures thereof;
a carotenoid-containing compound that is selected from among lycopene, lutein, zeaxanthin and mixtures of lutein and zeaxanthin; and
a micronutrient-containing compound that is selected from among yerba mate, ginkgo biloba and ginseng.

20. The composition of claim 1, wherein the amount of non-polar compound(s) in the composition is from 1% to 75%, by weight, of the composition.

21. The composition of claim 1, further comprising a polar solvent.

22. The composition of claim 21, wherein the polar solvent is a polar protic solvent.

23. The composition of claim 22, wherein the polar solvent is water or an edible alcohol or mixtures thereof.

24. The composition of claim 21, wherein the polar solvent is selected from among water, glycerin, propylene glycol, ethylene glycol, tetraethylene glycol, triethylene glycol and trimethylene glycol.

25. The composition of claim 21, wherein the polar solvent is present in an amount from more than 1% to 95%, by weight, of the composition.

26. The composition of claim 25, wherein the polar solvent is present in an amount from more than 45% to 80%, by weight, of the composition.

27. The composition of claim 25, comprising a co-surfactant present in an amount sufficient to stabilize the composition compared to the absence of the co-surfactant.

28. The composition of claim 27, wherein the co-surfactant is selected from among a phospholipid, a sucrose fatty acid ester, a polysorbate and a polysorbate analog.

29. The composition of claim 27, wherein the co-surfactant contains phosphatidylcholine.

30. The composition of claim 25, comprising an emulsion stabilizer present in an amount sufficient to stabilize the composition compared to the absence of the emulsion stabilizer.

31. The composition of claim 30, wherein the emulsion stabilizer is selected from among one or more of a blend of xanthan gum, guar gum and sodium alginate; modified gum acacia; and ester gum.

32. The composition of claim 1, comprising a flavor or flavoring agent.

33. The composition of claim 25, wherein the amount of the water-soluble vitamin E derivative mixture is from 16% to 30%, inclusive, by weight, of the composition.

34. A composition, consisting essentially of:
a) a water-soluble vitamin E derivative mixture present in an amount from 5% to 95%, by weight, of the composition, wherein:
the water-soluble vitamin E derivative mixture comprises from 25 wt% to 69 wt% water-soluble vitamin E monomer and from 13 wt% to 75 wt% water-soluble vitamin E dimer; and
the water-soluble vitamin E derivative is a polyalkylene glycol derivative of vitamin E;
b) a non-polar compound other than the water-soluble vitamin E derivative mixture, present in an amount from 1% to 75%, by weight, of the composition; and
c) a preservative present in an amount sufficient to preserve the composition.

35. A composition, consisting essentially of:
a) a water-soluble vitamin E derivative mixture present in an amount from 5% to 95%, by weight, of the composition, wherein:
the water-soluble vitamin E derivative mixture comprises from 25 wt% to 69 wt% water-soluble vitamin E monomer and from 13 wt% to 75 wt% water-soluble vitamin E dimer; and the water-soluble vitamin E derivative is a polyalkylene glycol derivative of vitamin E;

b) a non-polar compound other than the water-soluble vitamin E derivative mixture, present in an amount from 1% to 75%, by weight, of the composition;

c) a preservative present in an amount sufficient to preserve the composition; and d) a non-polar solvent that differs from the non-polar compound and is present in an amount at least sufficient to dissolve the non-polar compound.

36. The composition of claim 1, wherein the composition comprises between 5% and 50%, by weight, the non-polar compound.

37. A beverage, comprising the composition of claim 36 in a beverage base.

38. The beverage of claim 37, wherein the beverage base is water, soda, juice, carbonated water, flavored water or flavored carbonated water.

39. The beverage of claim 37, wherein the beverage base is a fruit, vegetable or berry juice, milk, a sports drink, a base that comprises a fruit flavor or flavoring agent, or a carbonated beverage.

40. The composition of claim 1, comprising a sweetener.

41. The composition of claim 40, wherein the sweetener is selected from among one or more of sucralose, sucrose, lactose, fructose, an acesulfame salt, aspartame, saccharin, stevia, stevioside and xylitol.

42. The composition of claim 1, comprising a stabilizer that is selected from among one or more of carbonates, bicarbonates, acids and antioxidants.

43. A method of making the composition of claim 1, comprising:

(a) mixing and heating initial ingredient(s) in a vessel, wherein:

the initial ingredient(s) comprise the water-soluble vitamin E derivative mixture present in an amount from 5% to 95%, by weight, of the composition;

(b) adding the non-polar compound at an amount from 1% to 75%, by weight, of the composition, and any other ingredients;

(c) homogenizing the ingredients; and (d) cooling the mixed ingredients to thereby generate a composition that comprises the water-soluble vitamin E derivative mixture.

44. The method of claim 43, further comprising, step (e) mixing the composition prepared in step (d) with an aqueous composition.

45. A method for preparing a beverage containing a non-polar compound, comprising adding the composition of claim 1 to a beverage base.

46. The method of claim 45, wherein the beverage base comprises a juice, water, a soda, a sports drink or a nutritional drink.

47. A composition for direct consumption, comprising in an aqueous beverage base:

(a) a non-polar ingredient in an amount between about 0.001% and about 0.1%, by weight; and (b) a water-soluble vitamin E derivative mixture in an amount between at or about 0.1% and 15%, by weight, of the composition, wherein:

the water-soluble vitamin E derivative mixture comprises at least 13 wt % water-soluble vitamin E derivative dimer and up to 87 wt % water-soluble vitamin E derivative monomer; and the water-soluble vitamin E derivative is a polyalkylene glycol derivative of vitamin E.

48. The composition of claim 47, wherein the amount of dimer in the water-soluble vitamin E derivative mixture is greater than 29%, by weight, and the total amount of the dimer and monomer in the water-soluble vitamin E derivative mixture is at least 95%, by weight, of the mixture.

49. The composition of claim 47, wherein the amount of the water-soluble vitamin E derivative mixture is between 0.1% and at or about 5%, by weight, of the composition.

50. The composition of claim 1, wherein the water-soluble vitamin E derivative mixture contains 29%-69%, inclusive, of the vitamin E derivative dimer, and contains less than 70% vitamin E derivative monomer.

* * * * *